US009309263B2

(12) United States Patent
White et al.

(10) Patent No.: US 9,309,263 B2
(45) Date of Patent: Apr. 12, 2016

(54) FUSED MULTI-CYCLIC SULFONE COMPOUNDS AS INHIBITORS OF BETA-SECRETASE AND METHODS OF USE THEREOF

(71) Applicant: AMGEN INC., Thousand Oaks, CA (US)

(72) Inventors: Ryan White, Somerville, MA (US); Jennifer R. Allen, Newbury Park, CA (US); Oleg Epstein, Belmont, MA (US); Fang-Tsao Hong, Thousand Oaks, CA (US); Zihao Hua, Andover, MA (US); Jason Brooks Human, Boston, MA (US); Patricia Lopez, Woodland Hills, CA (US); Philip R. Olivieri, Charlestown, MA (US); Karina Romero, Arlington, MA (US); Laurie Schenkel, Boston, MA (US); John Stellwagen, Beverly, MA (US); Nuria A. Tamayo, Newbury Park, CA (US); Xiao Mei Zheng, Natick, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/166,012

(22) Filed: Jan. 28, 2014

(65) Prior Publication Data

US 2014/0213581 A1 Jul. 31, 2014

Related U.S. Application Data

(60) Provisional application No. 61/758,175, filed on Jan. 29, 2013.

(51) Int. Cl.

| C07D 417/10 | (2006.01) |
|---|---|
| C07D 417/14 | (2006.01) |
| C07D 513/04 | (2006.01) |
| C07D 513/14 | (2006.01) |
| C07D 417/12 | (2006.01) |
| C07D 471/04 | (2006.01) |
| C07D 487/04 | (2006.01) |
| C07D 513/10 | (2006.01) |
| C07D 513/20 | (2006.01) |
| C07D 519/00 | (2006.01) |

(52) U.S. Cl.
CPC ............ *C07D 513/04* (2013.01); *C07D 417/12* (2013.01); *C07D 471/04* (2013.01); *C07D 487/04* (2013.01); *C07D 513/10* (2013.01); *C07D 513/14* (2013.01); *C07D 513/20* (2013.01); *C07D 519/00* (2013.01)

(58) Field of Classification Search
CPC .. C07D 417/14; C07D 417/10; C07D 513/14; C07D 513/04
See application file for complete search history.

(56) References Cited

U.S. PATENT DOCUMENTS

| 8,158,620 B2 | 4/2012 | Suzuki et al. |
|---|---|---|
| 2010/0075957 A1 | 3/2010 | Tamura et al. |
| 2012/0238557 A1 | 9/2012 | Masui et al. |
| 2012/0245157 A1 | 9/2012 | Masui et al. |

FOREIGN PATENT DOCUMENTS

| WO | 2011/005738 A1 | 1/2011 |
|---|---|---|
| WO | 2012/139425 A1 | 10/2012 |

(Continued)

OTHER PUBLICATIONS

West, Anthony R., Solid State Chemistry and Its Applications, Wiley, New York, 1988, 358.*

(Continued)

*Primary Examiner* — Erich A Leeser
(74) *Attorney, Agent, or Firm* — Markus Bergauer; Bernard P. Friedrichsen; G. Prabhakar Reddy

(57) ABSTRACT

The present invention provides a new class of compounds useful for the modulation of beta-secretase enzyme (BACE) activity. The compounds have a general Formula I:

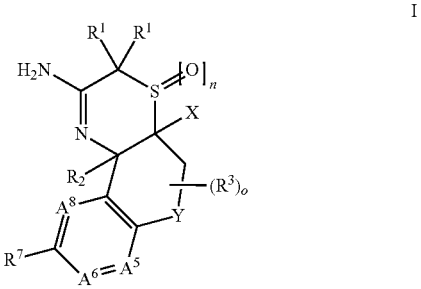

wherein variables $A^5$, $A^6$, $A^8$, $R^1$, $R^2$, $R^3$, $R^7$, X, Y, n and o of Formula I, independently, are defined herein. The invention also provides pharmaceutical compositions comprising the compounds, and corresponding uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formula II and sub-formula embodiments thereof, compounds of Formula III, intermediates and processes and methods useful for the preparation of compounds of Formulas I-III, and sub-Formulas thereof.

31 Claims, No Drawings

(56) References Cited

FOREIGN PATENT DOCUMENTS

| WO | 2012/162330 | A1 | | 11/2012 | |
|---|---|---|---|---|---|
| WO | 2012/162334 | A1 | | 11/2012 | |
| WO | WO 2012/162330 | | * | 11/2012 | ........... C07D 279/08 |
| WO | 2013/004676 | A1 | | 1/2013 | |
| WO | 2013/030713 | A1 | | 3/2013 | |
| WO | 2013/148851 | A1 | | 10/2013 | |
| WO | 2013164730 | A1 | | 11/2013 | |
| WO | 2013182638 | A1 | | 12/2013 | |
| WO | 2014/099788 | A1 | | 6/2014 | |
| WO | 2014/099794 | A1 | | 6/2014 | |
| WO | 2014099768 | A1 | | 6/2014 | |
| WO | 2014/150331 | A1 | | 9/2014 | |
| WO | 2014/150340 | A1 | | 9/2014 | |

OTHER PUBLICATIONS

Yan et al, Lancet Neurol 2014; 13: 319-29.
Joachim et al., *Alz. Dis. Assoc. Dis.*, 6:7-34 (1992).
Selkoe, Neuron, 6:487 (1991).
Seubert et al., Nature, 359:325-327 (1992).
Citron, Trends in Pharmacological Sciences, 25(2):92-97 (2004).
Nature Medicine (Jun. 22, 2008).
Nature, 402:537-554 (1999) (p. 510).
Sabbagh, M. et al., Alz. Dis. Rev. 3:1-19 (1997).
Cole, S.L., Vasser, R., Molecular Degeneration 2:22, 2007.
Luo et al., Nature Neuroscience, 4:231-232 (2001).
Bioorganic & Medicinal Chemistry Letters 20 (2010) 2068-2073.
J. Med. Chem. 2009.
Alzheimer's Research & Therapy 2009.
Expert Opin. Emerging Drugs (2008) 13(2):255-271.
J. Med. Chem. 2008, 51, 6259-6262.
Chem. Soc. Rev., 2009, 38, 2698-2715.
Sabbagh_ClinicalDev_2009.
J. Neurosci., Oct. 14, 2009 • 29(41):12787-12794.
Zhou_et_al_ARKIVOC_2010_vi_84-88.
Nowak_Bioorganic_Medicinal_Chemistry_Letters_2009.
Malamas_Bioorganic_Medicinal_Chemistry_Letters_2009.
Zhou_Bioorganic_Medicinal_Chemistry_Letters_2010.
Malamas_JMedChem2009.
Expert Opin. Ther. Targets (2010) 14(12);1273-1277.

* cited by examiner

FUSED MULTI-CYCLIC SULFONE COMPOUNDS AS INHIBITORS OF BETA-SECRETASE AND METHODS OF USE THEREOF

RELATED APPLICATIONS

This application claims the benefit of U.S. Provisional Patent Application No. 61/758,175, filed on Jan. 29, 2013, which specification is hereby incorporated herein by reference in its entirety.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, is in phase II clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology,* 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. For example, each of the following PCT publications: WO2012139425 and WO2012162330 describe inhibitors of BACE, useful for treating AD and other beta-secretase mediated disorders. Specifically, WO2012162330 describes tricyclic thiazine compounds as inhibitors for the beta amyloid, having the general formula:

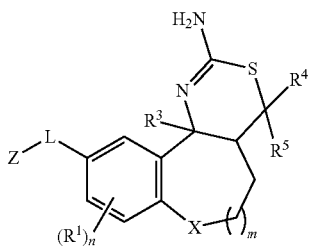

wherein X is selected from the group consisting of $CH_2$, O and $NR^2$.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knockout models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitrc oxide release from microglial cells. However, in the very same mice, it was also found that no atrophic change was detected in the retina of mice deficient in cathepsin B or L. *Mol. Cell. Neurosci,* 2003 Feb. 22(2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy,* 2007, September-October; 3(5):474-476. Finally, an adverse effect of the inhibition of Cat D is evident from the data presented in *PLoS One,* 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities (Alzheimer's Research Forum News, Mar. 31, 2011 reporting on Martin Citron's presentation at the AD/PD Conference March-2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

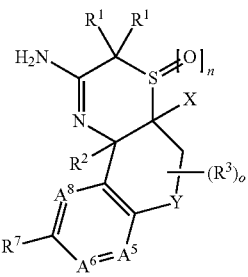

wherein each of $A^5$, $A^6$, $A^8$, $R^1$, $R^2$, $R^3$, $R^7$, X, Y, n and o of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In embodiment A of the invention, there are provided compounds, including stereoisomers, tautomers, hydrates, solvates and pharmaceutically acceptable salts thereof, which are generally defined by Formula I:

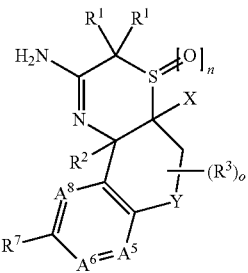

or a stereoisomer, tautomer, hydrate, solvate or pharmaceutically acceptable salt thereof, wherein
$A^5$ is $CR^5$ or N;
$A^6$ is $CR^6$ or N;
$A^8$ is $CR^8$ or N, provided that no more than one of $A^5$, $A^6$ and $A^8$ is N;
each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NHC(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —$NHC(O)R^{11}$— or —$C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;
X is H, F, $CH_3$, $CH_2CH_3$, cyclopropyl or CN;
Y is —$SCR^4R^4$—, —$CR^4R^4S$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;
n is 0, 1 or 2; and
o is 0, 1 or 2.

In embodiment A-1 of the invention, there are provided compounds, including stereoisomers, tautomers, hydrates, solvates and pharmaceutically acceptable salts thereof, which are generally defined by Formula I:

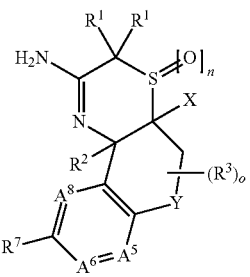

or a stereoisomer, tautomer, hydrate, solvate or pharmaceutically acceptable salt thereof, wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$allyl or $C_{1-3}$haloalkyl on the nitrogen atom;

$R^2$ is $C_{1-4}$alkyl or $C_{1-4}$haloalkyl;

each $R^3$, independently, is halo, $C_1$ alkyl, $OC_{1-4}$alkyl, $CH_2OC_{1-4}$allyl, $CH_2OH$, $C_{1-4}$haloalkyl or cyclopropyl, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$, —NH—C(=O)—$R^9$, —C(=O)NH—$R^9$, —O—$R^9$, S—$R^9$;

or $R^7$ is

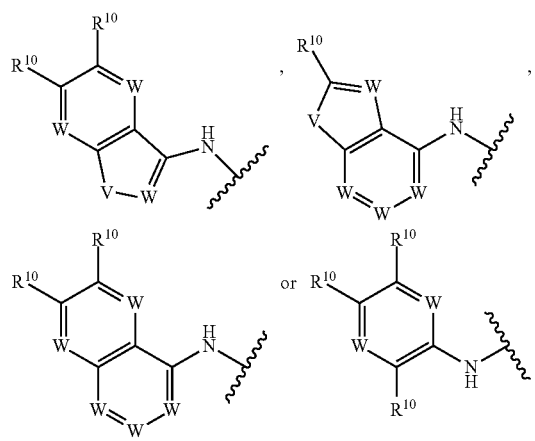

wherein V is $NR^{10}$, O or S; and each W, independently, is CH, CF, CCl or N.

$R^9$ is acetyl, $C_{1-6}$-alkyl, $C_2$ alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

X is H, F, $CH_3$, $CH_2CH_3$ or CN;

Y is —$SCR^4R^4$—, —$CR^4R^4S$—, —$OCR^4R^4$—, —$CR^4R^4O$— or —$CR^4R^4CR^4R^4$—, wherein each $R^4$, independently, is H, F, $C_{1-6}$alkyl, $OC_{1-6}$alkyl or $C_{1-6}$haloalkyl;

n is 0, 1 or 2; and o is 0, 1 or 2.

In embodiment 2 of the invention, there are provided compounds, including stereoisomers, tautomers, hydrates, solvates and pharmaceutically acceptable salts thereof, which are generally defined by Formula II:

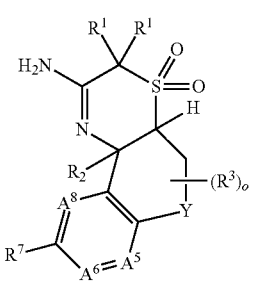

wherein $A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$-spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is $CH_3$, $CH_2F$ or $CHF_2$;

each $R^3$, independently, is halo, $C_1$ alkyl, $OC_{1-4}$alkyl, $CH_2OC_{1-4}$alkyl, $CH_2OH$, $C_{1-4}$haloalkyl or cyclopropyl, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$ or —NH—C(=O)—$R^9$;

or $R^7$ is

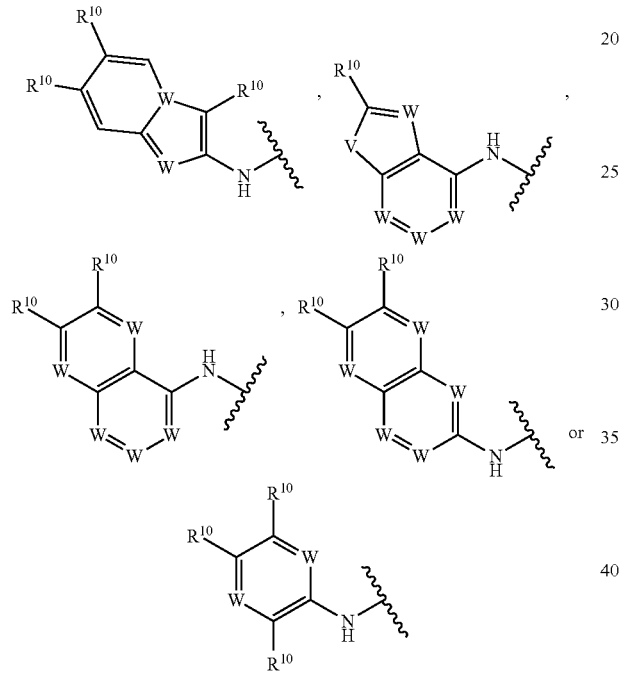

wherein V is $NR^{10}$ or S; and each W, independently, is CH, CF, CCl, $CCH_3$ or N;

$R^9$ is acetyl, $C_{1-6}$-alkyl, $C_2$ alkenyl, $C_{2-4}$alkynyl or a ring selected from phenyl, pyridyl, pyrimidyl, pyrazinyl, pyridazinyl, pyrazolyl, oxazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, imidazo-pyridyl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH_3, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and o is 0, 1 or 2.

In embodiment 2-A of the invention, there are provided compounds, including stereoisomers, tautomers, hydrates, solvates and pharmaceutically acceptable salts thereof, which are generally defined by Formula II-A:

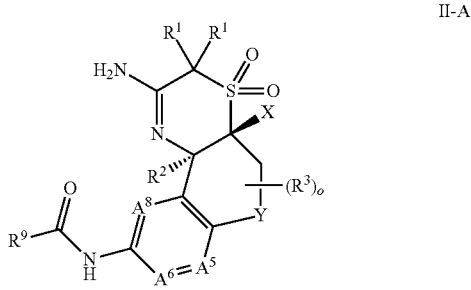

II-A wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is $CH_3$, $CH_2F$ or $CHF_2$;

each $R^3$, independently, is halo, $C_{1-4}$alkyl, $CH_2OC_{1-4}$alkyl, $CH_2OH$, $C_{1-4}$haloalkyl or cyclopropyl, wherein each of the $CH_2OC_{1-4}$alkyl and cyclopropyl is optionally substituted with 1-4 F atoms;

each of $R^5$, $R^6$ and $R^8$, independently, is H or F;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

X is H or F;

Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, $C_{1-3}$alkyl or $C_{1-3}$haloalkyl; and o is 0, 1 or 2.

In embodiment 2-B of the invention, there are provided compounds, including stereoisomers, tautomers, hydrates, solvates and pharmaceutically acceptable salts thereof, which are generally defined by Formula II-B:

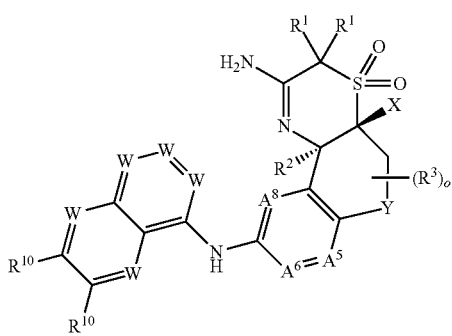

II-B wherein
$A^5$ is $CR^5$ or N;
$A^6$ is $CR^6$ or N;
$A^8$ is $CR^8$ or N, provided that no more than one of $A^5$, $A^6$ and $A^8$ is N;

each $R^1$, independently, is H, F, Cl, $C_{1-4}$-alkyl, $C_{2-4}$alkenyl, $C_{2-4}$alkynyl, CN, $CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is $CH_3$, $CH_2F$ or $CHF_2$;

each $R^3$, independently, is halo, $C_1$ alkyl, $CH_2OC_{1-4}$alkyl, $CH_2OH$, $C_{1-4}$haloalkyl or cyclopropyl, wherein each of the $CH_2OC_{1-4}$alkyl and cyclopropyl is optionally substituted with 1-4 F atoms;

each of $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

each W, independently, is CH, CF, CCl, $CCH_3$ or N;

X is H or F;

Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, $C_{1-3}$alkyl or $C_{1-3}$haloalkyl; and o is 0, 1 or 2.

In embodiment 2-C of the invention, there are provided compounds, including stereoisomers, tautomers, hydrates, solvates and pharmaceutically acceptable salts thereof, which are generally defined by Formula II-C:

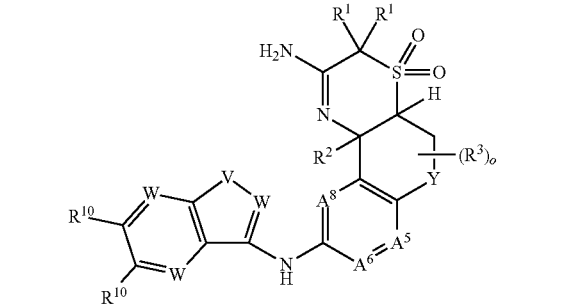

II-C wherein
$A^5$ is $CR^5$ or N;
$A^6$ is $CR^6$ or N;
$A^8$ is $CR^8$ or N, provided that no more than one of $A^5$, $A^6$ and $A^8$ is N;

each $R^1$, independently, is H, F, Cl, $C_{1-4}$-alkyl, $C_{2-4}$alkenyl, $C_{2-4}$alkynyl, CN, $CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is $CH_3$, $CH_2F$ or $CHF_2$;

each $R^3$, independently, is halo, $C_1$ alkyl, $CH_2OC_{1-4}$alkyl, $CH_2OH$, $C_{1-4}$haloalkyl or cyclopropyl, wherein each of the $CH_2OC_{1-4}$alkyl and cyclopropyl is optionally substituted with 1-4 F atoms;

each of $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy; morpholinyl, pyrazolyl, isoxazolyl, dihydropyranyl, pyrrolyl, pyrrolidinyl, tetrahydropyrrolyl, piperazinyl, oxetan-3-yl, dioxolyl, NHC(O)R$^{11}$— or C(O)NHR$^{11}$—, wherein each of the $C_{1-6}$allyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

each W, independently, is CH, CF, CCl, $CCH_3$ or N;

X is H or F;

Y is $SCR^4R^4$—, $S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and o is 0, 1 or 2.

In embodiment 2-D of the invention, there are provided compounds, including stereoisomers, tautomers, hydrates, solvates and pharmaceutically acceptable salts thereof, which are generally defined by Formula II-D:

II-D wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-4}$-alkyl, $C_{2-4}$alkenyl, $C_{2-4}$alkynyl, CN, $CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is $CH_3$, $CH_2F$ or $CHF_2$;

each $R^3$, independently, is halo, $C_{1-4}$alkyl, $CH_2OC_{1-4}$alkyl, $CH_2OH$, $C_{1-4}$haloalkyl or cyclopropyl, wherein each of the $CH_2OC_{1-4}$alkyl and cyclopropyl is optionally substituted with 1-4 F atoms;

each of $R^5$, $R^6$ and $R^8$, independently, is H or F;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy; morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy; morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

each W, independently, is CH, CF, CCl, $CCH_3$ or N;

X is H or F;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and o is 0, 1 or 2.

In embodiment 3-A of the invention, there are provided compounds, including stereoisomers, tautomers, hydrates, solvates and pharmaceutically acceptable salts thereof, which are generally defined by Formula III-A:

III-A wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_1$ alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$ or —NH—C(=O)—$R^9$;

or $R^7$ is

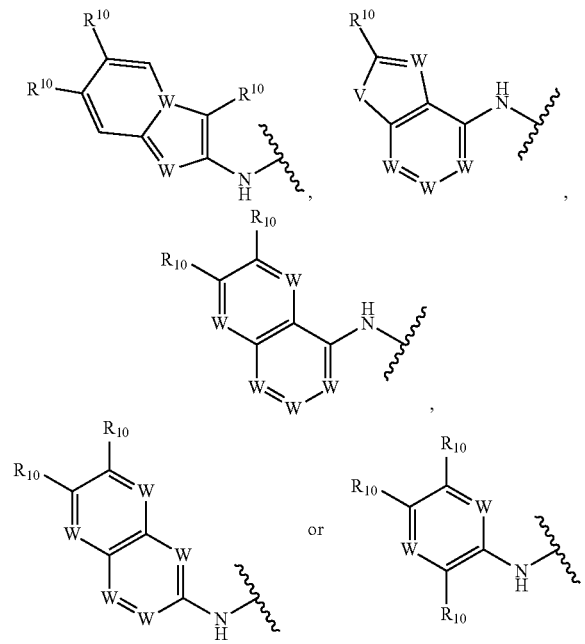

wherein V is $NR^{10}$ or S; and each W, independently, is CH, CF, CCl, $CCH_3$ or N;

$R^9$ is acetyl, $C_{1-6}$-alkyl, $C_2$ alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —$NHC(O)R^{11}$— or —$C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;

X is H, F, $CH_3$, $CH_2CH_3$, cyclopropyl or CN;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;

n is 0, 1 or 2; and o is 0, 1 or 2.

In embodiment 3-B of the invention, there are provided compounds, including stereoisomers, tautomers, hydrates, solvates and pharmaceutically acceptable salts thereof, which are generally defined by Formula III-B:

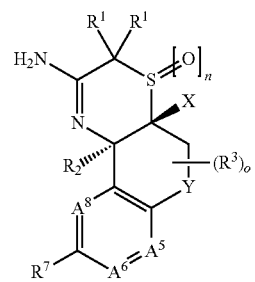

III-B wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_{1-4}$ alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$ or —NH—C(=O)—$R^9$;

or $R^7$ is

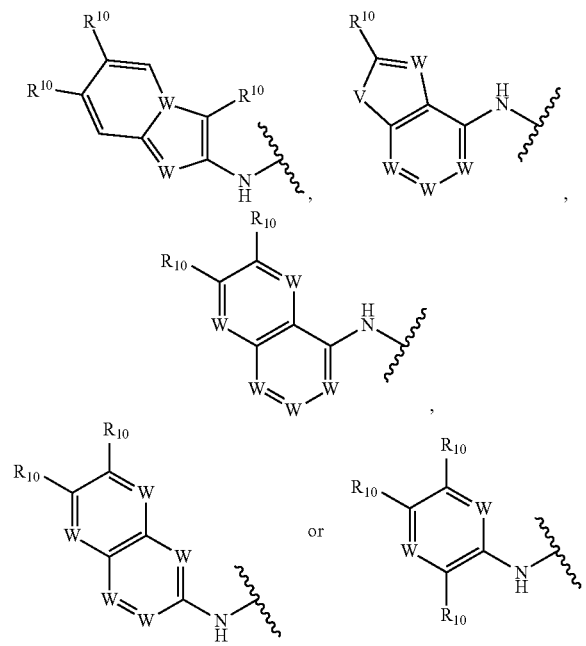

wherein V is $NR^{10}$ or S; and each W, independently, is CH, CF, CCl, $CCH_3$ or N;

$R^9$ is acetyl, $C_{1-6}$-alkyl, $C_2$ alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;

X is H, F, $CH_3$, $CH_2CH_3$, cyclopropyl or CN;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;

n is 0, 1 or 2; and o is 0, 1 or 2.

In embodiment 3-C of the invention, there are provided compounds, including stereoisomers, tautomers, hydrates, solvates and pharmaceutically acceptable salts thereof, which are generally defined by Formula III-C:

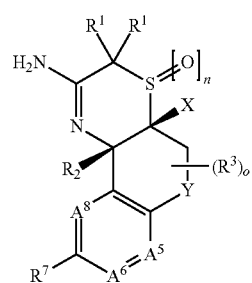

III-C wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_1$ alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$ or —NH—C(=O)—$R^9$;

or $R^7$ is

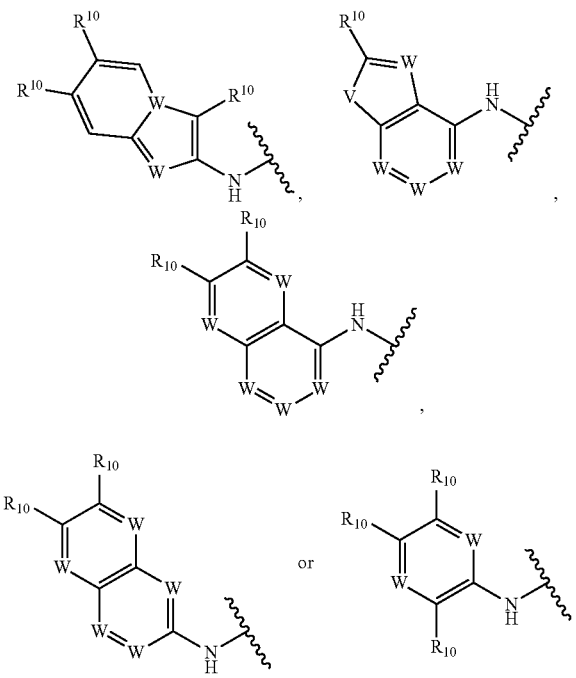

wherein V is $NR^{10}$ or S; and each W, independently, is CH, CF, CCl, $CCH_3$ or N;

$R^9$ is acetyl, $C_{1-6}$-alkyl, $C_2$ alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;

X is H, F, $CH_3$, $CH_2CH_3$, cyclopropyl or CN;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;

n is 0, 1 or 2; and o is 0, 1 or 2.

In embodiment 3-D of the invention, there are provided compounds, including stereoisomers, tautomers, hydrates, solvates and pharmaceutically acceptable salts thereof, which are generally defined by Formula III-D:

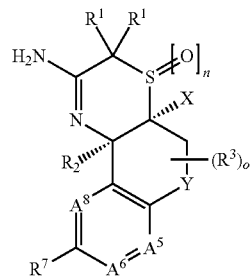

III-D wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_1$ alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is NH—$R^9$ or —NH—C(=O)—$R^9$;

or $R^7$ is

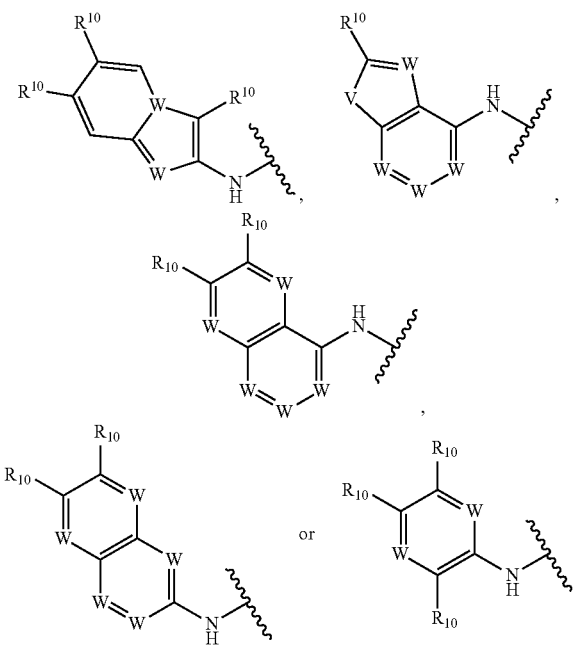

wherein V is $NR^{10}$ or S; and each W, independently, is CH, CF, CCl, $CCH_3$ or N;

$R^9$ is acetyl, $C_{1-6}$-alkyl, $C_2$ alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;

X is H, F, $CH_3$, $CH_2CH_3$, cyclopropyl or CN;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;

n is 0, 1 or 2; and o is 0, 1 or 2.

Similarly, in embodiments 2-A-1, 2-A-2, 2-A-3 and 2-A-4, (shown below), the invention provides compounds of sub-formulas II-A-1, II-A-2, II-A-3 and II-A-4, respectively, as described below.

II-A-1

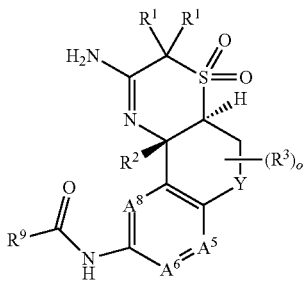

II-A-2

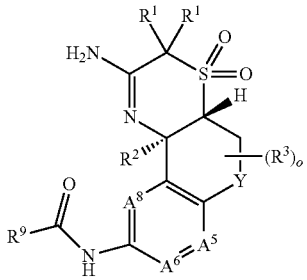

II-A-3

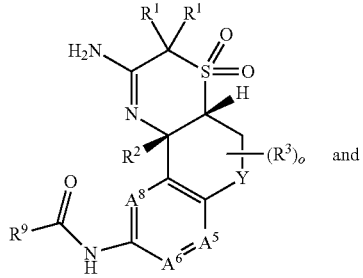

and

II-A-4

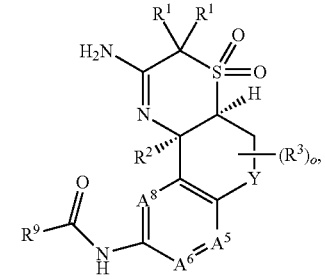

wherein each of the variables listed in II-A-1, II-A-2, II-A-3 and II-A-4, respectively, are as defined hereinabove and below with respect to Formula II and II-A; and

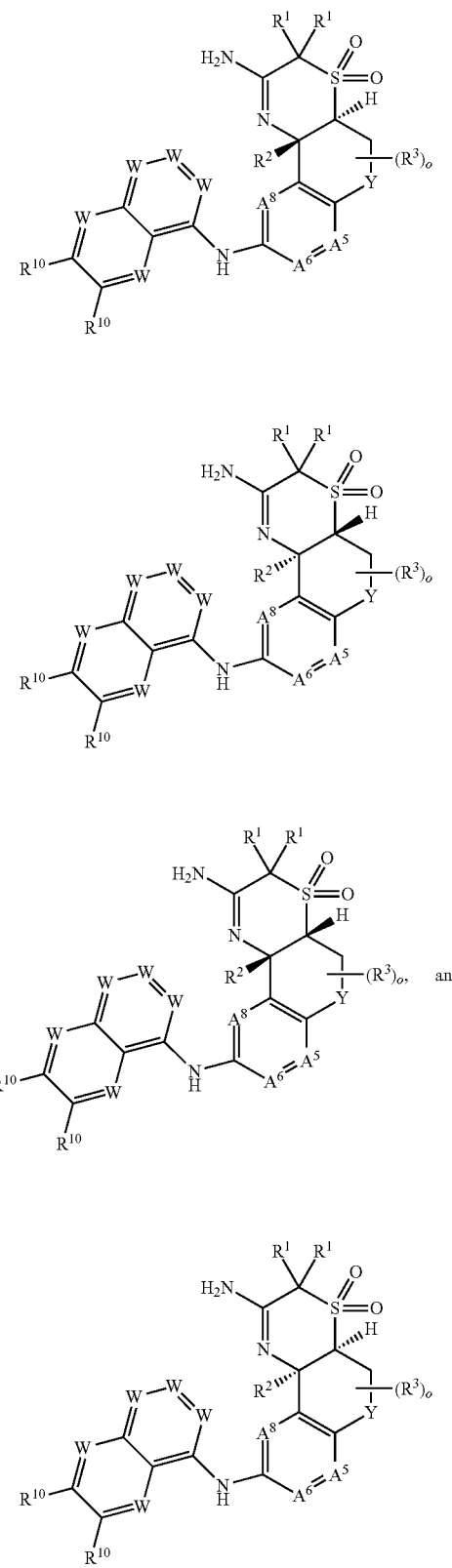

wherein each of the variables listed in II-B-1, II-B-2, II-B-3 and II-B-4, respectively, are as defined hereinabove and below with respect to Formula II and II-B; and

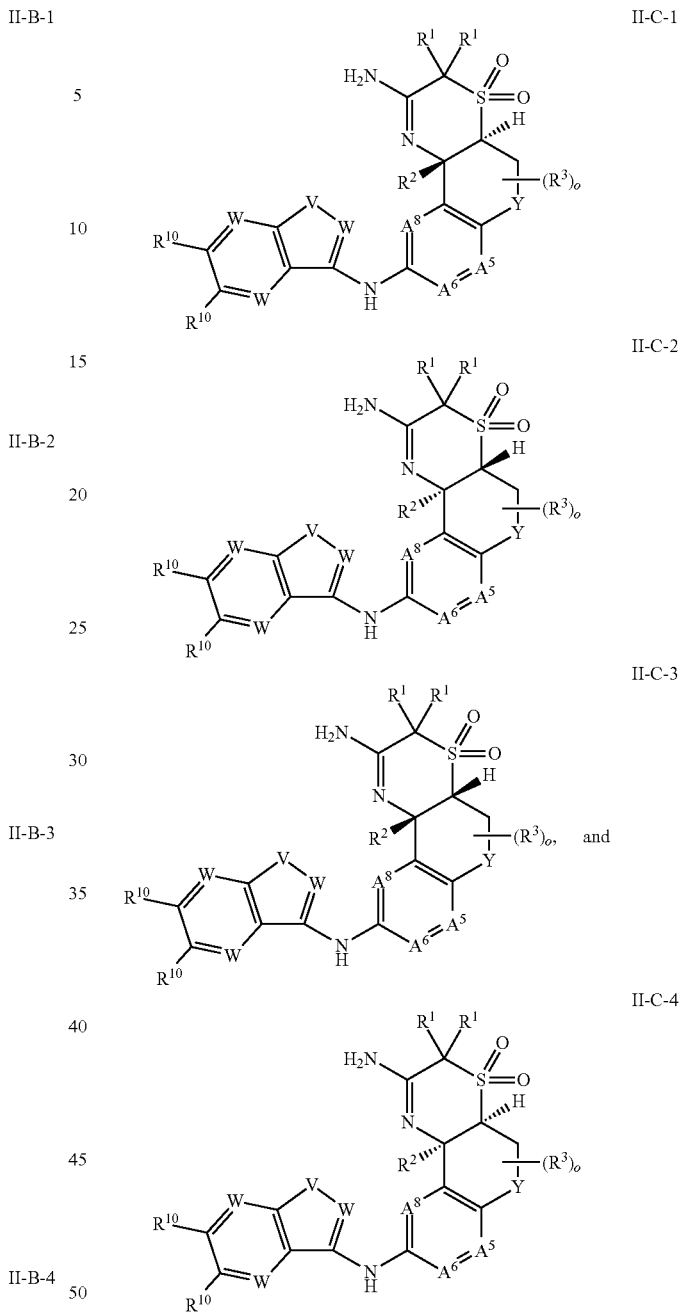

wherein each of the variables listed in embodiments 2-C-1, 2-C-2, 2-C-3 and 2-C-4 (Formulas II-C-1, II-C-2, II-C-3 and II-C-4), respectively, are as defined hereinabove and below with respect to Formula II and II-C, individually or in conjunction with any of the above or below embodiments, including those described in embodiments A, A-1 to A-4, B, B-1 to B-4, C, C-1 to C-7, D, D-1 to D-12, E, E-1 to E-5, F, F-1 to F-4, G, G-1 to G-4, H, H-1 to H-4, I, I-1 to I-9, J, J-1 to J-9, K, K-1, L, L-1 to L-3, M, M-1 to M-2, N, O, O-1 to O-4 and P-1 to P-2 described herein.

The present invention contemplates that the various different embodiments of Formulas I, II and III, and sub-Formulas II-A, II-B, II-C, III-A, III-B, III-C and III-D thereof, described herein, may comprise the following embodiments with respect to individual variables of $A^5, A^6, A^8, R^1, R^2, R^3,$ $R^7$, $R^9$, $R^{10}$, V, W, X and Y, n and o, where applicable, as described below. Hence, these embodiments with respect to individual variables $A^5$, $A^6$, $A^8$, $R^1$, $R^2$, $R^3$, $R^7$, $R^9$, $R^{10}$, V, W, X and Y, n and o, where applicable, may be applied "in conjunction with any of the other {above and below} embodiments" to create various embodiments of general Formulas I, II and III, and each sub-formula thereof, which are not literally or identically described herein. More specifically, the term "in conjunction with any of the above or below embodiments" includes embodiments A, A-1 to A-4, B, B-1 to B-4, C, C-1 to C-7, D, D-1 to D-12, E, E-1 to E-5, F, F-1 to F-4, G, G-1 to G-4, H, H-1 to H-4, I, I-1 to 1-9, J, J-1 to J-9, K, K-1, L, L-1 to L-3, M, M-1 to M-2, N, O, O-1 to O-4 and P-1 to P-2 described herein, as it applies to general Formulas I, II and III, and sub-formulas II-A, III-C and thereof, also described herein.

In another embodiment A, the invention includes compounds of Formula I, wherein n is 0, 1 or 2, in conjunction with any of the above or below embodiments.

In another embodiment A-1, the invention includes compounds of Formula I, wherein n is 1 or 2, in conjunction with any of the above or below embodiments.

In another embodiment A-2, the invention includes compounds of Formula I, wherein n is 2, in conjunction with any of the above or below embodiments.

In another embodiment A-3, the invention includes compounds of Formula I, wherein n is 1, in conjunction with any of the above or below embodiments.

In another embodiment A-4, the invention includes compounds of Formula I, wherein n is 0, in conjunction with any of the above or below embodiments.

In another embodiment B, the invention includes compounds of Formula I, wherein o is 0, 1 or 2, in conjunction with any of the above or below embodiments.

In another embodiment B-1, the invention includes compounds of Formula I, wherein o is 1 or 2, in conjunction with any of the above or below embodiments.

In another embodiment B-2, the invention includes compounds of Formula I, wherein o is 2, in conjunction with any of the above or below embodiments.

In another embodiment B-3, the invention includes compounds of Formula I, wherein o is 1, in conjunction with any of the above or below embodiments.

In another embodiment B-4, the invention includes compounds of Formula I, wherein o is 0, in conjunction with any of the above or below embodiments.

In another embodiment C, the invention includes compounds wherein each $R^1$, independently, is H, F, $C_{2-4}$alkenyl, $C_{2-4}$alkynyl, CN, —$CH_2OC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment C-1, the invention includes compounds wherein each $R^1$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment C-2, the invention includes compounds wherein each $R^1$, independently, is H, F, Cl, $CF_3$, $OCF_3$, methyl, ethyl, CN, OH, $OCH_3$, $SCH_3$, $NHCH_3$, $C(O)$ $CH_3$ or $CH_2OCHF_2$, in conjunction with any of the above or below embodiments.

In another embodiment C-3, the invention includes compounds wherein each $R^1$, independently, is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment C-4, the invention includes compounds wherein each $R^1$, independently, is H, F, Cl, $CF_3$, $CH_3$, $CF_2H$ or $CH_2F$, in conjunction with any of the above or below embodiments.

In another embodiment C-5, the invention includes compounds wherein each $R^1$, independently, is H, F, $CF_3$, $CH_3$, $CF_2H$ or $CH_2F$, in conjunction with any of the above or below embodiments.

In another embodiment C-6, the invention includes compounds wherein each $R^1$, independently, is H, F, $CF_3$ or $CH_3$, in conjunction with any of the above or below embodiments.

In another embodiment C-7, the invention includes compounds wherein each $R^1$, independently, is H, F or $CH_3$, in conjunction with any of the above or below embodiments.

In another embodiment C-8, the invention includes compounds wherein each $R^1$, independently, is $CH_3$, in conjunction with any of the above or below embodiments.

In another embodiment C-9, the invention includes compounds wherein each $R^1$, independently, is H, F or $CH_3$, or each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl, in conjunction with any of the above or below embodiments.

In another embodiment C-10, the invention includes compounds wherein each $R^1$, taken together with the carbon atom to which they are attached form a $C_{3-6}$ spirocarbocyclic ring optionally including one 0 heteroatom and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl, in conjunction with any of the above or below embodiments.

In another embodiment C-11, the invention includes compounds wherein each $R^1$, taken together with the carbon atom to which they are attached form a cyclopropyl, cyclobutyl or cyclopentyl ring optionally substituted with 1-4 F atoms on the carbon atoms, in conjunction with any of the above or below embodiments.

In another embodiment C-12, the invention includes compounds wherein each $R^1$, taken together with the carbon atom to which they are attached form a cyclopropyl or cyclopentyl ring optionally substituted with 1-4 F atoms on the carbon atoms, in conjunction with any of the above or below embodiments.

In another embodiment D, the invention includes compounds wherein $R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms, in conjunction with any of the above or below embodiments.

In another embodiment D-1, the invention includes compounds wherein $R^2$ is $C_{1-4}$alkyl, $C_{1-4}$haloalkyl, $CH_2OC_{1-4}$alkyl, $CH_2OC_{1-4}$haloalkyl or cyclopropyl, in conjunction with any of the above or below embodiments.

In another embodiment D-2, the invention includes compounds wherein $R^2$ is $CH_3$, $CH_2F$ or $CHF_2$, in conjunction with any of the above or below embodiments.

In another embodiment D-3, the invention includes compounds wherein each $R^2$, independently, is $CH_3$ or $CH_2F$, in conjunction with any of the above or below embodiments.

In another embodiment D-4, the invention includes compounds wherein each $R^2$, independently, is $CH_3$, $CF_3$ or $CH_2F$, in conjunction with any of the above or below embodiments.

In another embodiment D-5, the invention includes compounds wherein each $R^2$, independently, is $CF_3$ or $CH_3$, in conjunction with any of the above or below embodiments.

In another embodiment D-6, the invention includes compounds wherein each $R^2$, independently, is $CH_3$, in conjunction with any of the above or below embodiments.

In another embodiment D-7, the invention includes compounds wherein each $R^2$, independently, is H, in conjunction with any of the above or below embodiments.

In another embodiment E, the invention includes compounds wherein each $R^3$, independently, is halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms, in conjunction with any of the above or below embodiments.

In another embodiment E-1, the invention includes compounds wherein each $R^3$, independently, is halo, $C_{1-4}$alkyl, $C_{1-4}$haloalkyl, $CH_2OH$, $CH_2OCHF_2$ or cyclopropyl, wherein each of the $C_{1-4}$alkyl, and cyclopropyl is optionally substituted with 1-4 F atoms, in conjunction with any of the above or below embodiments.

In another embodiment E-2, the invention includes compounds wherein each $R^3$, independently, is F, $C_{1-4}$alkyl, $CH_2OH$, $CH_2OCH_2F$, $CH_2OCF_2H$, or cyclopropyl, wherein each of the $C_{1-4}$alkyl and cyclopropyl is optionally substituted with 1-2 F atoms, in conjunction with any of the above or below embodiments.

In another embodiment E-3, the invention includes compounds wherein each $R^3$, independently, is F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment E-4, the invention includes compounds wherein each $R^3$, independently, is F, $CH_3$, $CF_3$, $C_2H_5$, $CF_2H$ or $CH_2F$, in conjunction with any of the above or below embodiments.

In another embodiment E-5, the invention includes compounds wherein each $R^3$, independently, is F, $CF_3$, $CH_3$, $CF_2H$ or $CH_2F$, in conjunction with any of the above or below embodiments.

In another embodiment F, the invention includes compounds wherein $A^5$ is $CR^5$ wherein $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment F-1, the invention includes compounds wherein $A^5$ is $CR^5$ wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment F-2, the invention includes compounds wherein $A^5$ is $CR^5$ wherein $R^5$ is H, F, $CF_3$, $CF_2H$, $CH_2F$ or $CH_3$, in conjunction with any of the above or below embodiments.

In another embodiment F-3, the invention includes compounds wherein $A^5$ is $CR^5$ wherein $R^5$ is H or F, in conjunction with any of the above or below embodiments.

In another embodiment F-4, the invention includes compounds wherein $A^5$ is N, in conjunction with any of the above or below embodiments.

In another embodiment G, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment G-1, the invention includes compounds wherein $A^6$ is $CR^6$ wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment G-2, the invention includes compounds wherein $A^6$ is $CR^6$, wherein $R^6$ is H, F, $CF_3$, $CF_2H$, $CH_2F$ or $CH_3$, in conjunction with any of the above or below embodiments.

In another embodiment G-3, the invention includes compounds wherein $A^6$ is $CR^6$, wherein $R^6$ is H or F, in conjunction with any of the above or below embodiments.

In another embodiment G-4, the invention includes compounds wherein $A^6$ is N, in conjunction with any of the above or below embodiments.

In another embodiment H, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^8$ is $CR^8$ wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment H-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment H-3, the invention includes compounds wherein $A^8$ is $CR^8$ wherein $R^8$ is H or F, in conjunction with any of the above or below embodiments.

In another embodiment H-4, the invention includes compounds wherein $A^8$ is N, in conjunction with any of the above or below embodiments.

In another embodiment I, the invention includes compounds wherein no more than one of $A^5$, $A^6$ and $A^8$ is N, in conjunction with any of the above or below embodiments.

In another embodiment I-1, the invention includes compounds wherein no more than one of $A^5$ and $A^6$ is N, in conjunction with any of the above or below embodiments.

In another embodiment I-2, the invention includes compounds wherein $A^5$ is $CR^5$ or N, $A^6$ is $CR^6$ or N and $A^8$ is $CR^8$ or N, provided that no more than one of $A^5$, $A^6$ and $A^8$ is N, in conjunction with any of the above or below embodiments.

In another embodiment, the invention includes compounds wherein $A^5$ is $CR^5$ or N, $A^6$ is $CR^6$ and $A^8$ is $CR^8$, in conjunction with any of the above or below embodiments.

In another embodiment I-3, the invention includes compounds wherein $A^5$ is $CR^5$, $A^6$ is $CR^6$ and $A^8$ is $CR^8$, in conjunction with any of the above or below embodiments.

In another embodiment I-4, the invention includes compounds wherein $A^5$ is N, $A^6$ is $CR^6$, and $A^8$ is $CR^8$, in conjunction with any of the above or below embodiments.

In another embodiment I-5, the invention includes compounds wherein $A^5$ is $CR^5$, $A^6$ is N, and $A^8$ is $CR^8$, in conjunction with any of the above or below embodiments.

In another embodiment I-6, the invention includes compounds wherein $A^5$ is $CR^5$, $A^6$ is $CR^6$, and $A^8$ is N, in conjunction with any of the above or below embodiments.

In another embodiment I-7, the invention includes compounds of embodiments 1, 2 or 3, and sub-formulas thereof, wherein $A^5$ is $CR^5$ or N;

$A^6$ is $CR^6$ or N;

$A^8$ is $CR^8$ or N, provided that no more than one of $A^5$, $A^6$ and $A^8$ is N; and each of $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment 1-8, the invention includes compounds of embodiments 1, 2 or 3, and sub-formulas thereof, wherein $A^5$ is $CR^5$;

$A^6$ is $CR^6$; and $A^8$ is $CR^8$; wherein each of $R^5$, $R^6$ and $R^8$, independently, is H, F, $CF_3$, $CF_2H$, $CH_2F$ or $CH_3$, in conjunction with any of the above or below embodiments.

In another embodiment 1-9, the invention includes compounds of embodiments 1, 2 or 3, and sub-formulas thereof, wherein $A^5$ is CH, CF or N, $A^6$ is CH, CF or N, $A^8$ is CH, CF or N, one of $A^5$, $A^6$ and $A^8$ is N, in conjunction with any of the above or below embodiments.

In another embodiment J, the invention includes compounds wherein $R^7$ is —NH—$R^9$, —NH—C(=O)—$R^9$, —C(=O)NH—$R^9$, —O—$R^9$, S—$R^9$; or $R^7$ is

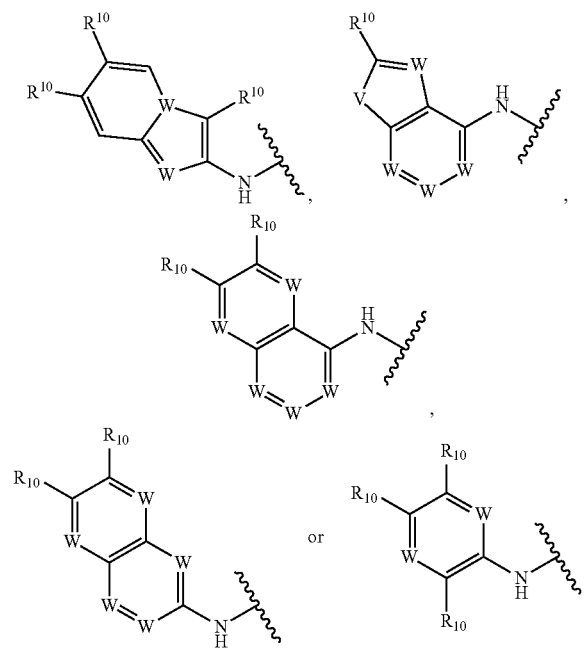

wherein V is $NR^{10}$, O or S; and each W, independently, is CH, CF, CCl or N, in conjunction with any of the above or below embodiments.

In another embodiment J-1, the invention includes compounds wherein $R^7$ is NH—$R^9$, —NH—C(=O)—$R^9$ or

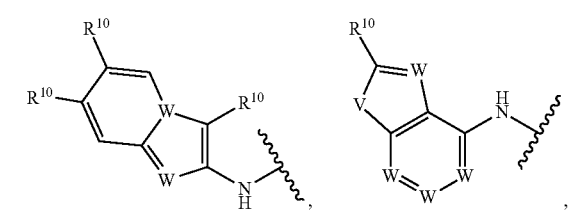

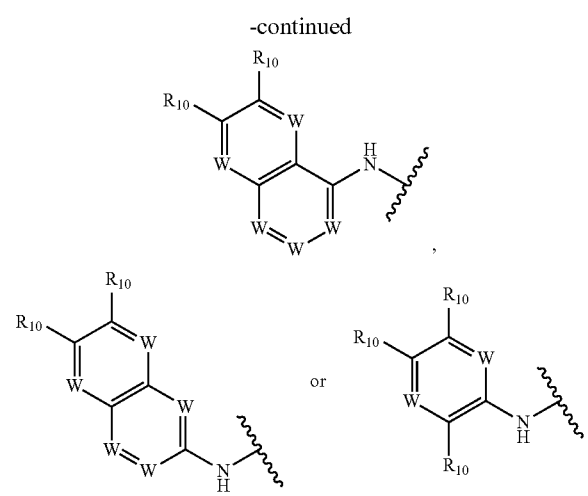

wherein V is $NR^{10}$ or S; and each W, independently, is CH, CF, CCl, $CCH_3$ or N, in conjunction with any of the above or below embodiments.

In another embodiment J-2, the invention includes compounds wherein $R^7$ is —NH—C(=O)—$R^9$ or

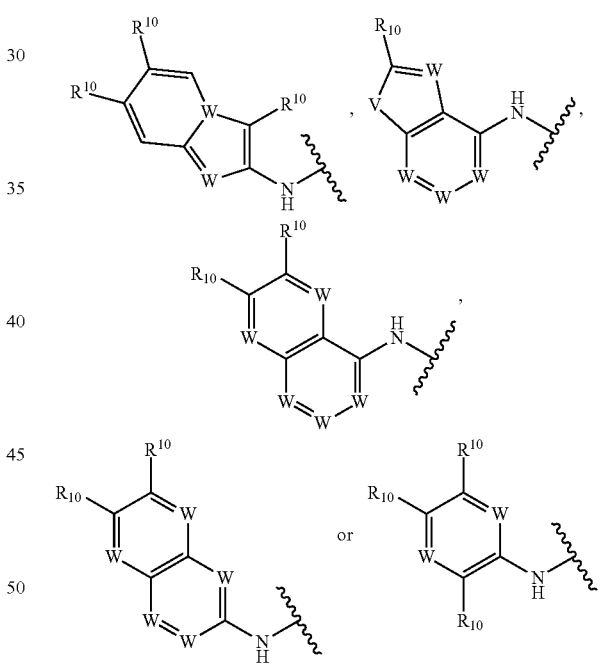

wherein V is $NR^{10}$ or S; and each W, independently, is CH, CF, CCl, $CCH_3$ or N, in conjunction with any of the above or below embodiments.

In another embodiment J-3, the invention includes compounds wherein $R^7$ is —NH—C(=O)—$R^9$, in conjunction with any of the above or below embodiments.

In another embodiment J-4, the invention includes compounds wherein $R^7$ is NH—$R^9$, in conjunction with any of the above or below embodiments.

In another embodiment J-5, the invention includes compounds wherein $R^7$ is

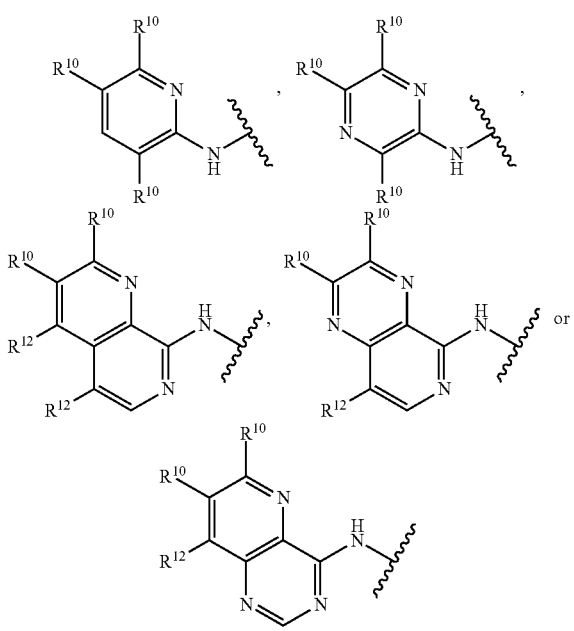

wherein each $R^{12}$, independently, is H, F or Cl, in conjunction with any of the above or below embodiments.

In another embodiment J-6, the invention includes compounds wherein $R^7$ is $R^7$ is —NH—C(=O)—$R^9$ or

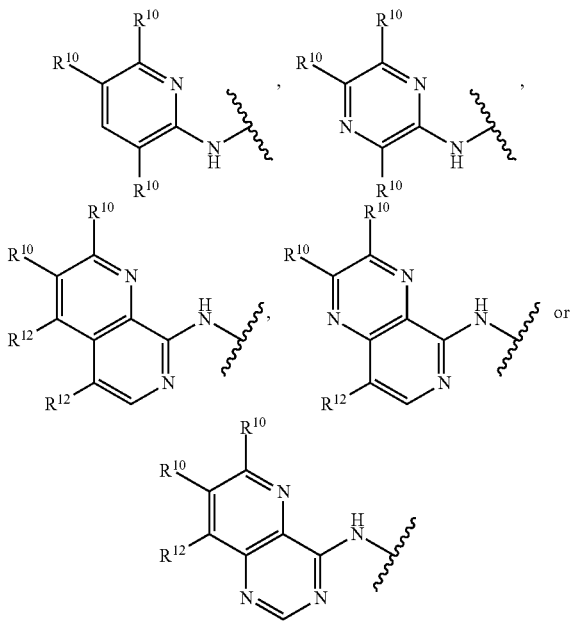

wherein each $R^{12}$, independently, is H, F or Cl, in conjunction with any of the above or below embodiments.

In another embodiment J-7, the invention includes compounds wherein $R^7$ is NH—$R^9$, —O—$R^9$ or S—$R^9$, in conjunction with any of the above or below embodiments.

In another embodiment J-8, the invention includes compounds wherein $R^7$ is —O—$R^9$ or S—$R^9$, in conjunction with any of the above or below embodiments.

In another embodiment J-9, the invention includes compounds wherein $R^7$ is NH—$R^9$ or —NH—C(=O)—$R^9$, wherein $R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K, the invention includes compounds wherein $R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K-1, the invention includes compounds wherein $R^7$ is NH—$R^9$ or —NH—C(=O)—$R^9$, wherein $R^9$ is, independently, is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_2$ alkenyl, $C_{2-4}$alkynyl and ring are optionally substituted, independently, with 1-5 substituents of $R^{10}$, in conjunction with any of the above or below embodiments.

In another embodiment K-2, the invention includes compounds wherein $R^7$ is NH—$R^9$ or —NH—C(=O)—$R^9$, wherein $R^9$ is a ring selected from phenyl, pyridyl, pyrimidyl, pyrazinyl, pyridazinyl, naphthyl, quinolinyl, isoquinolinyl, quinazolinyl, naphthyridinyl, phthalazinyl, imidazo[1,2-a]pyridyl, pyrido[3,4-b]pyrazin-5-yl or pyrido[3,2-d]pyrimidin-4-yl, wherein the ring is optionally substituted, independently, with 1-5 substituents of $R^{10}$, in conjunction with any of the above or below embodiments.

In another embodiment K-3, the invention includes compounds wherein $R^9$ is a ring selected from phenyl, pyridyl, pyrimidyl, pyrazinyl, pyridazinyl, naphthyl, quinolinyl, isoquinolinyl, quinazolinyl, naphthyridinyl, phthalazinyl, imidazo[1,2-a]pyridyl, pyrido[3,4-b]pyrazin-5-yl or pyrido[3,2-d]pyrimidin-4-yl, wherein the ring is optionally substituted, independently, with 1-5 substituents of $R^{10}$, in conjunction with any of the above or below embodiments.

In another embodiment L, the invention includes compounds wherein X is H, F, $CH_3$ or CN, in conjunction with any of the above or below embodiments.

In another embodiment L-1, the invention includes compounds wherein X is H, F or $CH_3$, in conjunction with any of the above or below embodiments.

In another embodiment L-2, the invention includes compounds wherein X is H or F, in conjunction with any of the above or below embodiments.

In another embodiment L-3, the invention includes compounds wherein X is H, in conjunction with any of the above or below embodiments.

In another embodiment M, the invention includes compounds wherein Y is —SCR$^4$R$^4$—, —CR$^4$R$^4$S—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, OH, C$_{1-6}$allyl, OC$_{1-6}$allyl or C$_{1-6}$haloalkyl, in conjunction with any of the above or below embodiments.

In another embodiment M-1, the invention includes compounds wherein Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, C$_{1-3}$allyl or C$_{1-3}$haloalkyl, in conjunction with any of the above or below embodiments.

In another embodiment M-2, the invention includes compounds wherein Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, CH$_3$, CH$_2$F or CHF$_2$, in conjunction with any of the above or below embodiments.

In another embodiment M-3, the invention includes compounds wherein Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H or CH$_3$, in conjunction with any of the above or below embodiments.

In another embodiment N, the present invention provides compounds, and solvates, tautomers, hydrates, stereoisomers and pharmaceutically acceptable salts thereof, as defined by Formulas I, II, II-A, II-B or II-C, III-A, III-B, III-D, II-A-1, II-A-2, II-A-3, II-A-4, II-B-1, II-B-2, II-B-3, II-B-4, II-C-1, II-C-2, II-C-3, II-C-4, II-D-1, II-D-2, II-D-3 or II-D-4, wherein A$^5$ is CR$^5$ or N;
A$^6$ is CR$^6$ or N;
A$^8$ is CR$^8$ or N, provided that no more than one of A$^5$, A$^6$ and A$^8$ is N;
each R$^1$, independently, is H, F, Cl, CF$_3$, OCF$_3$, methyl, ethyl, CN, OH, OCH$_3$, SCH$_3$, NHCH$_3$, C(O)CH$_3$ or CH$_2$OCHF$_2$;
R$^2$ is H, F, CH$_2$F or CH$_3$;
each R$^3$, independently, is C$_{1-4}$allyl, C$_{1-4}$haloalkyl, CH$_2$OH, CH$_2$OCHF$_2$ or cyclopropyl; and
each of R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment O, the present invention provides compounds, and solvates, tautomers, hydrates, stereoisomers and pharmaceutically acceptable salts thereof, as defined by Formulas I and II, wherein R$^7$ is NH—R$^9$ or —NH—C(=O)—R$^9$;
or R$^7$ is

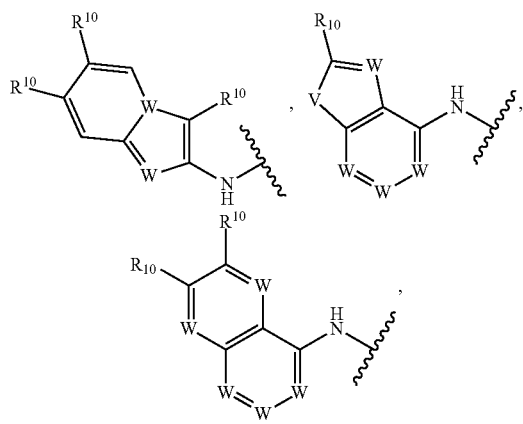

-continued

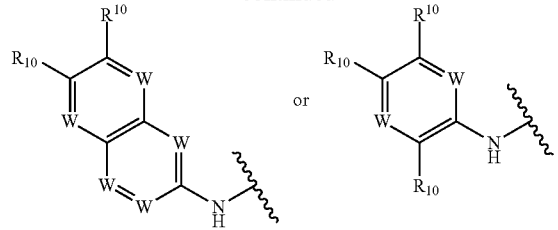

wherein V is NR$^{10}$ or S; and
each W, independently, is CH, CF, CCl, CCH$_3$ or N, in conjunction with any of the above or below embodiments.

In another embodiment O-1, the invention includes compounds of Formula II-A, II-B or II-C, or a sub-formula thereof, wherein
A$^5$ is CR$^5$ or N;
A$^6$ is CR$^6$ or N;
A$^8$ is CR$^8$ or N, provided that no more than one of A$^5$, A$^6$ and A$^8$ is N;
each R$^1$, independently, is H, F, Cl, C$_{1-4}$-alkyl, C$_{2-4}$alkenyl, C$_{2-4}$alkynyl, CN, —CH$_2$OC$_{1-3}$-alkyl, —OC$_{1-3}$-alkyl, wherein each of the C$_{1-4}$-alkyl, C$_{2-4}$alkenyl, C$_{2-4}$alkynyl and C$_{1-4}$-alkyl portion of —CH$_2$OC$_{1-3}$-alkyl and —OC$_{1-3}$-alkyl are optionally substituted with 1-4 substituents of F;
alternatively, each R$^1$ taken together with the carbon atom to which they are attached form a C$_{3-6}$ spirocarbocyclic ring optionally including one heteroatom selected from O and N and optionally substituted with 1-4 F atoms on the carbon atoms and a substituent of C$_{1-3}$alkyl, CH$_2$OC$_{1-2}$alkyl or C$_{1-3}$haloalkyl on the nitrogen atom;
R$^2$ is H, F, CH$_2$F or CH$_3$;
each R$^3$, independently, is halo, C$_1$ alkyl, CH$_2$OH, CH$_2$OC$_{1-4}$alkyl, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;
each of R$^5$, R$^6$ and R$^8$, independently, is H or F;
R$^9$ is acetyl, C$_{1-6}$-alkyl, C$_2$ alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo [2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

X is H or F;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and o is 0, 1 or 2.

In another embodiment O-2, the invention includes compounds of Formula II-A, II-B or II-C, or a sub-formula thereof, wherein $A^5$ is $CR^5$ or N;
$A^6$ is $CR^6$;
$A^8$ is $CR^8$;

each $R^1$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;

alternatively, each $R^1$ taken together with the carbon atom to which they are attached form a spirocyclobutyl ring optionally substituted with 1-3 F atoms;

$R^2$ is H, F, $CH_2F$ or $CH_3$;

each $R^3$, independently, is F, $CH_3$, $C_2H_5$, $CF_2H$ or $CH_2F$;

$R^9$ is acetyl, $C_{1-6}$-alkyl, $C_2$ alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —$NHC(O)R^{11}$— or —$C(O)NHR^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

X is H or F;

Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and o is 0, 1 or 2.

In another embodiment O-3, the invention includes compounds of Formula II-B or II-C, or a sub-formula thereof, wherein $A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

each $R^1$, independently, is H, F or $CH_3$;

alternatively, each $R^1$ taken together with the carbon atom to which they are attached form a $C_{3-6}$ spirocarbocyclic ring optionally including one heteroatom selected from O and N and optionally substituted with 1-3 F atoms;

$R^2$ is H, F or $CH_3$;

X is H or F; and

Y is $SCR^4R^4$—, $S(O)_2CR^4R^4$—, —$OCR^4R^4$—, —$CR^4R^4O$— or —$CR^4R^4CR^4R^4$—, wherein each $R^4$, independently, is H, F or $CH_3$; and o is 0, in conjunction with any of the above or below embodiments with respect to Formula II-B or II-C, or a sub-formula thereof.

In another embodiment O-4, the invention includes compounds of Formula II-A, II-B or II-C, or a sub-formula thereof, wherein $A^5$ is $CR^5$ or N;
$A^6$ is $CR^6$ or N;
$A^8$ is $CR^8$ or N, wherein each of $R^5$, $R^6$ and $R^8$, independently, is H or F and provided no more than one of $A^5$, $A^6$ and $A^8$ is N;

each $R^1$, independently, is H, F, Cl, $CF_3$, $CH_3$, $CF_2H$ or $CH_2F$;

$R^2$ is H or $CH_3$;

each $R^3$, independently, is $CF_3$, $CH_3$, $CF_2H$ or $CH_2F$;

X is H; and

Y is $SCR^4R^4$—, $S(O)_2CR^4R^4$—, —$OCR^4R^4$—, —$CR^4R^4O$— or —$CR^4R^4CR^4R^4$—, wherein each $R^4$, independently, is H, F or $CH_3$, in conjunction with any of the above or below embodiments with respect to Formula II-A, II-B or II-C, or a sub-formula thereof.

In another embodiment P-1, the invention includes compounds of Formula III-A, III B, III-C or III-D, wherein $A^5$ is $CR^5$;
$A^6$ is $CR^6$;
$A^8$ is $CR^8$; wherein each of $R^5$, $R^6$ and $R^8$, independently, is H, F, Cl, $CF_3$, $OCF_3$, Methyl or CN;

each $R^1$, independently, is H, F, $CH_3$, $C_2H_5$, $CF_2H$ or $CH_2F$;

alternatively, each $R^1$ taken together with the carbon atom to which they are attached form a spirocyclobutyl ring optionally substituted with 1-3 F atoms;

$R^2$ is H, F, $CH_2F$ or $CH_3$;

each $R^3$, independently, is $CH_3$, $C_2H_5$, $CF_2H$ or $CH_2F$;

X is H, F or $CH_3$; and

Y is $SCR^4R^4$—, $S(O)_2CR^4R^4$—, —$OCR^4R^4$—, —$CR^4R^4O$— or —$CR^4R^4CR^4R^4$—, wherein each $R^4$, independently, is H, F or $CH_3$, in conjunction with any of the above or below embodiments with respect to III-A, III-B, III-C or III-D.

In another embodiment P-2, the invention includes compounds of Formula III-A, III B, III-C or III-D, wherein $A^5$ is $CR^5$ or N;
$A^6$ is $CR^6$ or N;
$A^8$ is $CR^8$ or N, wherein each of $R^5$, $R^6$ and $R^8$, independently, is H or F and provided no more than one of $A^5$, $A^6$ and $A^8$ is N;

each $R^1$, independently, is H, F, Cl, $CF_3$, $CH_3$, $CF_2H$ or $CH_2F$; and $R^3$ is $CF_3$, $CH_3$, $CF_2H$ or $CH_2F$;
X is H, F or $CH_3$; and
Y is $—OCR^4R^4—$ or $—CR^4R^4O—$, wherein each $R^4$, independently, is H, F, $C_{1-6}$alkyl or $C_{1-6}$haloalkyl, in conjunction with any of the above or below embodiments with respect to Formula III-A, III-B, III-C or III-D.

In embodiment Q, the invention includes compounds, or a pharmaceutically acceptable salt thereof, of Formulas III-B-1:

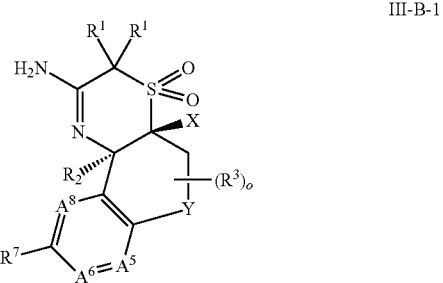

III-B-1 wherein $A^5$ is $CR^5$ or N;
$A^6$ is $CR^6$;
$A^8$ is $CR^8$, wherein each of $R^5$, $R^6$ and $R^8$, independently, is H or F;
each $R^1$, independently, is $CH_3$;
$R^2$ is $CH_3$ or $CH_2F$;
$R^7$ is $—NH—C(=O)—R^9$, or
$R^7$ is

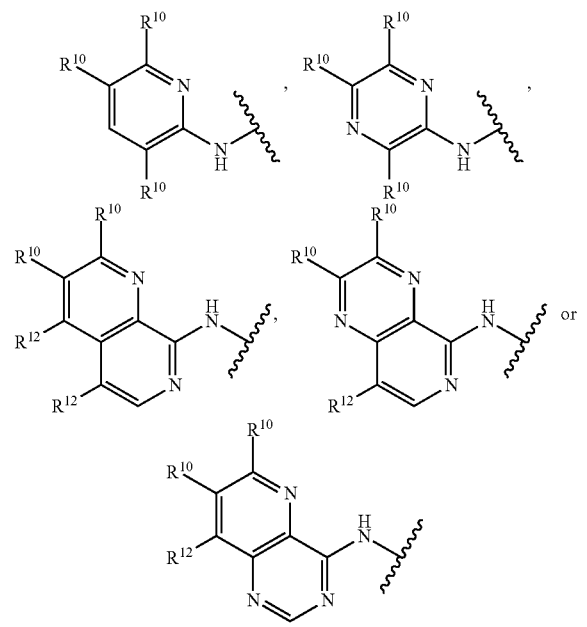

$R^9$ is a ring selected from phenyl, pyridyl, pyrimidyl, pyrazinyl, pyridazinyl, naphthyl, quinolinyl, isoquinolinyl, quinazolinyl, naphthyridinyl, phthalazinyl, imidazo[1,2-a]pyridyl, pyrido[3,4-b]pyrazin-5-yl or pyrido[3,2-d]pyrimidin-4-yl, wherein the ring is optionally substituted, independently, with 1-5 substituents of $R^{10}$;
each $R^{10}$, independently, is H, F, Cl, $C_{1-3}$alkyl, $C_{1-3}$haloalkyl, CN, OH, $C_{2-3}$alkenyl, $C_{2-3}$alkynyl, $C_{3-6}$cycloalkyl, $C_{1-6}$alkoxyl, $C_{1-6}$thioalkoxyl, 2-propyn-1-yloxy, 2-butyn-1-yloxy, wherein each of the $C_{1-6}$alkyl, $C_{2-3}$alkenyl, $C_{2-3}$alkynyl, $C_{3-6}$cycloalkyl, $C_{1-6}$alkoxyl, $C_{1-6}$thioalkoxyl, 2-propyn-1-yloxy or 2-butyn-1-yloxy, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;
each $R^{12}$, independently, is H, F, $C_1$ or $CH_3$;
X is H or F;
Y is $—SCR^4R^4—$, $—S(O)_2CR^4R^4—$, $—OCR^4R^4—$, $—CR^4R^4O—$ or $—CR^4R^4CR^4R^4—$, wherein each $R^4$, independently, is H, F, $CH_3$, $CH_2F$ or $CF_3$; and
o is 0.

In embodiment Q, the invention includes compounds, or a pharmaceutically acceptable salt thereof, of Formula III-B-2:

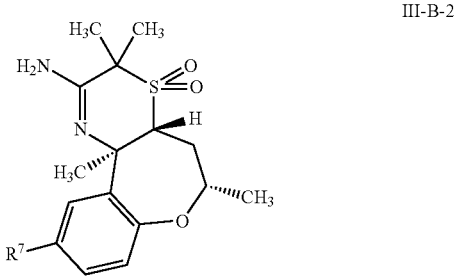

III-B-2 wherein $R^7$ is

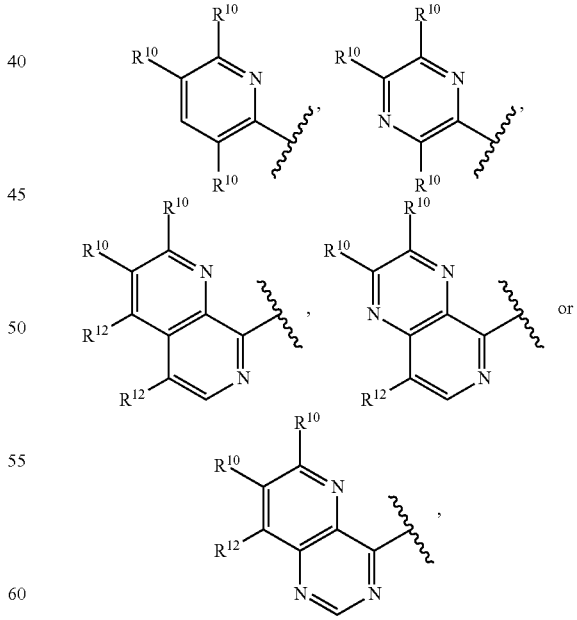

wherein each $R^{10}$, independently, is H, halo, haloalkyl, CN, OH, $NO_2$, $NH_2$, $SF_5$, acetyl, $—C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, —NHC(O)R$^{11}$— or —C(O)NHR$^{11}$—, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$; and each R$^{12}$, independently, is H, F or Cl.

All of the possible embodiments described herein for the various A, R, V, W, X and Y groups of the compounds of Formula I may be applied, as appropriate, to compounds of Formula II and any sub-formulas thereof, as well as to a compound of Formulas III-A, III-B, III-C and III-D.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

In another embodiment, the invention provides one or more of the compounds, or a pharmaceutically acceptable salt thereof, of Formulas I, II and III, and sub-formulas thereof, as exemplified and/or specifically disclosed or described herein.

In another embodiment, the invention provides a compound, or a stereoisomer, tautomer or pharmaceutically acceptable salt thereof, selected from

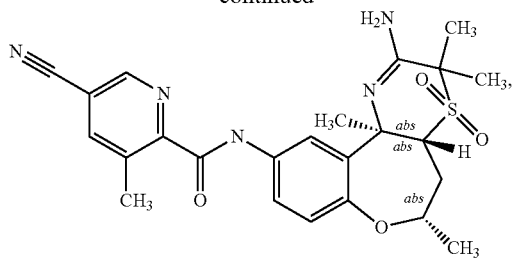

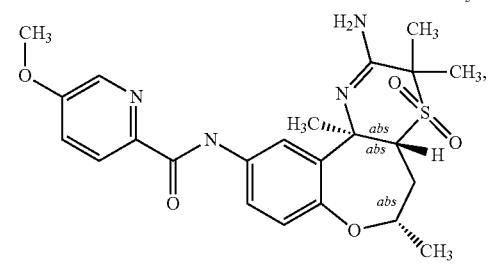

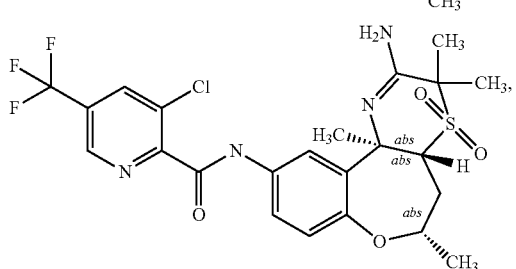

-continued

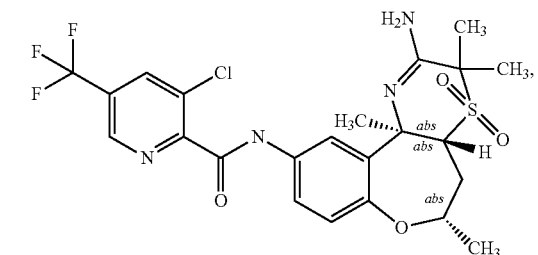

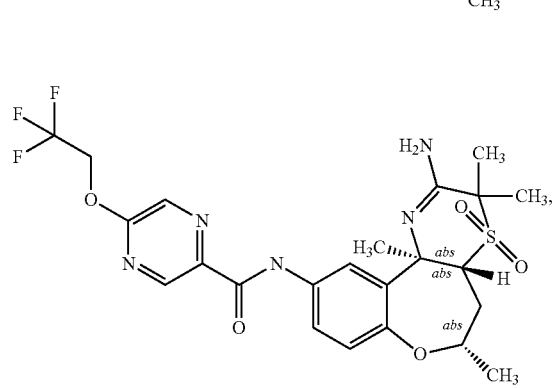

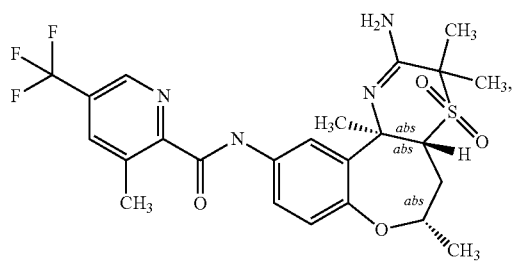

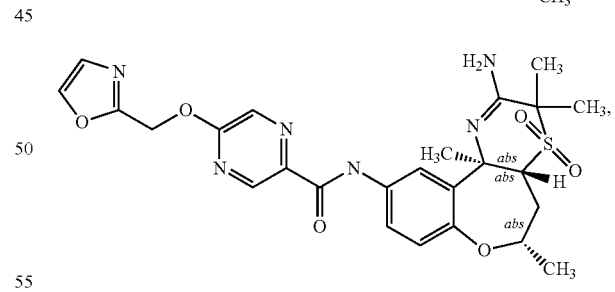

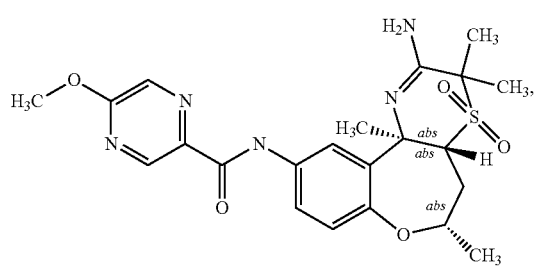

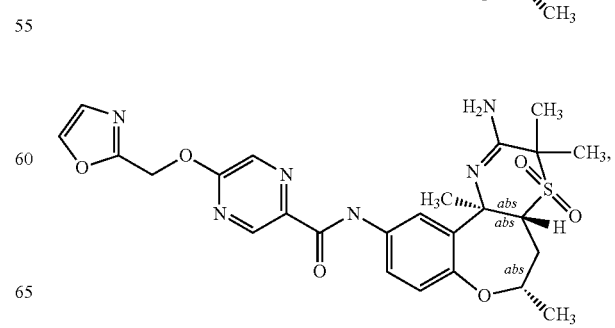

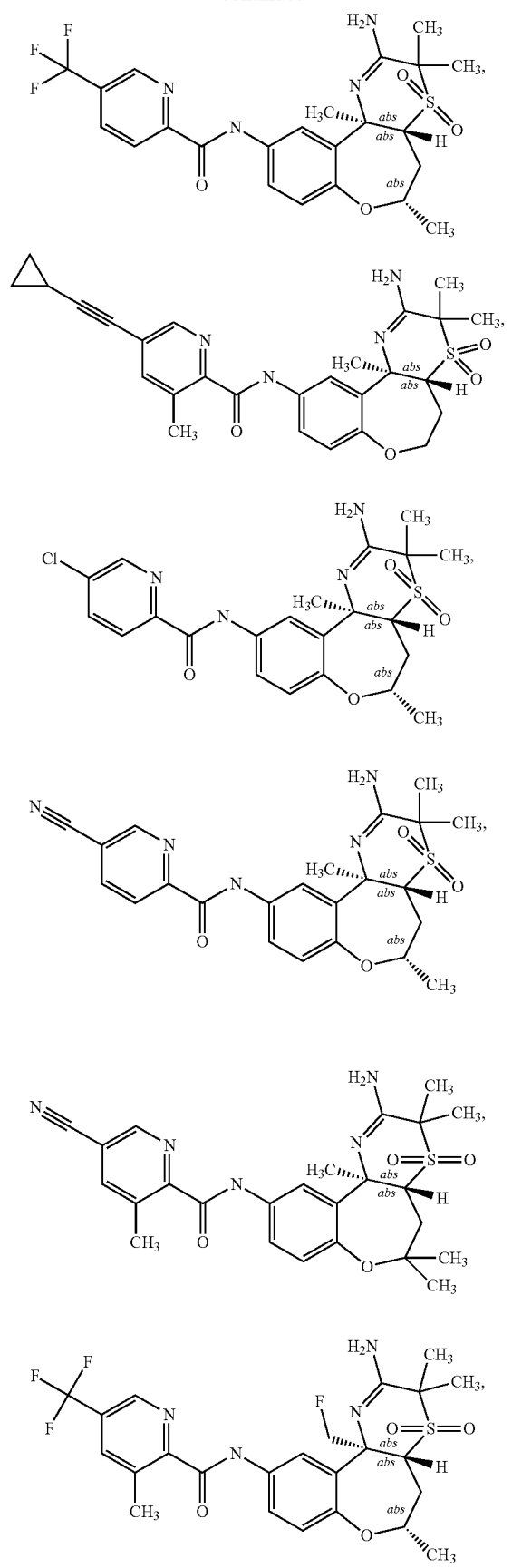
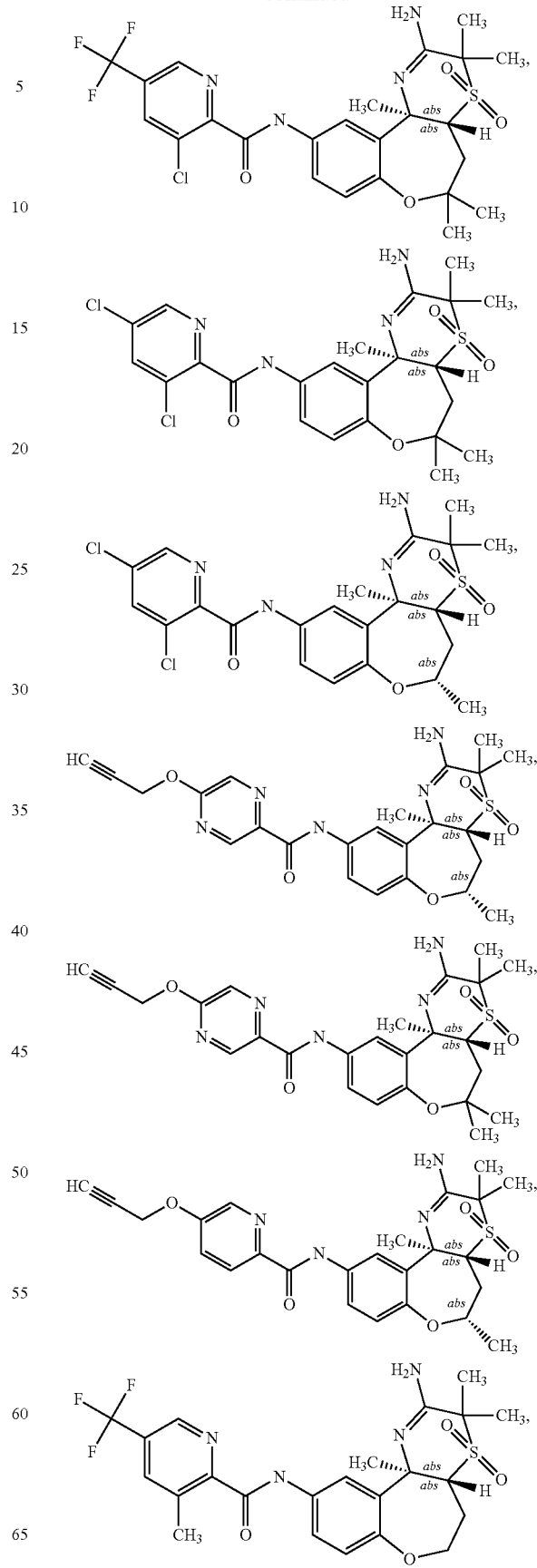

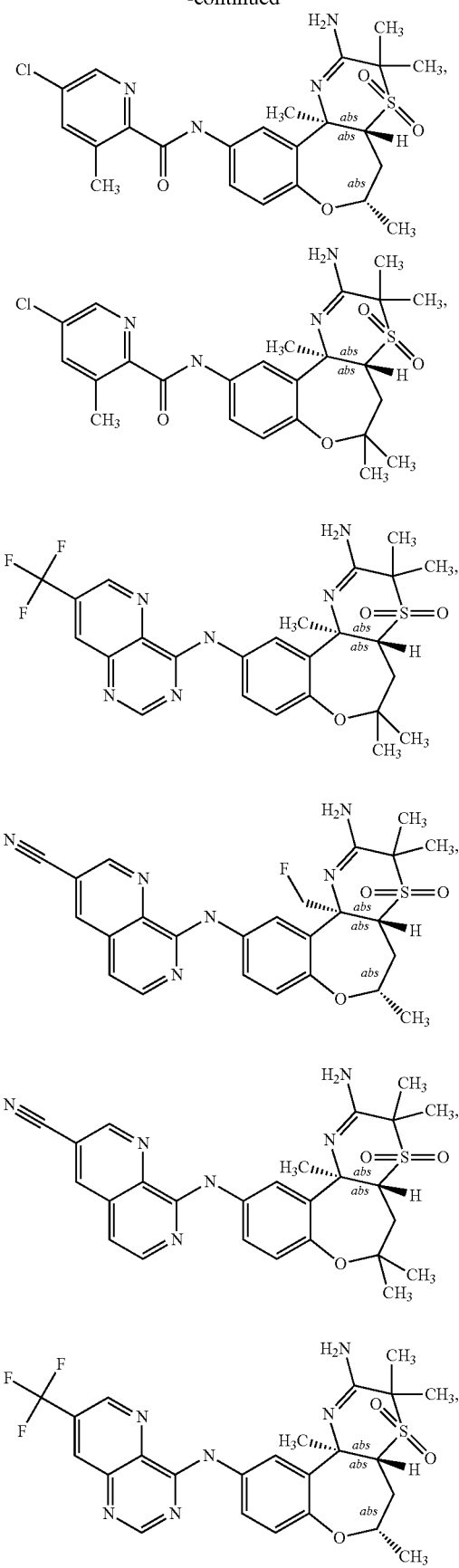
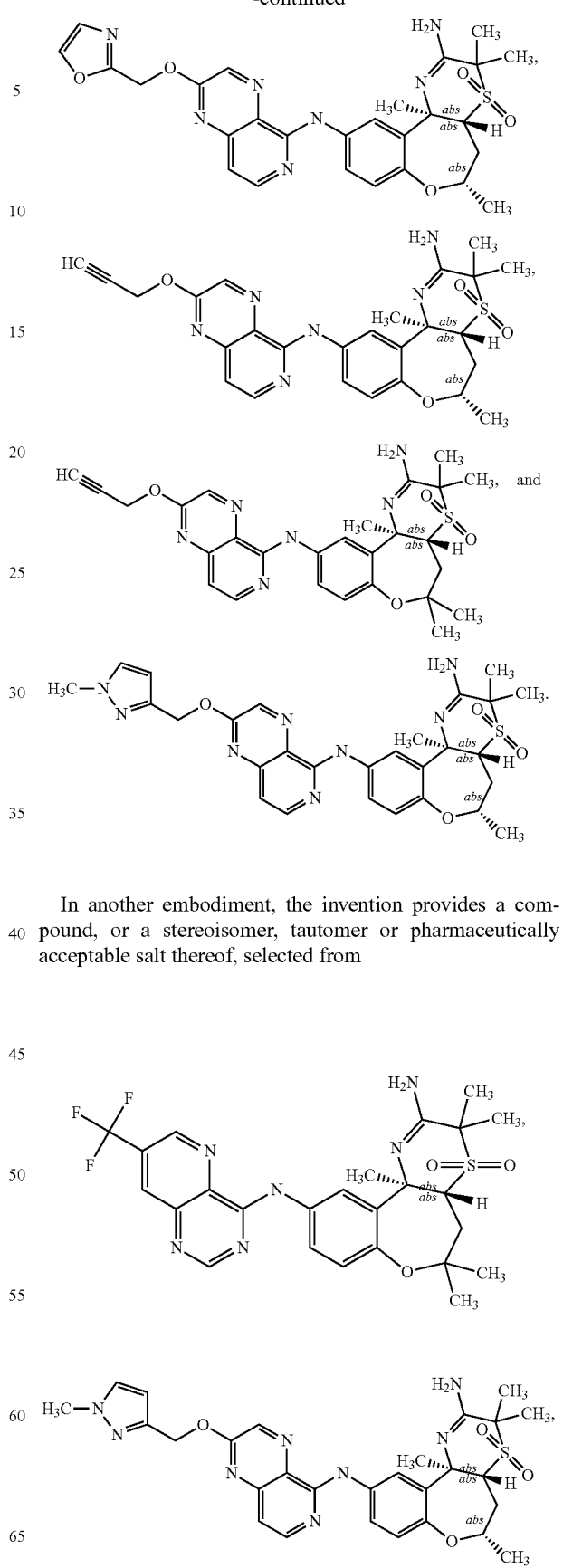
In another embodiment, the invention provides a compound, or a stereoisomer, tautomer or pharmaceutically acceptable salt thereof, selected from -continued

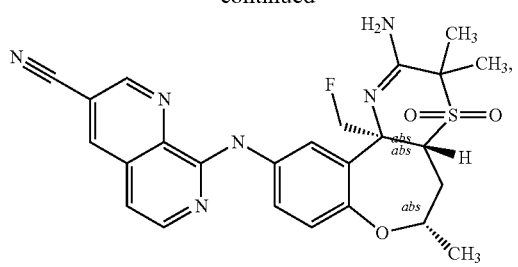

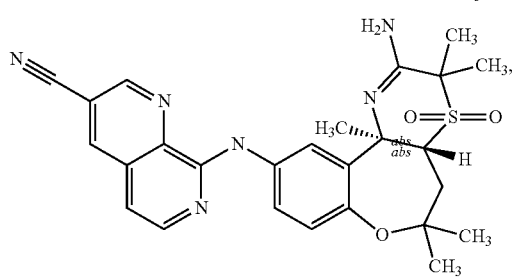

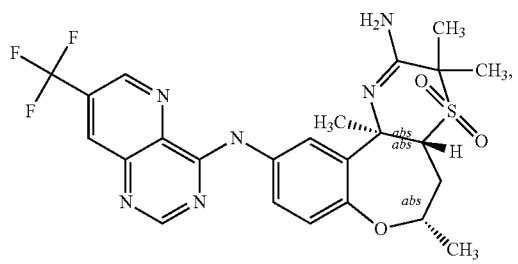

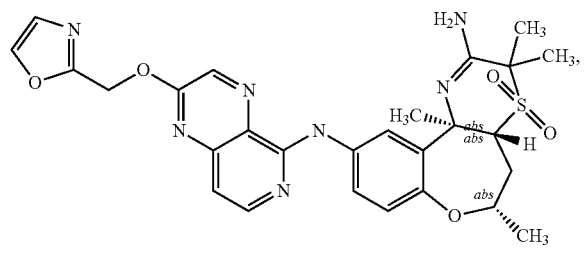

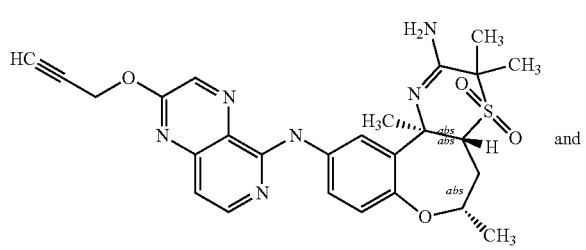

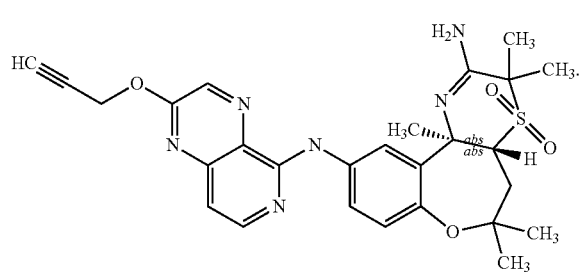

In another embodiment, the invention provides the compound of formula

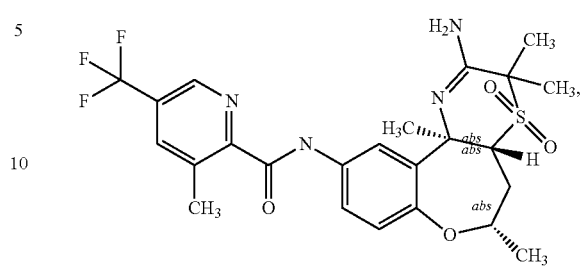

or a stereoisomer, tautomer or pharmaceutically acceptable salt thereof.

In another embodiment, the invention provides the compound of formula

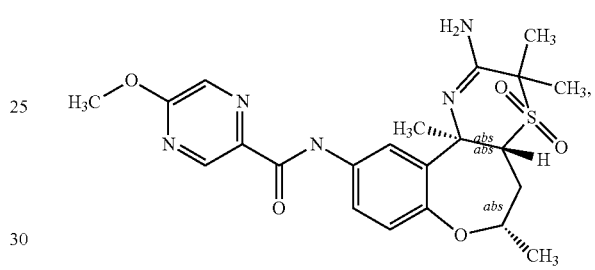

or a stereoisomer, tautomer or pharmaceutically acceptable salt thereof.

In another embodiment, the invention provides the compound of formula

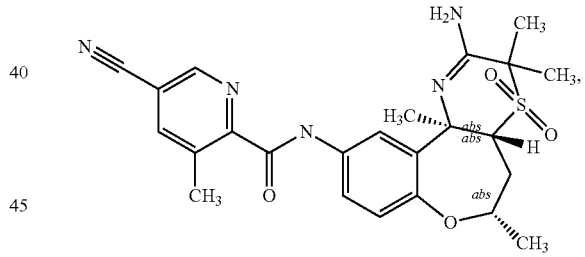

or a stereoisomer, tautomer or pharmaceutically acceptable salt thereof.

In another embodiment, the invention provides the compound of formula

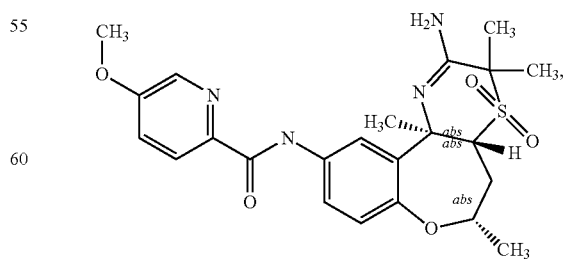

or a stereoisomer, tautomer or pharmaceutically acceptable salt thereof.

In another embodiment, the invention provides the compound of formula

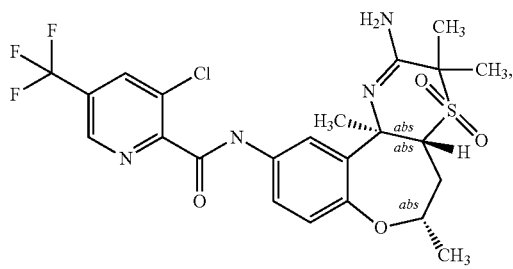

or a stereoisomer, tautomer or pharmaceutically acceptable salt thereof.

In another embodiment, the invention provides the compound of formula

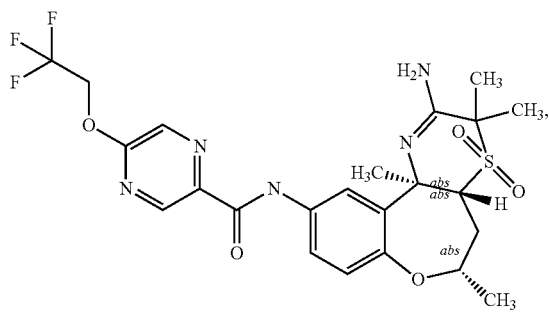

or a stereoisomer, tautomer or pharmaceutically acceptable salt thereof.

In another embodiment, the invention provides the compound of formula

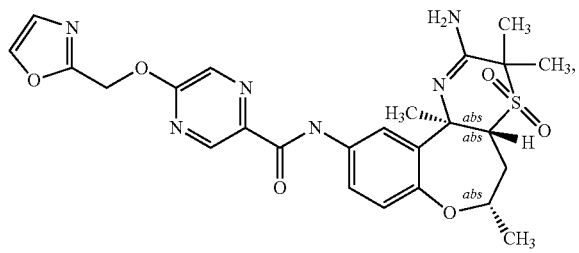

or a stereoisomer, tautomer or pharmaceutically acceptable salt thereof.

In another embodiment, the invention provides the compound of formula

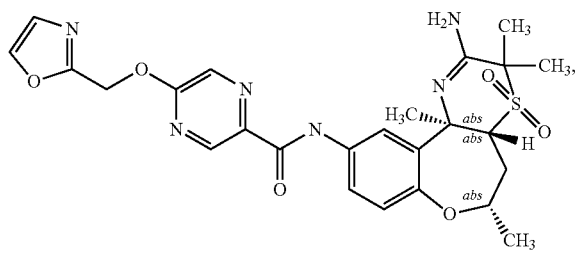

or a stereoisomer, tautomer or pharmaceutically acceptable salt thereof.

In another embodiment, the invention provides the compound of formula

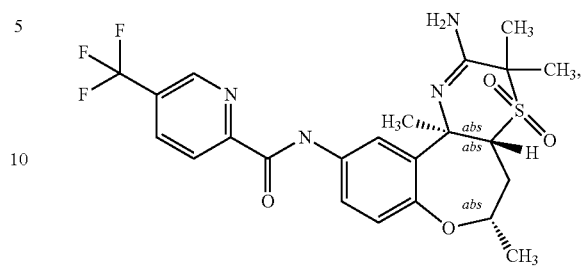

or a stereoisomer, tautomer or pharmaceutically acceptable salt thereof.

In another embodiment, the invention provides the compound of formula

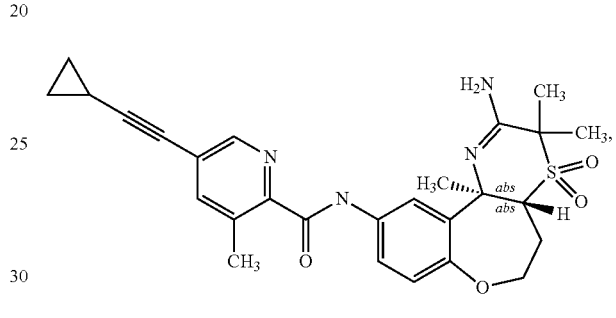

or a stereoisomer, tautomer or pharmaceutically acceptable salt thereof.

In another embodiment, the invention provides the compound of formula

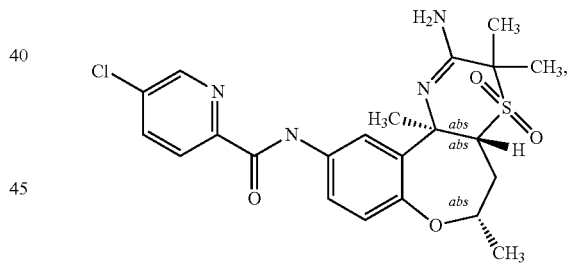

or a stereoisomer, tautomer or pharmaceutically acceptable salt thereof.

In another embodiment, the invention provides the compound of formula

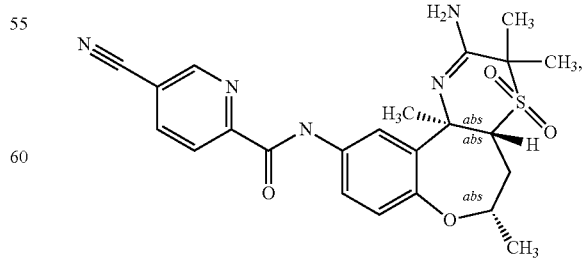

or a stereoisomer, tautomer or pharmaceutically acceptable salt thereof.

In another embodiment, the invention provides the compound of formula

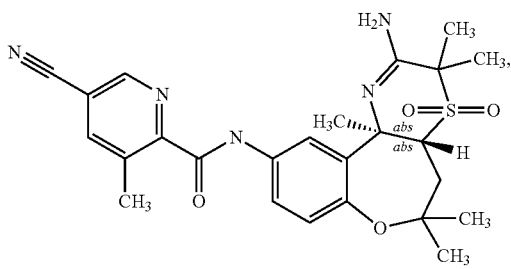

or a stereoisomer, tautomer or pharmaceutically acceptable salt thereof.

In another embodiment, the invention provides the compound of formula

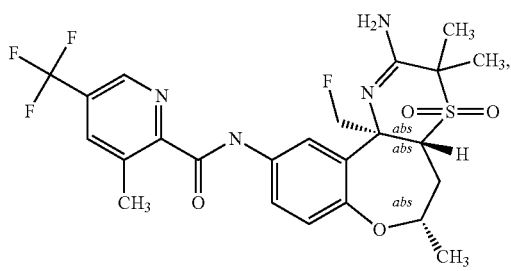

or a stereoisomer, tautomer or pharmaceutically acceptable salt thereof.

In another embodiment, the invention provides the compound of formula

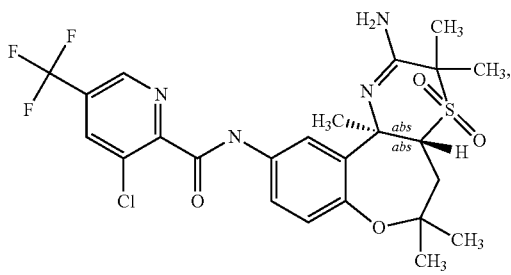

or a stereoisomer, tautomer or pharmaceutically acceptable salt thereof.

In another embodiment, the invention provides the compound of formula

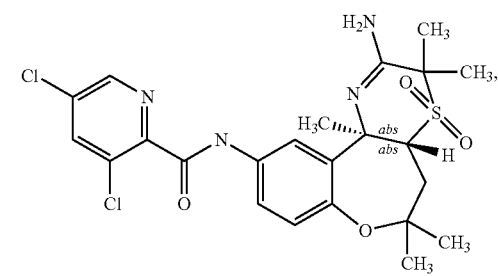

or a stereoisomer, tautomer or pharmaceutically acceptable salt thereof.

In another embodiment, the invention provides the compound of formula

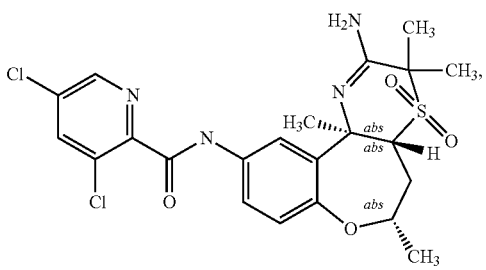

or a stereoisomer, tautomer or pharmaceutically acceptable salt thereof.

In another embodiment, the invention provides the compound of formula

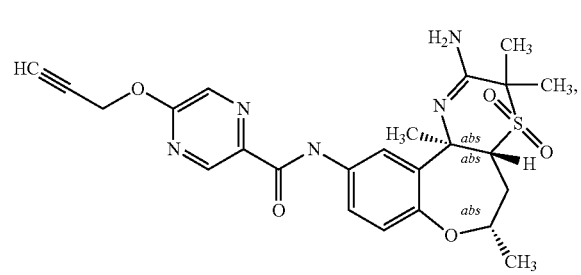

or a stereoisomer, tautomer or pharmaceutically acceptable salt thereof.

In another embodiment, the invention provides the compound of formula

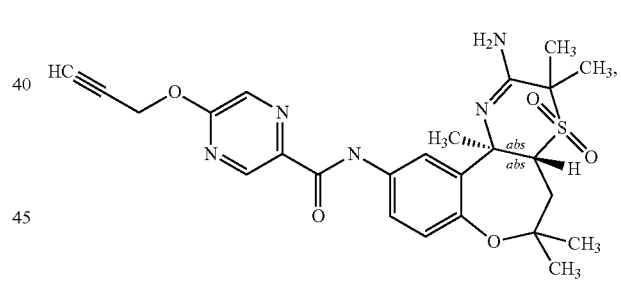

or a stereoisomer, tautomer or pharmaceutically acceptable salt thereof.

In another embodiment, the invention provides the compound of formula

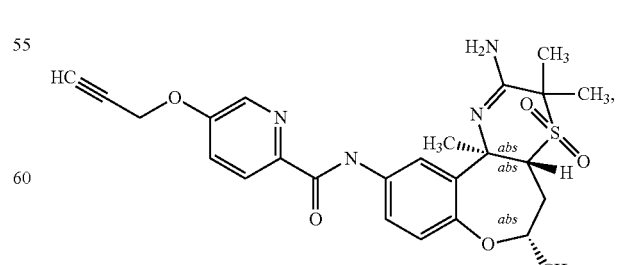

or a stereoisomer, tautomer or pharmaceutically acceptable salt thereof.

In another embodiment, the invention provides the compound of formula

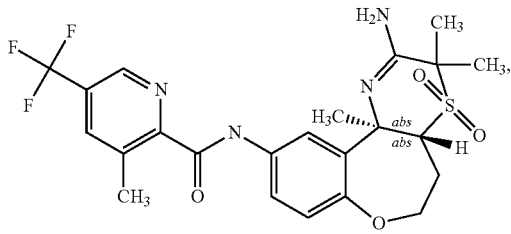

or a stereoisomer, tautomer or pharmaceutically acceptable salt thereof.

In another embodiment, the invention provides the compound of formula

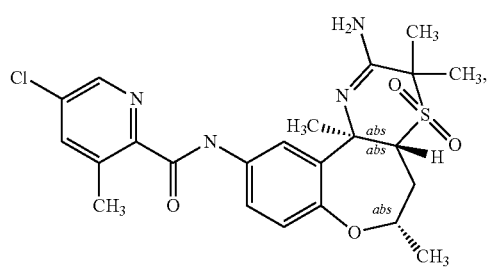

or a stereoisomer, tautomer or pharmaceutically acceptable salt thereof.

In another embodiment, the invention provides the compound of formula

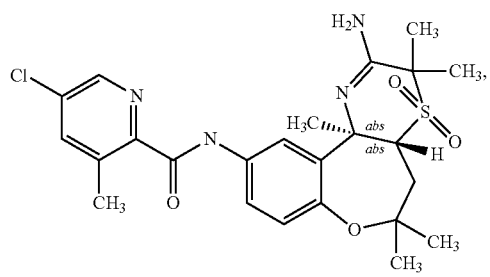

or a stereoisomer, tautomer or pharmaceutically acceptable salt thereof.

In another embodiment, the invention provides the compound of formula

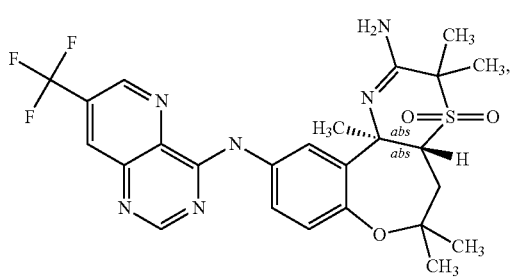

or a stereoisomer, tautomer or pharmaceutically acceptable salt thereof.

In another embodiment, the invention provides the compound of formula

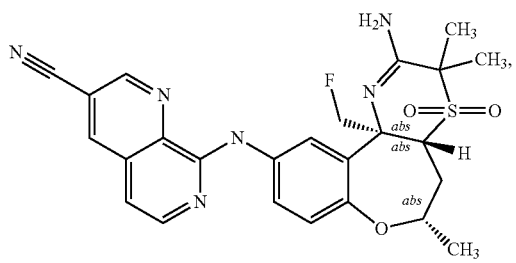

or a stereoisomer, tautomer or pharmaceutically acceptable salt thereof.

In another embodiment, the invention provides the compound of formula

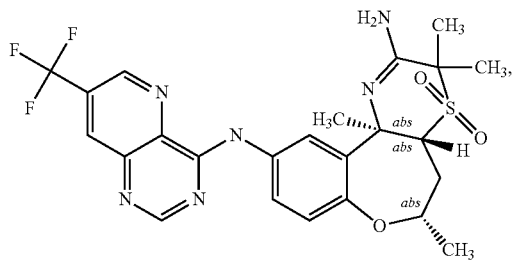

or a stereoisomer, tautomer or pharmaceutically acceptable salt thereof.

In another embodiment, the invention provides the compound of formula

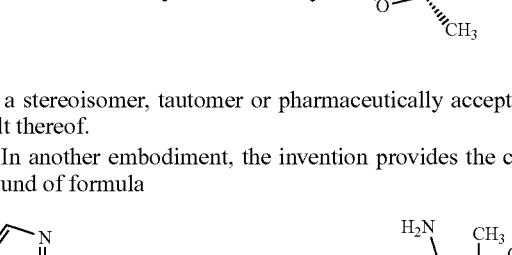

or a stereoisomer, tautomer or pharmaceutically acceptable salt thereof.

In another embodiment, the invention provides the compound of formula

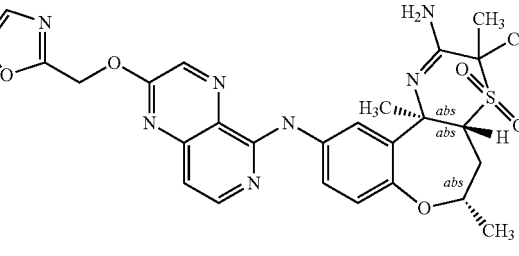

or a stereoisomer, tautomer or pharmaceutically acceptable salt thereof.

In another embodiment, the invention provides the compound of formula

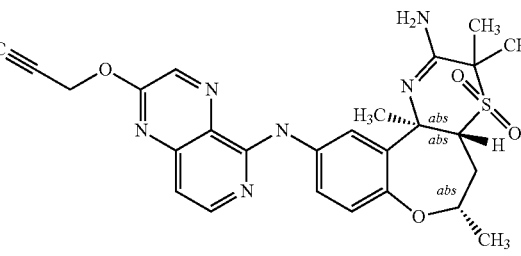

or a stereoisomer, tautomer or pharmaceutically acceptable salt thereof.

In another embodiment, the invention provides the compound of formula

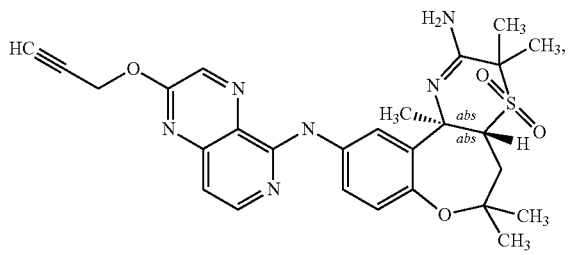

or a stereoisomer, tautomer or pharmaceutically acceptable salt thereof.

In another embodiment, the invention provides the compound of formula

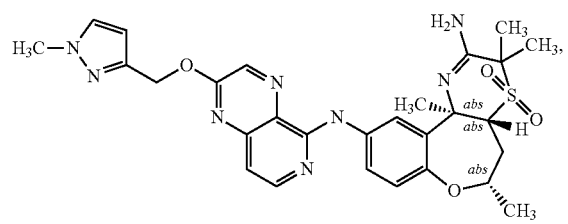

or a stereoisomer, tautomer or pharmaceutically acceptable salt thereof.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from α and β. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substituents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOC—tert-butoxycarbonyl
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
$Et_2O$—diethyl ether
EtOAc—ethyl acetate
FC—flash (column) chromatography
g, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
$Ph_3P$—triphenylphosphine
Pd/C—palladium on carbon
$Pd(PPh_3)_4$—palladium(0)triphenylphosphine tetrakis
$Pd(dppf)Cl_2$ palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RCM—ring-closing metathesis
RT, rt—room temperature
RBF, rbf—round bottom flask
TLC, tlc—thin layer chromatography
TBAF—Tetrabutylammonium fluoride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light Scheme 1-A

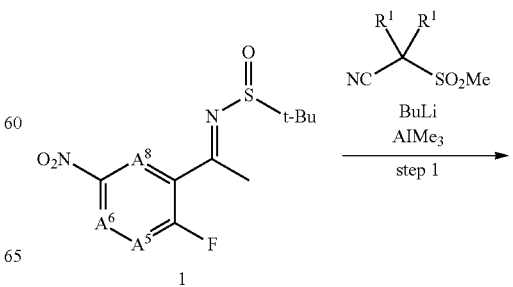

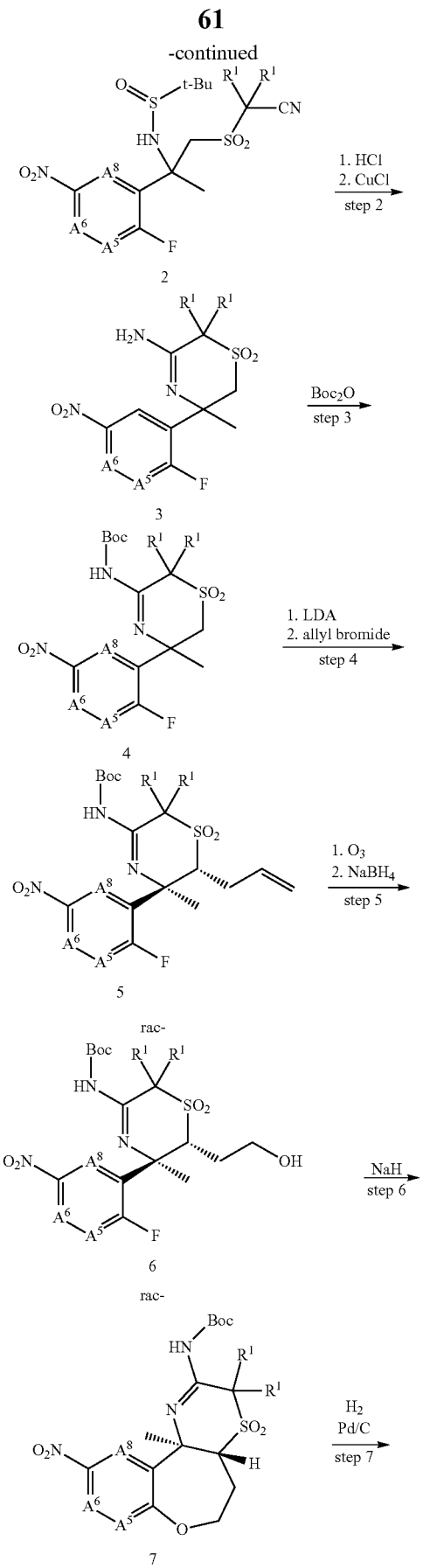
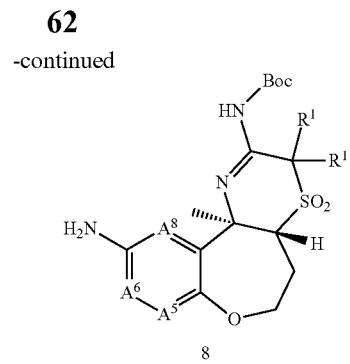
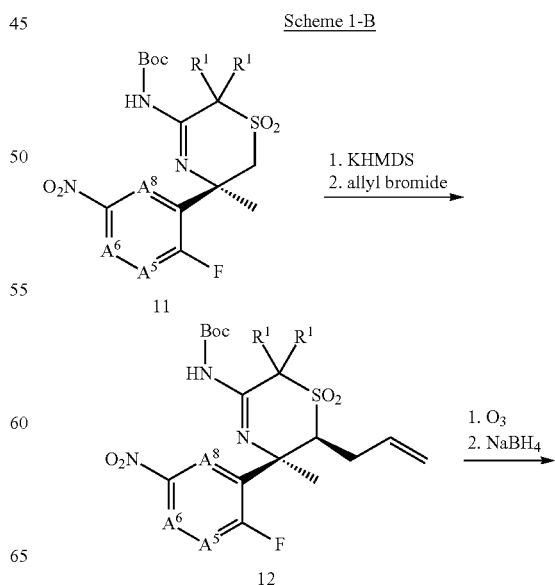

Scheme 1-A describes an exemplary method for preparing intermediate 8, enroute to preparing compounds of Formulas I, II and III, wherein Y is O—$CH_2$—, $R_2$ is $CH_3$, X is H and n is 2. Beginning with compound 1 (prepared by methods analogous to that described in example 2 below), one of ordinary skill in the art may react it with 2-methyl-2-(methylsulfonyl)propanenitrile to afford the adduct 3. Ring closure of nitrile intermediate 3 may be accomplished by reacting it with copper catalyst in the presence of acid, such as HCl, as shown above. The primary amine of intermediate 3 may then be Boc protected via conventional techniques and reagents known in the art, as described herein, under suitable conditions, to afford carbamate compound 4. The methyl group of the carbamate 4 may be converted to the corresponding allylic moiety using LDA and allyl bromide under suitable conditions, such as those described hereinabove, to generate olefin intermediate 5. The olefin of intermediate 5 may be reduced using common reducing reagents, such as borane reagents, to provide the corresponding alcohol intermediate 6. The second ring closure can be accomplished using a strong base, such as NaH, to activate the alcohol and enable ring closure to boc-protected intermediate 7. The nitro-group of intermediate 7 can then be reduced to the corresponding amino group using known techniques, such as palladium catalyzed hydrogenation, to provide the corresponding amine adduct 8. Amine adduct can then be used to synthesize desired compounds of formulas I, II and III, and sub-formulas thereof, with desired $R^7$, $R^9$ and $R^{10}$ groups.

Scheme 1-B

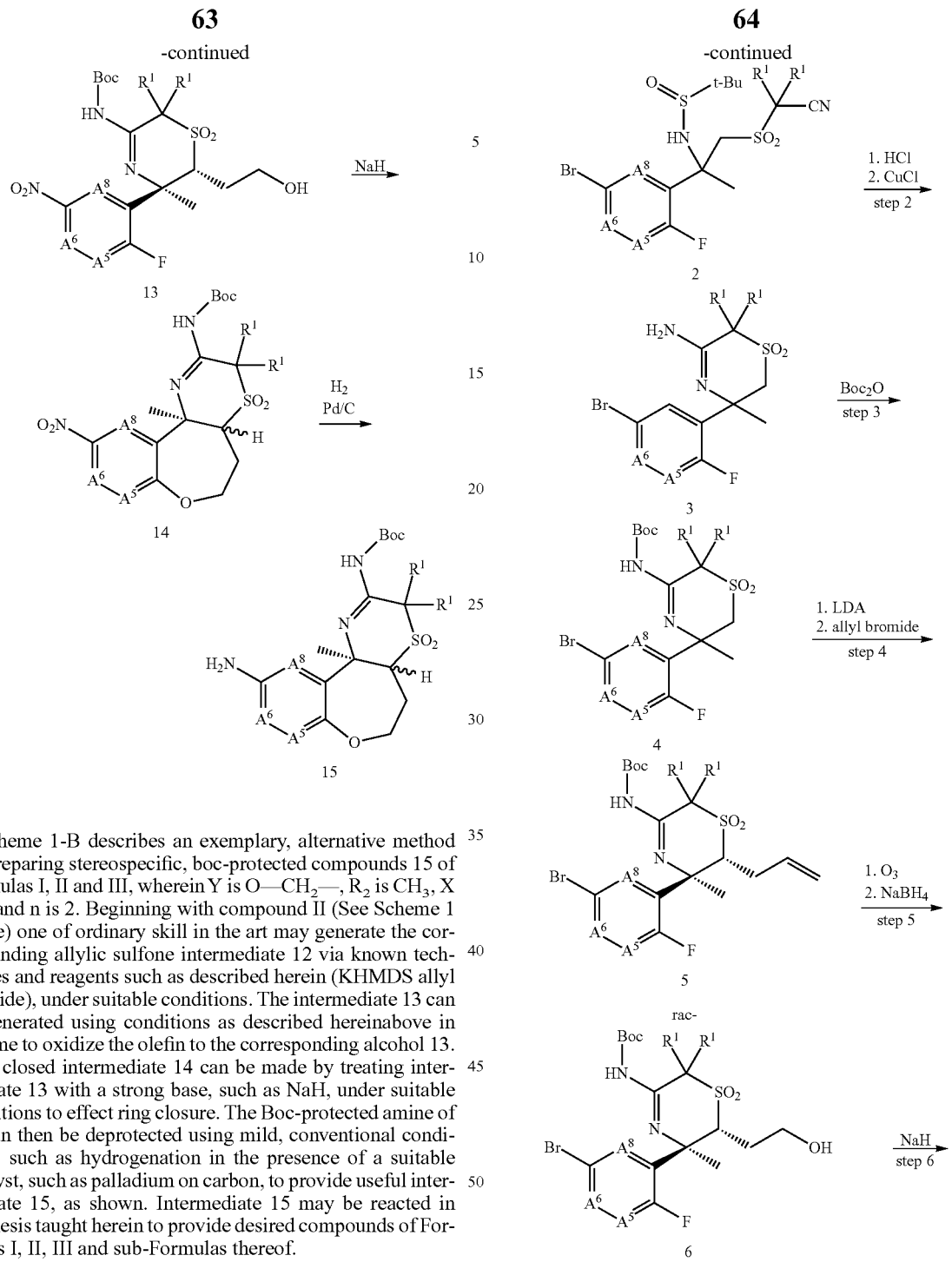

Scheme 1-B describes an exemplary, alternative method for preparing stereospecific, boc-protected compounds 15 of Formulas I, II and III, wherein Y is O—CH$_2$—, R$_2$ is CH$_3$, X is H and n is 2. Beginning with compound II (See Scheme 1 above) one of ordinary skill in the art may generate the corresponding allylic sulfone intermediate 12 via known techniques and reagents such as described herein (KHMDS allyl bromide), under suitable conditions. The intermediate 13 can be generated using conditions as described hereinabove in scheme to oxidize the olefin to the corresponding alcohol 13. Ring closed intermediate 14 can be made by treating intermediate 13 with a strong base, such as NaH, under suitable conditions to effect ring closure. The Boc-protected amine of 14 can then be deprotected using mild, conventional conditions, such as hydrogenation in the presence of a suitable catalyst, such as palladium on carbon, to provide useful intermediate 15, as shown. Intermediate 15 may be reacted in synthesis taught herein to provide desired compounds of Formulas I, II, III and sub-Formulas thereof.

Scheme 1-C

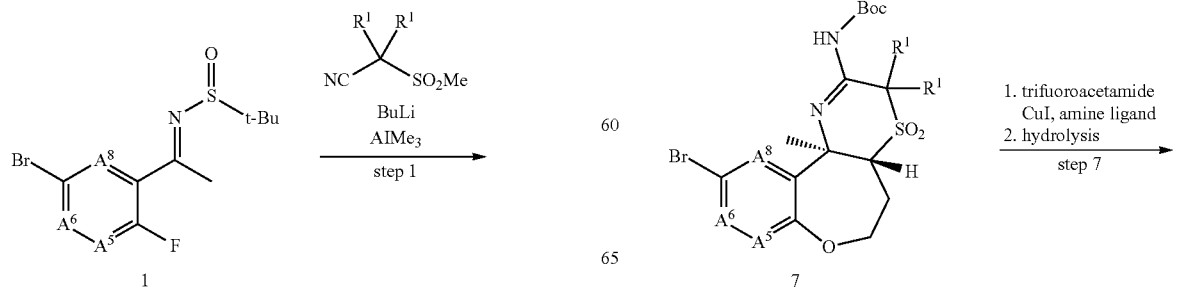

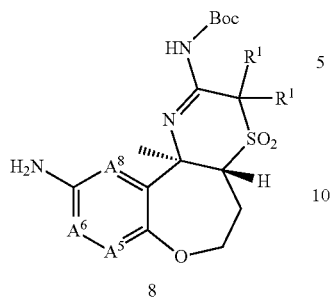

8

Compounds of Formulas I, II and III, wherein Y is O—CH$_2$—, R$_2$ is CH$_3$, X is H n is 2 and one of A$^5$, A$^6$ and A$^8$ is N, may be prepared as described in scheme 1-C above, but using a bromide (Br) in place of the nitro (NO$_2$) group in the starting materials used in scheme 1-A, step 1. The bromide can be carried on through steps 2-6 in an analogous fashion to that described in Scheme 1-A. The bromide intermediate equivalent of compound 7 (in scheme 1-A) may then be made into compounds of Formulas I, II and III using Grignard chemistry and forming the Grignard reagent, followed by displacement with a desirable amino-R$^9$ group (not shown). Alternatively, the bromide intermediate of compound 7 may be converted to the corresponding amine intermediate 8 using known method, such as displacement with trifluoroacetamide in the presence of copper catalyst, followed by hydrolysis of the trifluoroacetate, with under suitable conditions, to afford the primary amine 8, as shown.

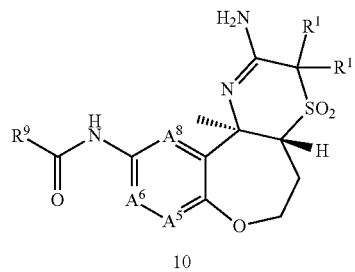

10

Scheme 1-B describes an exemplary method for preparing compounds 10 of Formulas I, II, II-A and III, wherein Y is O—CH$_2$—, R$_2$ is CH$_3$, X is H and n is 2. Beginning with compound 8 (see Scheme 2 above) one of ordinary skill in the art may activate a desired R$^9$-carboxylic acid in conjunction with an acid activating reagent, such as HATU, DCC, TATU, DMTMM and the like known in the art and commonly used acid activating agents/reagents (see Method 1 and 2 for Examples 4 & 6 in Table 1) to afford the desired boc-protected amide-linked adduct 9. Compound 9 can be deprotected using known conditions, such as with an acid, like TFA, to afford final compounds of Formula I, II, II-A and III.

Acid activating agents convert the OH of the acid into a strong leaving group "LG." Suitable leaving groups include halides, such as an iodide, bromide, chloride or fluoride. The LG may also be a non-halide moiety such as an alkylsulfonate or other known groups which generally form an electrophilic species (E$^+$). Coupling reactions generally occur more readily in one or a combination of solvents and a base. Suitable solvents include, without limitation, generally non-nucleophilic, anhydrous solvents such as toluene, CH$_2$Cl$_2$, THF, DMF, N,N-dimethylacetamide, pyridine and the like. The solvent may range in polarity, as appreciated by those skilled in the art. Suitable bases include, for example, tertiary amine bases such as DIEA, TEA, carbonate bases such as Na$_2$CO$_3$, K$_2$CO$_3$, Cs$_2$CO$_3$, hydrides such as NaH, KH and the like, alkoxides such as NaOCH$_3$, and the like. The base itself may also serve as a solvent. These coupling reactions are generally fast and conversion occurs typically in ambient conditions. However, depending upon the particular substrate, such reactions may require heat, as appreciated by those skilled in the art.

Scheme 2

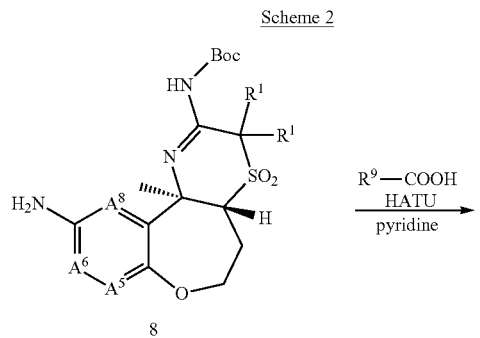

8

Scheme 3

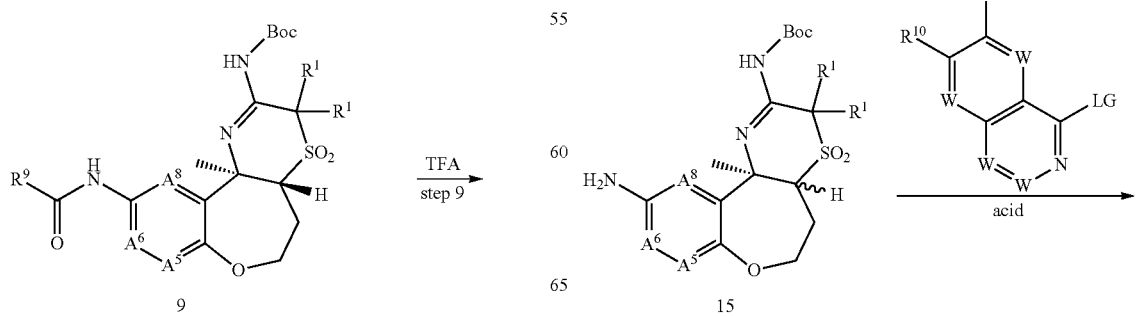

-continued

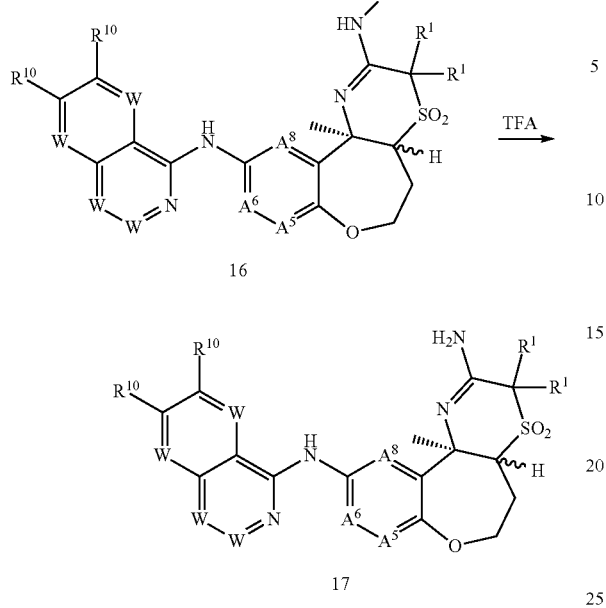

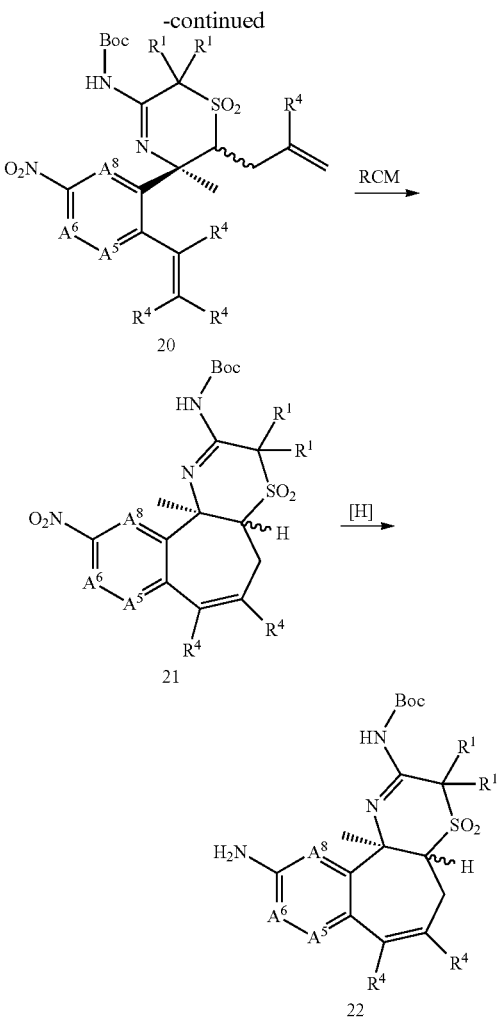

As shown, desired compounds 17 of Formula II and II-B can be prepared by treatment of intermediate amine 15 with a desired bicyclic $R^7$ group having a suitable leaving group, such as a chloride (Cl) or other aromatic leaving group, in the presence of a suitable acid, such as in the presence of sulfuric acid. This allows coupling of the bicyclic heteroaromatic $R^7$ group to the amine to form boc-protected intermediate 16. Intermediate 16 can then be treated with acid, such as TFA, to afford the desired amine-linked compounds of Formula II, and particularly II-B.

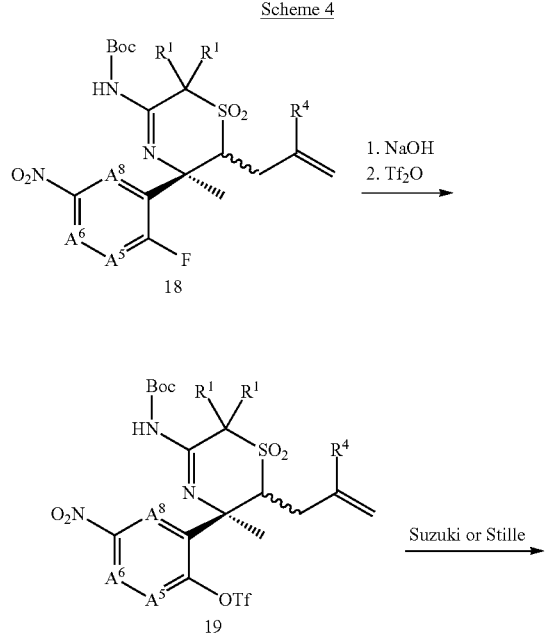

Scheme 4 describes a possible representative method for preparing each boc-protected stereoisomer (22) of Formulas I, II and III, wherein Y is —$CR^4R^4CR^4R^4$—, $R^2$ is $CH_3$, X is H and n is 2, but also broadly applicable to other embodiments. Beginning with sulfone isomers 18, analogous to previously described isomers 5 or 12 and obtained via similar methodology (see Schemes 1-A and 1-B), one of ordinary skill in the art may generate the corresponding phenol using hydroxide or equivalent hydrolytic conditions. Activation of the phenol to form a halogen equivalent, for example with triflic anhydride to give the corresponding triflate 19, would allow for metal catalyzed cross-coupling under a variety of standard conditions to access olefin 20. Ring-closing metathesis of 20 under standard conditions (Chem. Soc. Rev. (2010), 39, (8), 3305-3316) would give olefin 21, which could subsequently be reduced (e.g. metal-catalyzed hydrogenation) to afford 22. Subsequent functionalization of 22 in analogous manner as 15, would provide compounds of Formulas I, II and III wherein Y is —$CR^4R^4CR^4R^4$—, $R_2$ is $CH_3$, X is H and n is 2. Alternatively, any number of common carbon-carbon bond forming methods could be employed to establish the necessary substituted carbocycle containing the desired $R^4$ substitution (Organic Synthesis, Smith, M. B., McGraw-Hill, 1994).

Scheme 5

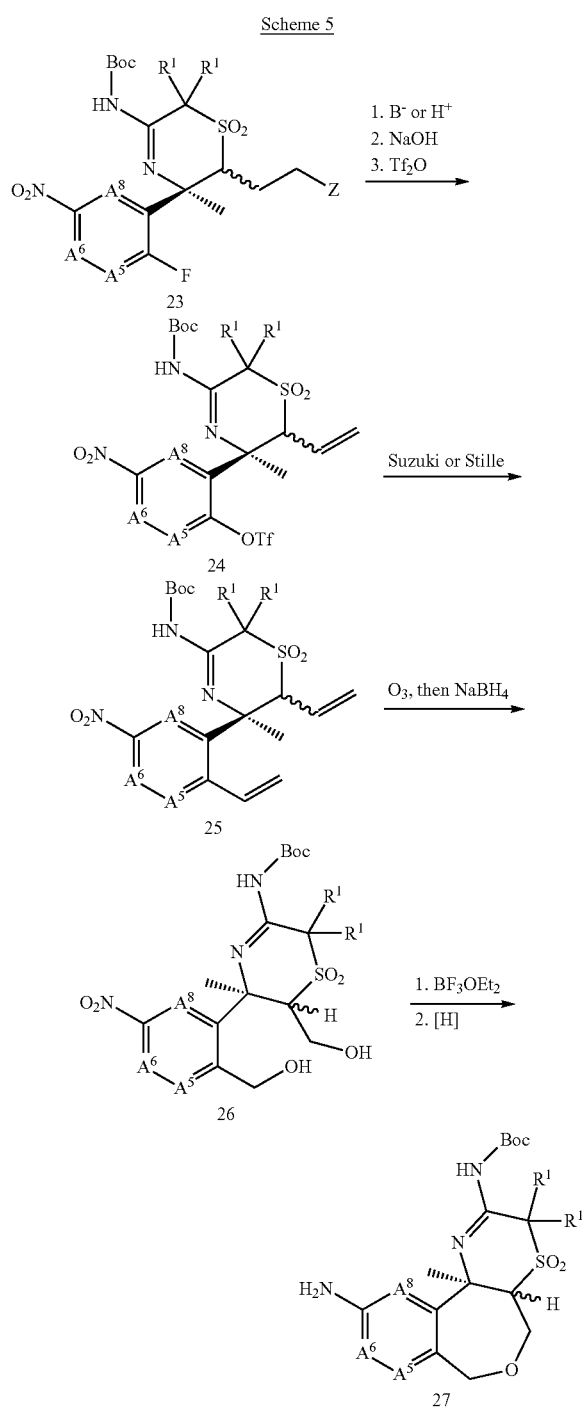

As described in Scheme 5, it is possible to prepare each boc-protected stereoisomer 27 of Formulas I, II and III, wherein Y is —CR$^4$R$^4$O—, R$_2$ is CH$_3$, X is H and n is 2. Beginning with compound 23, derived through alkylation in analogous manner as 18 where Z=halogen, hydroxyl, or a leaving group, one of ordinary skill in the art may effect elimination of "Z" to generate the corresponding olefin. Subsequent introduction of a second olefin as previously described herein could give 25. Treatment of 25 under ozonolysis or equivalent conditions could generate alcohol 26 after reductive workup (e.g. NaBH$_4$). Formation of cyclic ethers from diols is well precedented (Tetrahedron, 2002, 2009-7016) and can proceed under a variety of conditions including treatment with Lewis acids (e.g. BF$_3$OEt$_2$). Reduction of the nitro group to afford 27 and subsequent elaboration in analogous manner as 15, would provide compounds of Formulas I, II and III wherein Y is CH$_2$O—, R$_2$ is CH$_3$, X is H and n is 2.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, O-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs; ACD software or Accelrys Draw 4.0 (used to name bis-boc compounds & intermediates)).

Example 1

Intermediate 1

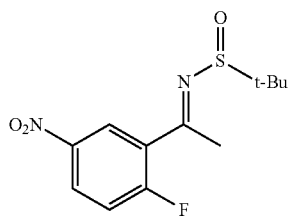 [SMILES: C/C(=N\S(=O)C(C)(C)C)c1cc([N+](=O)[O-])ccc1F]

Synthesis of N-(1-(2-fluoro-5-nitrophenyl)ethylidene)-2-methylpropane-2-sulfinamide A 250 ml RBF was charged with 2-methyl-2-propanesulfinamide (3.64 g, 30.0 mmol) and 1-(2-fluoro-5-nitrophenyl)ethanone (5.00 g, 27.3 mmol). THF (55 ml) was added and the resulting slurry was stirred for 5 min until full dissolution was observed. Titanium(IV) ethoxide, technical grade (11.30 ml, 54.6 mmol) was added and the mixture was stirred at 70° C. for 2 h. The mixture was cooled to RT and diluted with 70 ml brine. After stirring for 15 min, EtOAc (50 ml) was added to the mixture and the organic layer was decanted. The aqueous suspension was extracted twice with EtOAc, and the organic fractions were combined, washed with brine and concentrated in vacuo. The residue was purified by FC on 120 g RediSep Gold column using a solvent gradient of 5-50% EtOAc in heptane to afford N-(1-(2-fluoro-5-nitrophenyl)ethylidene)-2-methylpropane-2-sulfinamide (5.88 g, 20.54 mmol, 75% yield) as yellow oil, which crystallized slowly.

Example 2

Intermediate 2

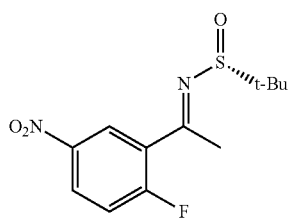 [SMILES: C/C(=N\[S@](=O)C(C)(C)C)c1cc([N+](=O)[O-])ccc1F]

Synthesis of (R)—N-(1-(2-fluoro-5-nitrophenyl)ethylidene)-2-methylpropane-2-sulfinamide The titled compound was prepared in a manner analogous to that of example 1, but using (R)-2-methyl-2-propanesulfinamide.

Example 3

Intermediate 3

Synthesis of 2-Methyl-2-(methylsulfonyl)propanenitrile

To a solution of 2-(methylsulfonyl)acetonitrile (60 g, 504 mmol) in DMF (252 mL) at 0° C. was added potassium carbonate (209 g, 1511 mmol) portion-wise, followed by iodomethane (136 mL, 1511 mmol). After 15 minutes, the ice bath was removed and the reaction was stirred at RT for 48 hours. The reaction mixture was filtered through a Celite pad, and the filter cake was rinsed with ethyl acetate and ether. The combined filtrates were concentrated and partitioned between ether and water. The organic portion was dried over sodium sulfate, filtered, and concentrated in vacuo to afford the titled intermediate (58 g, 78% yield) as an off-white solid.

Example 4

Method 1

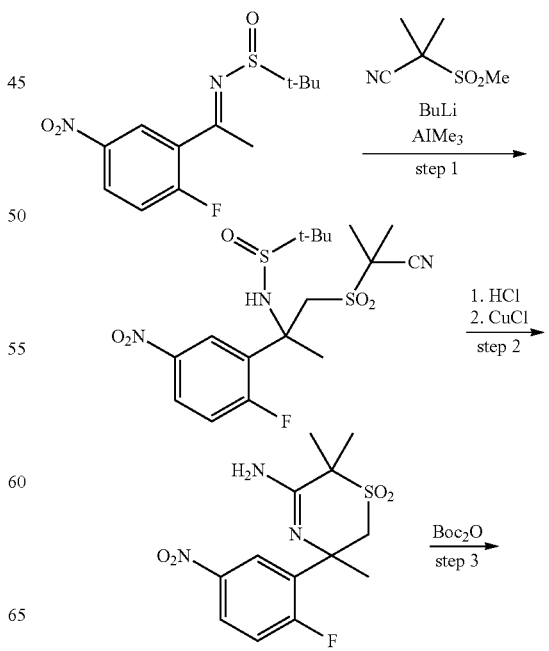

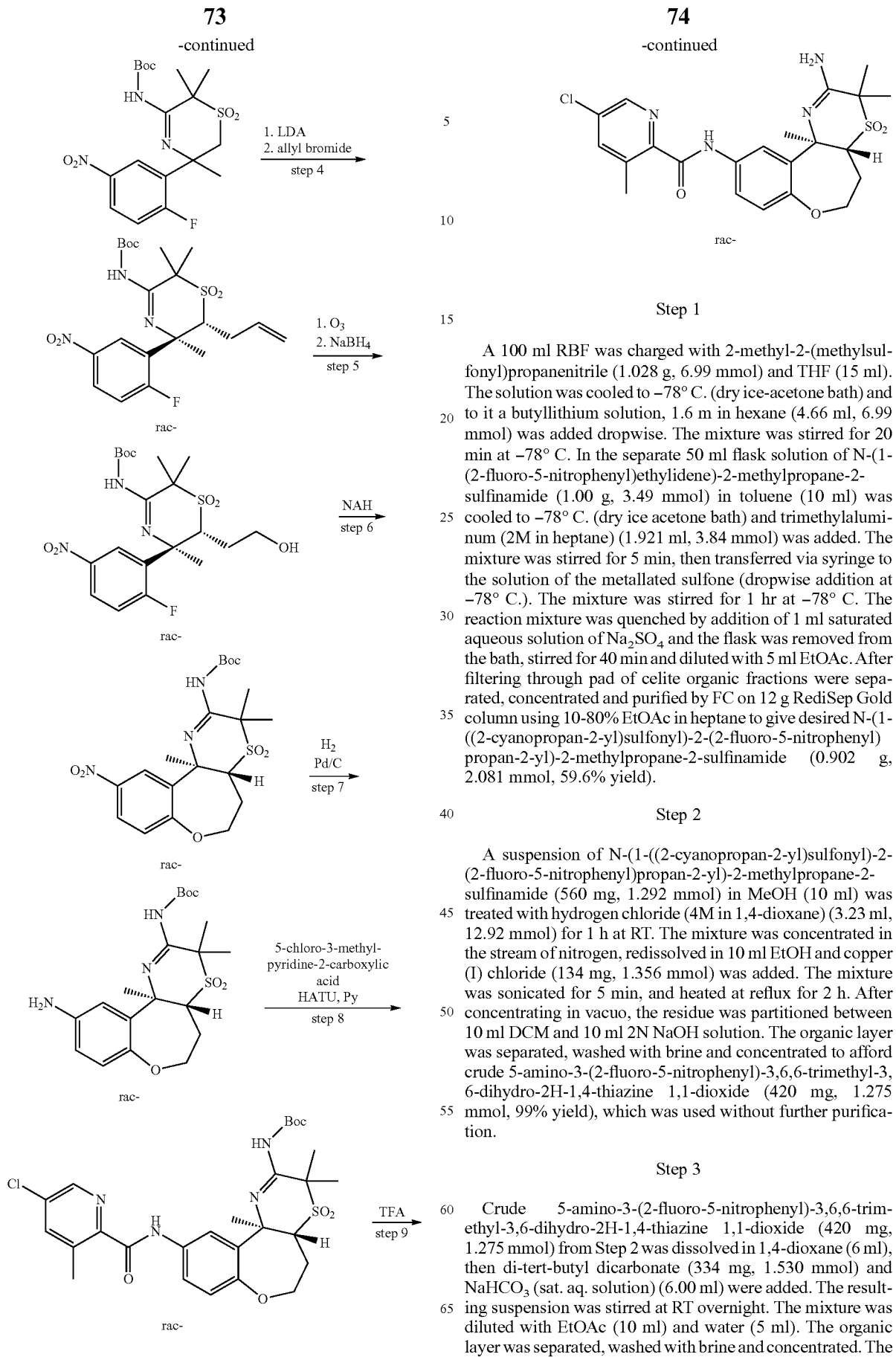

Step 1

A 100 ml RBF was charged with 2-methyl-2-(methylsulfonyl)propanenitrile (1.028 g, 6.99 mmol) and THF (15 ml). The solution was cooled to −78° C. (dry ice-acetone bath) and to it a butyllithium solution, 1.6 m in hexane (4.66 ml, 6.99 mmol) was added dropwise. The mixture was stirred for 20 min at −78° C. In the separate 50 ml flask solution of N-(1-(2-fluoro-5-nitrophenyl)ethylidene)-2-methylpropane-2-sulfinamide (1.00 g, 3.49 mmol) in toluene (10 ml) was cooled to −78° C. (dry ice acetone bath) and trimethylaluminum (2M in heptane) (1.921 ml, 3.84 mmol) was added. The mixture was stirred for 5 min, then transferred via syringe to the solution of the metallated sulfone (dropwise addition at −78° C.). The mixture was stirred for 1 hr at −78° C. The reaction mixture was quenched by addition of 1 ml saturated aqueous solution of $Na_2SO_4$ and the flask was removed from the bath, stirred for 40 min and diluted with 5 ml EtOAc. After filtering through pad of celite organic fractions were separated, concentrated and purified by FC on 12 g RediSep Gold column using 10-80% EtOAc in heptane to give desired N-(1-((2-cyanopropan-2-yl)sulfonyl)-2-(2-fluoro-5-nitrophenyl)propan-2-yl)-2-methylpropane-2-sulfinamide (0.902 g, 2.081 mmol, 59.6% yield).

Step 2

A suspension of N-(1-((2-cyanopropan-2-yl)sulfonyl)-2-(2-fluoro-5-nitrophenyl)propan-2-yl)-2-methylpropane-2-sulfinamide (560 mg, 1.292 mmol) in MeOH (10 ml) was treated with hydrogen chloride (4M in 1,4-dioxane) (3.23 ml, 12.92 mmol) for 1 h at RT. The mixture was concentrated in the stream of nitrogen, redissolved in 10 ml EtOH and copper (I) chloride (134 mg, 1.356 mmol) was added. The mixture was sonicated for 5 min, and heated at reflux for 2 h. After concentrating in vacuo, the residue was partitioned between 10 ml DCM and 10 ml 2N NaOH solution. The organic layer was separated, washed with brine and concentrated to afford crude 5-amino-3-(2-fluoro-5-nitrophenyl)-3,6,6-trimethyl-3,6-dihydro-2H-1,4-thiazine 1,1-dioxide (420 mg, 1.275 mmol, 99% yield), which was used without further purification.

Step 3

Crude 5-amino-3-(2-fluoro-5-nitrophenyl)-3,6,6-trimethyl-3,6-dihydro-2H-1,4-thiazine 1,1-dioxide (420 mg, 1.275 mmol) from Step 2 was dissolved in 1,4-dioxane (6 ml), then di-tert-butyl dicarbonate (334 mg, 1.530 mmol) and $NaHCO_3$ (sat. aq. solution) (6.00 ml) were added. The resulting suspension was stirred at RT overnight. The mixture was diluted with EtOAc (10 ml) and water (5 ml). The organic layer was separated, washed with brine and concentrated. The concentrated residue was purified by FC on 40 g RediSep Gold column using 5-50% EtOAc in heptane to afford tert-butyl (5-(2-fluoro-5-nitrophenyl)-2,2,5-trimethyl-1,1-dioxido-5,6-dihydro-2H-1,4-thiazin-3-yl)carbamate (460 mg, 1.071 mmol, 84% yield).

Step 4

To a solution of tert-butyl (5-(2-fluoro-5-nitrophenyl)-2,2,5-trimethyl-1,1-dioxido-5,6-dihydro-2H-1,4-thiazin-3-yl)carbamate (230 mg, 0.536 mmol) in THF (5 ml) was added lithium diisopropylamide, (2.0 M solution in tetrahydrofuran/heptane/ethylbenzene) (0.803 ml, 1.607 mmol) dropwise at −78° C. and the mixture was stirred for 20 min at the −78° C. To a resulting dark solution, allyl bromide (0.139 ml, 1.607 mmol) was added dropwise and the mixture was stirred for another 20 min. The reaction was quenched with NH$_4$Cl solution at −78° C., the flask was removed from the bath and allowed to reach RT. The mixture was extracted with ethyl acetate, organic layer was washed with brine, concentrated and the concentrated crude residue was separated on 12 g RediSep Gold column using 5-50% EtOAc in heptane solvent gradient to afford tert-butyl ((5RS,6RS)-6-allyl-5-(2-fluoro-5-nitrophenyl)-2,2,5-trimethyl-1,1-dioxido-5,6-dihydro-2H-1,4-thiazin-3-yl)carbamate (120 mg, 0.256 mmol, 47.7% yield) as major diastereomer and tert-butyl ((5RS,6SR)-6-allyl-5-(2-fluoro-5-nitrophenyl)-2,2,5-trimethyl-1,1-dioxido-5,6-dihydro-2H-1,4-thiazin-3-yl)carbamate (20 mg, 0.043 mmol, 7.9% yield) as minor diastereomer.

Step 5

A solution of tert-butyl ((5RS,6RS)-6-allyl-5-(2-fluoro-5-nitrophenyl)-2,2,5-trimethyl-1,1-dioxido-5,6-dihydro-2H-1,4-thiazin-3-yl)carbamate (120 mg, 0.256 mmol) in DCM (1.8 ml) and MeOH (0.6 ml) was cooled to −78° C., and sodium bicarbonate (42.9 mg, 0.511 mmol) was added and the mixture was ozonolyzed for 10 min. Oxygen was bubbled through the solution for 2 min, then solid sodium borohydride (14.5 mg, 0.383 mmol) was added to the mixture and the mixture was removed from the cooling bath and was allowed to reach RT and stirred for 30 min. The reaction was quenched with sat. solution of NH$_4$Cl and extracted with EtOAc. The organic layer was washed with brine, dried over MgSO$_4$ and concentrated to afford crude racemic tert-butyl ((5RS,6RS)-5-(2-fluoro-5-nitrophenyl)-6-(2-hydroxyethyl)-2,2,5-trimethyl-1,1-dioxido-5,6-dihydro-2H-1,4-thiazin-3-yl)carbamate (120 mg, 0.253 mmol, 99% yield) which was used without further purification.

Step 6

To a solution of tert-butyl ((5RS,6RS)-5-(2-fluoro-5-nitrophenyl)-6-(2-hydroxyethyl)-2,2,5-trimethyl-1,1-dioxido-5,6-dihydro-2H-1,4-thiazin-3-yl)carbamate (120 mg, 0.253 mmol) in the mixture of THF (2 ml) and DMF (0.2 ml) sodium hydride (60% dispersion in mineral oil) (25.3 mg, 0.634 mmol) was added and the mixture was stirred for 10 min at RT. The reaction mixture was quenched with saturated NH$_4$Cl solution and extracted with EtOAc. The organic layer was washed with brine and concentrated. The residue was purified by FC on 12 g RediSep Gold column using 10-100% EtOAc/heptane to afford tert-butyl ((4aRS,11bRS)-3,3,11b-trimethyl-10-nitro-4,4-dioxido-4a,5,6,11b-tetrahydro-3H-benzo[6,7]oxepino[4,5-b][1,4]thiazin-2-yl)carbamate (100 mg, 0.221 mmol, 87% yield).

Step 7

A solution of tert-butyl ((4aRS,11bRS)-3,3,11b-trimethyl-10-nitro-4,4-dioxido-4a,5,6,11b-tetrahydro-3H-benzo[6,7]oxepino[4,5-b][1,4]thiazin-2-yl)carbamate (100 mg, 0.221 mmol) in EtOAc (2 ml) and EtOH (2 ml) was hydrogenated under hydrogen balloon in the presence of palladium, 10% wt. on activated carbon (50 mg, 0.047 mmol) for 30 min. The mixture was filtered through the plug of Celite, filter cake was washed with ethyl acetate. The combined filtrate was concentrated ton afford crude tert-butyl ((4aRS,11bRS)-10-amino-3,3,11b-trimethyl-4,4-dioxido-4a,5,6,11b-tetrahydro-3H-benzo[6,7]oxepino[4,5-b][1,4]thiazin-2-yl)carbamate (70 mg, 0.165 mmol, 75.0% yield) which was used without further purification.

Step 8

Crude tert-butyl ((4aRS,11bRS)-10-amino-3,3,11b-trimethyl-4,4-dioxido-4a,5,6,11b-tetrahydro-3H-benzo[6,7]oxepino[4,5-b][1,4]thiazin-2-yl)carbamate (70 mg, 0.165 mmol) was suspended in DMF (2 ml) and sonicated for 1 min. 5-Chloro-3-methylpyridine-2-carboxylic acid (34.0 mg, 0.198 mmol), pyridine (0.04 ml, 0.496 mmol) and HATU (94 mg, 0.248 mmol) were added and resulting suspension was stirred for 45 min at RT. The mixture was diluted with EtOAc (8 ml) and saturated NaHCO$_3$ solution (3 ml). Water was added to dissolve precipitated solids. The organic layer was separated, washed with water and concentrated, and the resulting concentrate/residue was purified by FC on 12 g RediSep Gold column using 10-80% EtOAc in heptane to afford tert-butyl ((4aRS,11bRS)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (76 mg, 0.132 mmol, 80% yield) as white solid.

Step 9

A solution of tert-butyl ((4aRS,11bRS)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (76 mg, 0.132 mmol) in 2 ml DCM was treated with TFA (1 ml, 13.46 mmol) and the mixture was stirred for 1 hr at RT. The mixture was concentrated, and the residue was redissolved in 0.5 ml MeOH and basified with 3 ml sat. aq. NaHCO$_3$ solution. The precipitated solid was extracted with EtOAc, the extract was washed with brine, filtered through pad of celite and concentrated to afford N-((4aRS,11bRS)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide (Example 1) (57 mg, 0.120 mmol, 90% yield).

LC/MS (ESI$^+$) m/z=477

$^1$H NMR (400 MHz, DMSO-d$_6$) δ 10.35 (br s, 1H), 8.57 (dd, J=0.5, 2.3 Hz, 1H), 8.02 (dd, J=0.7, 2.3 Hz, 1H), 7.76-7.83 (m, 2H), 6.96 (d, J=8.31 Hz, 1H), 5.77-6.00 (br s, 2H), 4.51-4.66 (m, 1H), 3.60-3.72 (m, 1H), 3.45-3.58 (m, 1H), 2.56 (s, 3H), 2.26-2.46 (m, 2H), 1.60 (s, 3H), 1.53 (s, 3H), 1.52 (s, 3H).

Example 5

Intermediate 4

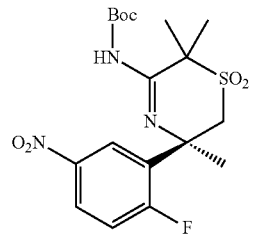 [SMILES: CC(C)(C)OC(=O)NC1=N[C@](C)(c2cc([N+](=O)[O-])ccc2F)CS(=O)(=O)C1(C)C]

Example 5 (intermediate 4), (R)-tert-butyl (5-(2-fluoro-5-nitrophenyl)-2,2,5-trimethyl-1,1-dioxido-5,6-dihydro-2H-1,4-thiazin-3-yl)carbamate, was prepared from (R)—N-(1-(2-fluoro-5-nitrophenyl)ethylidene)-2-methylpropane-2-sulfinamide (Intermediate 2) according to steps 1-3 in Example 4, Method 1.
Examples 6a & 6b
Method 2
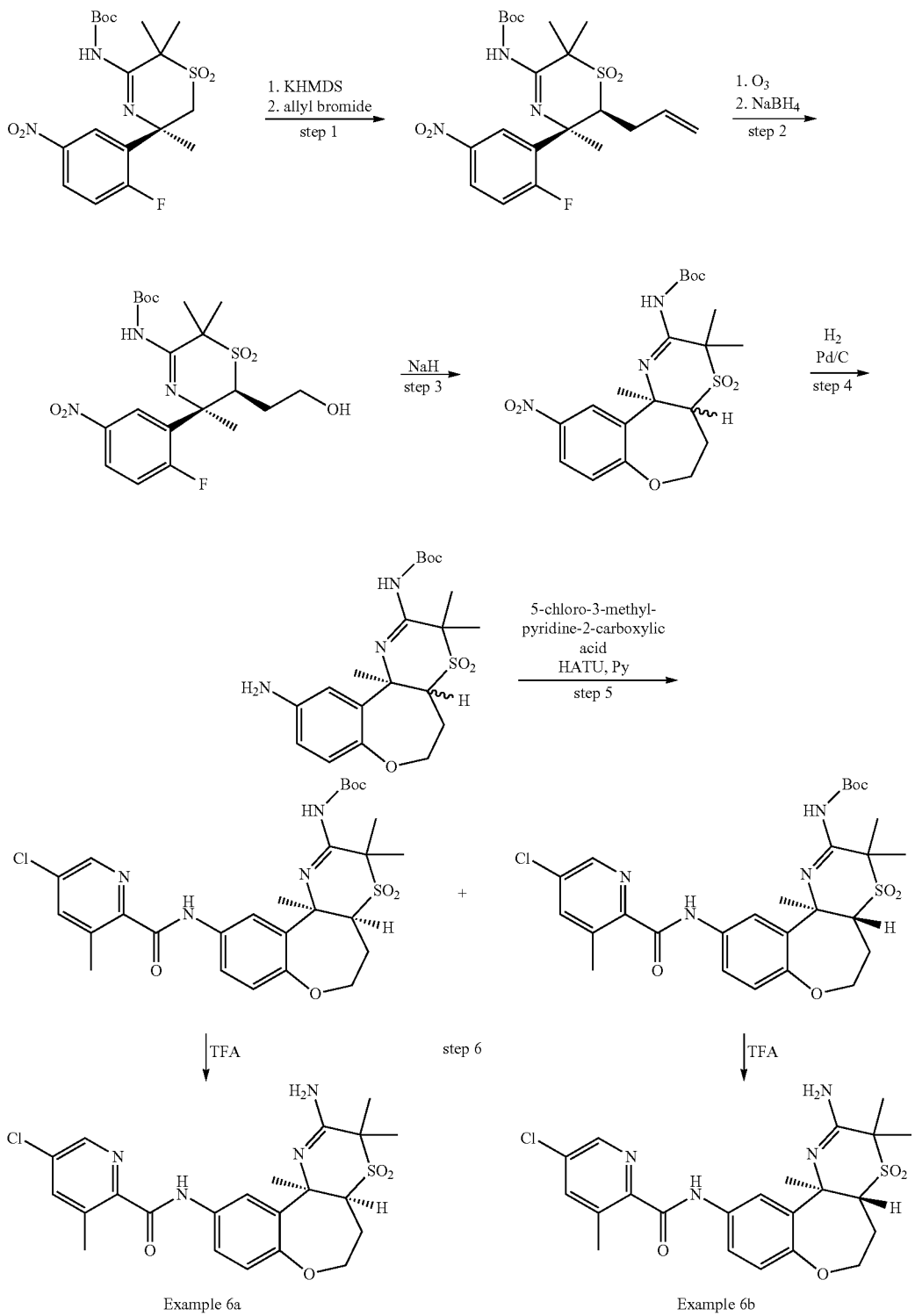

Step 1

To a solution of (R)-tert-butyl (5-(2-fluoro-5-nitrophenyl)-2,2,5-trimethyl-1,1-dioxido-5,6-dihydro-2H-1,4-thiazin-3-yl)carbamate (600 mg, 1.397 mmol) in THF (14 ml) was added potassium bis(trimethylsilyl)amide, (1M in THF) (8.38 ml, 8.38 mmol) dropwise at −78° C. and the mixture was stirred for 30 min at −78° C. Neat allyl bromide (0.363 ml, 4.19 mmol) was then added dropwise and the mixture was stirred for 30 min. The reaction mixture was quenched with sat. aq. $NH_4Cl$ solution at −78° C., then allowed to reach RT and extracted with ethyl acetate. The organic extracts were washed with brine and concentrated. The residue was separated by silica gel chromatography on a 40 g RediSep Gold column using 10-60% EtOAc/heptane solvent gradient to afford less polar trans-isomer tert-butyl ((5R,6R)-6-allyl-5-(2-fluoro-5-nitrophenyl)-2,2,5-trimethyl-1,1-dioxido-5,6-dihydro-2H-1,4-thiazin-3-yl)carbamate (170 mg, 0.362 mmol, 25.9% yield), and more polar cis-isomer tert-butyl ((5R,6S)-6-allyl-5-(2-fluoro-5-nitrophenyl)-2,2,5-trimethyl-1,1-dioxido-5,6-dihydro-2H-1,4-thiazin-3-yl)carbamate (263 mg, 0.560 mmol).

Step 2

To a solution of tert-butyl ((5R,6S)-6-allyl-5-(2-fluoro-5-nitrophenyl)-2,2,5-trimethyl-1,1-dioxido-5,6-dihydro-2H-1,4-thiazin-3-yl)carbamate (250 mg, 0.532 mmol) (cis-isomer from Step 1) in DCM (4 ml) and MeOH (1.3 ml), was added sodium bicarbonate (89 mg, 1.065 mmol) and the mixture was cooled to −78° C. The resulting mixture was ozonolized for about 10 min or until analysis showed no starting material present. The stream of oxygen was passed through the solution for 5 min, then solid sodium borohydride (40.3 mg, 1.065 mmol) was added to the mixture. The flask was removed from the bath and allowed to reach RT and stirred for 30 min. The reaction was quenched with saturated $NH_4Cl$ solution (caution: there is evolution of gas), diluted with water to dissolve solids and extracted into EtOAc. The organic layer was washed with brine, dried over $MgSO_4$, filtered and concentrated to afford tert-butyl ((5R,6S)-5-(2-fluoro-5-nitrophenyl)-6-(2-hydroxyethyl)-2,2,5-trimethyl-1,1-dioxido-5,6-dihydro-2H-1,4-thiazin-3-yl)carbamate which was used in the next step without further purification.

Step 3

A solution of crude tert-butyl ((5R,6S)-5-(2-fluoro-5-nitrophenyl)-6-(2-hydroxyethyl)-2,2,5-trimethyl-1,1-dioxido-5,6-dihydro-2H-1,4-thiazin-3-yl)carbamate (250 mg, 0.528 mmol) in THF (5 ml) and DMF (0.5 ml) was treated portionwise with NaH (60% suspension in mineral oil) (52.8 mg, 1.320 mmol). After initial gas evolution the reaction mixture became dark red. The mixture was stirred at RT for 10 min. The mixture was quenched with $NH_4Cl$ solution and diluted with EtOAc. Water was added to dissolve solids, and the organic layer was separated, washed with brine and concentrated. The residue was purified by FC on 12 g RedSep Gold column using 10-100% EtOAc in heptane. All the fractions containing both epimers were combined and concentrated to afford tert-butyl ((11bR)-3,3,11b-trimethyl-10-nitro-4,4-dioxido-4a,5,6,11b-tetrahydro-3H-benzo[6,7]oxepino[4,5-b][1,4]thiazin-2-yl)carbamate (196 mg, 0.432 mmol, 82% yield) as a mixture of epimers at C4. Ratio by NMR 2:1 favoring trans-isomer.

Step 4

A solution of tert-butyl ((11bR)-3,3,11b-trimethyl-10-nitro-4,4-dioxido-4a,5,6,11b-tetrahydro-3H-benzo[6,7]oxepino[4,5-b][1,4]thiazin-2-yl)carbamate (190 mg, 0.419 mmol) (1.9:1 mixture of trans/cis epimers) in EtOAc (3 ml) and EtOH (1.000 ml) was hydrogenated (balloon) in the presence of palladium (10% wt. on activated carbon) (44.6 mg, 0.042 mmol) for 2 hr at rt. Additional palladium, 10% wt. on activated carbon (44.6 mg, 0.042 mmol) was added and hydrogenation continued for additional 2 h. The mixture was filtered through the plug of celite and washed 3 times with 3 ml portions of EtOAc. The filtrate was concentrated in vacuo to give tert-butyl ((11bR)-10-amino-3,3,11b-trimethyl-4,4-dioxido-4a,5,6,11b-tetrahydro-3H-benzo[6,7]oxepino[4,5-b][1,4]thiazin-2-yl)carbamate as a mixture of diastereomers which was used in the next step without purification.

Step 5

To the crude tert-butyl ((11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (190 mg, 0.449 mmol) from Step 4 (~2:1 trans/cis mixture) dissolved in DMF (2 ml), was added 5-chloro-3-methylpyridine-2-carboxylic acid (92 mg, 0.538 mmol), pyridine (0.109 ml, 1.346 mmol) and HATU (256 mg, 0.673 mmol) and resulting solution was stirred for 1 hr at RT. The mixture was diluted with EtOAc (8 ml) and saturated $NaHCO_3$ solution (3 ml). Water was added to dissolve precipitated solids. The organic layer was separated, washed with water, brine and concentrated. The residue was and purified by silica gel chromatography on 12 g RediSep Gold column using 10-70% EtOAc in heptane to afford major less polar trans-isomer tert-butyl ((4aR,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (110 mg, 0.191 mmol, 42.5% yield and more polar minor cis-isomer tert-butyl ((4aS,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (70 mg, 0.121 mmol, 27% yield).

Step 6

A solution of trans-isomer tert-butyl ((4aR,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (110 mg, 0.191 mmol) in DCM (2 ml) was treated with TFA (0.7 ml, 9.53 mmol) for 10 min at RT. The mixture was concentrated to dryness, redissolved in 0.5 ml of MeOH and neutralized with saturated solution $NaHCO_3$. The precipitated material was extracted with ethyl acetate, organic extract was washed with water, brine, filtered through pad of celite and concentrated to afford N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide (Example 6a) (89 mg, 0.187 mmol, 98% yield).

LC/MS (ESI$^+$) m/z=477

$^1$H NMR (400 MHz, DMSO-d$_6$) §10.35 (br s, 1H), 8.57 (dd, J=0.5, 2.3 Hz, 1H), 8.02 (dd, J=0.7, 2.3 Hz, 1H), 7.76-7.83 (m, 2H), 6.96 (d, J=8.31 Hz, 1H), 5.77-6.00 (br s, 2H), 4.51-4.66 (m, 1H), 3.60-3.72 (m, 1H), 3.45-3.58 (m, 1H), 2.56 (s, 3H), 2.26-2.46 (m, 2H), 1.60 (s, 3H), 1.53 (s, 3H), 1.52 (s, 3H).

In a deprotection step analogous to step 6 hereinabove, the cis-isomer tert-butyl ((4aS,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (70 mg, 0.121 mmol) was converted to N-((4aS, 11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide (Example 6b) (55 mg, 0.115 mmol, 95% yield).

LC/MS (ESI⁺) m/z=477

$^1$H NMR (400 MHz, DMSO-$d_6$) δ 10.32 (br. s, 1H), 8.56 (dd, J=0.6, 2.3 Hz, 1H), 8.00 (dd, J=0.6, 2.3 Hz, 1H), 7.70 (dd, J=2.3, 8.4 Hz, 1H), 7.46 (d, J=2.3 Hz, 1H), 6.86 (d, J=8.4 Hz, 1H), 5.96-6.13 (m, 2H), 4.22-4.35 (m, 1H), 3.81-3.94 (m, 1H), 3.66-3.79 (m, 1H), 2.53 (s, 3H), 2.30-2.45 (m, 2H), 1.62 (s, 3H), 1.61 (s, 3H), 1.41 (s, 3H).

Intermediate 5

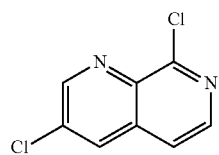 [SMILES: Clc1cnc2c(Cl)nccc2c1]

Synthesis of 3,8-Dichloro-1,7-naphthyridine

Step 1: 3-Bromo-5-chloropicolinonitrile

A microwave vial was charged with copper (I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 hours. The solution was concentrated, diluted with DCM (25 mL), and filtered. The filtrate was concentrated, and the residue was purified by silica gel chromatography, eluting with 0-30% EtOAc in heptanes, to afford the title compound (2 g, 9.20 mmol). MS m/z=219 (M+H).

Step 2: 5-Chloro-3-((trimethylsilyl)ethynyl)picolinonitrile

A pressure vessel was charged with triethylamine (7.65 mL, 55.2 mmol), ethynyltrimethylsilane (2.32 mL, 16.6 mmol), copper (I) iodide (0.263 g, 1.380 mmol), palladium (0) tetrakis(triphenylphosphine) (0.558 g, 0.483 mmol), 3-bromo-5-chloropicolinonitrile (3.0 g, 13.8 mmol), and N,N-dimethylformamide (50 ml). The vessel was flushed with argon, sealed, stirred at ambient temperature for 15 minutes, and then heated at 50° C. for 4 hours. The solution was diluted with water and extracted with ethyl acetate. The combined organic layers were concentrated, and the residue was purified by silica-gel chromatography, eluting 0-50% ethyl acetate in hexane, to afford the title compound (1.3 g, 5.5 mmol). MS m/z=235 (M+H).

Step 3: 5-Chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in methanol, 42.6 mL, 21.30 mmol), sealed, and stirred at 55° C. for one hour. The solution was concentrated, and the residue was purified via silica gel chromatography, eluting with 10% methanol in DCM to afford the title compound (1.7 g, 7.50 mmol). MS m/z=227 (M+H).

Step 4: 3-Chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with dichloromethane. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 ethyl acetate/methanol/ammonium hydroxide) in ethyl acetate, to the title intermediate (1.1 g, 6.1 mmol). MS m/z=181 (M+H).

Step 5: 3,8-Dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H).

Intermediate 6

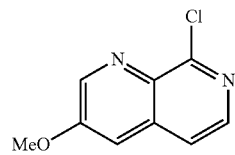

Synthesis of 8-Chloro-3-methoxy-1,7-naphthyridine

Step 1: 3-chloro-5-methoxypicolinonitrile

To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 minutes at 0° C., then allowed to warm to RT and stir for 30 minutes. The solution was partitioned between water and EtOAc. The organic layer was washed with water and concentrated. The crude product was purified via silica gel chromatography, eluting with 0-75% ethyl acetate in heptanes, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H).

Step 2: 5-Methoxy-3-((triethylsilyl)ethynyl)picolinonitrile

A sealed vessel was charged with bis(acetonitrile)palladium (II) chloride (0.154 g, 0.593 mmol), dicyclohexyl(2',4',6'-triisopropyl-[1,1'-biphenyl]-2-yl)phosphine (0.848 g, 1.780 mmol), cesium carbonate (25.1 g, 77 mmol), the product of Intermediate 9, step 1 (5 g, 29.7 mmol), and ACN (60 mL). The vessel was flushed with argon, sealed, and stirred at RT for 25 minutes. To the reaction was added triethyl(ethynyl)silane (5.41 g, 38.6 mmol), and the vessel was resealed and stirred at 90° C. for 3 hours. The solution was concentrated, and the residue was purified via silica gel chromatography, eluting with 0-50% ethyl acetate in heptanes, to afford the title compound (3.8 g, 13.9 mmol). MS m/z=273 (M+H).

Step 3:
3-(2,2-Dimethoxyethyl)-5-methoxypicolinonitrile

A pressure vessel was charged with 5-methoxy-3-((triethylsilyl)ethynyl)picolinonitrile (3.8 g, 13.95 mmol) and sodium methoxide (0.5 M in methanol, 69.7 mL, 34.9 mmol). The vessel was sealed and stirred at 55° C. for 2 hours. The reaction was concentrated to afford the title intermediate (3.1 g, 13.95 mmol).

Step 4: 8-chloro-3-methoxy-1,7-naphthyridine

Using an analogous sequence of reactions to those described in Intermediate 5, steps 4-5, 3-(2,2-dimethoxyethyl)-5-methoxypicolinonitrile (3.4 g, 15.30 mmol) was converted to the title compound (552 mg, 2.84 mmol). MS m/z=195 (M+H).

Intermediate 7

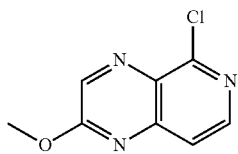

Synthesis of
5-Chloro-2-methoxypyrido[3,4-b]pyrazine

Step 1: 5-Chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in ethanol (34.8 mL) was stirred at reflux for 24 hours. The solution was cooled to −20° C. for 16 hours, and the resulting precipitate was collected by vacuum filtration and rinsed with ethanol. The crude product was purified via reverse-phase HPLC, eluting with 5-50% acetonitrile/ 0.1% trifluoroacetic acid in water/0.1% trifluoroacetic acid, to afford the title compound (570 mg, 3.14 mmol). MS m/z=182 (M+H).

Step 2: 2,5-Dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in dichloromethane, washed with saturated sodium bicarbonate, dried over anhydrous sodium sulfate, filtered, and concentrated to afford the title compound (580 mg, 2.90 mmol). MS m/z=200 (M+H).

Step 3: 5-Chloro-2-methoxypyrido[3,4-b]pyrazine

To a solution of 2,5-dichloropyrido[3,4-b]pyrazine (580 mg, 2.90 mmol) in N,N-dimethylformamide (10 mL) was added a 0.5-M solution of sodium methoxide in methanol (6.09 mL, 3.04 mmol), and the reaction was stirred at room temperature for 5 minutes. The solution was diluted with water and extracted with ethyl acetate. The organic layer was dried with sodium sulfate, filtered and concentrated to afford the title compound (550 mg, 2.81 mmol). MS m/z=196 (M+H).

Intermediate 8

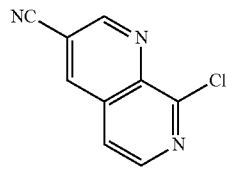 [SMILES: N#Cc1cnc2c(Cl)nccc2c1]

Synthesis of
8-Chloro-1,7-naphthyridine-3-carbonitrile

A screw-cap vial was charged with 3-chloro-1,7-naphthyridin-8(7H)-one (100 mg, 0.554 mmol), zinc cyanide (97.6 mg, 0.831 mmol), 2-dieyelohexylphosphino-2',6'-dimethoxybiphenyl (45.5 mg, 0.111 mmol), tris(dibenzylideneacetone)dipalladium(0) (40.6 mg, 0.044 mmol), DMF (2.74 mL) and water (28 μL). The vial was purged with argon, sealed, and stirred at 110° C. for 1 hour. The mixture was filtered through a pad of Celite, which was rinsed with methanol and dimethylsulfoxide. The combined filtrates were concentrated, and a few drops of water were added. The resulting solids were collected by vacuum filtration, rinsed with water and dried.

The solids were suspended in toluene (3.5 mL), and phosphorus oxychloride (98 pt, 1.052 mmol) and DIPEA (122 pt, 0.701 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptanes, to provide the title compound (50 mg, 0.264 mmol) as a white solid. LC/MS (ESI+) m/z=190 (M+H).

Intermediate 9

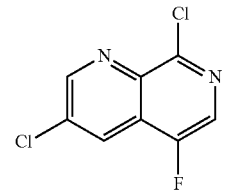 [SMILES: Fc1cnc(Cl)c2ncc(Cl)cc12]

Synthesis of 3,8-Dichloro-5-fluoro-1,7-naphthyridine

Step 1: 3-chloro-5-fluoro-6-methoxy-6,7-dihydro-1, 7-naphthyridin-8(5H)-one

A pressure bottle was charged with 3-chloro-1,7-naphthyridin-8(7H)-one (15 g, 83 mmol), methanol (34.6 mL), ACN (173 mL) and 1-chloromethyl-4-fluoro-1,4-diazoniabicyclo [2.2.2]octane bis(tetrafluoroborate) (30.9 g, 87 mmol), and the mixture was heated at 45° C. for 15 hours. Water and ethyl acetate were added, and the layers were separated. The aqueous portion was extracted twice with ethyl acetate and once with DCM, and the combined organic layers were dried with anhydrous sodium sulfate, filtered and concentrated. The crude solid was triturated with a minimum amount of ethyl acetate and filtered. The title intermediate was isolated as an off-white solid (15.34 g, 80%) as a 3:1 mixture of diastereomers.

Step 2: 3,8-dichloro-5-fluoro-1,7-naphthyridine

A vial was charged with 3-chloro-5-fluoro-6-methoxy-6,7-dihydro-1,7-naphthyridin-8(5H)-one (7.5 g, 32.5 mmol), acetonitrile (130 mL) and phosphorus oxychloride (9.09 mL, 98 mmol), and the mixture was stirred at 75° C. for 15 hours. The mixture was concentrated, and the crude material was purified by silica gel chromatography, eluting with 0-50% ethyl acetate in heptanes, to provide the title compound (5.57 g, 25.7 mmol, 79% yield) as a white solid. LC/MS (ESI$^+$) m/z=217 (M+H).

Intermediate 10

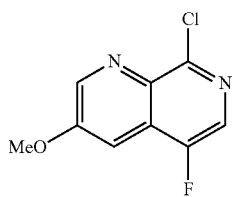 [SMILES: COc1cnc2c(Cl)ncc(F)c2c1]

Synthesis of
8-Chloro-5-fluoro-3-methoxy-1,7-naphthyridine

Using an analogous sequence of reactions to those described for Intermediate 9,5-fluoro-3-methoxy-1,7-naphthyridin-8(7H)-one was converted to the title compound. LC/MS (ESI$^+$) m/z=213 (M+H).

Intermediate 11

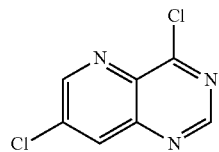 [SMILES: Clc1cnc2c(Cl)ncnc2c1]

Synthesis of 4,7-Dichloropyrido[3,2-d]pyrimidine

Step 1: 3-Amino-5-chloropicolinamide

To a suspension of 5-chloro-2-cyano-3-nitropyridine (1.274 mL, 10.9 mmol) in water (22 mL) was added 28% aqueous ammonium hydroxide (3.94 mL, 28.3 mmol), and the reaction was stirred at RT for 20 minutes. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. $^1$H-NMR (400 MHz, DMSO-d$_6$): δ 7.88 (br. s, 1H), δ 7.73 (s, 1H), δ 7.39 (br. s, 1H), δ 7.23 (s, 1H), δ 7.06 (br. s, 2H). LC/MS (ESI$^+$) m/z=172 (M+H).

Step 2: 7-Chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 hours. After cooling to RT, the yellow precipitate was collected by vacuum filtration and washed with hexanes to yield the title intermediate (1.03 g, 5.67 mmol) as a yellow solid. $^1$H NMR (400 MHz, DMSO-d$_6$) δ ppm 8.20 (s, 1H) 8.27 (d, J=2.35 Hz, 1H) 8.80 (d, J=2.25 Hz, 1H) 12.68 (br. s., 1H). LC/MS (ESI m/z=182 (M+H).

Step 3: 4,7-Dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 hour. After cooling to RT, the reaction mixture was concentrated to provide the title compound. LC/MS (ESI$^+$) m/z=200 (M+H).

Intermediate 12

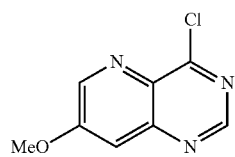 [SMILES: COc1cnc2c(Cl)ncnc2c1]

Synthesis of
4-Chloro-7-methoxypyrido[3,2-d]pyrimidine

Step 1: 7-Methoxypyrido[3,2-d]pyrimidin-4(1H)-one

A microwave vial was charged with 7-chloropyrido[3,2-d]pyrimidin-4(1H)-one (110 mg, 0.606 mmol), a 0.5 M solution of sodium methoxide in methanol (3.65 mL, 1.817 mmol) and sodium methoxide (327 mg, 6.06 mmol). The vial was capped and irradiated in a microwave reactor at 145° C. for 30 minutes. The reaction was neutralized with saturated aqueous ammonium chloride (3 mL), concentrated, and diluted with cold water. The resulting precipitate was collected by vacuum filtration and dried in vacuo to provide the title compound (107 mg, 0.604 mmol) as pink solid. $^1$H NMR (400 MHz, DMSO-d$_6$) δ ppm 3.95 (s, 3H) 7.49 (d, J=2.74 Hz, 1H) 8.11 (s, 1H) 8.47 (d, J=2.74 Hz, 1H). LC/MS (ESI$^+$) m/z=178 (M+H).

Step 2: 4-Chloro-7-methoxypyrido[3,2-d]pyrimidine

Using an analogous reaction to that described for Intermediate 11, step 3, 7-methoxypyrido[3,2-d]pyrimidin-4(1H)-one was converted to the title compound. LC/MS (ESI$^+$) m/z=196 (M+H).

Intermediate 13

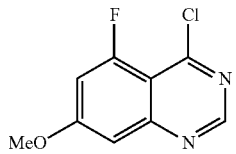 [SMILES: COc1cc(F)c2c(Cl)ncnc2c1]

Synthesis of
4-Chloro-5-fluoro-7-methoxyquinazoline

Step 1: 2-Amino-6-fluoro-4-methoxybenzonitrile

Ammonia gas was bubbled through a solution of 2,6-difluoro-4-methoxybenzonitrile (1.0 g, 5.91 mmol) in dimethylsulfoxide (11.83 mL) for 10 minutes. The reaction was then sealed and stirred at 90° C. for 24 hours. The reaction mixture was cooled to ambient temperature and concentrated in vacuo to afford a tan residue. The residue was triturated with water, collected be vacuum filtration, and dried in vacuo to afford the title intermediate (0.9 g, 5.42 mmol) as a white solid. LC/MS (ESI$^+$) m/z=167 (M+H).

Step 2: 5-Fluoro-7-methoxyquinazolin-4-ol

To a mixture of formic acid (11.43 mL, 298 mmol) and sulfuric acid (0.866 mL, 16.25 mmol) was added 2-amino-6-fluoro-4-methoxybenzonitrile (0.9 g, 5.42 mmol) in portions. The reaction mixture was stirred at 100° C. for 1 hour, cooled to ambient temperature, and poured into 80 mL of an ice-water mixture. The resulting precipitate was collected by vacuum filtration and dried in vacuo to provide the title intermediate (0.8 g, 4.12 mmol) as an off-white solid. LC/MS (ESI$^+$) m/z=195 (M+H).

Step 3: 4-Chloro-5-fluoro-7-methoxyquinazoline

To a suspension of 5-fluoro-7-methoxyquinazolin-4-ol (0.125 g, 0.644 mmol) in thionyl chloride (1.410 mL, 19.31 mmol) was added N,N-dimethylformamide (0.028 mL, 0.361 mmol). The reaction was stirred at 80° C. for 6 hours and concentrated in vacuo. The residue was suspended in saturated aqueous sodium bicarbonate and extracted with dichloromethane. The organic layer was concentrated in vacuo to generate the title compound (0.13 g, 0.611 mmol) as a yellow solid. LC/MS (ESI$^+$) m/z=213 (M+H).

Intermediate 14

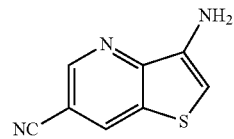 [SMILES: N#Cc1cnc2c(N)csc2c1]

Synthesis of
3-Aminothieno[3,2-b]pyridine-6-carbonitrile

Step 1: Sodium
(E)-2-cyano-3,3-dimethoxyprop-1-en-1-olate

To a suspension of NaH (60% dispersion in mineral oil, 2.52 g, 63.0 mmol) in diethylether (75 mL) was added 3,3-dimethoxypropanenitrile (6.17 mL, 55.0 mmol) followed by methyl formate (6.74 mL, 110 mmol). The solution was stirred for 3 days at RT. The resulting solid was collected by vacuum filtration and washed with ether to afford sodium (E)-2-cyano-3,3-dimethoxyprop-1-en-1-olate (4.2 g, 25.4 mmol).

Step 2: 3-Aminothieno[3,2-b]pyridine-6-carbonitrile

To a solution of sodium (E)-2-cyano-3,3-dimethoxyprop-1-en-1-olate (1012 mg, 6.13 mmol) in methanol (12 mL) was added concentrated hydrochloric acid (503 µL 6.13 mmol). The solution was stirred for 5 minutes, and then a solution of thiophene-3,4-diamine (700 mg, 6.13 mmol) in methanol (12 mL) was added. The solution was stirred at reflux for 3 hours, and then a solution of concentrated HCl (1.0 mL) in methanol (2 mL) was added. The reaction was stirred at reflux for an additional two hours, quenched with TEA (3 mL), and concentrated. The crude product was purified via silica gel chromatography, eluting with 0-100% ethyl acetate in heptanes, to provide the title compound (250 mg, 1.427 mmol). MS m/z=176 (M+H).

Intermediate 15

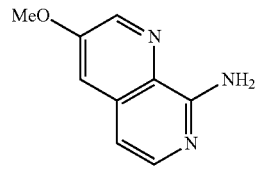 [SMILES: COc1cnc2c(N)nccc2c1]

Synthesis of 3-Methoxy-1,7-naphthyridin-8-amine

Step 1: 3-Methoxy-N-(4-methoxybenzyl)-1,7-naphthyridin-8-amine

To a solution of 8-chloro-3-methoxy-1,7-naphthyridine (1 g, 5.14 mmol) in N,N-dimethylformamide (10.28 mL) was added potassium carbonate (1.42 g, 10.28 mmol) followed by 4-methoxybenzylamine (1.47 ml, 11.3 mmol). The reaction was stirred at 100° C. for 24 hours and then concentrated to generate a brown residue. This was partitioned between ethyl acetate and water. The organic layer was concentrated and purified by silica-gel chromatography, eluting with 1-5% methanol in DCM, to provide the title compound (1.37 g, 4.63 mmol) as a tan solid. LC/MS (ESI+) m/z=296 (M+H).

Step 2: 3-methoxy-1,7-naphthyridin-8-amine

To a solution of N-(4-methoxybenzyl)-1,7-naphthyridin-8-amine (340 mg, 1.15 mmol) in 1,2-dichloroethane (5.80 mL) was added TFA (2.67 mL, 34.5 mmol). The reaction was stirred at 75° C. for 8 hours and then concentrated. The residue was partitioned between DCM and aqueous sodium bicarbonate. The organic layer was concentrated and purified by silica-gel chromatography, eluting with 50-100% EtOAc in DCM, to provide the title compound (171.7 mg, 0.98 mmol) as an off-white solid. LC/MS (ESI+) m/z=176 (M+H).

Intermediate 16

Synthesis of 5-(Difluoromethyl)picolinic acid

Step 1: 5-Formylpicolinonitrile

A suspension of 2-bromo-5-formylpyridine (940 mg, 5.05 mmol) and copper (I) cyanide (679 mg, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with ethyl acetate. The combined organic layers were washed with brine, dried over anhydrous magnesium sulfate, filtered and concentrated. The crude product was purified by silica-gel chromatography, eluting with a gradient of 40%-60% (40% ethyl acetate in heptane) in heptane, to provide the title compound (236 mg, 1.786 mmol) as white solid. LC/MS (ESI+) m/z=133 (M+H).

Step 2: 5-(Difluoromethyl)picolinonitrile

To a solution of 5-formylpicolinonitrile (74 mg, 0.560 mmol) in toluene (0.25 mL) was added bis(2-methoxyethyl)aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM. The organic layer was washed with brine, dried over anhydrous magnesium sulfate, filtered, and concentrated. The crude material was purified by silica-gel chromatography, eluting with a gradient of 40% to 60% (40% ethyl acetate/heptane) in heptane, to provide the title compound (48 mg, 0.311 mmol) as white solid. LC/MS (ESI+) m/z=155 (M+H).

Step 3: 5-(difluoromethyl)picolinic acid

A suspension of 5-(difluoromethyl)picolinonitrile (48 mg, 0.311 mmol) in 12 N aqueous hydrochloric acid (4.3 mL, 140 mmol) was stirred at 110° C. for 1.5 hours. After cooling to ambient temperature, the reaction mixture was concentrated and treated with DIPEA (2 mL). The mixture was concentrated and dried in vacuo to provide the title compound in quantitative yield. LC/MS (ESI+) m/z=174 (M+H).

Intermediate 17

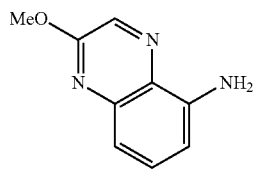 [SMILES: COc1cnc2c(N)cccc2n1]

Synthesis of 2-Methoxyquinoxalin-5-amine

To a suspension of 5-aminoquinoxalin-2(1H)-one (440 mg, 2.73 mmol) in methanol (1 mL), DCM (8 mL) and acetonitrile (8 mL), at 0° C., was added TEA (1.14 mL, 8.19 mmol), followed by (trimethylsilyl)diazomethane (2 mL, 4.10 mmol; 2.0M in hexanes). The reaction mixture was allowed to warm to RT and stirred for additional 3 hours. The suspension was filtered, and the filtrate was concentrated under reduced pressure. The crude product was purified by silica gel chromatography, eluting with 10%-50% ethyl acetate in hexane, to provide the title compound (167 mg, 0.953 mmol) as a light-yellow powder. LC/MS (ESI+) m/z=176 (M+H).

Intermediate 18

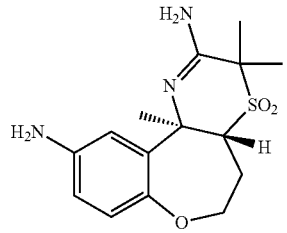 [SMILES: CC1(C)C(N)=N[C@]2(C)c3cc(N)ccc3OCC[C@H]2S1(=O)=O]

Synthesis of (4aR,11bR)-3,3,11b-trimethyl-4,4-dioxo-5,6-dihydro-4aH-[1]benzoxepino[4,5-b][1,4]thiazine-2,10-diamine A solution of tert-butyl ((4aR,11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (intermediate 19) (308 mg, 0.727 mmol) in DCM (5.5 ml) was treated with trifluoroacetic acid (2.70 ml, 36.4 mmol) for 15 min. The mixture was concentrated, redissolved in DCM, diluted with water and free-based with a saturated solution of NaHCO₃. The mixture was extracted with DCM, organic extract was washed with brine, filtered through pad of celite and concentrated to afford (4aR,11bR)-3,3,11b-trimethyl-4,4-dioxo-5,6-dihydro-4aH-[1]benzoxepino[4,5-b][1,4]thiazine-2,10-diamine (180 mg, 0.557 mmol, 77% yield) as an off-white solid. LC/MS (ESI⁺) m/z=324.2 (M+H).

Intermediate 19-Cis and 19-Trans

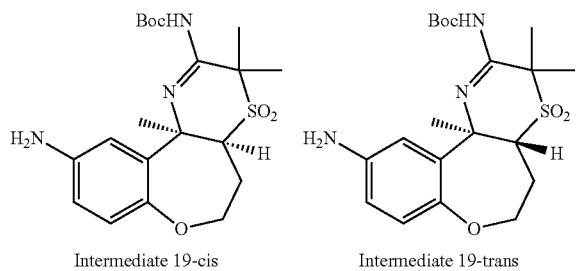 [SMILES: CC(C)(C)OC(=O)NC1=N[C@]2(C)c3cc(N)ccc3OCC[C@@H]2S(=O)(=O)C1(C)C ; CC(C)(C)OC(=O)NC1=N[C@]2(C)c3cc(N)ccc3OCC[C@H]2S(=O)(=O)C1(C)C]

Intermediate 19-cis      Intermediate 19-trans

The preparation of Intermediates 19-cis and 19-trans is detailed in Method 2. tert-butyl ((11bR)-3,3,11b-trimethyl-10-nitro-4,4-dioxido-4a,5,6,11b-tetrahydro-3H-benzo[6,7]oxepino[4,5-b][1,4]thiazin-2-yl)carbamate (Prepared in Step 3, Method 2) can be purified via silica gel chromatography, using a gradient of 0-50% EtOAc in heptane to provide the cis and trans diastereomers, which can be hydrogenated separately according to Step 4, Method 2, to provide Intermediate 19-cis and Intermediate 19-trans. LC/MS (ESI⁺) m/z=476.1 (M+Na) for both diastereomers.

Intermediate 20

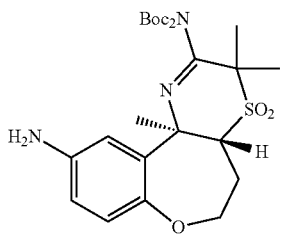

Synthesis of tert-butyl N-[(4aR,11bR)-10-amino-3,3,11b-trimethyl-4,4-dioxo-5,6-dihydro-4aH-[1]benzoxepino[4,5-b][1,4]thiazin-2-yl]-N-tert-butoxycarbonyl-carbamate Step 1: tert-utyl N-[(4aR,11bR)-3,3,11b-trimethyl-10-nitro-4,4-dioxo-5,6-dihydro-4aH-[1]-benzoxepino[4,5-b][1,4]thiazin-2-yl]-N-tert-butoxycarbonyl-carbamate To a 10-mL RBF was added tert-butyl ((4aR,11bR)-3,3,11b-trimethyl-10-nitro-4,4-dioxido-4a,5,6,11b-tetrahydro-3H-benzo[6,7]oxepino[4,5-b][1,4]thiazin-2-yl)carbamate (0.25 g, 0.55 mmol), di-tert-butyl dicarbonate (0.24 g, 1.10 mmol), triethylamine (0.23 mL, 1.66 mmol), DMAP (81 mg, 0.66 mmol) and DCM (3.0 ml). The resulting mixture was stirred at ambient temp for 2 h. The mixture was diluted with EtOAc and washed with brine. The organic portion was concentrated and purified in 10-50% EtOAc/heptanes (12 g column) to give tert-butyl N-[(4aR,11bR)-3,3,11b-trimethyl-10-nitro-4,4-dioxo-5,6-dihydro-4aH-[1]benzoxepino[4,5-b][1,4]thiazin-2-yl]-N-tert-butoxycarbonyl-carbamate (0.27 g, 88% yield) as a white solid. m/z (ESI) 576.0 (M+Na)⁺.

Step 2: tert-butyl N-[(4aR,11bR)-10-amino-3,3,11b-trimethyl-4,4-dioxo-5,6-dihydro-4aH-[1]benzoxepino[4,5-b][1,4]thiazin-2-yl]-N-tert-butoxycarbonyl-carbamate To an argon flushed flask was added tert-butyl N-[(4aR,11bR)-3,3,11b-trimethyl-10-nitro-4,4-dioxo-5,6-dihydro-4aH-[1]benzoxepino[4,5-b][1,4]thiazin-2-yl]-N-tert-butoxycarbonyl-carbamate (1.94 g, 3.50 mmol) and THF (35 ml), followed by a slurry of palladium on carbon (0.75 g, 0.70 mmol) in EtOAc (5 ml). The gas in flask was replaced with hydrogen balloon for three times. The mixture was stirred under an atmosphere of hydrogen at room temperature overnight. The mixture was filtered through celite plug and concentrated to give tert-butyl N-[(4aR,11bR)-10-amino-3,3,11b-trimethyl-4,4-dioxo-5,6-dihydro-4aH-[1]benzoxepino[4,5-b][1,4]thiazin-2-yl]-N-tert-butoxycarbonyl-carbamate (1.80 g, 98% yield) as an off-white solid. m/z (ESI) 524.2 (M+H)⁺.

Intermediate 21-Trans

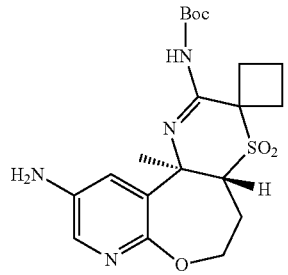 [SMILES: CC(C)(C)OC(=O)NC1=N[C@]2(C)c3cc(N)cnc3OCC[C@H]2S(=O)(=O)C12CCC2]

Synthesis of tert-butyl ((4a'R,11b'R)-10'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate Step 1: N—((R)-2-(5-bromo-2-fluoropyridin-3-yl)-1-((1-cyanocyclobutyl)sulfonyl)propan-2-yl)-2-methylpropane-2-sulfinamide A solution of 1-(methylsulfonyl)cyclobutanecarbonitrile (8 g, 50.4 mmol) in THF (50 mL) was brought to −78° C. followed by the dropwise addition of butyllithium solution, 2.5M in hexanes (20.17 mL, 50.4 mmol). The resulting mixture was stirred at this temperature for 20 min. A solution of (R,E)-N-(1-(5-bromo-2-fluoropyridin-3-yl)ethylidene)-2-methylpropane-2-sulfinamide (9.0 g, 28.02 mmol) in toluene (40 mL) at −78° C. was treated with trimethylaluminum solution, 2.0 M in toluene (14 ml, 28.02 mmol) for 10 min. This solution was added dropwise to the previous mixture containing the nitrile and the resulting mixture was stirred at −78° C. for 1 h. The mixture was quenched with saturated NH₄Cl and extracted with EtOAc. The combined organics were dried over Na₂SO₄, filtered, concentrated and chromatographed on silica gel using 0-100% EtOAc/hexanes to afford an off-white solid as N—((R)-2-(5-bromo-2-fluoropyridin-3-yl)-1-((1- cyanocyclobutyl)sulfonyl)propan-2-yl)-2-methylpropane-2-sulfinamide (7.07 g, 14.72 mmol, 59.1% yield). LC/MS (ESI$^+$) m/z=479.8 (M+H).

Step 2: (R)-9-amino-7-(5-bromo-2-fluoropyridin-3-yl)-7-methyl-5-thia-8-azaspiro[3.5]non-8-ene 5,5-dioxide To a solution of N—((R)-2-(5-bromo-2-fluoropyridin-3-yl)-1-((1-cyanocyclobutyl)sulfonyl)propan-2-yl)-2-methylpropane-2-sulfinamide (7.0 g, 14.57 mmol) in MeOH (10 mL) was added hydrogen chloride, 1 m in diethyl ether (58.3 ml, 58.3 mmol) and stirred at room temperature for 30 min until starting material was consumed. The mixture was concentrated, diluted with DCM and neutralized with 10% Na$_2$CO$_3$ and 1 N NaOH. The organic phase was dried over Na$_2$SO$_4$, filtered and concentrated to afford a pale yellow oil as (R)-1-((2-amino-2-(5-bromo-2-fluoropyridin-3-yl)propyl)sulfonyl)cyclobutanecarbonitrile. This product was dissolved in DCE (40 mL), placed in a water bath at room temperature and trimethylaluminum solution, 2.0M in toluene (11.66 ml, 23.31 mmol) was added dropwise. After the addition was completed, the water bath was removed and the resulting mixture was stirred at room temperature for 17 h. The mixture was cooled to 0° C. and 1N aqueous hydrochloric acid (43.7 ml, 43.7 mmol) was added dropwise via an addition funnel (slowly at first until vigorous reaction subsided) and stirred at room temperature. The aqueous solution was extracted with DCM. The pH of the aq. phase was adjusted to pH>10 with 10 N NaOH and extracted with DCM. The combined organic extracts were washed with brine, dried over Na$_2$SO$_4$, filtered, concentrated and chromatographed on silica gel using 0-100% EtOAc/hexanes to afford a light yellow solid as (R)-9-amino-7-(5-bromo-2-fluoropyridin-3-yl)-7-methyl-5-thia-8-azaspiro[3.5]non-8-ene 5,5-dioxide (3.9 g, 10.37 mmol, 71.1% yield). LC/MS (ESI$^+$) m/z=375.6 (M+H).

Step 3: (R)-tert-butyl (7-(5-bromo-2-fluoropyridin-3-yl)-7-methyl-5,5-dioxido-5-thia-8-azaspiro[3.5]non-8-en-9-yl)carbamate To a solution of (R)-9-amino-7-(5-bromo-2-fluoropyridin-3-yl)-7-methyl-5-thia-8-azaspiro[3.5]non-8-ene 5,5-dioxide (1.02 g, 2.71 mmol) in THF (20 mL) was added triethylamine (0.415 ml, 2.98 mmol) followed by di-tert-butyl dicarbonate (0.638 ml, 2.98 mmol). The resulting mixture was stirred at rt for 17 h. The mixture was diluted with EtOAc and washed with saturated NH$_4$Cl. The organic phase was dried over Na$_2$SO$_4$, filtered and concentrated to afford a light yellow oil as (R)-tert-butyl (7-(5-bromo-2-fluoropyridin-3-yl)-7-methyl-5,5-dioxido-5-thia-8-azaspiro[3.5]non-8-en-9-yl)carbamate (1.3 g, 2.73 mmol, 101% yield). LC/MS (ESI$^+$) m/z=497.8 (M+H).

Step 4: tert-butyl ((6R,7R)-6-allyl-7-(5-bromo-2-fluoropyridin-3-yl)-7-methyl-5,5-dioxido-5-thia-8-azaspiro[3.5]non-8-en-9-yl)carbamate and tert-butyl ((6S,7R)-6-allyl-7-(5-bromo-2-fluoropyridin-3-yl)-7-methyl-5,5-dioxido-5-thia-8-azaspiro[3.5]non-8-en-9-yl)carbamate A solution of (R)-tert-butyl (7-(5-bromo-2-fluoropyridin-3-yl)-7-methyl-5,5-dioxido-5-thia-8-azaspiro[3.5]non-8-en-9-yl)carbamate (5.0 g, 10.50 mmol) in THF (100 mL) was brought to −78° C. followed by the dropwise addition of potassium bis(trimethylsilyl)amide, 1 m in tetrahydrofuran (63.0 ml, 63.0 mmol). The resulting mixture was stirred at this temperature for 40 min then neat allyl bromide (2.72 ml, 31.5 mmol) was added dropwise. The mixture was kept at this temperature for 40 min. Then, it was quenched with saturated NH$_4$Cl at −78° C. and brought to rt, and extracted with EtOAc. The combined organics were washed with brine, dried over Na$_2$SO$_4$, filtered, concentrated and chromatographed on silica gel using 0-25% Et$_2$O/heptane to afford a white solid as tert-butyl ((6R,7R)-6-allyl-7-(5-bromo-2-fluoropyridin-3-yl)-7-methyl-5,5-dioxido-5-thia-8-azaspiro[3.5]non-8-en-9-yl)carbamate (2.02 g, 3.91 mmol, 37.3% yield). LC/MS (ESI$^+$) m/z=537.8 (M+H) and tert-butyl ((6S,7R)-6-allyl-7-(5-bromo-2-fluoropyridin-3-yl)-7-methyl-5,5-dioxido-5-thia-8-azaspiro[3.5]non-8-en-9-yl)carbamate (1.06 g, 2.053 mmol, 19.56% yield). LC/MS (ESI) m/z=537.8 (M+H).

Step 5: tert-butyl ((6R,7R)-7-(5-bromo-2-fluoropyridin-3-yl)-6-(2-hydroxyethyl)-7-methyl-5,5-dioxido-5-thia-8-azaspiro[3.5]non-8-en-9-yl)carbamate To a solution of tert-butyl ((6R,7R)-6-allyl-7-(5-bromo-2-fluoropyridin-3-yl)-7-methyl-5,5-dioxido-5-thia-8-azaspiro[3.5]non-8-en-9-yl)carbamate (2.0 g, 3.87 mmol) in DCM (40 mL) and MeOH (10 mL) was added sodium bicarbonate (0.651 g, 7.75 mmol) and the resulting mixture was brought to −78° C. To this mixture was bubbled O$_3$ for 15 min until the starting material was consumed. A stream of oxygen was passed through the solution for 5 min, then solid sodium borohydride (0.293 g, 7.75 mmol) was added to the mixture. The flask was removed from the bath and allowed to reach rt and stirred for 30 min. The mixture was carefully quenched with saturated NH$_4$Cl, water was added and extracted with DCM. The combined organics were dried over Na$_2$SO$_4$, filtered, and concentrated to afford a white solid as tert-butyl ((6R,7R)-7-(5-bromo-2-fluoropyridin-3-yl)-6-(2-hydroxyethyl)-7-methyl-5,5-dioxido-5-thia-8-azaspiro[3.5]non-8-en-9-yl)carbamate (2.035 g, 3.91 mmol, 101% yield). LC/MS (ESI$^+$) m/z=541.8 (M+H).

Step 6: tert-butyl ((4a'R,11b'R)-10'-bromo-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate A solution of tert-butyl ((6R,7R)-7-(5-bromo-2-fluoropyridin-3-yl)-6-(2-hydroxyethyl)-7-methyl-5,5-dioxido-5-thia-8-azaspiro[3.5]non-8-en-9-yl)carbamate (1.04 g, 1.998 mmol) in THF/DMF (20/2 mL) was brought to 0° C. followed by the addition of sodium hydride, 60% dispersion in mineral oil (0.200 g, 5.00 mmol) in one portion. After one min stirring at 0° C. the ice bath was removed. The reaction became yellow. More sodium hydride, 60% dispersion in mineral oil (0.200 g, 5.00 mmol) was added at rt and stirred for 20 min more. The reaction went to completion (3:1 mixture of epimers). The mixture was brought to 0° C. and carefully quenched with saturated NH$_4$Cl and water was added. The reaction mixture was extracted with EtOAc and the combined organics were dried over Na$_2$SO$_4$, filtered, concentrated and chromatographed on silica gel using 0-30% EtOAc/hexanes to afford each isomer as a white solid tert-butyl ((4a'S,11b'R)-10'-bromo-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate (0.46 g, 0.919 mmol, 46.0% yield). LC/MS (ESI$^+$) m/z=521.8 (M+H).

Step 7: 4a 11b'R)-2'-amino-10'-bromo-11b'-methyl-4a',5',6',11b'-tetrahydrospiro[cyclobutane-1,3'-pyrido[3',2':6,7]oxepino[4,5-b][1,4]thiazine]-4',4'-dioxide A flask was charged with tert-butyl ((4a'R,11b'R)-10'-bromo-11b'-methyl-4',4'-dioxido-4a',5',6',11b'-tetrahydrospiro[cyclobutane-1,3'-pyrido[3',2': 6,7]oxepino[4,5-b][1,4]thiazin]-2'-yl)carbamate (0.0306 g, 0.061 mmol) followed by the addition of TFA (1.0 ml, 13.46 mmol). The resulting mixture was stirred at rt for 15 min, quenched with water and the pH was brought to >10 using saturated NaHCO₃ and 1 N NaOH, and extracted with DCM. The combined organics were dried over Na₂SO₄, filtered and concentrated to afford a white solid as (4a'R,11b'R)-2'-amino-10'-bromo-11b'-methyl-4a',5',6',11b'-tetrahydrospiro[cyclobutane-1,3'-pyrido[3',2': 6,7]oxepino[4,5-b][1,4]thiazine]-4',4'-dioxide (0.0192 g, 0.048 mmol, 78% yield). LC/MS (ESI) m/z=399.8 (M+H).

Step 8: (4a'R,11b'R)-2',10'-diamino-11b'-methyl-4a',5',6',11b'-tetrahydrospiro[cyclobutane-1,3'-pyrido[3',2':6,7]oxepino[4,5-b][1,4]thiazine]-4',4'-dioxide A mixture of (4a'R,11b'R)-2'-amino-10'-bromo-11b'-methyl-4a',5',6',11b'-tetrahydrospiro[cyclobutane-1,3'-pyrido[3',2':6,7]oxepino[4,5-b][1,4]thiazine]-4',4'-dioxide (1.08 g, 2.70 mmol), (+)-sodium 1-ascorbate (0.053 g, 0.270 mmol), sodium azide (0.526 g, 8.09 mmol), and copper(i) iodide (0.103 g, 0.540 mmol) was purged with N₂ followed by the addition of (1r,2r)-(−)-n,n"-dimethylcyclohexane-1,2-diamine (0.128 ml, 0.809 mmol) and EtOH/water (2/0.5 mL). The resulting mixture was heated at 95° C. for 3 h. The mixture was brought to rt, poured into a 9:1 mixture of saturated NH₄Cl/NH₄OH and extracted with EtOAc. The combined organics were dried over Na₂SO₄, filtered and concentrated to afford (4a'R,11b'R)-2'-amino-10'-azido-11b'-methyl-4a',5',6',11b'-tetrahydrospiro[cyclobutane-1,3'-pyrido[3',2':6,7]oxepino[4,5-b][1,4]thiazine]-4',4'-dioxide to be used without further purification. This product was dissolved in THF (20 mL) and DMF (10 mL) followed by the addition of triethylamine (0.450 ml, 3.24 mmol) and di-tert-butyl dicarbonate (0.707 g, 3.24 mmol) and the resulting mixture was stirred at rt over the weekend. The mixture was poured into saturated NH₄Cl and extracted with EtOAc. The combined organics were dried over Na₂SO₄, filtered and concentrated to afford tert-butyl ((4a'R,11b'R)-10'-azido-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate as a yellow product. The yellow residue was poured into water (50 mL) and extracted again with EtOAc to remove DMF. The combined organics were dried over Na₂SO₄, filtered and concentrated. The yellow oil obtained was dissolved in THF/water (10/5 mL) followed by the addition of trimethyl phosphine (0.559 ml, 5.40 mmol) and the resulting mixture was stirred at rt for 1.5 h. Some starting material was still observed, so more trimethyl phosphine (0.559 ml, 5.40 mmol) was added and stirred for 1 h more. The reaction was poured into water and extracted with EtOAc. The combined organics were dried over Na₂SO₄, filtered, concentrated and chromatographed on silica gel using 0-100% EtOAc/hexanes to afford a pale yellow solid as tert-butyl ((4a'R,11b'R)-10'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate (0.300 g, 0.687 mmol, 25.5% yield). LC/MS (ESI⁺) m/z=437 (M+H).

Intermediate 21-Cis

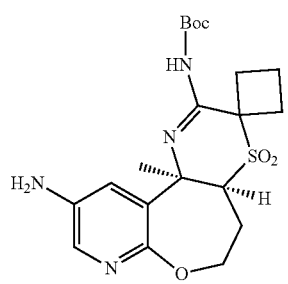 [SMILES: CC(C)(C)OC(=O)NC1=N[C@]2(C)c3cc(N)cnc3OCC[C@@H]2S(=O)(=O)C12CCC2]

Synthesis of tert-butyl ((4a'S,11b'R)-10'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate The same procedure was used as for Intermediate 21-trans except Steps 5-8 were performed using tert-butyl ((6S,7R)-7-(5-bromo-2-fluoropyridin-3-yl)-6-(2-hydroxyethyl)-7-methyl-5,5-dioxido-5-thia-8-azaspiro[3.5]non-8-en-9-yl) carbamate (isolated in Step 4). LC/MS (ESI⁺) m/z=437 (M+H).

Intermediate 22-Cis

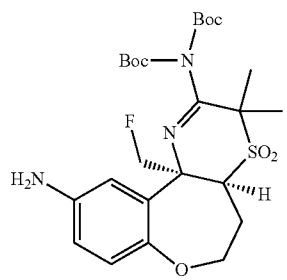 [SMILES: CC(C)(C)OC(=O)N(C(=O)OC(C)(C)C)C1=N[C@]2(CF)c3cc(N)ccc3OCC[C@@H]2S(=O)(=O)C1(C)C]

Synthesis of tert-butyl N-[(4aS,11bS)-11b-(fluoromethyl)-3,3-dimethyl-10-amino-4,4-dioxo-5,6-dihydro-4aH-[1]benzoxepino[4,5-b][1,4]thiazin-2-yl]-N-tert-butoxycarbonyl-carbamate Step 1:
1-(5-Bromo-2-fluorophenyl)-2-fluoroethanone A 2.0 M solution of LDA in heptane/THF/ethylbenzene (100 mL, 200 mmol) was added dropwise via syringe to a solution of 1-bromo-4-fluorobenzene (20 mL, 182 mmol) in THF (600 mL) at −78° C. After stirring for 2.5 hours at −78° C., ethyl monofluoroacetate (18.47 mL, 191 mmol) was added dropwise via syringe, and the reaction was stirred at −78° C. for 20 minutes and then stirred at −45° C. for 30 minutes before being quenched with saturated aqueous ammonium chloride at −45° C. The mixture was diluted with water and ethyl acetate. The layers were separated and the aqueous layer was extracted with ethyl acetate. The combined organic extracts were washed with saturated aqueous ammonium chloride, water, and saturated aqueous sodium chloride, dried over anhydrous magnesium sulfate, filtered, and concentrated. The crude product was dissolved in a minimal amount of methanol and placed in a −20° C. freezer overnight. The resulting solid was collected and washed with cold methanol to afford the title intermediate (12.07 g, 51.6 mmol, 28% yield) as a white solid.

Step 2: (R,Z)—N-(1-(5-Bromo-2-fluorophenyl)-2-fluoroethylidene)-2-methylpropane-2-sulfinamide Titanium (IV) ethoxide (4.05 mL, 19.6 mmol) was added via syringe to a solution of 1-(5-bromo-2-fluorophenyl)-2-fluoroethanone (2.3 g, 9.79 mmol) and (R)-(+)-2-methyl-2-propanesulfinamide (2.37 g, 19.57 mmol) in tetrahydrofuran (20 ml) at RT. The reaction was stirred for 18 hours and then the reaction was slowly poured into a vigorously stirred water/EtOAc mixture. After stirring 15 minutes, the mixture was filtered through a Celite pad, which was rinsed with ethyl acetate, and the phases were separated. The aqueous layer was extracted with ethyl acetate; the combined organic extracts were washed with brine, dried over anhydrous sodium sulfate, filtered and concentrated. The crude product was purified by silica-gel chromatography, eluting with 10% EtOAc in hexanes, to provide the title compound (2.81 g, 8.31 mmol, 85% yield) as a yellow oil. LC/MS (ESI$^+$) m/z=338, 340 (M+H; 2 bromine isotopes).

Step 3: (R)—N-(2-(5-Bromo-2-fluorophenyl)-1-((2-cyanopropan-2-yl)sulfonyl)-3-fluoropropan-2-yl)-2-methylpropane-2-sulfinamide To a solution of 2-methyl-2-(methylsulfonyl)propanenitrile (1.654 g, 11.24 mmol) in THF (14 mL) at −78° C. was added a 2.5 M solution of n-butyllithium in hexanes (4.49 mL, 11.24 mmol) dropwise via syringe. After 30 minutes at −78° C., a 0° C. solution of (R,Z)—N-(1-(5-bromo-2-fluorophenyl)-2-fluoroethylidene)-2-methylpropane-2-sulfinamide (1.9 g, 5.62 mmol) in THF (14.00 mL), which had been pretreated with boron trifluoride diethyl etherate (0.693 mL, 5.62 mmol) at 0° C. for 15 minutes, was added dropwise via cannula. The reaction was stirred for 2 hours at −78° C., and then quenched with saturated aqueous ammonium chloride at −78° C. and diluted with water and ethyl acetate. The layers were separated and the aqueous layer was extracted with EtOAc. The combined organic extracts were washed with water and saturated aqueous sodium chloride, and dried over sodium sulfate. The solution was filtered, concentrated, and purified by silica-gel chromatography, eluting with 25% ethyl acetate in hexanes followed by 40% ethyl acetate hexane to provide the title compound. The product was isolated as a 2:1 mixture of diastereomers. LC/MS (ESI$^+$) m/z=485, 487 (M+H; 2 bromine isotopes).

Step 4: 5-amino-3-(5-bromo-2-fluorophenyl)-3-(fluoromethyl)-6,6-dimethyl-3,6-dihydro-2H-thiopyran 1,1-dioxide To a solution of N-(2-(5-bromo-2-fluorophenyl)-1-((2-cyanopropan-2-yl)sulfonyl)-3-fluoropropan-2-yl)-2-methylpropane-2-sulfinamide (45 g, 93 mmol) in dioxane (800 mL) was added hydrochloric acid, 4.0M solution in 1,4-dioxane (107 mL, 428 mmol). The reaction mixture was heated to 100° C. for 2 d. The reaction was allowed to cool to RT, concentrated, and dried under high vacuum to give a light brown solid. The solids were triturated in DCM, filtered, rinsed, and dried to give a white solid. The compound was separated into its enantiomers via prep-scale supercritical fluid chromatography using a Chiralpak AD-H column with an isocratic 75% carbon dioxide/25% methanol with 0.2% ammonia solvent system to yield (R)-5-amino-3-(5-bromo-2-fluorophenyl)-3-(fluoromethyl)-6,6-dimethyl-3,6-dihydro-2H-1,4-thiazine 1,1-dioxide (41.4 g, 109 mmol, 78% yield) and (S)-5-amino-3-(5-bromo-2-fluorophenyl)-3-(fluoromethyl)-6,6-dimethyl-3,6-dihydro-2H-1,4-thiazine 1,1-dioxide (38.6 g, 101 mmol, 73%) LC/MS (ESI$^+$) m/z=380.9; 382.9 for both diastereomers. (M+H; 2 bromine isotopes).

Step 5: (S)-5-amino-3-(fluoromethyl)-3-(2-fluorophenyl)-6,6-dimethyl-3,6-dihydro-2H-1,4-thiazine 1,1-dioxide To a solution of (S)-5-amino-3-(5-bromo-2-fluorophenyl)-3-(fluoromethyl)-6,6-dimethyl-3,6-dihydro-2H-1,4-thiazine 1,1-dioxide (3.22 g, 8.44 mmol) in ethanol (15 mL) and ethyl acetate (5 mL) was added sodium bicarbonate (138 mg, 1.69 mmol) and 10 wt % palladium on carbon (0.90 g, 8.44 mmol). The flask was evacuated and backfilled with hydrogen three times, and stirred at room temperature under a hydrogen atmosphere for 2 hours. The reaction mixture was filtered through a Celite pad, and the filter cake was rinsed with ethyl acetate and ethanol. The combined filtrates were concentrated in vacuo and the residue was redissolved in ethyl acetate, washed with saturated aqueous sodium bicarbonate, dried over sodium sulfate, filtered and evaporated to provide the title compound (2.49 g, 8.23 mmol) as an off-white solid. LC/MS (ESI$^+$) m/z=303 (M+H).

Step 6: (S)-5-amino-3-(2-fluoro-5-nitrophenyl)-3-(fluoromethyl)-6,6-dimethyl-3,6-dihydro-2H-1,4-thiazine 1,1-dioxide To a solution of (S)-5-amino-3-(fluoromethyl)-3-(2-fluorophenyl)-6,6-dimethyl-3,6-dihydro-2H-1,4-thiazine 1,1-dioxide (1.98 g, 6.55 mmol) in sulfuric acid (8.73 mL, 0.16 mol) at 0° C. was added potassium nitrate (0.69 g, 6.88 mmol) portion wise. When the addition was completed, the reaction mixture was allowed to warm to room temperature and the mixture was stirred at room temperature for 30 min. The reaction mixture was carefully poured over ice-water (100 mL) and neutralized by the addition of aqueous ammonium hydroxide. The mixture was diluted with water (10 mL) and extracted with ethyl acetate (2×50 mL). The combined organic extracts were washed with brine, dried over sodium sulfate, filtered, and concentrated under vacuum to give the title compound (2.27 g, 6.64 mmol) as an off-white solid. $^1$H NMR (400 MHz, DMSO-d$_6$) δ 8.43 (dd, J=3.03, 6.75 Hz, 1H), 8.25 (td, J=3.55, 8.95 Hz, 1H), 7.51 (dd, J=9.00, 11.35 Hz, 1H), 6.58 (br. s., 2H), 4.59 (q, J=8.80 Hz, 1H), 4.48 (q, J=8.80 Hz, 1H), 3.68-3.87 (m, 2H), 1.61 (s, 3H), 1.47 (s, 3H). LC/MS (ESI$^+$) m/z=348 (M+H).

Step 7: tert-butyl N-tert-butoxycarbonyl-N-[(3S)-3-(fluoromethyl)-3-(2-fluoro-5-nitro-phenyl)-6,6-dimethyl-1,1-dioxo-2H-1,4-thiazin-5-yl]carbamate To a solution of (S)-5-amino-3-(2-fluoro-5-nitrophenyl)-3-(fluoromethyl)-6,6-dimethyl-3,6-dihydro-2H-1,4-thiazine 1,1-dioxide (710 mg, 2.04 mmol) in THF (10 mL) was added triethyl amine (0.72 mL, 5.11 mmol) followed by di-tert-butyl dicarbonate (981 mg, 4.50 mmol). The reaction mixture was stirred at RT for 18 h and diluted with EtOAc and water.

The aqueous phase was extracted with EtOAc (2×). The combined organic extracts were washed with brine (1×), dried over Na$_2$SO$_4$, filtered, concentrated in vacuo to give tert-butyl N-tert-butoxycarbonyl-N-[(3S)-3-(fluoromethyl)-3-(2-fluoro-5-nitro-phenyl)-6,6-dimethyl-1,1-dioxo-2H-1,4-thiazin-5-yl]carbamate (922 mg, 82%) as an off-white solid which was taken to next step without further purification. LC/MS (ESI$^+$) m/z=570 (M+Na).

Step 8: tert-butyl N-[(3S)-2-allyl-3-(fluoromethyl)-3-(2-fluoro-5-nitro-phenyl)-6,6-dimethyl-1,1-dioxo-2H-1,4-thiazin-5-yl]-N-tert-butoxycarbonyl-carbamate To a solution of tert-butyl N-tert-butoxycarbonyl-N-[(3S)-3-(fluoromethyl)-3-(2-fluoro-5-nitro-phenyl)-6,6-dimethyl-1,1-dioxo-2H-1,4-thiazin-5-yl]carbamate (2.79 g, 5.10 mmol) in THF (30 mL) at −78° C. under a nitrogen atmosphere was added lithium bis(trimethylsilyl)amide, (7.65 mL, 7.65 mmol, 1M in THF) dropwise. The reaction mixture was stirred at −78° C. for 1 h and then allyl bromide (1.77 mL, 20.41 mmol) was added dropwise. The reaction mixture was stirred at −78° C. for 2 h and quenched by the addition of satd. aqueous NH$_4$Cl at −78° C., then allowed to warm to RT and extracted with EtOAc. The organic extracts were washed with brine, dried over Na$_2$SO$_4$, filtered and concentrated in vacuo. The crude mixture was purified by silica gel chromatography on a 80 g RediSep Gold column using a 0-30% EtOAc/hexanes gradient to afford tert-butyl N-[(3S)-2-allyl-3-(fluoromethyl)-3-(2-fluoro-5-nitro-phenyl)-6,6-dimethyl-1,1-dioxo-2H-1,4-thiazin-5-yl]-N-tert-butoxycarbonyl-carbamate (2.0 g, 67%) as an off-white solid and a mixture of cis and trans (2:1) isomers. LC/MS (ESI$^+$) m/z=610 (M+Na).

Step 9: tert-butyl N-tert-butoxycarbonyl-N-[(3S)-3-(fluoromethyl)-3-(2-fluoro-5-nitro-phenyl)-2-(3-hydroxypropyl)-6,6-dimethyl-1,1-dioxo-2H-1,4-thiazin-5-yl]carbamate To a solution of tert-butyl N-[(3S)-2-allyl-3-(fluoromethyl)-3-(2-fluoro-5-nitro-phenyl)-6,6-dimethyl-1,1-dioxo-2H-1,4-thiazin-5-yl]-N-tert-butoxycarbonyl-carbamate (1.95 g, 3.33 mmol) in DCM (60 mL) and MeOH (20 mL) was added sodium bicarbonate (0.56 g, 6.65 mmol). The reaction mixture was cooled to −78° C. and ozonolized for about 15 min or until analysis showed no starting material present. A stream of oxygen was passed through the solution for 5 min, and then solid sodium borohydride (252 mg, 6.65 mmol) was added to the mixture. The flask was removed from the bath and allowed to reach RT and stirred for 1 h. The reaction was quenched with satd. aqueous NH$_4$Cl, diluted with water to dissolve solids, and extracted with EtOAc. The organic layer was washed with brine, dried over Na$_2$SO$_4$, filtered, and concentrated in vacuo to give tert-butyl N-tert-butoxycarbonyl-N-[(3S)-3-(fluoromethyl)-3-(2-fluoro-5-nitro-phenyl)-2-(3-hydroxypropyl)-6,6-dimethyl-1,1-dioxo-2H-1,4-thiazin-5-yl]carbamate which was taken to next step without further purification. LC/MS (ESI$^+$) m/z=614 (M+Na).

Step 10: tert-butyl N-[(4aS,11bS)-11b-(fluoromethyl)-3,3-dimethyl-10-nitro-4,4-dioxo-5,6-dihydro-4aH-[1]benzoxepino[4,5-b][1,4]thiazin-2-yl]-N-tert-butoxycarbonyl-carbamate To a solution of tert-butyl N-tert-butoxycarbonyl-N-[(3S)-3-(fluoromethyl)-3-(2-fluoro-5-nitro-phenyl)-2-(3-hydroxypropyl)-6,6-dimethyl-1,1-dioxo-2H-1,4-thiazin-5-yl]carbamate (1.95 g, 3.30 mmol) in THF:DMF (10:1, 44 mL) at 0° C. was added NaH (264 mg, 6.60 mmol, 60% suspension in mineral oil) portion wise. The reaction mixture was stirred at RT for 1 h and an additional amount of NaH was added (264 mg, 6.60 mmol, 60% suspension in mineral oil). The reaction mixture was stirred at RT for 1 h, quenched with satd. aqueous NH$_4$Cl, and diluted with EtOAc. Water was added to dissolve solids, and the organic layer was separated. The organic extracts were washed with brine, dried over Na$_2$SO$_4$, filtered, and concentrated in vacuo. The crude mixture was purified by silica gel chromatography using a 0-25% EtOAc/hexanes gradient to afford the less polar cis-isomer, tert-butyl N-[(4aS,11bS)-11b-(fluoromethyl)-3,3-dimethyl-10-nitro-4,4-dioxo-5,6-dihydro-4aH-[1]benzoxepino[4,5-b][1,4]thiazin-2-yl]-N-tert-butoxycarbonyl-carbamate (647 mg, 34%) as a white solid, LC/MS (ESI$^+$) m/z=594 (M+Na), and the more polar trans-isomer, tert-butyl N-[(4aS,11bS)-11b-(fluoromethyl)-3,3-dimethyl-10-nitro-4,4-dioxo-5,6-dihydro-4aH-[1]benzoxepino[4,5-b][1,4]thiazin-2-yl]-N-tert-butoxycarbonyl-carbamate (594 mg, 31%) as a white solid. LC/MS (ESI$^+$) m/z=594 (M+Na).

Step 11: tert-butyl N-[(4aS,11bS)-11b-(fluoromethyl)-3,3-dimethyl-10-amino-4,4-dioxo-5,6-dihydro-4aH-[1]benzoxepino[4,5-b][1,4]thiazin-2-yl]-N-tert-butoxycarbonyl-carbamate A solution of tert-butyl N-[(4aS,11bS)-11b-(fluoromethyl)-3,3-dimethyl-10-nitro-4,4-dioxo-5,6-dihydro-4aH-[1]benzoxepino[4,5-b][1,4]thiazin-2-yl]-N-tert-butoxycarbonyl-carbamate (647 mg, 1.13 mmol) in EtOAc (15 mL) and EtOH (5 mL) was hydrogenated at 1 atm. in the presence of palladium (10% wt. on activated carbon) (120 mg, 1.13 mmol) for 5 h at RT. The mixture was filtered through the pad of celite and washed 3 times with EtOAc. The filtrate was concentrated in vacuo to give tert-butyl N-[(4aS,11bS)-11b-(fluoromethyl)-3,3-dimethyl-10-amino-4,4-dioxo-5,6-dihydro-4aH-[1]benzoxepino[4,5-b][1,4]thiazin-2-yl]-N-tert-butoxycarbonyl-carbamate (613 mg, 100%) as a white solid. LC/MS (ESI$^+$) m/z=564 (M+Na).

Intermediate 22-Trans

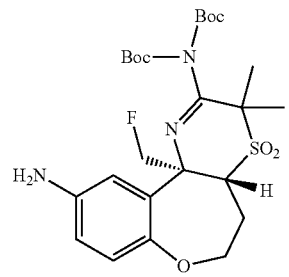 [SMILES: CC(C)(C)OC(=O)N(C(=O)OC(C)(C)C)C1=N[C@]2(CF)c3cc(N)ccc3OCC[C@H]2S(=O)(=O)C1(C)C]

Synthesis of tert-butyl N-[(4aR,11bS)-10-amino-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate In a reduction step analogous to step 11 above, tert-butyl N-[(4aR,11bS)-11b-(fluoromethyl)-3,3-dimethyl-10-nitro-4,4-dioxo-5,6-dihydro-4aH-[1]benzoxepino[4,5-b][1,4]thiazin-2-yl]-N-tert-butoxycarbonyl-carbamate (Isolated in Step 10) was converted to tert-butyl N-[(4aR,11bS)-10-amino-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate (564 mg, 100%) white solid. LC/MS (ESI+) m/z=564 (M+Na).

Intermediate 23-Trans

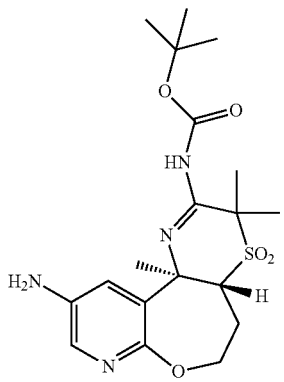 [SMILES: CC(C)(C)OC(=O)NC1=N[C@]2(C)c3cc(N)cnc3OCC[C@H]2S(=O)(=O)C1(C)C]

Synthesis of tert-butyl ((4aR,11bR)-10-amino-3,3,11b-trimethyl-4,4-dioxido-4a,5,6,11b-tetrahydro-3H-pyrido[3',2':6,7]oxepino[4,5-b][1,4]thiazin-2-yl)carbamate Step 1: 1-(5-bromo-2-fluoropyridin-3-yl)ethanol To a solution of 5-bromo-2-fluoronicotinaldehyde (10 g, 49 mmol) in THF (100 mL) at −78° C. was added dropwise methylmagnesium bromide (3.0 M solution in diethyl ether, 24.5 mL, 73.5 mmol). After the addition, the reaction was warmed to room temperature and stirred for 17 h. The mixture was carefully quenched with saturated ammonium chloride and extracted with EtOAc. The combined organic extracts were washed with brine, dried over $Na_2SO_4$, filtered, and concentrated. Purification by flash column chromatography on silica gel (eluted with 0-10% EtOAc/hexanes) gave 1-(5-bromo-2-fluoropyridin-3-yl)ethanol (10.8 g, 49.1 mmol, 100% yield) as a yellow oil. LC/MS (ESI+) m/z=220 (M+H).

Step 2: 1-(5-bromo-2-fluoropyridin-3-yl)ethanone

A solution of pyridinium dichromate (55.4 g, 147 mmol) in DCM (100 mL) was brought to 0° C. and a solution of 1-(5-bromo-2-fluoropyridin-3-yl)ethanol (10.8 g, 49.1 mmol) in DCM (30 mL) was added. The reaction was allowed to warmed to room temperature and stirred for 48 h. The mixture was filtered through Celite, washed with DCM and concentrated to afford 1-(5-bromo-2-fluoropyridin-3-yl)ethanone (11 g, 51 mmol, 100% yield) as a light yellow solid. LC/MS (ESI+) m/z=218 (M+H).

Step 3: (R,Z)—N-(1-(5-bromo-2-fluoropyridin-3-yl)ethylidene)-2-methylpropane-2-sulfinamide A mixture of 1-(5-bromo-2-fluoropyridin-3-yl)ethanone (11 g, 51 mmol), (R)-2-methylpropane-2-sulfinamide (12.2 g, 101 mmol) and titanium (IV) ethoxide (26.1 mL, 126 mmol) in THF (100 mL) was heated to reflux for 2 h. The mixture was cooled to room temperature, brine was added and the mixture was stirred for 10 min. The suspension was filtered through silica gel. The organic phase was separated and the aqueous phase was extracted with EtOAc. The combined organic extracts were washed with brine, dried over $Na_2SO_4$, filtered, and concentrated. Purification by flash column chromatography on silica gel (eluted with 0-20% EtOAc/hexanes) gave (R,Z)—N-(1-(5-bromo-2-fluoropyridin-3-yl)ethylidene)-2-methylpropane-2-sulfinamide (16 g, 50 mmol, 99% yield) as a bright yellow oil. LC/MS (ESI) m/z=321 (M+H).

Step 4: N—((R)-2-(5-bromo-2-fluoropyridin-3-yl)-1-((2-cyanopropan-2-yl)sulfonyl)propan-2-yl)-2-methylpropane-2-sulfinamide A solution of 2-methyl-2-(methylsulfonyl)propanenitrile (2.74 g, 18.61 mmol) in THF (50 mL) was cooled to −78° C. and n-butyllithium (1.6 M in hexanes, 11.63 mL, 18.61 mmol) was added dropwise. The resulting mixture was stirred at this temperature for 20 min. In a separate flask, a solution of (R,Z)—N-(1-(5-bromo-2-fluoropyridin-3-yl)ethylidene)-2-methylpropane-2-sulfinamide (4.27 g, 13.3 mmol) in toluene (50 mL) at −78° C. was treated with trimethylaluminum (2 M in toluene, 6.65 mL, 13.3 mmol) for 10 min. This solution was added dropwise to the previous solution and the resulting mixture was stirred at −78° C. for 3 h. The reaction was quenched with saturated $NH_4Cl$ and extracted with EtOAc. The combined organic extracts were dried over $Na_2SO_4$, filtered, and concentrated. Purification by flash column chromatography on silica gel (eluted with 0-100% EtOAc/hexanes) gave N#R)-2-(5-bromo-2-fluoropyridin-3-yl)-1-((2-cyanopropan-2-yl)sulfonyl)propan-2-yl)-2-methylpropane-2-sulfinamide (1.63 g, 3.48 mmol, 26% yield) as a pale yellow oil. LC/MS (ESI) m/z=468 (M+H).

Step 5: (R)-5-amino-3-(5-bromo-2-fluoropyridin-3-yl)-3,6,6-trimethyl-3,6,-dihydro-2H-1,4-thiazine 1,1-dioxide To a solution of N#R)-2-(5-bromo-2-fluoropyridin-3-yl)-1-((2-cyanopropan-2-yl)sulfonyl)propan-2-yl)-2-methylpropane-2-sulfinamide (1.63 g, 3.48 mmol) in methanol (25 mL) was added hydrogen chloride (4.0 M in 1,4-dioxane, 4.35 mL, 17.4 mmol) and stirred at room temperature for 40 min until the starting material was consumed. The mixture was concentrated, diluted with DCM, and neutralized with 10% aqueous $Na_2CO_3$ and 1 M NaOH. The organic phase was dried over $Na_2SO_4$, filtered, and concentrated to afford (R)-2-((2-amino-2-(5-bromo-2-fluoropyridin-3-yl)propyl)sulfonyl)-2-methylpropanenitrile as a pale yellow oil. The (R)-2-((2-amino-2-(5-bromo-2-fluoropyridin-3-yl)propyl)sulfonyl)-2-methylpropanenitrile was dissolved in 1,2-dichloroethane (100 mL) and trimethylaluminum (2 M in toluene, 2.78 mL, 5.57 mmol) was added dropwise. The resulting mixture was stirred at room temperature for 17 h. The mixture was cooled to 0° C. and hydrochloric acid (1 M, 17.40 mL, 17.40 mmol) was added dropwise via an addition funnel (slowly at first until the vigorous reaction subsided) and stirred at room temperature. The aqueous solution was extracted with DCM. The pH of the aqueous phase was adjusted to pH>10 with 10 M NaOH and extracted with DCM. The combined organic extracts were washed with brine, dried over $Na_2SO_4$, filtered, and concentrated. Purification by flash column chromatography on silica gel (eluted with 0-100% EtOAc/hexanes) gave (R)-5-amino-3-(5-bromo-2-fluoropyridin-3-yl)-3,6,6-trimethyl-3,6-dihydro- 2H-1,4-thiazine 1,1-dioxide (1.0 g, 2.8 mmol, 79% yield) as a light yellow solid. LC/MS (ESI) m/z=364 (M+H).

Step 6: (R)-tert-butyl (5-(5-bromo-2-fluoropyridin-3-yl)-2,2,5-trimethyl-1,1-dioxido-5,6-dihydro-2H-1,4-thiazin-3-yl)carbamate To a solution of (R)-5-amino-3-(5-bromo-2-fluoropyridin-3-yl)-3,6,6-trimethyl-3,6-dihydro-2H-1,4-thiazine 1,1-dioxide (3.91 g, 10.7 mmol) in dioxane (50 mL) at room temperature was added saturated aqueous NaHCO$_3$ (50 mL) and di-tert-butyldicarbonate (2.83 g, 13.0 mmol). The reaction mixture was stirred at room temperature for 22 h and diluted with EtOAc and water. The aqueous phase was extracted with EtOAc (2×). The combined organic extracts were washed with brine (1×), dried over MgSO$_4$, filtered, concentrated. Purification by flash column chromatography on silica gel (80 g, 20% EtOAc in hexanes) gave (R)-tert-butyl (5-(5-bromo-2-fluoropyridin-3-yl)-2,2,5-trimethyl-1,1-dioxido-5,6-dihydro-2H-1,4-thiazin-3-yl)carbamate (4.92 g, 10.6 mmol, 99% yield) as a white solid. LC/MS (ESI$^+$) m/z=464 (M+H).

Step 7: tert-butyl ((5R,6R)-6-allyl-5-(5-bromo-2-fluoropyridin-3-yl)-2,2,5-trimethyl-1,1-dioxido-5,6-dihydro-2H-1,4-thiazin-3-yl)carbamate and tert-butyl ((5R,6S)-6-allyl-5-(5-bromo-2-fluoropyridin-3-yl)-2,2,5-trimethyl-1,1-dioxido-5,6-dihydro-2H-1,4-thiazin-3-yl)carbamate To a solution of (R)-tert-butyl (5-(5-bromo-2-fluoropyridin-3-yl)-2,2,5-trimethyl-1,1-dioxido-5,6-dihydro-2H-1,4-thiazin-3-yl)carbamate (1.02 g, 2.197 mmol) in THF (13 mL) at −78° C. was added potassium bis(trimethylsilyl)amide (1 M in THF, 13.2 mL, 13.2 mmol) dropwise. The solution was stirred at −78° C. for 30 min and allyl bromide (0.570 mL, 6.59 mmol) was added. The reaction mixture was stirred at −78° C. for 70 min, quenched with saturated NH$_4$Cl, warmed to room temperature and diluted with EtOAc and water. The aqueous phase was extracted with EtOAc (2×). The combined organic extracts were washed with brine (1×), dried over MgSO$_4$, filtered, concentrated. Purification by flash column chromatography on silica gel (40 g, 10% to 40% EtOAc in hexanes) gave tert-butyl ((5R,6R)-6-allyl-5-(5-bromo-2-fluoropyridin-3-yl)-2,2,5-trimethyl-1,1-dioxido-5,6-dihydro-2H-1,4-thiazin-3-yl)carbamate (0.703 g, 1.39 mmol, 63% yield) as a white solid, LC/MS (ESI$^+$) m/z=504 (M+H); and tert-butyl ((5R,6S)-6-allyl-5-(5-bromo-2-fluoropyridin-3-yl)-2,2,5-trimethyl-1,1-dioxido-5,6-dihydro-2H-1,4-thiazin-3-yl)carbamate (0.280 g, 0.555 mmol, 25% yield) as white solid, LC/MS (ESI$^+$) m/z=504 (M+H). The two products were recombined and used in the next step.

Step 8: tert-butyl ((5R)-5-(5-bromo-2-fluoropyridin-3-yl)-6-(2-hydroxyethyl)-2,2,5-trimethyl-1,1-dioxido-5,6-dihydro-2H-1,4-thiazin-3-yl)carbamate To a solution of tert-butyl ((5R)-6-allyl-5-(5-bromo-2-fluoropyridin-3-yl)-2,2,5-trimethyl-1,1-dioxido-5,6-dihydro-2H-1,4-thiazin-3-yl)carbamate (0.988 g, 1.96 mmol) in MeOH (5 mL) and DCM (15 mL) at room temperature was added sodium bicarbonate (0.333 g, 3.96 mmol). The reaction mixture was cooled to −78° C. and ozone was bubbled through the solution. After 15 min, the solution turned blue and oxygen was bubbled through the mixture for 5 min. Sodium borohydride (0.154 g, 4.07 mmol) was added and the reaction mixture was removed from the −78° C. bath. The solution was warmed to room temperature, stirred for 1 h, and quenched with saturated NH$_4$Cl, and diluted with EtOAc water. The aqueous phase was extracted with EtOAc (2×). The combined organic extracts were washed with brine (1×), dried over MgSO$_4$, filtered, concentrated. Purification by flash column chromatography on silica gel (40 g, 20% to 60% EtOAc in hexanes) gave tert-butyl ((5R)-5-(5-bromo-2-fluoropyridin-3-yl)-6-(2-hydroxyethyl)-2,2,5-trimethyl-1,1-dioxido-5,6-dihydro-2H-1,4-thiazin-3-yl)carbamate (0.913 g, 1.80 mmol, 92% yield) as a mixture of isomers that was used in the next step without separation. LC/MS (ESI$^+$) m/z=508 (M+H).

Step 9: tert-butyl ((4aR,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate and tert-butyl ((4aS,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate To a solution of tert-butyl 45R)-5-(5-bromo-2-fluoropyridin-3-yl)-6-(2-hydroxyethyl)-2,2,5-trimethyl-1,1-dioxido-5,6-dihydro-2H-1,4-thiazin-3-yl)carbamate (3.65 g, 7.18 mmol) in THF (70 mL) and DMF (7 mL) at 0° C. was added sodium hydride (60% weight dispersion in mineral oil, 0.729 g, 18.2 mmol). The reaction mixture was warmed to room temperature and stirred for 25 min. The reaction was quenched with saturated NH$_4$Cl and diluted with EtOAc and water. The aqueous phase was extracted with EtOAc (2×). The combined organic extracts were washed with brine (1×), dried over MgSO$_4$, filtered, and concentrated. Purification by flash column chromatography on silica gel (120 g, 20% to 70% EtOAc in hexanes) gave tert-butyl ((4aR,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate (2.66 g, 5.45 mmol, 76% yield) as a white solid, LC/MS (ESI$^+$) m/z=488 (M+H); and tert-butyl ((4aS,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate (0.686 g, 1.41 mmol, 20% yield) as a white solid. LC/MS (ESI$^+$) m/z=488 (M+H).

Step 10: tert-butyl 44aR,11bR)-10-amino-3,3,11b-trimethyl-4,4-dioxido-4a,5,6,11b-tetrahydro-3H-pyrido[3',2':6,7]oxepino[4,5-b][1,4]thiazin-2-yl)carbamate To a mixture of tert-butyl 44aR,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate (0.615 g, 1.26 mmol), sodium azide (0.247 g, 3.80 mmol) and sodium (R)-2-((S)-1,2-dihydroxyethyl)-4-hydroxy-5-oxo-2,5-dihydrofuran-3-olate (0.032 g, 0.16 mmol) was added EtOH (2 mL) and water (1.2 mL). The mixture was degassed by bubbling argon through the solution and copper(I) iodide (0.053 g, 0.28 mmol) and (1R,2R)-(−)-N,N"-dimethylcyclohexane-1,2-diamine (0.060 mL, 0.38 mmol) were added. The reaction mixture was heated to 70° C. After 30 min, the temperature was lowered to 60° C. After 5 h, the reaction mixture was cooled to room temperature and additional sodium (R)-2-((S)-1,2-dihydroxyethyl)-4-hydroxy-5-oxo-2,5-dihydrofuran-3-olate (35 mg, 0.18 mmol), copper(I) iodide (51 mg, 0.27 mmol), sodium azide (280 mg, 4.3 mmol), and trans-N,N"-dimethylcyclohexane-1,2-diamine (0.060 mL, 0.38 mmol) were added. The reaction mixture was heated to 70° C. for 30 min and cooled to room temperature. The reaction was poured into a 9:1 mixture of aqueous saturated ammonium chloride/ammonium hydroxide and diluted with EtOAc. The layers were separated and the aqueous layer was extracted with EtOAc (3×). The combined organic extracts were washed with brine (1×), dried over MgSO₄, filtered, and concentrated to give a yellow solid. Purification by flash column chromatography on silica gel (24 g, 50% to 100% EtOAc in hexanes) gave tert-butyl ((4aR,11bR)-10-amino-3,3,11b-trimethyl-4,4-dioxido-4a,5,6,11b-tetrahydro-3H-pyrido[3',2':6,7]oxepino[4,5-b][1,4]thiazin-2-yl)carbamate (0.290 g, 0.683 mmol, 54% yield) as a white solid. LC/MS (ESI⁺) m/z=425 (M+H).

Intermediate 23-Cis

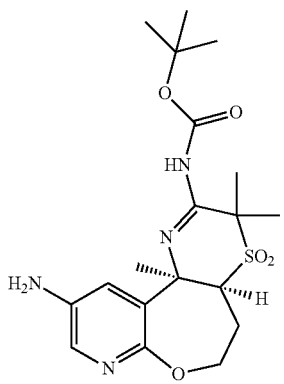 [SMILES: CC(C)(C)OC(=O)NC1=N[C@]2(C)c3cc(N)cnc3OCC[C@@H]2S(=O)(=O)C1(C)C]

Synthesis of tert-butyl ((4aS,11bR)-10-amino-3,3,11b-trimethyl-4,4-dioxido-4a,5,6,11b-tetrahydro-3H-pyrido[3',2':6,7]oxepino[4,5-b][1,4]thiazin-2-yl)carbamate The titled compound was prepared in a manner analogous to that of intermediate 23-trans, but using tert-butyl ((4aS,11bR)-10-bromo-3,3,11b-trimethyl-4,4-dioxido-4a,5,6,11b-tetrahydro-3H-pyrido[3',2':6,7]oxepino[4,5-b][1,4]thiazin-2-yl)carbamate (the minor cis-bromo-isomer, 0.81 g, 1.658 mmol, from Step 9 in the synthesis of intermediate 23-trans). The crude product (0.290, 41%) was used directly for the next reaction without further purification. LC/MS (ESI⁺) m/z=425 (M+H).

Intermediate 24 (Cis)

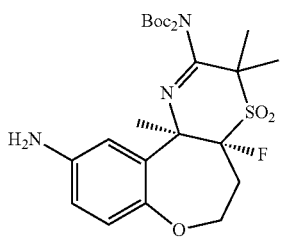

Synthesis of tert-butyl N-[(4aS,11bR)-10-amino-4a-fluoro-3,3,11b-trimethyl-4,4-dioxo-5,6-dihydro-[1]-benzoxepino[4,5-b][1,4]thiazin-2-yl]-N-tert-butoxycarbonyl-carbamate Step 1: Tert-butyl N-[(4aS,11bR)-3,3,11b-trimethyl-10-nitro-4,4-dioxo-5,6-dihydro-4aH-[1]-benzoxepino[4,5-b][1,4]thiazin-2-yl]-N-tert-butoxycarbonyl-carbamate To a solution of tert-butyl N-[(4aS,11bR)-3,3,11b-trimethyl-10-nitro-4,4-dioxo-5,6-dihydro-4aH-[1]benzoxepino[4,5-b][1,4]thiazin-2-yl]carbamate (130 mg, 0.287 mmol) (Prepared in Method 2) in dichloromethane (1.4 mL) was added di-tert-butyl dicarbonate (94 mg, 0.430 mmol), triethylamine (59.8 µl, 0.430 mmol), and DMAP (35.0 mg, 0.287 mmol). The reaction was stirred at ambient temperature for 2 hours. The reaction mixture was partitioned between water and ethyl acetate and the organic layer was concentrated. The crude residue was purified by column chromatography, eluting with 10-50% ethyl acetate/heptane to give the title compound (82 mg, 0.148 mmol, 52% yield) as a white foam. MS m/z=576.2 (M+Na).

Step 2: Tert-butyl N-[(4aS,11bR)-4a-fluoro-3,3,11b-trimethyl-10-nitro-4,4-dioxo-5,6-dihydro-[1]benzoxepino[4,5b][1,4]thiazin-2-yl]-N-tert-butoxycarbonyl-carbamate A solution of tert-butyl N-[(4aS,11bR)-3,3,11b-trimethyl-10-nitro-4,4-dioxo-5,6-dihydro-4aH-[1]benzoxepino[4,5-b][1,4]thiazin-2-yl]-N-tert-butoxycarbonyl-carbamate (60 mg, 0.11 mmol) in THF (1.0 mL) was cooled to −78° C. and KHMDS (1.0 M in THF; 0.33 mL, 0.33 mmol) was added dropwise via syringe. The reaction was stirred at this temperature for 45 minutes and N-fluorobenzenesulfonimide (103 mg, 0.33 mmol) was added as a solution in THF (0.3 mL). The reaction was stirred at −78° C. for 30 minutes. The reaction was quenched with aqueous ammonium chloride solution and extracted with ethyl acetate. The organic portion was concentrated and the resulting crude was purified by column chromatography, eluting with 10-50% ethyl acetate/heptane to give the title compound (20 mg, 0.035 mmol, 32% yield) as a white solid. MS m/z=594.3 (M+Na).

Step 3: Tert-butyl N-[(4aS,11bR)-10-amino-4a-fluoro-3,3,11b-trimethyl-4,4-dioxo-5,6-dihydro-[1]benzoxepino[4,5-b][1,4]thiazin-2-yl]-N-tert-butoxycarbonyl-carbamate A mixture of tert-butyl N-[(4aS,11bR)-4a-fluoro-3,3,11b-trimethyl-10-nitro-4,4-dioxo-5,6-dihydro-[1]benzoxepino[4,5-b][1,4]thiazin-2-yl]-N-tert-butoxycarbonyl-carbamate (20 mg, 0.035 mmol) and 10% Pd on carbon (18.62 mg, 0.017 mmol) in Ethanol (0.2 mL) was stirred under hydrogen atmosphere for 2 hours. The mixture was passed through a celite cake and rinsed with ethyl acetate and ethanol. The filtrate was concentrated in vacuo to afford the title compound (19 mg, 0.035 mmol, 100% yield) as a yellow oil. MS m/z=564.2 (M+Na).

Intermediate 24 (Trans)

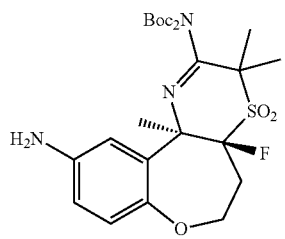

Synthesis of tert-butyl N-[(4aR,11bR)-10-amino-4a-fluoro-3,3,11b-trimethyl-4,4-dioxo-5,6-dihydro-[1]-benzoxepino[4,5-b][1,4]thiazin-2-yl]-N-tert-butoxycarbonyl-carbamate Step 1: tert-Butyl N-tert-butoxycarbonyl-N-[(3R)-2-fluoro-3-(2-fluoro-5-nitro-phenyl)-3,6,6-trimethyl-1,1-dioxo-2H-1,4-thiazin-5-yl]carbamate A solution of tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (bis-boc intermediate) (2.03 g, 3.83 mmol)) in THF (24 mL) was cooled to −78° C. LHMDS (1.0 M in THF; 4.02 ml, 4.02 mmol) was added dropwise and the reaction was stirred at −78° C. for 1 hour. To this was added N-fluorobenzenesulfonimide (1.813 g, 5.75 mmol) as a solution in THF (4 mL). The reaction was stirred at −78° C. for 30 minutes. The reaction was treated with aqueous ammonium chloride solution and extracted with ethyl acetate. The organic portion was e dried over $Na_2SO_4$, filtered, concentrated and purified by column chromatography, eluting with 0-40% tert-butyl methyl ether in Heptanes to afford the title compound (1.1 g, 2.01 mmol, 52.4% yield) as a mixture of diastereomers. MS m/z=570.0 (M+Na).

Step 2: tert-Butyl N-[(4aR,11bR)-4a-fluoro-3,3,11b-trimethyl-10-nitro-4,4-dioxo-5,6-dihydro-[1]benzoxepino[4,5b][1,4]thiazin-2-yl]-N-tert-butoxycarbonyl-carbamate A solution of tert-butyl N-tert-butoxycarbonyl-N-[(3R)-2-fluoro-3-(2-fluoro-5-nitro-phenyl)-3,6,6-trimethyl-1,1-dioxo-2H-1,4-thiazin-5-yl]carbamate (1.1 g, 2.05 mmol) in THF (3.1 ml, 3.07 mmol) was cooled to −78° C. and to this was added LHMDS (1.0 M in THF; 3.07 ml, 3.07 mmol). The reaction was stirred at −78° C. for 45 minutes and then oxirane (1M in THF; 3.41 ml, 4.09 mmol) was added dropwise via syringe. The reaction was stirred at −78° C. for 30 minutes and then at ambient temperature for 16 hours. The reaction was treated with aqueous $NH_4Cl$ solution and extracted with ethyl acetate. The organic portion was dried over $Na_2SO_4$, filtered, concentrated and purified by column chromatography, eluting with 0-40% EtOAc/Heptanes to give the title compound as a white solid. (490 mg, 0.857 mmol, 41.9% yield). MS m/z=494.1 (M+Na).

Step 3: tert-Butyl N-[(4aR,11bR)-10-amino-4a-fluoro-3,3,11b-trimethyl-4,4-dioxo-5,6-dihydro-[1]-benzoxepino[4,5-b][1,4]thiazin-2-yl]-N-tert-butoxycarbonyl-carbamate A mixture of tert-butyl N-[(4aR,11bR)-4a-fluoro-3,3,11b-trimethyl-10-nitro-4,4-dioxo-5,6-dihydro-[1]benzoxepino[4,5-b][1,4]thiazin-2-yl]-N-tert-butoxycarbonyl-carbamate (490 mg, 0.857 mmol) and pd/c (274 mg, 0.257 mmol) in THF (5.7 mL) was stirred under hydrogen atmosphere for 16 hours. The mixture was passed through a celite cake and rinsed with ethyl acetate and ethanol. The filtrate was concentrated in vacuo to afford the title compound (460 mg, 0.850 mmol, 99% yield) as a white foam. MS m/z=564.2 (M+Na).

Intermediate 25

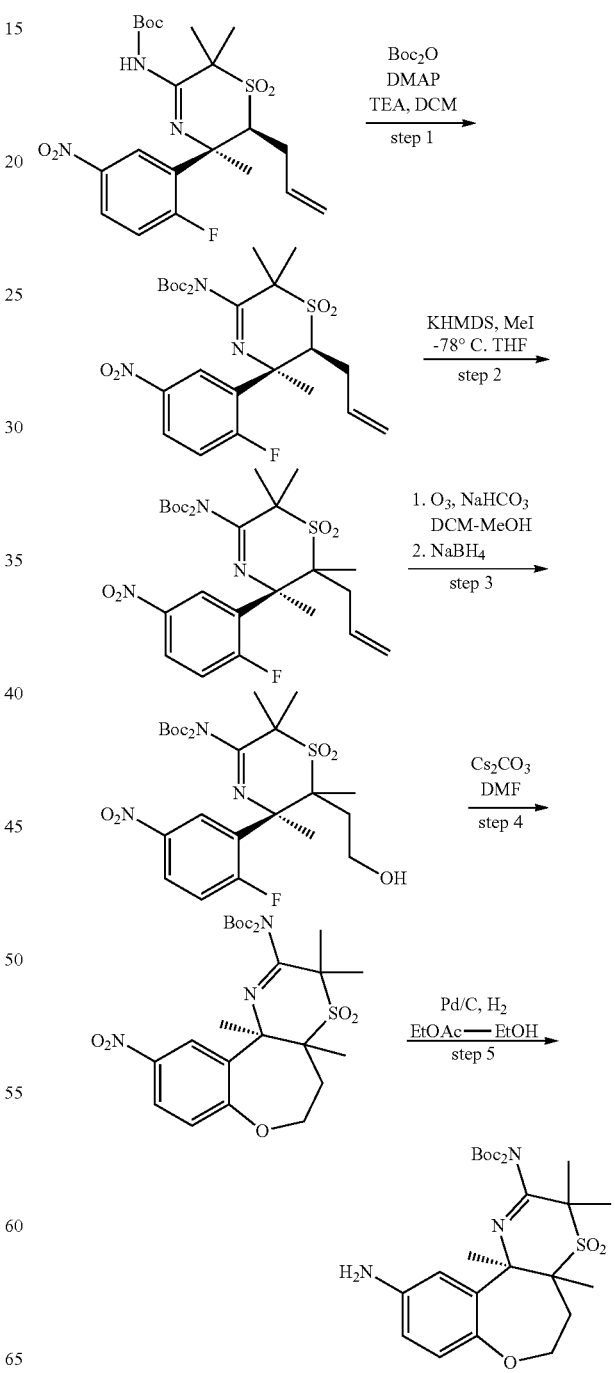

Synthesis of tert-butyl N-[(11bR)-10-amino-3,3,4a,
11b-tetramethyl-4,4-dioxo-5,6-dihydro-[1]benzox-
epino[4,5b][1,4]thiazin-2-yl]-N-tert-butoxycarbonyl-
carbamate Step 1: Tert-butyl N-[(2S,3R)-2-allyl-3-(2-fluoro-5-
nitro-phenyl)-3,6,6-trimethyl-1,1-dioxo-2H-1,4-thi-
azin-5-yl]-N-tert-butoxycarbonyl-carbamate To a 10-mL round-bottomed flask was added tert-butyl ((5R,6S)-6-allyl-5-(2-fluoro-5-nitrophenyl)-2,2,5-trimethyl-1,1-dioxido-5,6-dihydro-2H-1,4-thiazin-3-yl)carbamate (0.30 g, 0.64 mmol), di-tert-butyl dicarbonate (0.28 g, 1.28 mmol), triethylamine (0.27 ml, 1.92 mmol), DMAP (0.086 g, 0.70 mmol) and DCM (3.2 ml). The resulting mixture was stirred at ambient temp overnight. The mixture was concentrated and purified in 5-40% EtOAc/heptanes (12 g column) to give tert-butyl N-[(2S,3R)-2-allyl-3-(2-fluoro-5-nitro-phenyl)-3,6,6-trimethyl-1,1-dioxo-2H-1,4-thiazin-5-yl]-N-tert-butoxycarbonyl-carbamate (0.30 g, 82% yield) as a yellow solid. m/z (ESI) 593.0 (M+Na)$^+$.

Step 2: Tert-butyl N-[(5R)-6-allyl-5-(2-fluoro-5-
nitro-phenyl)-2,2,5,6-tetramethyl-1,1-dioxo-1,4-thi-
azin-3-yl]-N-tert-butoxycarbonyl-carbamate To a mixture of tert-butyl N-[(2S,3R)-2-allyl-3-(2-fluoro-5-nitro-phenyl)-3,6,6-trimethyl-1,1-dioxo-2H-1,4-thiazin-5-yl]-N-tert-butoxycarbonyl-carbamate (0.22 g, 0.38 mmol) in THF (2 mL) at −78° C. was added potassium bis(trimethylsilyl)amide, 1M in THF (1.13 ml, 1.13 mmol) and the solution was stirred for 15 minutes. Iodomethane (0.070 ml, 1.13 mmol) was added and the mixture was stirred at −78° C. for 0.5 h. The reaction was quenched by water, extracted with ethyl acetate. The combined extracts were washed with brine, dried and concentrated. The crude material was absorbed onto a plug of silica gel and purified by chromatography through a BioTage column (25 g), eluting with a gradient of 5% to 40% EtOAc in hexane, to provide tert-butyl N-[(5R)-6-allyl-5-(2-fluoro-5-nitro-phenyl)-2,2,5,6-tetramethyl-1,1-dioxo-1,4-thiazin-3-yl]-N-tert-butoxycarbonyl-carbamate (0.19 g, 85% yield) as a white solid. m/z (ESI) 606.1 (M+Na)$^+$.

Step 3: tert-butyl N-tert-butoxycarbonyl-N-[(5R)-5-
(2-fluoro-5-nitro-phenyl)-6-(2-hydroxyethyl)-2,2,5,
6-tetramethyl-1,1-dioxo-1,4-thiazin-3-yl]carbamate A solution of tert-butyl N-[(5R)-6-allyl-5-(2-fluoro-5-nitro-phenyl)-2,2,5,6-tetramethyl-1,1-dioxo-1,4-thiazin-3-yl]-N-tert-butoxycarbonyl-carbamate (0.18 g, 0.31 mmol) in DCM (2.4 ml) and MeOH (0.8 ml) was added sodium bicarbonate (0.053 g, 0.63 mmol) and then cooled in dry ice-acetone bath. A mixture of $O_3$ in oxygen gas was bubbled through the solution until the blue color persisted. The excess ozone was removed by bubbling through oxygen gas for 5 minutes. Sodium borohydride (0.018 g, 0.47 mmol) was added and the mixture was stirred and allowed to warm to 0° C. After 30 minutes, the reaction was quenched by sat.NH$_4$Cl and extracted with DCM. The combined extracts were washed with brine, dried and concentrated to give crude tert-butyl N-tert-butoxycarbonyl-N-[(5R)-5-(2-fluoro-5-nitro-phenyl)-6-(2-hydroxyethyl)-2,2,5,6-tetramethyl-1,1-dioxo-1,4-thiazin-3-yl]carbamate as a white solid. m/z (ESI) 611.0 (M+Na)$^+$.

Step 4: tert-butyl N-[(11bR)-3,3,4a,11b-tetramethyl-
10-nitro-4,4-dioxo-5,6-dihydro-[1]benzoxepino[4,5-
b][1,4]thiazin-2-yl]-N-tert-butoxycarbonyl-carbam-
ate To a solution of crude tert-butyl N-tert-butoxycarbonyl-N-[(5R)-5-(2-fluoro-5-nitro-phenyl)-6-(2-hydroxyethyl)-2,2,5,6-tetramethyl-1,1-dioxo-1,4-thiazin-3-yl]carbamate (0.18 g, 0.31 mmol) in DMF (1.8 ml) was added cesium carbonate (0.25 g, 0.77 mmol). The resulting mixture was stirred at ambient temperature for 7 h. Extra cesium carbonate (0.36 g) was added and the mixture was stirred at ambient temperature overnight. The reaction mixture was diluted with 30 ml of saturated NH$_4$Cl and extracted with EtOAc. The organic extract was washed with brine and dried over MgSO$_4$. The solution was filtered and concentrated in vacuo to give the crude material as an orange oil. The crude material was absorbed onto a plug of silica gel and purified by chromatography through a Biotage column (25 g), eluting with a gradient of 5% to 40% EtOAc in hexane, to provide tert-butyl N-[(11bR)-3,3,4a,11b-tetramethyl-10-nitro-4,4-dioxo-5,6-dihydro-[1]benzoxepino[4,5-b][1,4]thiazin-2-yl]-N-tert-butoxycarbonyl-carbamate (0.076 g, 43% yield) as a light-yellow solid. m/z (ESI) 591.1 (M+Na)$^+$.

Step 5: tert-butyl N-[(11bR)-10-amino-3,3,4a,11b-
tetramethyl-4,4-dioxo-5,6-dihydro-[1]-benzoxepino
[4,5-b][1,4]thiazin-2-yl]-N-tert-butoxycarbonyl-car-
bamate A solution of tert-butyl N-[(11bR)-3,3,4a,11b-tetramethyl-10-nitro-4,4-dioxo-5,6-dihydro-[1]benzoxepino[4,5-b][1,4]thiazin-2-yl]-N-tert-butoxycarbonyl-carbamate (0.076 g, 0.13 mmol) in EtOAc (0.9 ml) and EtOH (0.5 ml) was stirred under hydrogen balloon in the presence of palladium, 10% wt. on activated carbon (0.036 g, 0.033 mmol) for 15 h. The mixture was filtered through the plug of Celite, filter cake was washed with ethyl acetate. The combined filtrate was concentrated to afford crude tert-butyl N-[(11bR)-10-amino-3,3,4a,11b-tetramethyl-4,4-dioxo-5,6-dihydro-[1]benzoxepino[4,5-b][1,4]thiazin-2-yl]-N-tert-butoxycarbonyl-carbamate as mixture of trans and cis diasteromers (~1:3 ratio) which was used without further purification. m/z (ESI) 560.0 (M+Na)$^+$.

Intermediate 26

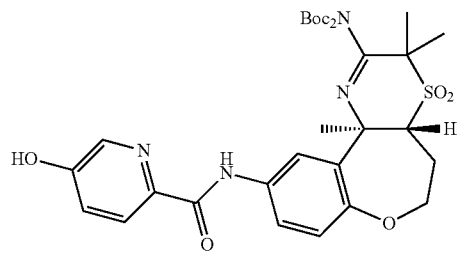

Synthesis of Tert-butyl N-[(4aR,11bR)-10-[(5-hy-
droxypyridine-2-carbonyl)amino]-3,3,11b-trimethyl-
4,4-dioxo-5,6-dihydro-4aH-[1]benzoxepino[4,5-b][1,
4]thiazin-2-yl]-N-tert-butoxycarbonyl-carbamate tert-Butyl N-[(4aR,11bR)-10-[(5-hydroxypyridine-2-carbonyl)amino]-3,3,11b-trimethyl-4,4-dioxo-5,6-dihydro- 4aH-[1]benzoxepino[4,5-b][1,4]thiazin-2-yl]-N-tert-butoxycarbonyl-carbamate was prepared via General Method 3, Step 1 using Intermediate 20 and 5-hydroxy-pyridine-2-carboxylic acid (Combi-blocks) in 93% yield as a red solid. LC/MS (ESI+) m/z=667.2 (M+Na).

Intermediate 27-Cis and 27-Trans

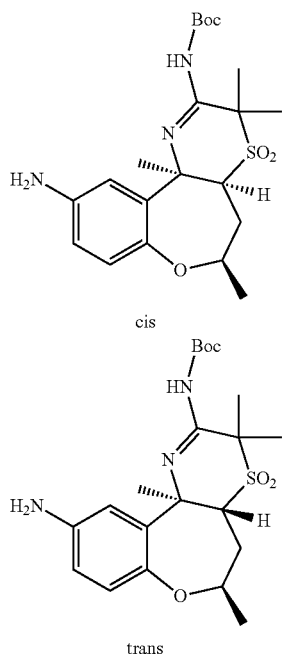

cis trans

Synthesis of tert-butyl ((4aR/S,6R,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate Step 1: tert-butyl ((4aR/S,6R,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate To a dry flask was added tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (200 mg, 0.378 mmol) and dry THF (2.5 ml). The reaction mixture was cooled to −78° C. and LHMDS (1 M in THF; 0.94 ml, 0.944 mmol) was added. The mixture was stirred for t 0 min and then (r)-(+)-1,2-epoxypropane (53 µl, 0.755 mmol) was added. The reaction mixture was stirred for 1 hr at −78° C. and then dry ice/acetone bath was removed. The mixture was allowed to warm up to RT and stirred for 1 h. It was quenched by 3 ml of sat. aq.NH₄Cl. The reaction mixture was diluted with water and extracted with EtOAc. The organic extract was washed with brine and dried over MgSO4. The solution was filtered and concentrated to give the crude material as a brown oil. The crude mixture was dissolved in 2 ml tBuOH and potassium tert-butoxide, 1.0 M solution THF (1.1 ml, 1.1 mmol). It was stirred at RT. 20 min later, 5 mL of sat. aq. NH₄Cl was added and it was extracted with EtOAc. It was concentrated and was purified by silica gel chromatography eluting with 20% to 35% to 50% EtOAc in heptane to give tert-butyl ((4aR,6R,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (50 mg, 0.107 mmol, 28.3% yield) and tert-butyl ((4aS,6R,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (27 mg, 0.058 mmol, 15.29% yield). MS m/z=490.0 (M+23).

Step 2: Tert-butyl ((4aR/S,6R,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate A solution of tert-butyl ((4aR,6R,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (50 mg, 0.107 mmol) in THF (1 ml) was hydrogenated under hydrogen balloon in the presence of palladium 10 wt. % on activated carbon (34.1 mg, 0.032 mmol) for 1.5 h. The mixture was filtered through the plug of Celite, filter cake was washed with ethyl acetate. The combined filtrate was concentrated to afford crude tert-butyl ((4aR,6R,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate (46 mg, 0.105 mmol, 98% yield) which was used without further purification. MS m/z=438.3 (M+H).

Under similar conditions, tert-butyl ((4aS,6R,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (27 mg, 0.058 mmol) was converted to the cis epimer tert-butyl ((4aS,6R,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate (24 mg, 0.055 mmol, 51.3% yield). MS m/z=438.2 (M+H).

Intermediates 28-Cis and 28-Trans

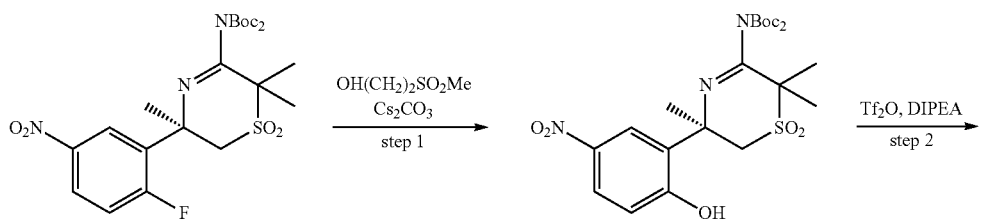

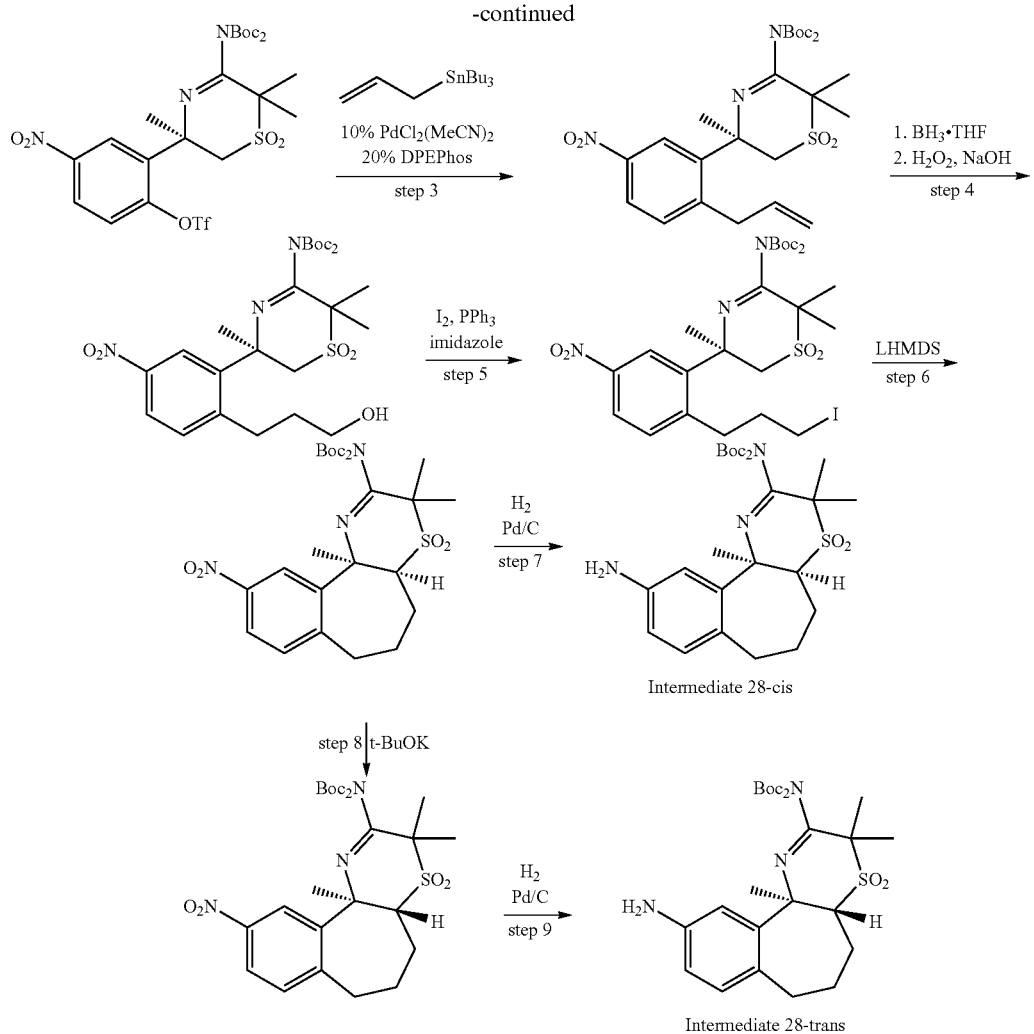

Intermediate 28-cis

Intermediate 28-trans

Synthesis of tert-butyl-N-((4aS,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate and tert-butyl-N-((4aR,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate Step 1: (R)-tert-butyl-N-(5-(2-hydroxy-5-nitrophenyl)-2,2,5-trimethyl-1,1-dioxido-5,6-dihydro-2H-1,4-thiazin-3-yl)-N-tert-butoxylcarbonyl-carbamate To a solution of (R)-tert-butyl-N-(5-(2-fluoro-5-nitrophenyl)-2,2,5-trimethyl-1,1-dioxido-5,6-dihydro-2H-1,4-thiazin-3-yl)-N-tert-butoxycarbonyl-carbamate (1.00 g, 1.888 mmol) (prepared according to the procedure detailed in Intermediate 32, Step 1) in DMF (8 ml) 2-(methylsulphonyl)ethanol (0.49 g, 3.95 mmol) and cesium carbonate (1.28 g, 3.93 mmol) were added and the mixture was stirred overnight at rt. Additional $Cs_2CO_3$ (610 mg, 1 eq) and 2-(methylsulphonyl)ethanol (250 mg, 1 eq) were added and stirring continued for additional 2 hrs. The mixture was diluted with EtOAc and saturated ammonium chloride. Organic layer was separated and washed twice with water, then with brine and concentrated. The residue was purified by FC on 40 g RediSep Gold column using 5-100% EtOAc in heptane to afford (R)-tert-butyl-N-(5-(2-hydroxy-5-nitrophenyl)-2,2,5-trimethyl-1,1-dioxido-5,6-dihydro-2H-1,4-thiazin-3-yl)-N-tert-butoxylcarbonyl-carbamate (940 mg, 1.782 mmol, 94% yield). LC/MS (ESI$^+$) m/z=550 (M+Na)

Step 2: (R)-2-(5-((bis-(tert-butoxycarbonyl))amino)-3,6,6-trimethyl-1,1-dioxido-3,6-dihydro-2H-1.4 thiazin-3-yl)-4-nitrophenyl trifluoromethanesulfonate 100 ml RBF was charged with (R)-tert-butyl-N-(5-(2-hydroxy-5-nitrophenyl)-2,2,5-trimethyl-1,1-dioxido-5,6-dihydro-2H-1,4-thiazin-3-yl)-N-tert-butoxylcarbonyl-carbamate (940 mg, 1.782 mmol) in DCM (18 ml) and N,N-diisopropylethylamine (0.930 ml, 5.35 mmol) was added. The mixture was stirred until full dissolution observed and cooled to −78° C. (dry ice-acetone bath). Trifluoromethanesulfonic anhydride (0.449 ml, 2.67 mmol) was added dropwise and the mixture was stirred for 20 min at −78° C. The reaction was quenched with sat $NaHCO_3$ solution, allowed to warm to rt and diluted with EtOAc. Organic layer was separated, washed with brine and concentrated. The residue was purified by FC on 40 g RediSep Gold column using 5-60% EtOAc in heptane to give (R)-2-(5-((bis-(tert-butoxycarbonyl))amino)-3,6,6- trimethyl-1,1-dioxido-3,6-dihydro-2H-1,4-thiazin-3-yl)-4-nitrophenyl trifluoromethanesulfonate (924 mg, 1.401 mmol, 79% yield). LC/MS (ESI$^+$) m/z=682 (M+Na).

Step 3: (R)-tert-butyl-N-(5-(2-allyl-5-nitrophenyl)-2,2,5-trimethyl-1,1-dioxido-5,6-dihydro-2H-1,4-thiazin-3-yl)-N-tert-butoxycarbonyl-carbamate 100 ml RBF was charged with (R)-2-(5-((bis-(tert-butoxycarbonyl))amino)-3,6,6-trimethyl-1,1-dioxido-3,6-dihydro-2H-1,4-thiazin-3-yl)-4-nitrophenyl trifluoromethanesulfonate (794 mg, 1.204 mmol), bis(acetonitrile)palladium (II)dichloride (31.2 mg, 0.120 mmol), (oxydi-2,1-phenylene)bis(diphenylphosphine) (130 mg, 0.241 mmol) and DMF (6 ml). The mixture was stirred for 2 min until all solids dissolved. Allyltri-n-butylstannane (0.746 ml, 2.407 mmol) was added, the vial was sealed and stirred at 75° C. (heating block) for 30 min. The mixture was concentrated in vacuo and purified by FC on 40 g RediSep Gold column using 5-70% EtOAc in heptane to afford (R)-tert-butyl-N-(5-(2-allyl-5-nitrophenyl)-2,2,5-trimethyl-1,1-dioxido-5,6-dihydro-2H-1,4-thiazin-3-yl)-N-tert-butoxycarbonyl-carbamate (623 mg, 1.129 mmol, 94% yield). LC/MS (ESI$^+$) m/z=574 (M+Na).

Step 4: (R)-tert-butyl-N-(5-(2-(3-hydroxypropyl)-5-nitrophenyl)-2,2,5-trimethyl-1,1-dioxido-5,6-dihydro-2H-1,4-thiazin-3-yl)-N-tert-butoxycarbonyl-carbamate A solution of (R)-tert-butyl-N-(5-(2-allyl-5-nitrophenyl)-2,2,5-trimethyl-1,1-dioxido-5,6-dihydro-2H-1,4-thiazin-3-yl)-N-tert-butoxycarbonyl-carbamate (623 mg, 1.129 mmol), in THF (11 ml) was cooled to 0° C. and borane tetrahydrofuran complex, 1.0 M in THF (1.13 ml, 1.13 mmol) was added dropwise. The mixture was stirred for 1.5 h at 0° C., then quenched with water (1 ml) and allowed to warm up to rt. The mixture was recooled to 0° C. and hydrogen peroxide (30% solution) (1.15 ml, 11.29 mmol) and sodium hydroxide (2N solution) (1.129 ml, 2.259 mmol) then were added and stirred at rt for 30 min. The mixture was partitioned between EtOAc (20 ml) and water (10 ml), organic layer was washed with brine and concentrated. The residue was purified by FC on 12 g RediSep Gold column using 20-100% EtOAc in heptane to afford (R)-tert-butyl-N-(5-(2-(3-hydroxypropyl)-5-nitrophenyl)-2,2,5-trimethyl-1,1-dioxido-5,6-dihydro-2H-1,4-thiazin-3-yl)-N-tert-butoxycarbonyl-carbamate (385 mg, 0.676 mmol, 60% yield). LC/MS (ESI$^+$) m/z=592 (M+Na).

Step 5: (R)-tert-butyl-N-(5-(2-(3-iodopropyl)-5-nitrophenyl)-2,2,5-trimethyl-1,1-dioxido-5,6-dihydro-2H-1,4-thiazin-3-yl)-N-tert-butoxycarbonyl-carbamate A solution of imidazole (64.5 mg, 0.948 mmol) and triphenylphosphine (99 mg, 0.379 mmol) in 1.5 ml DCM was cooled to 0° C. and iodine (96 mg, 0.379 mmol) was added. The mixture was stirred for 2 min at 0° C., then solution of (R)-tert-butyl-N-(5-(2-(3-hydroxypropyl)-5-nitrophenyl)-2,2,5-trimethyl-1,1-dioxido-5,6-dihydro-2H-1,4-thiazin-3-yl)-N-tert-butoxycarbonyl-carbamate (180 mg, 0.316 mmol) in 0.5 ml DCM was added. The mixture was removed from cooling bath and stirred at rt for 20 min. The mixture was directly loaded onto 12 g RediSep Gold column and eluted with 5-50% EtOAc in heptane to afford (R)-tert-butyl-N-(5-(2-(3-iodopropyl)-5-nitrophenyl)-2,2,5-trimethyl-1,1-dioxido-5,6-dihydro-2H-1,4-thiazin-3-yl)carbamate-N-tert-butoxycarbonyl-carbamate (173 mg, 0.255 mmol, 81% yield). LC/MS (ESI$^+$) m/z=524 (M Boc–t-Bu).

Step 6: tert-butyl-N-((4aS,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate A solution of (R)-tert-butyl-N-(5-(2-(3-iodopropyl)-5-nitrophenyl)-2,2,5-trimethyl-1,1-dioxido-5,6-dihydro-2H-1,4-thiazin-3-yl)-N-tert-butoxycarbonyl-carbamate (172 mg, 0.253 mmol) in THF (2.5 ml) was cooled down to −78° C. and lithium bis(trimethylsilyl)amide (1M solution in THF) (0.40 ml, 0.40 mmol) was added dropwise. The bright yellow mixture was stirred at −78° C. for 20 min, then transferred to −45° C. bath (acetonitrile-dry ice) and stirred for extra 5 min. Saturated NH$_4$Cl (2 ml) solution was added, the mixture was removed from the bath and allowed to reach rt, diluted with EtOAc (5 ml) and water to dissolve solids. Organic layer was washed with brine and concentrated. The residue was purified by FC on 12 g RediSep column using 20-70% EtOAc in heptane to afford tert-butyl-N-((4aS,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (105 mg, 0.190 mmol, 75% yield) as white solid. LC/MS (ESI$^+$) m/z=574 (M+Na).

Step 7: tert-butyl-N-((4aS,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (Intermediate 28-cis)

A solution of tert-butyl-N-((4aS,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (125 mg, 0.227 mmol) in THF (2 ml) was hydrogenated in the presence of palladium (10% wt.) on activated carbon (48.2 mg, 0.045 mmol) for 1 h (hydrogen balloon). The mixture was filtered through plug of celite, filter cake was washed with EtOAc, filtrate was concentrated to afford tert-butyl-N-((4aS,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (116 mg, 0.222 mmol, 98% yield), which was used without further purification. LC/MS (ESI$^+$) m/z=522 (M+H).

Step 8: tert-Butyl-N-((4aR,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate A solution of tert-butyl-N-((4aS,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (806 mg, 1.461 mmol) in THF (10 ml) was treated with potassium tert-butoxide (1M in THF) (0.584 ml, 0.584 mmol) dropwise at rt. The mixture became dark after first few drops added. After 5 min stirring the reaction was quenched by 3 ml sat NH$_4$Cl solution, stirred for 5 min, then diluted with water (2 ml) and EtOAc (3 ml). Organic layer was washed with brine and concentrated. The residue was purified by FC using 40 g RediSep Gold column (10-70% EtOAc in heptane) to afford tert-butyl-N-((4aR,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tertbutoxycarbonyl-carbamate (615 mg, 1.115 mmol, 76% yield). LC/MS (ESI$^+$) m/z=574 (M+Na).

Step 9: tert-butyl-N-((4aR,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (Intermediate 28-trans)

A solution of tert-butyl-N-((4aR,11bR)-10-nitro-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (390 mg, 0.707 mmol) in THF (5 ml) was hydrogenated using a balloon in the presence of palladium (10% wt.) on activated carbon (150 mg, 0.141 mmol) for 1.5 h. The mixture was filtered through pad of celite, filter cake was washed with THF, filtrate was concentrated to afford tert-butyl-N-((4aR,11bR)-10-amino-3,3,11b-trimethyl-4,4-dioxido-3,4a,5,6,7,11b-hexahydrobenzo[3,4]cyclohepta[1,2-b][1,4]thiazin-2-yl)-N-tert-butoxycarbonyl-carbamate (340 mg, 0.652 mmol, 92% yield) which was used in the next step without purification. LC/MS (ESI$^+$) m/z=522 (M+H).

Intermediate 29-Cis

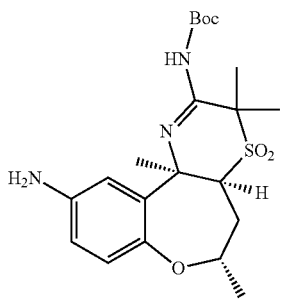 [SMILES: C[C@H]1C[C@H]2[C@](C)(N=C(NC(=O)OC(C)(C)C)C(C)(C)S2(=O)=O)c2cc(N)ccc2O1]

Synthesis of tert-butyl ((4aS,6S,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate Step 1: tert-butyl ((4aR,6S,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate and tert-butyl ((4aS,6S,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate To a 25-mL round-bottomed dry flask was added tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (420 mg, 0.793 mmol) in THF (5 ml). The reaction solution was cooled to −78° C., then LHMDS (1 M in THF; 2.0 ml, 2.0 mmol) was added slowly. It was stirred for 20 min, then (S)-2-methyloxirane (92 µl, 1.586 mmol) was added at −78° C. The reaction mixture was stirred from −78° C. to 0° C. After 15 min, it was quenched by sat. aq. NH$_4$Cl. The reaction mixture was diluted with water and extracted with EtOAc. The organic extract was washed with brine and dried over MgSO$_4$. The solution was filtered and concentrated to give the crude material as a brown oil. The crude mixture was dissolved in 4 ml tBuOH and potassium tert-butoxide, 1.0M solution in THF (2.4 ml, 2.4 mmol) was added. It was stirred at RT. 50 min later, 5 ml of sat. NH$_4$Cl was added and the reaction mixture was extracted with EtOAc. It was concentrated and was purified by silica gel chromatography using 20% to 35% to 50% EtOAc/heptane to give 70 mg of tert-butyl ((4aR,6S,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (less polar peak by TLC) and 50 mg of tert-butyl ((4aS,6S,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate (more polar peak by TLC). MS m/z=490.2 (M+23).

Step 2: tert-butyl ((4aS,6S,11bR)-10-amino-3,3,6,11b-tetramethyl-4,4-dioxido-4a,5,6,11b-tetrahydro-3H-benzo[6,7]oxepino[4,5-b][1,4]thiazin-2-yl)carbamate The title compound was prepared according to the procedure described in the preparation of intermediate 27, step 2, using tert-butyl ((4a-5,6S,11bR)-3,3,6,11b-tetramethyl-10-nitro-4,4-dioxido-4a,5,6,11b-tetrahydro-3H-benzo[6,7]oxepino[4,5-b][1,4]thiazin-2-yl)carbamate. MS m/z=438.3 (M+H).

Intermediate 30

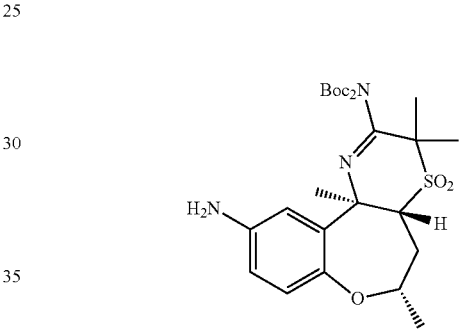

Synthesis of tert-butyl N-[(4aR,6S,11bR)-10-amino-3,3,6,11b-tetramethyl-4,4-dioxo-5,6-dihydro-4aH-[1]benzoxepino[4,5-b][1,4]thiazin-2-yl]-N-tert-butoxycarbonyl-carbamate Step 1: tert-butyl N-tert-butoxycarbonyl-N-[(2R,3R)-3-(2-fluoro-5-nitro-phenyl)-2-[(2S)-2-hydroxypropyl]-3,6,6-trimethyl-1,1-dioxo-2H-1,4-thiazin-5-yl]carbamate and tert-butyl N-tert-butoxycarbonyl-N-[(2S,3R-3-(2-fluoro-5-nitro-phenyl)-2-[(2S)-2-hydroxypropyl]-3,6,6-trimethyl-1,1-dioxo-2H-1,4-thiazin-5-yl]carbamate To a 15-mL round-bottom dry flask under nitrogen atmosphere was added tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (2.0 g, 3.78 mmol) and THF (20 ml). The reaction solution was cooled to −78° C., then LHMDS (7.55 ml, 7.55 mmol) was added slowly via syringe. The resulting deep red solution was stirred at −78° C. for 60 minutes. To this was then added (S)-2-methyloxirane (0.529 ml, 7.55 mmol) dropwise via syringe, and then BF$_3$—OEt$_2$ (0.957 ml, 7.55 mmol) in 7 ml THF was added slowly dropwise. The mixture was stirred at −78° C. for 1 h and the solution became light yellow. The rxn was quenched with saturated ammonium chloride and diluted with water. The solution was extracted with ethyl acetate twice and the combined organic layers were washed with brine and dried over anhydrous sodium sulfate, filtered and concentrated. The product was purified via silica gel column chromatography (120 g column) using 5-70% ethyl acetate in heptane to afford a mixture of cis and trans isomers, tert-butyl N-tert-butoxycarbonyl-N-[(2R,3R)-3-(2-fluoro-5-nitro-phenyl)-2-[(2S)-2-hydroxypropyl]-3,6,6-trimethyl-1,1-dioxo-2H-1,4-thiazin-5-yl]carbamate and tert-butyl N-tert-butoxycarbonyl-N-[(2S,3R)-3-(2-fluoro-5-nitro-phenyl)-2-[(2S)-2-hydroxypropyl]-3,6,6-trimethyl-1,1-dioxo-2H-1,4-thiazin-5-yl]carbamate (2.2 g, 3.75 mmol, 99%). MS m/z=610 [M+Na].

Step 2: tert-butyl N-[(4aR,6S,11bR)-3,3,6,11b-tetramethyl-10-nitro-4,4-dioxo-5,6-dihydro-4aH-[1]benzoxepino[4,5-b][1,4]thiazin-2-yl]-N-tert-butoxycarbonyl-carbamate A mixture of cis and trans isomers, tert-butyl N-tert-butoxycarbonyl-N-[2R,3R)-3-(2-fluoro-5-nitro-phenyl)-2-[(2S)-2-hydroxypropyl]-3,6,6-trimethyl-1,1-dioxo-2H-1,4-thiazin-5-yl]carbamate and tert-butyl N-tert-butoxycarbonyl-N-[(2S,3R)-3-(2-fluoro-5-nitro-phenyl)-2-[(2S)-2-hydroxypropyl]-3,6,6-trimethyl-1,1-dioxo-2H-1,4-thiazin-5-yl]carbamate (1.8 g, 3.06 mmol) and cesium carbonate (4.99 g, 15.32 mmol) were combined in DMSO (15 ml) and stirred at room temperature for 6 h. The solution was diluted with water and the precipitate was collected by filtration, washed with water, and dried under vacuum. The product was purified via silica gel column chromatography (80 g column) using 10-50% ethyl acetate in heptane to afford to afford tert-butyl N-[(4aR,6S,11bR)-3,3,6,11b-tetramethyl-10-nitro-4,4-dioxo-5,6-dihydro-4aH-[1]benzoxepino[4,5-b][1,4]thiazin-2-yl]-N-tert-butoxycarbonyl-carbamate (1.62 g, 2.85 mmol, 93% yield). MS m/z=590 [M+Na].

Step 3: tert-butyl N-[(4aR,6S,11bR)-10-amino-3,3,6,11b-tetramethyl-4,4-dioxo-5,6-dihydro-4aH-[1]benzoxepino[4,5-b][1,4]thiazin-2-yl]-N-tert-butoxycarbonyl-carbamate Tert-butyl N-[(4aR,6S,11bR)-3,3,6,11b-tetramethyl-10-nitro-4,4-dioxo-5,6-dihydro-4aH-[1]benzoxepino[4,5-b][1,4]thiazin-2-yl]-N-tert-butoxycarbonyl-carbamate (7.3 g, 12.86 mmol) and palladium on carbon (10%), wet (1 g, 0.470 mmol) were combined in ethyl acetate (60 ml) with 5 ml of MeOH under hydrogen atmosphere and stirred at room temp for 1 h. The solution was filtered thru celite, the Pd solids were washed with DCM and MeOH, then the organics were concentrated to afford tert-butyl N-[(4aR,6S,11bR)-10-amino-3,3,6,11b-tetramethyl-4,4-dioxo-5,6-dihydro-4aH-[1]benzoxepino[4,5-b][1,4]thiazin-2-yl]-N-tert-butoxycarbonyl-carbamate (6.5 g, 12.09 mmol, 94% yield) as a white solid. MS m/z=560 [M+Na].

Intermediate 31-Trans

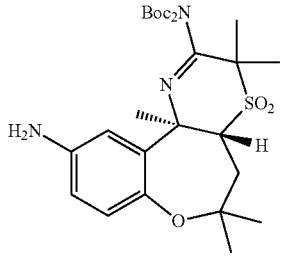

Synthesis of tert-butyl N-[(4aR,11bR)-10-amino-3,3,6,6,11b-pentamethyl-4,4-dioxo-4a,5-dihydro-[1]benzoxepino[4,5-b][1,4]thiazin-2-yl]-N-tert-butoxycarbonyl-carbamate Step 1: of tert-butyl N-tert-butoxycarbonyl-N-[(3R)-3-(2-fluoro-5-nitro-phenyl)-2-(2-hydroxy-2-methyl-propyl)-3,6,6-trimethyl-1,1-dioxo-2H-1,4-thiazin-5-yl]carbamate A solution of tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (0.4 g, 0.756 mmol) in THF (3.8 mL) was cooled to −78° C. and to this was added LHMDS (1.0M in THF; 1.51 ml, 1.51 mmol) dropwise via syringe. The reaction was stirred at −78° C. for 1 hr. 2,2-dimethyloxirane (0.134 ml, 1.51 mmol) was then added followed by BF3.OEt2 (1.44 ml, 1.44 mmol) as a solution in 2 mL of THF. The reaction was stirred at −78° C. for 1 hr. The reaction was treated with aqueous ammonium chloride solution and extracted with ethyl acetate. The organic portion was dried over Na2SO4, filtered, concentrated and purified by column chromatography, eluting with 0-40% EtOAc/Heptanes to give the title compound (376 mg, 0.624 mmol, 83% yield) as a white solid. MS m/z=624.2 (M+Na).

Step 2: tert-butyl N-[(11bR)-3,3,6,6,11b-pentamethyl-10-nitro-4,4-dioxo-4a,5-dihydro-[1]-benzoxepino[4,5-b][1,4]thiazin-2-yl]-N-tert-butoxycarbonyl-carbamate A mixture of tert-butyl N-tert-butoxycarbonyl-N-[(3R)-3-(2-fluoro-5-nitro-phenyl)-2-(2-hydroxy-2-methyl-propyl)-3,6,6-trimethyl-1,1-dioxo-2H-1,4-thiazin-5-yl]carbamate (230 mg, 0.382 mmol) and cesium carbonate (498 mg, 1.529 mmol) in DMSO (2 mL) was stirred at 65° C. for 5 hrs. The reaction was partitioned between water and ethyl acetate. The organic portion was dried over Na2SO4, filtered, concentrated and purified by column chromatography, eluting with 10-40% EtOAc/Heptanes to give tert-butyl N-[(4aR,11bR)-10-amino-3,3,6,6,11b-pentamethyl-4,4-dioxo-4a,5-dihydro-[1]benzoxepino[4,5-b][1,4]thiazin-2-yl]-N-tert-butoxycarbonyl-carbamate (trans stereoisomer; 108 mg, 0.186 mmol, 48.6% yield) and tert-butyl N-[(4aS,11bR)-10-amino-3,3,6,6,11b-pentamethyl-4,4-dioxo-4a,5-dihydro-[1]benzoxepino[4,5-b][1,4]thiazin-2-yl]-N-tert-butoxycarbonyl-carbamate (cis stereoisomer; 70 mg, 0.120 mmol, 31.5% yield) products. MS m/z=604.3 (M+Na).

Step 3: tert-butyl N-[(4aR,11bR)-10-amino-3,3,6,6,11b-pentamethyl-4,4-dioxo-4a,5-dihydro-[1]benzoxepino[4,5-b][1,4]thiazin-2-yl]-N-tert-butoxycarbonyl-carbamate A mixture of tert-butyl N-[(4aR,11bR)-3,3,6,6,11b-pentamethyl-10-nitro-4,4-dioxo-4a,5-dihydro-[1]benzoxepino[4,5-b][1,4]thiazin-2-yl]-N-tert-butoxycarbonyl-carbamate (105 mg, 0.180 mmol) and 10% Pd/C (58 mg, 0.054 mmol) in EtOAc (1.1 mL) and MeOH (1.1 mL) was stirred under hydrogen atmosphere for 16 hours. The mixture was passed through a celite cake and rinsed with ethyl acetate and ethanol. The filtrate was concentrated in vacuo to afford the title compound (99 mg, 0.180 mmol, 100% yield) as a white foam. MS m/z=574.3 (M+Na).

Intermediate 31-Cis

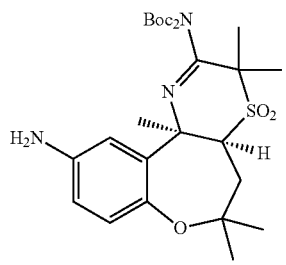

Synthesis of tert-butyl N-[(4aS,11bR)-10-amino-3,3, 6,6,11b-pentamethyl-4,4-dioxo-4a,5-dihydro-[1] benzoxepino[4,5-b][1,4]thiazin-2-yl]-N-tert-butoxy- carbonyl-carbamate A mixture of tert-butyl N-[(4aS,11bR)-3,3,6,6,11b-pen- tamethyl-10-nitro-4,4-dioxo-4a,5-dihydro-[1]benzoxepino [4,5-b][1,4]thiazin-2-yl]-N-tert-butoxycarbonyl-carbamate (70 mg, 0.120 mmol) (Prepared following the procedure for Intermediate 31 (trans), Step 1 and 2) and 10% Pd/C (38.6 mg, 0.036 mmol) in EtOAc (1.1 mL) and MeOH (1.1 mL) was stirred under hydrogen atmosphere for 16 hours. The mixture was passed through a celite cake and rinsed with ethyl acetate and ethanol. The filtrate was concentrated in vacuo to afford the title compound (66 mg, 0.120 mmol, 100% yield) as a white foam. MS m/z=574.3 (M+Na).

Intermediate 32-Cis and 32-Trans

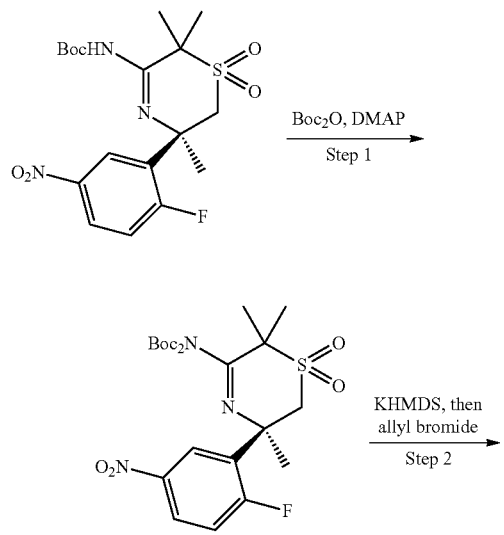

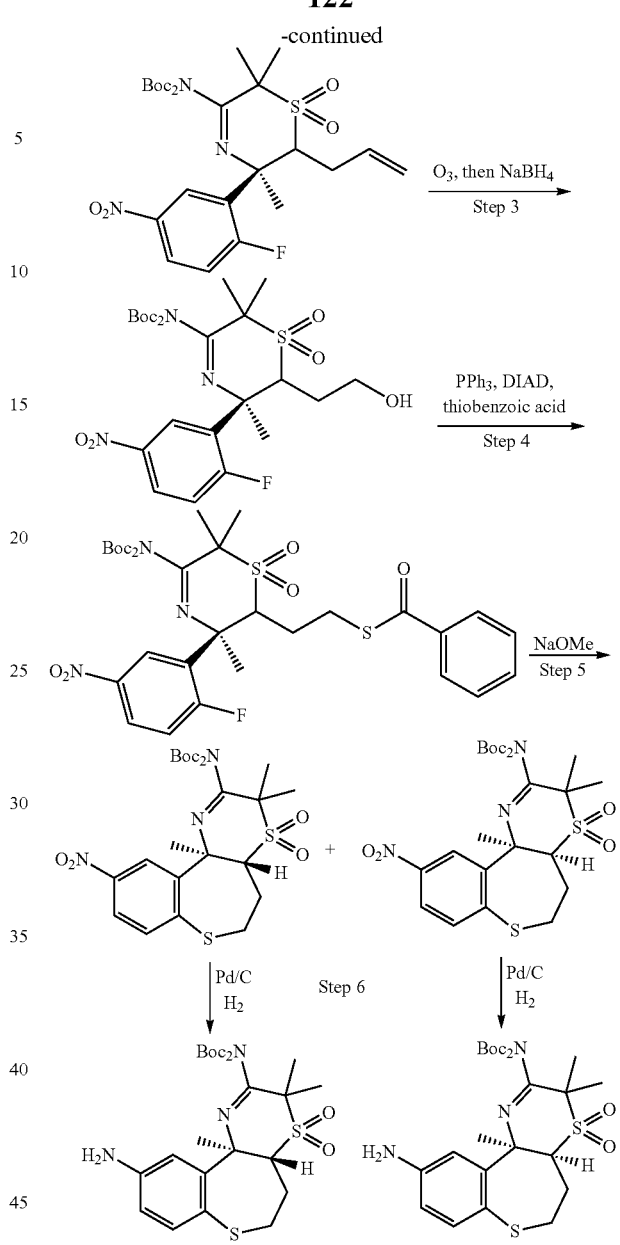

Synthesis of tert-butyl N-[(4aR,11bR)-10-amino-3,3, 11b-trimethyl-4,4-dioxo-5,6-dihydro-4aH-[1]ben- zothiepino[4,5-b][1,4]thiazin-2-yl]-N-tert-butoxycar- bonyl-carbamate and tert-butyl N-[(4aS,11bR)-10- amino-3,3,11b-trimethyl-4,4-dioxo-5,6-dihydro- 4aH-[1]-benzothiepino[4,5-b][1,4]thiazin-2-yl]-N- tert-butoxycarbonyl-carbamate Step 1: tert-Butyl N-tert-butoxycarbonyl-N-[(3R)-3- (2-fluoro-5-nitro-phenyl)-3,6,6-trimethyl-1,1-dioxo- 2H-1,4-thiazin-5-yl]carbamate A round bottom flask was charged with a solution of (R)- tert-butyl (5-(2-fluoro-5-nitrophenyl)-2,2,5-trimethyl-1,1- dioxido-5,6-dihydro-2H-1,4-thiazin-3-yl)carbamate (2.27 g, 5.29 mmol) in DCM (25 ml). Boc₂O (1.384 g, 6.34 mmol) and 4-(dimethylamino)pyridine (0.775 g, 6.34 mmol) were added and the mixture was stirred at RT for 30 min. (Gas evolution was observed after addition of DMAP). The mixture was concentrated to half volume and loaded onto 20 ml silica gel pre-column. Purification via silica gel chromatography using 0-60% EtOAc in heptane afforded tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (2.7 g, 5.10 mmol, 96% yield). LC/MS (ESI$^+$) m/z=552.1 (M+Na).

Step 2: tert-Butyl N-[(3R)-2-allyl-3-(2-fluoro-5-nitro-phenyl)-3,6,6-trimethyl-1,1-dioxo-2H-1,4-thiazin-5-yl]-N-tert-butoxycarbonyl-carbamate A 3-necked RBF equipped with a mechanical stirrer, Claisen adapter with thermocouple and a nitrogen inlet was charged with tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (8.8 g, 16.62 mmol) and THF (80 mL). The yellow solution was cooled to Tinternal−72+/−1° C. using a dry ice/IPA bath. KHMDS, 1M in THF (24.93 mL, 24.93 mmol) was added dropwise via cannula over ~15 min keeping Tinternal<−72+/−1° C. The reaction mixture became dark brown, and was stirred at Tinternal−−72+/−1° C. for 45 min. Allyl bromide (2.157 mL, 24.93 mmol) was added via syringe over 3 min, and stirring was continued at Tinternal<−75° C. for 75 min. 10 mL saturated aq. NH$_4$Cl was added, the cooling bath was removed, and the reaction mixture was allowed to warm to RT. Water was added until all solids were dissolved, and the layers were separated. The organic layer was dried over MgSO$_4$, filtered, and concentrated in vacuo. The crude material was purified via silica gel chromatography (heptane/EtOAc: 100/0 to 40/60+5% DCM isocratic) to provide tert-butyl N-[(3R)-2-allyl-3-(2-fluoro-5-nitro-phenyl)-3,6,6-trimethyl-1,1-dioxo-2H-1,4-thiazin-5-yl]-N-tert-butoxycarbonyl-carbamate (8.93 g, 2.85:1 ratio of diastereomers) as an off-white solid. LC/MS (ESI$^+$) m/z=592.2 (M+Na).

Step 3: tert-Butyl N-tert-butoxycarbonyl-N-[(3R)-3-(2-fluoro-5-nitro-phenyl)-2-(2-hydroxyethyl)-3,6,6-trimethyl-1,1-dioxo-2H-1,4-thiazin-5-yl]carbamate A 3-necked round bottom flask equipped with a mechanical stirrer, Claisen adapter with thermocouple and a nitrogen inlet was charged with tert-butyl N-[(3R)-2-allyl-3-(2-fluoro-5-nitro-phenyl)-3,6,6-trimethyl-1,1-dioxo-2H-1,4-thiazin-5-yl]-N-tert-butoxycarbonyl-carbamate (4.00 g, 7.02 mmol, 2.85:1 ratio of diastereomers), sodium bicarbonate (1.180 g, 14.04 mmol), DCM (30 mL) and MeOH (10.00 mL), and the resulting solution was cooled to Tinternal<−65+/−1° C. Ozone was bubbled through the reaction mixture until starting material was consumed according to LCMS (~1.5 h). The solution was purged with oxygen and then nitrogen, and sodium borohydride (0.531 g, 14.04 mmol) added in one portion. The cooling bath was removed, and the reaction mixture was allowed to warm to RT overnight. 2 mL acetone was added, followed by 10 mL sat. aq.NH$_4$Cl. After stirring for 10 min, 5 mL water was added and the layers were separated. The organic portion was dried over magnesium sulfate, filtered and concentrated in vacuo to provide tert-butyl N-tert-butoxycarbonyl-N-[(3R)-3-(2-fluoro-5-nitro-phenyl)-2-(2-hydroxyethyl)-3,6,6-trimethyl-1,1-dioxo-2H-1,4-thiazin-5-yl]carbamate (4.04 g, 2.85:1 ratio of diastereomers) as a white solid that was used without further purification. LC/MS (ESI$^+$) m/z=596.2 (M+Na).

Step 4: S-[2-[(3R)-5-[bis(tert-butoxycarbonyl)amino]-3-(2-fluoro-5-nitro-phenyl)-3,6,6-trimethyl-1,1-dioxo-2H-1,4-thiazin-2-yl]ethyl]benzenecarbothioate A round bottom flask was charged with triphenylphosphine (1.342 g, 5.12 mmol) and THF (15.99 ml) and this solution was cooled to 0° C. under nitrogen. DIAD (0.819 ml, 4.16 mmol) was added and the mixture was stirred for 30 min at 0° C. A precipitate formed within 5 min. Tert-butyl N-tert-butoxycarbonyl-N-[(3R)-3-(2-fluoro-5-nitro-phenyl)-2-(2-hydroxyethyl)-3,6,6-trimethyl-1,1-dioxo-2H-1,4-thiazin-5-yl]carbamate (as a 2.85:1 diastereomeric mixture) (1.835 g, 3.20 mmol) dissolved in minimum THF was added, followed by thiobenzoic acid (0.599 ml, 5.12 mmol). The reaction became homogeneous and was allowed to warm to RT. After stirring for 3 h at RT, the mixture was concentrated. The crude material was purified via silica gel chromatography using a gradient of 0-40% EtOAc in heptane to provide S-[2-[(3R)-5-[bis(tert-butoxycarbonyl)amino]-3-(2-fluoro-5-nitro-phenyl)-3,6,6-trimethyl-1,1-dioxo-2H-1,4-thiazin-2-yl]ethyl]benzenecarbothioate, as a 2.85:1 mixture of diastereomers, as a white solid. (2.00 g, 90% yield). LC/MS (ESI$^+$) m/z=716.2 (M+Na).

Step 5: tert-butyl N-[(4aR,11bR)-3,3,11b-trimethyl-10-nitro-4,4-dioxo-5,6-dihydro-4aH-[1]-benzothiepino[4,5-b][1,4]thiazin-2-yl]-N-tert-butoxycarbonyl-carbamate A round bottom flask was charged with S-[2-[(3R)-5-[bis(tert-butoxycarbonyl)amino]-3-(2-fluoro-5-nitro-phenyl)-3,6,6-trimethyl-1,1-dioxo-2H-1,4-thiazin-2-yl]ethyl]benzenecarbothioate (2.06 g, 2.97 mmol, 2.85:1 mixture of diastereomers), MeOH (14.85 ml) and sodium methoxide (0.679 ml, 2.97 mmol), and the reaction was stirred at RT. After 10 min the mixture was partitioned between EtOAc and water, and the layers were separated. The aqueous portion was extracted with additional EtOAc, and the combined organic portions were dried with Na$_2$SO$_4$, filtered and concentrated. The crude material was purified by silica gel chromatography using a gradient of 0-50% EtOAc in heptane, to provide the product diastereomers cleanly as light yellow foamy solids. Tert-butyl N-[(4aR,11bR)-3,3,11b-trimethyl-10-nitro-4,4-dioxo-5,6-dihydro-4aH-[1]benzothiepino[4,5-b][1,4]thiazin-2-yl]-N-tert-butoxycarbonyl-carbamate: 1.18 g, 70% yield. LC/MS (ESI$^+$) m/z=592.2 (M+H).

tert-Butyl N-[(4aS,11bR)-3,3,11b-trimethyl-10-nitro-4,4-dioxo-5,6-dihydro-4aH-[1]benzothiepino[4,5-b][1,4]thiazin-2-yl]-N-tert-butoxycarbonyl-carbamate: 0.35 g, 21% yield. LC/MS (ESI$^+$) m/z=592.2 (M+Na).

Step 6: tert-Butyl N-[(4aR,11bR)-10-amino-3,3,11b-trimethyl-4,4-dioxo-5,6-dihydro-4aH-[1]benzothiepino[4,5-b][1,4]thiazin-2-yl]-N-tert-butoxycarbonyl-carbamate A flask was charged with tert-butyl N-[(4aR,11bR)-3,3,11b-trimethyl-10-nitro-4,4-dioxo-5,6-dihydro-4aH-[1]benzothiepino[4,5-b][1,4]thiazin-2-yl]-N-tert-butoxycarbonyl-carbamate (1.18 g, 2.071 mmol), 10 wt. % Pd/C (0.220 g, 0.207 mmol), EtOAc (4.14 ml) and MeOH (4.14 ml). The flask was purged with nitrogen, evacuated, and filled with hydrogen. The reaction was stirred at RT under hydrogen atmosphere for 16 h. The reaction was incomplete, so another 100 mg of 10 wt. % Pd/C was added, and stirring under hydrogen was continued. After 8 h, the reaction was complete. The mixture was filtered through Celite and washed with EtOAc. The filtrate was concentrated to provide tert-butyl N-[(4aR,11bR)-10-amino-3,3,11b-trimethyl-4,4-dioxo-5,6-dihydro-4aH-[1]benzothiepino[4,5-b][1,4]thiazin-2-yl]-N-tert-butoxycarbonyl-carbamate (1.00 g, 89%) as a dark foamy solid. LC/MS (ESI$^+$) m/z=562.2 (M+Na). tert-Butyl N-[(4aS,11bR)-10-amino-3,3,11b-trimethyl-4,4-dioxo-5,6-dihydro-4aH-[1]benzothiepino[4,5-b][1,4]thiazin-2-yl]-N-tert-butoxycarbonyl-carbamate was prepared following the same hydrogenation procedure. The product was isolated as a dark foamy solid in 90% yield. LC/MS (ESI$^+$) m/z=562.2 (M+Na).

Intermediate 33-Trans

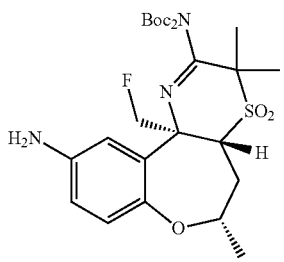

Synthesis of tert-butyl N-[(4aR,6S,11bS)-10-amino-11b-(fluoromethyl)-3,3,6-trimethyl-4,4-dioxo-5,6-dihydro-4aH-[1]benzoxepino[4,5-b][1,4]thiazin-2-yl]-N-tert-butoxycarbonyl-carbamate In an analogous sequence of reactions to that described in the preparation of trans intermediate 31, but using (S)-2-methyloxirane instead of 2,2-dimethyloxirane, tert-butyl N-tert-butoxycarbonyl-N-[(3S)-3-(fluoromethyl)-3-(2-fluoro-5-nitro-phenyl)-6,6-dimethyl-1,1-dioxo-2H-1,4-thiazin-5-yl]carbamate (preparation described in the synthesis of intermediate 22) was converted to the title compound (420 mg, 0.756 mmol, 36.5%) as a white foam. MS m/z=578.0 (M+Na).

Intermediate 33-Cis

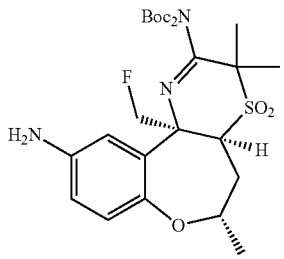

Synthesis of tert-butyl N-[(4a-5,6S,11bS)-10-amino-11b-(fluoromethyl)-3,3,6-trimethyl-4,4-dioxo-5,6-dihydro-4aH-[1]benzoxepino[4,5-b][1,4]thiazin-2-yl]-N-tert-butoxycarbonyl-carbamate In an analogous sequence of reactions to those described in the preparation of cis Intermediate 31, but using (S)-2-methyloxirane instead of 2,2-dimethyloxirane, tert-butyl N-tert-butoxycarbonyl-N-[(3S)-3-(fluoromethyl)-3-(2-fluoro-5-nitro-phenyl)-6,6-dimethyl-1,1-dioxo-2H-1,4-thiazin-5-yl] carbamate (preparation described in the synthesis of intermediate 22) was converted to the title compound (430 mg, 0.774 mmol, 37.4%) as a white foam. MS m/z=578.0 (M+Na).

Intermediate 34

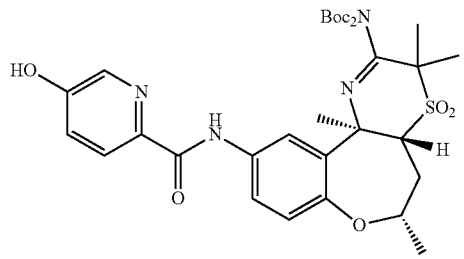

Synthesis of tert-Butyl N-[(4aR,6S,11bR)-10-[(5-hydroxypyridine-2-carbonyl)amino]3,3,6,11b-tetramethyl-4,4-dioxo-5,6-dihydro-4aH-[1]benzoxepino[4,5-b][1,4]thiazin-2-yl]-N-tert-butoxycarbonyl-carbamate To a solution of tert-butyl N-[(4aR,6S,11bR)-10-amino-3,3,6,11b-tetramethyl-4,4-dioxo-5,6-dihydro-4aH-[1]benzoxepino[4,5-b][1,4]thiazin-2-yl]-N-tert-butoxy carbonyl-carbamate (300 mg, 0.56 mmol), 5-hydroxypicolinic acid (93 mg, 0.67 mmol) and triethylamine (0.16 mL, 1.1 mmol) in DMF (5 mL) was added HATU (276 mg, 0.725 mmol). The reaction was stirred at ambient temperature. After 1 hour, the reaction mixture was partitioned between water and ethyl acetate; the organic layer was concentrated. The crude product was purified by column chromatography, eluting with 20-100% ethyl acetate in heptane, to provide the title compound (160 mg, 0.24 mmol, 43.5% yield) as an off-white solid. LC/MS (ESI$^+$) m/z: 682.0 (M+Na$^+$).

Intermediate 35

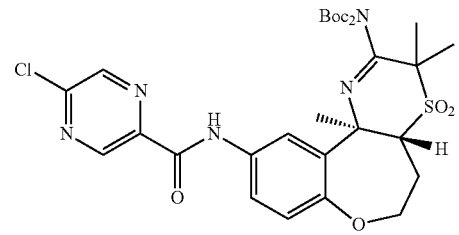

Synthesis of tert-butyl ((4aR,11bR)-10-(5-chloropyrazine-2-carboxamido)-3,3,11b-trimethyl-4,4-dioxido-4a,5,6,11b-tetrahydro-3H-benzo[6,7]oxepino[4,5-b][1,4]thiazin-2-yl)carbamate Using general method 3 (step 1), trans intermediate 19 (150 mg, 0.354 mmol) and 5-chloropyrazine-2-carboxylic acid (67.4 mg, 0.425 mmol) were combined to afford the title compound (140 mg, 0.248 mmol, 70.1%) as a white solid. MS m/z=564.0 (M+H).

Intermediate 36

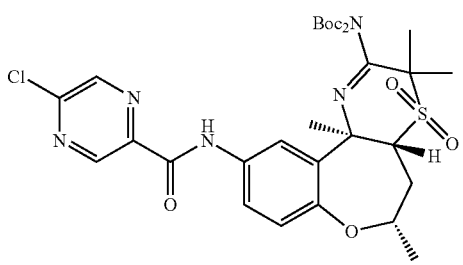

Synthesis of tert-butyl N-[(4aR,6S,11bR)-10-[(5-chloropyrazine-2-carbonyl)amino]-3,3,6,11b-tetramethyl-4,4-dioxo-5,6-dihydro-4aH-[1]benzoxepino[4,5-b][1,4]thiazin-2-yl]-N-tert-butoxycarbonyl-carbamate In a sealed tube, Intermediate 30 (0.58 g, 1.079 mmol) was dissolved in DMF (5.39 mL). To the resulting solution was added 5-chloropyrazine-2-carboxylic acid (0.188 g, 1.187 mmol), HATU (0.615 g, 1.618 mmol), and pyridine (0.262 mL, 3.24 mmol). The reaction was stirred at 20° C. for 2 hours. The reaction was extracted into ethyl acetate, washed once with water, once with brine, dried with sodium sulfate, filtered through a fritted funnel, and concentrated. The crude material was eluted through a silica gel column using 0-50% EtOAc/Heptane. The desired fractions were combined and concentrated to yield tert-butyl N-[(4aR,6S,11bR)-10-[(5-chloropyrazine-2-carbonyl)amino]-3,3,6,11b-tetramethyl-4,4-dioxo-5,6-dihydro-4aH-[1]benzoxepino[4,5-b][1,4]thiazin-2-yl]-N-tert-butoxycarbonyl-carbamate (0.640 g, 0.944 mmol, 87% yield) as an off-white solid.

Intermediate 37

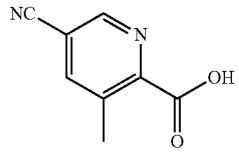

Synthesis of 5-cyano-3-methylpicolinic acid

Step 1: Synthesis of tert-butyl 5-bromo-3-methylpicolinate

To a 50-mL round-bottomed flask were added 5-bromo-3-methylpicolinic acid (7.95 g, 36.8 mmol) and di-tert-butyl dicarbonate (16.6 g, 73.6 mmol) in THF (73 ml) followed by addition of 4-(dimethylamino)pyridine (0.450 g, 3.68 mmol). It was stirred at RT for 3 h. It was quenched with sat. NaHCO₃ and extracted with EtOAc (3×80 ml). The organic phase was then washed with sat. NaHCO₃ again, and washed with brine and dried over MgSO4. The solution was filtered and concentrated in to give the crude material as a yellow oil. The crude material was purified by silica gel chromatography eluting with a gradient of 10% to 20% to 30% (40% EtOAc in Heptane) in Heptane, to provide tert-butyl 5-bromo-3-methylpicolinate (9.81 g, 36.0 mmol, 98% yield) as clear colorless oil. MS m/z=294.0/296.1 (M+Na)

Step 2: Synthesis of tert-butyl 5-cyano-3-methylpicolinate

A mixture of tert-butyl 5-bromo-3-methylpicolinate (7.47 g, 27.4 mmol), zinc cyanide (2.26 g, 19.21 mmol) and zinc dust (0.179 g, 2.74 mmol) was suspended in DMF (55 ml). The suspension was purged with N₂ and finally tri-tert-butylphosphine, 1.0M in toluene (2.196 ml, 2.196 mmol) was added under N₂ gas. The reaction mixture was heated to 80° C. for 2.5 h. Then 0.8 g of tri-tert-butylphosphine was added to reaction mixture and it was heated to 80° C. for another 5.5 h. The mixture was then cooled to RT and the grey suspension was filtered out. Then 175 ml of MTBE and 40 ml of water were added. The aqueous layer was washed with 75 ml of MTBE. The organic layer was then washed with 100 ml of water and brine. It was dried on MgSO₄ and concentrated. The crude material was concentrated to yield a yellow oil which was purified by chromatography through a Redi-Sep pre-packed silica gel column (330 g), eluting with a gradient of 20% to 30% to 40% (40% EtOAc in heptane) in heptane, to provide tert-butyl 5-cyano-3-methylpicolinate (3.72 g, 17.04 mmol, 62.1% yield) as white solid. MS m/z=241.2 (M+Na).

Step 3: Synthesis of 5-cyano-3-methylpicolinic acid

To a solution of tert-butyl 5-cyano-3-methylpicolinate (4.18 g, 19.15 mmol) in DCM (96 ml) was added TFA (148 ml, 1915 mmol), and the brown solution was stirred at RT for 2 h. The reaction mixture was concentrated. To the brown red residue was added EtOAc and it changed into a yellow slurry. It was concentrated again and dried on high vacuum. The reaction was triturated with 30 mL of MTBE and 50 ml of hexanes to yield 5-cyano-3-methylpicolinic acid (2.91 g, 17.95 mmol, 94% yield) as yellow solid. MS m/z=163.2 (M+H).

Intermediate 38

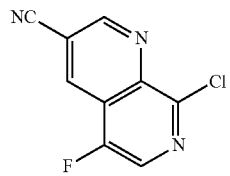 [SMILES: N#Cc1cnc2c(Cl)ncc(F)c2c1]

Synthesis of 8-chloro-5-fluoro-1,7-naphthyridine-3-carbonitrile

Step 1: 3-chloro-5-fluoro-6-methoxy-6,7-dihydro-1,7-naphthyridin-8(5H)-one

A pressure bottle was charged with 3-chloro-1,7-naphthyridin-8(7H)-one (15 g, 83 mmol), MeOH (34.6 ml), acetonitrile (173 ml) and Selectfluor (30.9 g, 87 mmol). The bottle was sealed and the mixture was heated at 50° C. for 6 h. An additional 2.5 g Selectfluor was added, and stirring was continued at 50° C. for 17 h. Upon cooling to RT, water and EtOAc were added, and the layers were separated. The aqueous portion was extracted two more times with EtOAc, and the combined organic portions were dried over sodium sulfate, filtered and concentrated. The crude solids were triturated with a minimum amount of EtOAc and filtered, which provided 15.34 g of product as a white solid. Upon standing for 17 h, additional solids precipitated out of the aqueous layer. These were filtered, washed with water and dried. 3-chloro-5-fluoro-6-methoxy-6,7-dihydro-1,7-naphthyridin-8(5H)-one was isolated with a combined yield of 18.62 g (96% yield) as a white solid. LC/MS (ESI$^+$) m/z=231.0 (M+H).

Step 2: 5-fluoro-6-methoxy-8-oxo-5,6,7,8-tetrahydro-1,7-naphthyridine-3-carbonitrile A pressure bottle was charged with Pd$_2$ dba$_3$ (1.032 g, 1.127 mmol), S-Phos (1.157 g, 2.82 mmol), ZnCN$_2$ (2.482 g, 21.14 mmol), 3-chloro-5-fluoro-6-methoxy-6,7-dihydro-1,7-naphthyridin-8(5H)-one (3.25 g, 14.09 mmol) and DMF (70.5 ml). The bottle was purged with argon and sealed, and the reaction mixture was heated at 110° C. for 1 h. Upon cooling to RT the crude reaction mixture was filtered through Celite and washed with MeOH. The filtrate was concentrated. The crude solids were triturated with DCM, filtered, washed with DCM and air-dried. 5-fluoro-6-methoxy-8-oxo-5,6,7,8-tetrahydro-1,7-naphthyridine-3-carbonitrile (2.27 g, 10.26 mmol, 72.8% yield) was isolated as an off white solid. LC/MS (ESI$^+$) m/z=222.0 (M+H).

Step 3: 8-chloro-5-fluoro-1,7-naphthyridine-3-carbonitrile

A pressure bottle was charged with 5-fluoro-6-methoxy-8-oxo-5,6,7,8-tetrahydro-1,7-naphthyridine-3-carbonitrile (2.27 g, 10.26 mmol), acetonitrile (41.1 ml) and POCl$_3$ (3.35 ml, 35.9 mmol). The bottle was sealed and the reaction was heated at 75° C. for 17 h. Upon cooling to RT the mixture was concentrated and the crude material was purified by silica gel chromatography, using a gradient of 0-20% 90/10 DCM/MeOH in DCM. 8-chloro-5-fluoro-1,7-naphthyridine-3-carbonitrile (1.2 g, 5.78 mmol, 56.3% yield) was isolated as a white solid. LC/MS (ESI$^+$) m/z=208.0 (M+H).

Intermediate 39

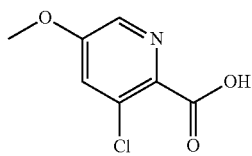

Synthesis of 3-chloro-5-methoxypicolinic acid

Step 1: Synthesis of methyl 3-chloro-5-methoxypicolinate

In a 1-L round bottom flask, the methyl 3-chloro-5-hydroxypicolinate (25.00 g, 133 mmol) and cesium carbonate (87 g, 267 mmol) were taken up in DMF (200 ml), and iodomethane (41.7 ml, 666 mmol) was added. A water-cooled condenser was attached, and the reaction vessel was heated in a 55° C. oil bath. After 3 h, the reaction was concentrated. The residue was taken up in 1.2 L of 80% EtOAc-hexane and 500 ml of brine. Not all the solids went in, so the mixture was filtered through Celite. The resulting filtrate's organic layer was separated, washed with brine (100 ml), dried over MgSO4 and concentrated. The residue was purified through silica gel using 30% to 40% EtOAc in hexane, affording 19.1 g (95 mmol) of a tan solid (71% yield). MS m/z=202 (M+H).

Step 2: Synthesis of 3-chloro-5-methoxypicolinic acid

In a 2-L round bottom flask, the methyl 3-chloro-5-methoxypicolinate (19.1 g, 95 mmol) was suspended in MeOH (104 ml). Aqueous 1N sodium hydroxide (104 ml, 104 mmol) was added. An air-cooled condenser was attached, and the reaction flask was heated in a 50° C. oil bath. After 1.5 h, the reaction was concentrated to remove the MeOH until a yellow sludge remained. The sludge was dissolved in 110 ml of water. The aqueous phase was extracted with diethyl ether (50 ml), which was discarded. The aqueous phase was acidified with aqueous hydrogen chloride (23 ml, 114 mmol), which caused extensive precipitation. The sludgy aqueous mixture was extracted with DCM in 6×250 ml. The organic layer were dried over MgSO$_4$ and concentrated to yield 3-chloro-5-methoxypicolinic acid (17.88 g, 95 mmol, 100%) as a yellow solid. MS m/z=188 (M+H).

Intermediate 40

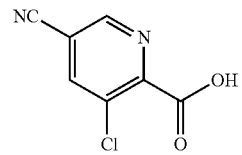 [SMILES: N#Cc1cnc(C(=O)O)c(Cl)c1]

Synthesis of 3-chloro-5-cyanopicolinic acid

Step 1: tert-butyl 5-bromo-3-chloropicolinate

To a 50-mL round-bottomed flask was added 5-bromo-3-chloropicolinic acid (1 g, 4.23 mmol) and di-tert-butyl dicarbonate (1.96 ml, 8.46 mmol) in THF (8.5 ml) followed by addition of 4-(dimethylamino)pyridine (0.052 g, 0.423 mmol). It was heated to 70° C. for 0.5 hr. It was quenched with sat. aq. NaHCO$_3$ and extracted with EtOAc. The organic phase was washed by sat. aq. NaHCO$_3$ and washed with brine and dried over MgSO$_4$. The solution was filtered and concentrated to give the crude material as a yellow oil. The crude material was absorbed onto a plug of silica gel and purified by chromatography through a Redi-Sep pre-packed silica gel column (40 g), eluting with a gradient of 15% to 25% to 35% (40% EtOAc in Heptane) in Heptane, to provide tert-butyl 5-bromo-3-chloropicolinate (1.15 g, 3.93 mmol, 93% yield) as clear colorless oil. MS m/z=314.0/316.0 (M+Na)

Step 2: Synthesis of tert-butyl 3-chloro-5-cyanopicolinate

A mixture of tert-butyl 5-bromo-3-chloropicolinate (12 g, 41.0 mmol), dicyanozinc (3.37 g, 28.7 mmol), and zinc (0.375 g, 5.74 mmol) were suspended in DMF (82 ml) in round bottom flak. The suspension was purged with N2 and finally Pd$_2$(dba)$_3$ (1.878 g, 2.051 mmol), tri-tert-butylphosphine (6.2 ml, 6.15 mmol) and neat tri-tert-butylphosphine (300 mg), was added under the Ar. The rxn mixture was heated to 95° C. for 3 h. Then another 2.8 g of Pd$_2$(dba)$_3$ and 1.2 g of neat P ligand were added. 3.5 h later, it was cooled to RT and black precipitate was filtered out by filtration. The filtrate was diluted with 150 ml of MTBE. The organic layer was washed with 100 ml of water and brine. It was dried on MgSO$_4$ and concentrated which was carried over to next step directly. MS m/z=261.0/263.0 (M+Na).

Step 3: Synthesis of 3-chloro-5-cyanopicolinic acid

To a solution of tert-butyl 3-chloro-5-cyanopicolinate (1.4 g, 3.23 mmol) in DCM (10.75 ml) was added TFA (25 ml, 323 mmol). The orange solution was stirred at RT for 1 hr. It was concentrated. Then the residue was passed through a PEAX column and the acid was eluted with 2% conc. HCl in MeOH (0.3 mL in 15 mL MeOH) to yield 3-chloro-5-cyanopicolinic acid (0.55 g, 3.01 mmol, 93% yield) as yellow solid. MS m/z=183 (M+H).

Intermediate 41

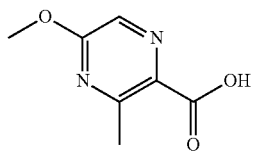

Synthesis of
5-ethoxy-3-methylpyrazine-2-carboxylic acid

Step 1: Methyl 3-methylpyrazine-2-carboxylate

A solution of 3-methylpyrazine-2-carboxylic acid (10 g, 72.4 mmol) in 80 mL methanol and sulfuric acid, 95% (5 ml, 90 mmol) was heated to 60° C. for 4 h. The solution was concentrated to remove MeOH, the residue was dissolved in 50 mL of water and neutralized with 10% aq Na$_2$CO$_3$ solution to pH 12. The resulting solution was extracted with ethyl acetate. The combined organics were dried and concentrated to give crude methyl 3-methylpyrazine-2-carboxylate (9.1 g, 83% yield) which was used for next step without further purification.

Step 2: 2-(Methoxycarbonyl)-3-methylpyrazine
1-oxide

To a solution of methyl 3-methylpyrazine-2-carboxylate (9.1 g, 59.8 mmol) in DCM (100 mL) at 0° C., was added urea hydrogen peroxide adduct, 97% (7.81 g, 83 mmol) and trifluoroacetic acid anhydride (10.8 ml, 78 mmol) dropwise. The resulting mixture was stirred at 0° C. for 1 h, and at room temperature for 18 h. The reaction was diluted with DCM and quenched with saturated Na$_2$SO$_3$ solution; the aqueous layer was back-extracted with DCM. The combined organic extracts were dried (MgSO4), filtered and concentrated in vacuo. The crude mixture was purified with ISCO (20% to 80% EtOAc/Hexanes) to afford a mixture of products: 2-(methoxycarbonyl)-3-methylpyrazine 1-oxide (5.2 g, 51.7% yield) and 3-(methoxycarbonyl)-2-methylpyrazine 1-oxide. The mixture was taken to next step without further purification.

Step 3: Methyl
6-chloro-3-methylpyrazine-2-carboxylate

A solution of mixture of 2-(methoxycarbonyl)-3-methylpyrazine 1-oxide compound with 3-(methoxycarbonyl)-2-methylpyrazine 1-oxide (1:1) (5.1 g, 15.17 mmol) in toluene (50 mL) was cooled to 0° C. To the mixture was added phosphorus oxychloride (2.78 ml, 30.3 mmol) under nitrogen followed by n,n'-dimethylformamide (0.117 ml, 1.517 mmol). The reaction mixture was stirred at room temperature for 4 h and then was heated to 65° C. for 18 h. The mixture was cooled to room temperature, diluted with EtOAc and washed with saturated NaHCO$_3$ solution. The aqueous layer was back-extracted with EtOAc. The combined organic extracts were dried (MgSO4), filtered and concentrated in vacuo. The mixture was purified with ISCO (0% to 50% EtOAc/Hexanes) to afford both isomers: methyl 5-chloro-3-methylpyrazine-2-carboxylate (0.68 g, 48.1% yield) and methyl 6-chloro-3-methylpyrazine-2-carboxylate (1.5 g, 106% yield).

Step 4:
5-Chloro-3-(methoxycarbonyl)-2-methylpyrazine
1-oxide

To a solution of methyl 6-chloro-3-methylpyrazine-2-carboxylate (8.6 g, 46.1 mmol) and hydrogen peroxide urea adduct (8.1 g, 86 mmol) in dichloromethane (100 mL) was added 2,2,2-trifluoroacetic anhydride (10.9 ml, 78 mmol) dropwise. The resulting mixture was stirred at room temperature for 2 h. The reaction mixture was diluted with DCM and quenched with water. The aqueous layer was extracted with DCM. The combined organic extracts were dried (MgSO$_4$), filtered and concentrated in vacuo to give the crude product 5-chloro-3-(methoxycarbonyl)-2-methylpyrazine 1-oxide (8.83 g, 43.6 mmol, 95% yield) which was used without further purification. $^1$H NMR (300 MHz, CDCl$_3$) δ ppm 8.31 (1H, s), 4.02 (3H, s), 2.65 (3H, s).

Step 5: Methyl
5,6-dichloro-3-methylpyrazine-2-carboxylate

To a solution of 5-chloro-3-(methoxycarbonyl)-2-methylpyrazine 1-oxide (8.83 g, 43.6 mmol) in toluene (100 mL) at 0° C. was added phosphorus oxychloride (10 ml, 109 mmol) and DMF (1 ml, 12.91 mmol). The reaction mixture was stirred at room temperature for 1 h, and then was heated to 85° C. fort 8 h. The mixture was cooled to RT and concentrated. The residue was diluted with EtOAc and washed with saturated NaHCO$_3$ solution. The combined organic extracts were dried (MgSO4), filtered and concentrated in vacuo. The crude mixture was purified with ISCO (0% to 10% EtOAc/Hexanes) to afford the desired methyl 5,6-dichloro-3-methylpyrazine-2-carboxylate (6.51 g, 68% yield). $^1$H NMR (300 MHz, CDCl$_3$) δ ppm 4.00 (3H, s), 2.83 (3H, s)

Step 6: Methyl
6-chloro-5-methoxy-3-methylpyrazine-2-carboxylate

To a solution of methyl 5,6-dichloro-3-methylpyrazine-2-carboxylate (6.17 g, 27.9 mmol) in anhydrous methanol (100 ml, 2.47 mol) at 0° C. was added potassium carbonate (4.30 g, 31.1 mmol) slowly. The suspension was stirred at 0° C. for 30 minutes and warmed to ambient temperature in 1 h. The solid was filtered and the filtrate was concentrated to give crude methyl 6-chloro-5-methoxy-3-methylpyrazine-2-carboxylate (6.2 g, 103% yield) which was used in next step without further purification.

Step 7: Methyl 5-methoxy-3-methylpyrazine-2-carboxylate

To a mixture of methyl 6-chloro-5-methoxy-3-methylpyrazine-2-carboxylate (6.5 g, 30.0 mmol) and palladium, 10% wt. on activated carbon (3.19 g, 3.00 mmol) in a 500 mL flask under nitrogen, was added acetone (200 mL) carefully. The flask was cooled to 0° C. and triethylamine (30 mL, 216 mmol) was added followed by formic acid (96%) (5.66 mL, 150 mmol) dropwise. The suspension was warmed to room temperature with stirring and then heated at 40° C. for 1 h. The reaction mixture was concentrated, diluted with saturated sodium hydrogenocarbonate solution and extracted with DCM. The organic layer was dried and concentrated. The crude product was purified by ISCO column chromatography using 0-20% EtOAc in DCM to give methyl 5-methoxy-3-methylpyrazine-2-carboxylate (5.2 g, 95% yield). $^1$H NMR (300 MHz, CDCl$_3$) δ ppm 8.11 (1H, s), 4.02 (3H, s), 3.97 (3H, s), 2.80 (3H, s)

Step 8: 5-Methoxy-3-methylpyrazine-2-carboxylic acid

To a solution of methyl 5-methoxy-3-methylpyrazine-2-carboxylate (5.1 g, 28.0 mmol) in MeOH (50 mL) was added sodium hydroxide 1.0 N solution (30.8 mL, 30.8 mmol). The reaction was heated to 40° C. for 2 h. The reaction mixture was concentrated, diluted with water and pH adjusted to 4. The solid that precipitated was filtered and dried. The remaining acidic solution was extracted with EtOAc and DCM. The combined organics were dried with Na$_2$SO$_4$, and concentrated in vacuo to give another batch of solid. The solids were combined and dried to give 5-methoxy-3-methylpyrazine-2-carboxylic acid (4.5 g, 96% yield). $^1$H NMR (300 MHz, DMSO-d$_6$) δ 13.00 (br. s., 1H), 8.18 (s, 1H), 3.96 (s, 3H), 2.67 (s, 3H).

Intermediate 42

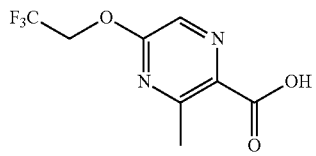 [SMILES: Cc1nc(OCC(F)(F)F)cnc1C(=O)O]

Synthesis of 3-methyl-5-(2,2,2-trifluoroethoxy)pyrazine-2-carboxylic acid

Sodium, which had been stored in mineral oil, was rinsed in hexane and cut into approximately 70-mg slivers. Those slivers of sodium (0.37 g, 16.08 mmol) were loaded into a 150-mL resealable vessel. The vessel was purged with argon, placed in a water bath, and 2,2,2-trifluoroethanol (31.2 mL, 429 mmol) was added. Bubbling ensued immediately. Bubbling had ceased and sodium had disappeared around 30 minutes. The mixture was stirred at room temperature for another 30 minutes. To this mixture was added methyl 5-chloro-3-methylpyrazine-2-carboxylate (1.00 g, 5.36 mmol). The vial was sealed and heated at 45° C. overnight. After addition of 1 M sodium hydroxide (5.90 mL, 5.90 mmol), the mixture was stirred at 45° C. overnight. The reaction mixture was concentrated to remove most of the trifluoroethanol. The residue was dissolved in the minimum amount of water (300 mL), and the aqueous phase was washed with diethyl ether (2×30 mL). The aqueous phase was acidified with 5 M HCl (5 mL). The aqueous phase was extracted with DCM until TLC (15% MeOH-DCM) showed product wasn't coming out any more. The organics were combined, dried over MgSO$_4$ and concentrated to give 3-methyl-5-(2,2,2-trifluoroethoxy)pyrazine-2-carboxylic acid (1.28 g, 100% yield). $^1$H NMR (300 MHz, CDCl$_3$) δ ppm 10.57 (br, 1H), 8.15 (s, 1H), 4.87 (qt, 2H, J=8.2), 2.93 (s, 3H).

Intermediate 43

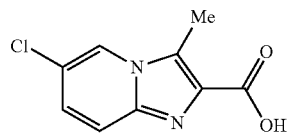 [SMILES: Cc1c(C(=O)O)nc2ccc(Cl)cn12]

Synthesis of 6-chloro-3-methylimidazo[1,2-a]pyridine-2-carboxylic acid

Step 1: Methyl 2-oxobutanoate

To a solution of 2-ketobutyric acid (6.72 g, 65.8 mmol) in 2,2-dimethoxypropane (100 ml, 816 mmol) and methanol (25 mL, 617 mmol) was added chlorotrimethylsilane (0.840 mL, 6.62 mmol). The reaction mixture was stirred at RT for 3 days and concentrated to give methyl 2-oxobutanoate (6.72 g, 57.9 mmol, 88% yield) as an orange liquid.

Step 2: Methyl 3-bromo-2-oxobutanoate

To a solution of methyl 2-oxobutanoate (6.92 g, 59.6 mmol) in DCM (60 mL) at 0° C. was added bromine (3.10 mL, 60.3 mmol). The reaction mixture was warmed to room temperature and stirred for 2 h, diluted with EtOAc, washed with saturated NaHCO$_3$ (2×), water (1×), brine (1×), dried over MgSO$_4$, filtered, and concentrated. The product, methyl 3-bromo-2-oxobutanoate, (8.26 g, 42.4 mmol, 71% yield) was used in the next step without further purification.

Step 3: Methyl 3-(5-chloro-2-iminopyridin-1-(2H)-yl)-2-oxobutanoate hydrobromide To a solution of methyl 3-bromo-2-oxobutanoate (8.26 g, 42.4 mmol) in DME (33 mL) at room temperature was added 2-amino-5-chloropyridine (5.45 g, 42.4 mmol). The reaction mixture was stirred at room temperature for 20 h. The solid was collected by filtration, washed with EtOAc (2×), and dried under high vacuum to give methyl 3-(5-chloro-2-iminopyridin-1(2H)-yl)-2-oxobutanoate hydrobromide (8.51 g, 26.3 mmol, 62% yield) as a white solid.

Step 4: Methyl 6-chloro-3-methylimidazo[1,2-a]pyridine-2-carboxylate

A solution of methyl 3-(5-chloro-2-iminopyridin-1(2H)-yl)-2-oxobutanoate hydrobromide (8.51 g, 26.3 mmol) in MeOH (50 mL) was heated to reflux for 16 h, cooled to room temperature, and concentrated to give a white solid. The solid was dissolved in a mixture of EtOAc and saturated NaHCO₃, the aqueous phase was discarded and the organic phase was washed with saturated NaHCO₃ (1×), water (1×), brine (1×), dried over MgSO₄, filtered, and concentrated to give methyl 6-chloro-3-methylimidazo[1,2-a]pyridine-2-carboxylate (5.68 g, 25.3 mmol, 96% yield) as an off white solid.

Step 5: 6-chloro-3-methylimidazo[1,2-a]pyridine-2-carboxylic acid

To a solution of methyl 6-chloro-3-methylimidazo[1,2-a]pyridine-2-carboxylate (1.01 g, 4.50 mmol) in MeOH (18 mL) at room temperature was added potassium hydroxide (407 mg, 7.25 mmol). The reaction mixture was heated to 50° C. for 15 h, and additional KOH (293 mg) was added. The reaction mixture was heated to reflux for 1 h, cooled to room temperature and 5 M HCl (2.5 mL) was added and the reaction mixture was concentrated. toluene (25 mL) was added to the concentrate and the toluene was evaporated under reduced pressure. This was repeated a second time and the concentrate was dried under high vacuum to give 6-chloro-3-methylimidazo[1,2-a]pyridine-2-carboxylic acid as an off white solid. MS m/z=210.9 [M+H]

Intermediate 44

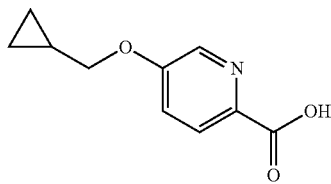 [SMILES: O=C(O)c1ccc(OCC2CC2)cn1]

Synthesis of 5-(cyclopropylmethoxy)picolinic acid

Step 1: Synthesis of 5-(cyclopropylmethoxy)picolinonitrile

To a disposable tube were added cyclopropylmethanol (0.44 ml, 5.41 mmol) in DMF (2 ml) and followed by addition of sodium hydride (60% dispersion in mineral oil) (260 mg, 6.50 mmol) slowly. It was stirred at RT for 15 min. Then 5-chloro-2-cyanopyridine (500 mg, 3.61 mmol) was added. It was stirred at RT for 1 h. Then the reaction mixture was diluted with water and extracted with EtOAc and tBuOMe. The organic extract was washed with brine and dried over MgSO4. The solution was filtered and concentrated to give the crude material as a dark brown oil. The crude material was absorbed onto a plug of silica gel and purified by chromatography through a Redi-Sep pre-packed silica gel column (40 g), eluting with a gradient of 15% to 30% to 45% EtOAc in heptane, to provide 5-(cyclopropylmethoxy)picolinonitrile as white solid mixed with cyclopropylmethanol. It was washed by heptane/tBuOMe (~5:1), and the white precipitate was collected by filtration to yield 5-(cyclopropylmethoxy) picolinonitrile (380 mg, 2.181 mmol, 60.4% yield) as white crystals. MS m/z=175.2 (M+H).

Step 2: Synthesis of 5-(cyclopropylmethoxy)picolinic acid

To a reaction vial was added 5-(cyclopropylmethoxy)picolinonitrile (120 mg, 0.689 mmol) in EtOH (2 ml) and 6N NaOH (2.9 ml, 17.22 mmol) was added. The mixture was heated to 90° C. for 1.5 h. The reaction mixture was concentrated and to the resulting residue was added 6N HCl until pH 2. The precipitate was collected to provide 5-(cyclopropylmethoxy)picolinic acid (50 mg, 0.259 mmol, 37.6% yield). MS m/z=194 (M+H).

Intermediate 45

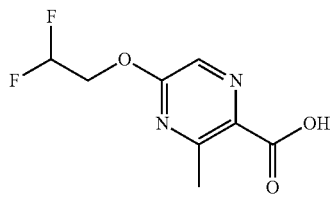

Synthesis of 5-(2,2-difluoroethoxy)-3-methylpyrazine-2-carboxylic acid

Step 1: Methyl 3-methylpyrazine-2-carboxylate

In a 2-L flask, 3-methylpyrazine-2-carboxylic acid (Matrix, 19.95 g, 144 mmol) was suspended in MeOH (500 mL). The suspension was cooled in an ice-water bath, and concentrated sulfuric acid (Fluka, 27.3 mL, 506 mmol) was added over a time period of 5 min. The reaction mixture was heated to 80° C. for 5 h. The reaction mixture was concentrated under reduced pressure and the residue was taken up in DCM (750 mL). The excess acid was neutralized carefully with aqueous NaOH (5M, 200 mL). The aqueous layer was separated and extracted with DCM (250 mL). The combined organic layers were combined, dried over MgSO₄ and concentrated to afford the title compound (16.15 g, 106 mmol, 73%). MS m/z=153 (M+H).

Step 2: 3-(Methoxycarbonyl)-2-methylpyrazine 1-oxide

In a 1-L flask, the methyl 3-methylpyrazine-2-carboxylate (step 1, 16.08 g, 106 mmol) was suspended in CHCl₃ (300 mL). 3-chlorobenzoperoxoic acid (Aldrich, 24.62 g, 143 mmol) was added. The reaction mixture was heated to 70° C. for 16 h. The reaction mixture was quenched with saturated NaHCO₃ (200 mL). The layers were separated, and the aqueous layer was further extracted with DCM (2×100 mL). The combined organic layers were dried over MgSO₄, and the filtrate was concentrated to afford the title compound. MS m/z=169 (M+H).

Step 3: Methyl 5-chloro-3-methylpyrazine-2-carboxylate

In a 1-L flask, the crude 3-(methoxycarbonyl)-2-methylpyrazine 1-oxide (step 2, 17.77 g, 106 mmol) was dissolved in DMF (300 mL). Neat phosphoryl trichloride (29.6 mL, 317 mmol) was added. The reaction mixture was heated to 100° C. After 1 h, the reaction mixture was concentrated to remove most of the DMF. The flask was cooled in an ice water bath, and 1 M aqueous Na₂CO₃ (300 mL) was added slowly, followed by 80% EtOAc-hexane (400 mL). The mixture was filtered through Celite. The resulting filtrate was partitioned and the aqueous phase was extracted further with 80%

EtOAc-hexane (2×250 mL). The combined organic layers were dried over MgSO$_4$ and concentrated. The material was purified through silica gel using 11% EtOAc-hexane to afford the title compound (4.29 g, 23 mmol, 22%). MS m/z=187 (M+H).

Step 4: methyl 5-(2,2-difluoroethoxy)-3-methylpyrazine-2-carboxylate

To a mixture of methyl 5-chloro-3-methylpyrazine-2-carboxylate (255 mg, 1.367 mmol) in 2,2-difluoroethanol (0.52 mL, 8.20 mmol) was added potassium carbonate (227 mg, 1.640 mmol). The reaction was stirred at ambient temperature for 1.5 hrs. The reaction was treated with water and extracted with ethyl acetate. The organic portion was dried over Na$_2$SO$_4$, filtered, concentrated and purified by column chromatography, eluting with 0-2% MeOH/DCM to give the title compound (63.8 mg, 0.275 mmol, 20.1%). MS m/z=233.1 (M+H).

Step 5: 5-(2,2-difluoroethoxy)-3-methylpyrazine-2-carboxylic acid

A mixture of methyl 5-(2,2-difluoroethoxy)-3-methylpyrazine-2-carboxylate (63.8 mg, 0.275 mmol) in aqueous 2N HCl (1 mL) and Dioxane (2 mL) was stirred at ambient temperature for 20 hrs. The reaction was concentrated and the resulting solid was rinsed with acetonitrile. The filtrate was collected and concentrated in vacuo to give the title compound (60 mg, 0.275 mmol, 100%) as a white solid. MS m/z=219.1 (M+H).

Intermediate 46

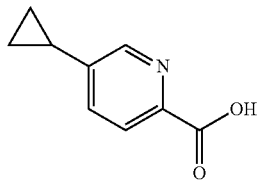 [SMILES: O=C(O)c1ccc(C2CC2)cn1]

Synthesis of 5-cyclopropylpicolinic acid

Step 1: Synthesis of methyl 5-cyclopropylpicolinate

To a sealed tube were added methyl 5-bromopicolinate (700 mg, 3.24 mmol) in THF (10 ml). The reaction mixture was purged with Ar followed by addition of tetrakis(triphenylphosphine)palladium (187 mg, 0.162 mmol) and finally cyclopropylzinc bromide solution 0.5 m in tetrahydrofuran (7.78 mL, 3.89 mmol). The tube was sealed and heated to 80° C. for 1.5 hrs. Then it was diluted with water, and extracted with EtOAc. The organic layer was washed with brine and concentrated to give crude product. The crude material was purified by chromatography through a Redi-Sep pre-packed silica gel column (40 g), eluting with a gradient of 25% to 40% to 60% EtOAc in Heptane, to provide methyl 5-cyclopropylpicolinate (420 mg, 2.370 mmol, 73.1% yield) as off-white solid. MS m/z=178.2 (M+H).

Step 2: Synthesis of 5-cyclopropylpicolinic acid

To a reaction vial were added methyl 5-cyclopropylpicolinate (370 mg, 2.088 mmol) and potassium hydroxide (258 mg, 4.59 mmol) in MeOH (7 ml). The reaction mixture was heated to 50° C. for 1 h. It was concentrated and was treated with small amount of water, and acidified by 6N HCl until pH 2. Then the mixture was concentrated and MeOH was added. The white salt was filtered out and the filtrate was passed through silica plug to yield desired product as yellow solid which still contains some salt. It was used directly for next step. MS m/z=164.2 (M+H).

Intermediate 47

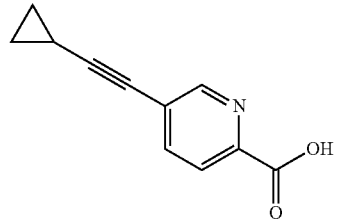 [SMILES: O=C(O)c1ccc(C#CC2CC2)cn1]

Synthesis of 5-(cyclopropylethynyl)picolinic acid

Step 1: Synthesis of methyl 5-(cyclopropylethynyl)picolinate

To a sealed tube were added methyl 5-bromopyridine-2-carboxylate (450 mg, 2.083 mmol) in THF (4 ml) followed by tetrakis(triphenylphosphine)palladium (193 mg, 0.167 mmol), copper(i) iodide (20 mg, 0.104 mmol), triethylamine (2.3 ml, 16.66 mmol) under N2. Finally cyclopropylacetylene (275 mg, 4.17 mmol) was added. The yellow mixture was stirred at 40° C. for overnight. The reaction mixture was diluted with water and extracted with EtOAc. The organic layer was washed with brine and dried over MgSO4. The solution was filtered and concentrated to give the crude material as an orange oil. The crude material was purified by chromatography through a Redi-Sep pre-packed silica gel column (40 g), eluting with a gradient of 15% to 30% to 45% EtOAc in Heptane, to provide methyl 5-(cyclopropylethynyl) picolinate (390 mg, 1.938 mmol, 93% yield) as an orange solid. MS m/z=202.2 (M+H).

Step 2: Synthesis of 5-(cyclopropylethynyl)picolinic acid

To a small flask were added methyl 5-(cyclopropylethynyl) picolinate (240 mg, 1.193 mmol) and potassium hydroxide (147 mg, 2.62 mmol) in MeOH (4 ml). The mixture was stirred at 50° C. for 20 min. It was cooled to RT and the solvent was reduced. The white solid was treated with small amount of water (~1.5 mL), and acidified by 6N HCl to pH 2. The light brown precipitate was formed and the resulting mixture was cooled to 0° C. by ice bath. The brown precipitate was collected by filtration to yield 5-(cyclopropylethynyl) picolinic acid (163 mg, 0.871 mmol, 73.0% yield) as light

Intermediate 48

Synthesis of 5-(methoxymethyl)picolinic acid

Step 1: 2-chloro-5-(methoxymethyl)pyridine

To a solution of 2-chloro-5-hydroxymethylpyridine (1 g, 6.97 mmol) in THF (34.8 ml) was added sodium hydride (60% wt) (0.418 g, 10.45 mmol). The reaction was stirred for 10 minutes and treated with methyl iodide (0.653 ml, 10.45 mmol). The reaction was stirred at ambient temperature for 4 hrs. The reaction mixture was quenched with saturated NH$_4$Cl and extracted with EtOAc. The organic portion was concentrated and purified in 10-40% EtOAc/Heptanes to give the title compound (880 mg, 5.58 mmol, 80% yield) as a tan solid. MS m/z=157.9 (M+H).

Step 2: 5-(methoxymethyl)picolinonitrile

A mixture of 2-chloro-5-(methoxymethyl)pyridine (0.831 g, 5.27 mmol), tetrakis (1.219 g, 1.055 mmol), dicyanozinc (0.929 g, 7.91 mmol) and DMF (17.58 ml) was stirred at 100° C. for 3 hrs. The reaction was treated with water and extracted with EtOAc. The organic portion was dried over Na$_2$SO$_4$, filtered, and concentrated in vacuo. The crude material was purified by column chromatography, eluting with 10-40% EtOAc/Heptanes to give the title compound (550 mg, 3.71 mmol, 70.4%). MS m/z=149.1 (M+H).

Step 3: 5-(methoxymethyl)picolinic acid

A mixture of 5-(methoxymethyl)picolinonitrile (207 mg, 1.397 mmol) in NaOH (aq. 5N) (2794 µl, 13.97 mmol) and EtOH (5588 µl) was stirred at 80° C. for 16 hrs. The reaction was concentrated to half its volume and treated with 2N HCl until the pH reached ~5. The product was extracted with ethyl acetate. The organic portion was dried over Na$_2$SO$_4$, filtered and concentrated in vacuo to give the title compound (210 mg, 1.26 mmol, 90%) as an off-white solid. MS m/z=167.9 (M+H).

Intermediate 49

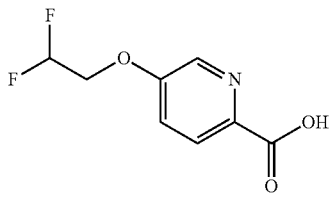 [SMILES: O=C(O)c1ccc(OCC(F)F)cn1]

Synthesis of 5-(2,2-difluoroethoxy)picolinic acid

To a mixture of 5-hydroxy-2-pyridinecarboxylic acid methyl ester (0.253 mL, 2.122 mmol), cesium carbonate (1.11 g, 3.40 mmol) and DMF (4.25 mL) was added 2,2-difluoroethyl trifluoromethanesulfonate (0.682 mL, 3.18 mmol). The reaction was stirred at ambient temperature for 3 hrs. The reaction was partitioned between water and ethyl acetate. The organic portion was concentrated and the residue was treated with 5 mL of THF and LiOH (Aq. 2N) (3.18 mL, 6.37 mmol). The reaction was stirred at ambient temperature for 16 hrs. The reaction was treated with 6N HCl until the pH reached ~2 and then diluted with ethyl acetate. The organic portion was dried over Na$_2$SO$_4$, filtered and concentrated in vacuo to give the title compound (370 mg, 1.821 mmol, 86%) as a tan solid. MS m/z=204.1 (M+H).

Intermediate 50

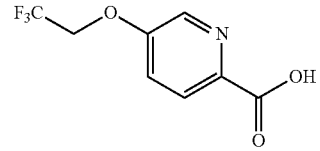 [SMILES: O=C(O)c1ccc(OCC(F)(F)F)cn1]

Synthesis of 5-(2,2,2-trifluoroethoxy)picolinic acid

Analogous to the preparation of intermediate 49, 5-hydroxy-2-pyridinecarboxylic acid methyl ester (0.253 mL, 2.122 mmol) and 2,2,2-trifluoroethyl trifluoromethanesulfonate (0.739 mL, 3.18 mmol) were combined to afford the title compound (390 mg, 1.764 mmol, 83%) as a white solid. MS m/z=222.1 (M+H).

Intermediate 51

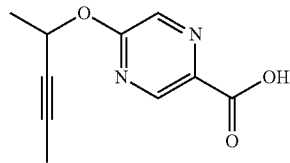

Synthesis of 5-(Pent-3-yn-2-yloxy)pyrazine-2-caboxylic acid 50 ml RBF was charged with 3-pentyn-2-ol (2.063 ml, 22.08 mmol) in DMF (10 ml) and potassium t-butoxide (1.24 g, 11.04 mmol) was added portionwise while stirring (cooling in water bath). The mixture was stirred at room temperature for 10 min until all t-BuOK went into solution, then 5-chloropyrazine-2-carboxylic acid (500 mg, 3.15 mmol) was added in portions and the resulting brown suspension was heated at 75° C. for 45 min. The mixture was cooled to room temperature and diluted with water (~20 ml) until all solids dissolved, then acidified with 2M HCl solution (~5.5 ml) to pH 2. The resulting solution was extracted with EtOAc, organic layer was washed with water twice then with brine, filtered through pad of celite and concentrated in vacuo. The (continued from previous: yellow solid. It was dried in high vacuum for overnight and was used directly for next step. MS m/z=188.1 (M+H).)

resulting suspension was diluted with 3 ml heptane/EtOAc (20:1) mixture then filtered. The solid was washed with heptane and dried in vacuo to afford 5-(pent-3-yn-2-yloxy)pyrazine-2-carboxylic acid (424 mg, 2.056 mmol, 65.2% yield) as tan solid. LC/MS (ESI+) m/z=207 (M+H).

Intermediate 52

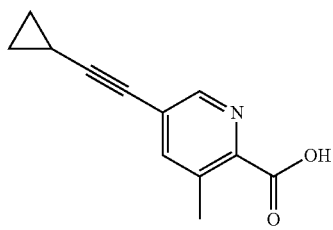

Synthesis of 5-(cyclopropylethynyl)-3-methylpicolinic acid

To a glass pressure vessel was added 5-bromo-3-methylpicolinic acid (0.250 g, 1.157 mmol), copper(i) iodide (0.033 g, 0.174 mmol), and PdCl$_2$(dppf)-CH$_2$Cl$_2$ adduct (0.066 g, 0.081 mmol). The flask was purged with nitrogen and DMF (3.86 mL), cyclopropylacetylene (0.196 mL, 2.314 mmol), and diisopropylamine (0.825 mL, 5.79 mmol) were added. The flask was purged again with nitrogen, sealed and stirred at 70° C. for 30 minutes. The reaction was cooled to room temperature. Water and ethyl acetate were added to the reaction and the layers were separated. The aqueous layer was then acidified to ~pH 6 by the addition of 2 N hydrochloric acid and extracted into ethyl acetate, washed once with water, once with sodium chloride, dried with sodium sulfate, filtered through a fritted funnel, and concentrated down to yield the desired acid as a brown oil. The crude material was eluted through a reverse phase column using 0-75% 1% TFA in MeCN/1% TFA in water, extracted into ethyl acetate, washed once with water, dried with sodium sulfate, filtered through a flitted funnel, and concentrated to yield 5-(cyclopropylethynyl)-3-methylpicolinic acid (0.110 g, 0.547 mmol, 47.2% yield) as a tan solid. LC/MS (ESI+) m/z=202.1.

Intermediate 53

Synthesis of (rac)-8-chloro-5-fluoro-3-(pent-3-yn-2-yloxy)-1,7-naphthyridine and (rac)-8-bromo-5-fluoro-3-(pent-3-yn-2-yloxy)-1,7-naphthyridine Step 1: (rac)-8-chloro-5-fluoro-1,7-naphthyridin-3-ol and (rac)-8-bromo-5-fluoro-1,7-naphthyridin-3-ol A pressure-resistant vessel was charged with 8-chloro-5-fluoro-3-methoxy-1,7-naphthyridine, Intermediate 10 (0.75 g, 3.53 mmol) and DCE (3.53 mL). To this was added BBr$_3$ (1.0 M in dichloromethane) (17.64 mL, 17.64 mmol) slowly via syringe. The resulting heterogeneous mixture was heated to 70° C. and stirred overnight. The reaction was quenched by slow addition to a beaker containing methanol on ice. The resulting yellow solution was concentrated down. The crude material was eluted through a silica gel column using 0-15% DCM:MeOH:NH$_4$OH (90:10:1)/DCM. The desired fractions were combined and concentrated down to yield a mixture of (rac)-8-chloro-5-fluoro-1,7-naphthyridin-3-ol and (rac)-8-bromo-5-fluoro-1,7-naphthyridin-3-ol. The material was used without further purification.

Step 2: (rac)-8-chloro-5-fluoro-3-(pent-3-yn-2-yloxy)-1,7-naphthyridine and (rac)-8-bromo-5-fluoro-3-(pent-3-yn-2-yloxy)-1,7-naphthyridine A sealed tube was charged with (rac)-8-chloro-5-fluoro-1,7-naphthyridin-3-ol and (rac)-8-bromo-5-fluoro-1,7-naphthyridin-3-o (0.300 g, 1.511 mmol) and pent-3-yn-2-ol (0.418 mL, 4.53 mmol) in THF (5.04 mL) followed by triphenylphosphine (1.19 g, 4.53 mmol). The reaction mixture was cooled to 0° C. and stirred for several minutes and diisopropyl azodicarboxylate (0.891 mL, 4.53 mmol) was added slowly. The ice bath was removed and the mixture was stirred at ambient temperature for 10 minutes. The reaction was quenched with water and extracted into ethyl acetate, washed once with water, once with sodium chloride, dried with sodium sulfate, filtered through a fritted funnel, and concentrated down. The crude material was eluted through a silica gel column using 0-50% EtOAc/Heptane. The desired fractions were combined and concentrated down to yield product as a mixture of (rac)-8-chloro-5-fluoro-3-(pent-3-yn-2-yloxy)-1,7-naphthyridine and (rac)-8-bromo-5-fluoro-3-(pent-3-yn-2-yloxy)-1,7-naphthyridine (0.320 g, 1.21 mmol, 80% yield). LC/MS (ESI+) m/z=265.1 and 309.0.

Intermediate 54

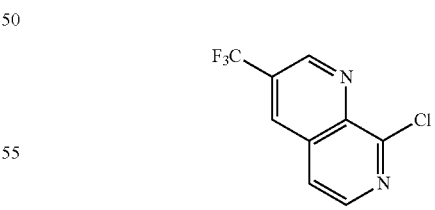

Synthesis of 8-chloro-3-(trifluoromethyl)-1,7-naphthyridine

A pressure vial was charged with 3-(trifluoromethyl)-1,7-naphthyridin-8(7H)-one (Anichem) (75 mg, 0.350 mmol), toluene (1401 μl), and Hunig's base (184 μl, 1.051 mmol). To this mixture was added POCl$_3$ (98 μl, 1.051 mmol), and the vial was sealed. The reaction was heated at 115° C. for 2 h.

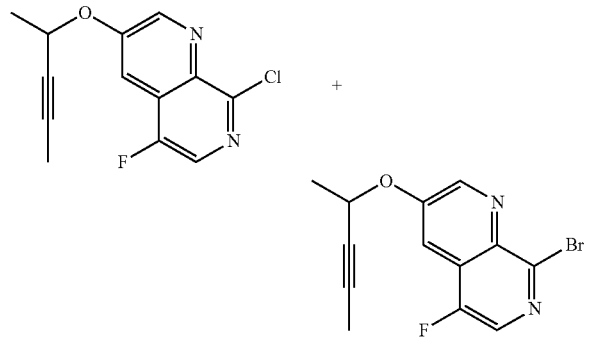

After 6 h, some unreacted starting material remained. The temperature was increased to 125° C. and the reaction was stirred overnight. Upon cooling to RT, EtOAc and water were added, and the layers were separated. The aqueous portion was extracted with additional EtOAc, and the combined organic portions were dried over sodium sulfate, filtered and concentrated. The crude material was purified by silica gel chromatography using a gradient of 0-50% EtOAc in heptane to provide 8-chloro-3-(trifluoromethyl)-1,7-naphthyridine (78 mg, 0.335 mmol, 96%) as a tan solid. LC/MS (ESI⁺) m/z=233.1 (M+H).

Intermediate 55

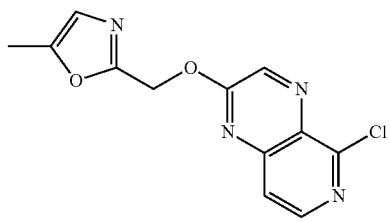 [SMILES: Cc1cnc(COc2cnc3c(Cl)nccc3n2)o1]

Synthesis of 2-(((5-Chloropyrido[3,4-b]pyrazin-2-yl)oxy)methyl)-5-methyloxazole

Step 1: 5-Chloropyrido[3,4-b]pyrazin-2-ol

A pressure-resistant vessel was charged with 5-chloro-2-methoxypyrido[3,4-b]pyrazine (5.0 g, 26 mmol) and DCE (25 mL). To this was added a 1M solution of boron tribromide in dichloromethane (82 mL, 82 mmol) slowly via syringe. The vessel was sealed, and the reaction was stirred at ambient temperature overnight. After 16 hours, the reaction was quenched by slow addition of the reaction mixture into a beaker containing methanol (100 mL) and ice. The resulting yellow solution was concentrated to a tan slurry, which was triturated with ethyl acetate (50 mL). The off-white precipitate was collected by vacuum filtration, washed with ethyl acetate, and dried in vacuo to provide the title compound (7.2 g, 40 mmol, 155% yield) along with some bromide salts. LC/MS (ESI⁺) m/z: 182.1 (M+H⁺).

Step 2: 2-(((5-Chloropyrido[3,4-b]pyrazin-2-yl)oxy)methyl)-5-methyloxazole

To a solution of 5-chloropyrido[3,4-b]pyrazin-2-ol (200 mg, 1.1 mmol) and (5-methyloxazol-2-yl)methanol (187 mg, 1.6 mmol) in tetrahydrofuran (5 mL) was added triphenylphosphine (433 mg, 1.6 mmol). The reaction mixture was cooled to 0° C. and diisopropyl azodicarboxylate (0.33 mL, 1.6 mmol) was added slowly. The reaction was stirred at 0° C. for 1 hour, and then allowed to warm to ambient temperature overnight. After 16 hours, the reaction was quenched with water and extracted into ethyl acetate. The organic layer was concentrated, and the crude product was purified by column chromatography, eluting with 20-80% (3:1 ethyl acetate/ethanol) in heptane. The less-polar isomer was isolated to provide the title compound (120 mg, 0.43 mmol, 79% yield) as a white solid. LC/MS (ESI⁺) m/z: 277.0 (M+H⁺).

Intermediate 56

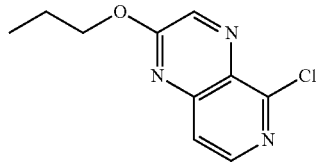

Synthesis of 5-Chloro-2-propoxypyrido[3,4-b]pyrazine

The title compound was prepared as described for Intermediate 55, except that 1-propanol was used instead of (5-methyloxazol-2-yl)methanol in Step 2, in 50% yield. LC/MS (ESI⁺) m/z: 224.1 (M+H⁺).

Intermediate 57

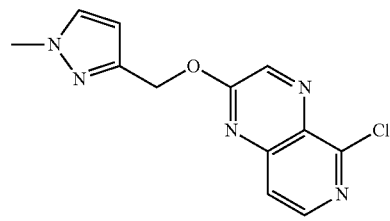 [SMILES: Cn1ccc(COc2cnc3c(Cl)nccc3n2)n1]

Synthesis of 5-Chloro-2-((1-methyl-1H-pyrazol-3-yl)methoxy)pyrido[3,4-b]pyrazine The title compound was prepared as described for Intermediate 55, except that (1-methyl-1H-pyrazol-3-yl)methanol was used instead of (5-methyloxazol-2-yl)methanol in Step 2, in 40% yield. LC/MS (ESI⁺) m/z: 276.0 (M+H⁺).

Intermediate 58

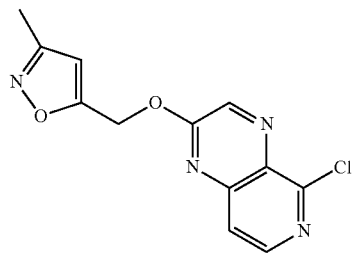 [SMILES: Cc1cc(COc2cnc3c(Cl)nccc3n2)on1]

Synthesis of 5-(((5-Chloropyrido[3,4-b]pyrazin-2-yl)oxy)methyl)-3-methylisoxazole The title compound was prepared as described for Intermediate 55, except that (3-methylisoxazol-5-yl)methanol was used instead of (5-methyloxazol-2-yl)methanol in Step 2, in 39% yield. LC/MS (ESI⁺) m/z: 277.0 (M+H⁺).

Intermediate 59

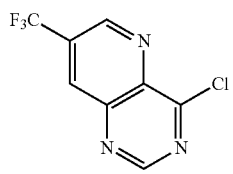 [SMILES: FC(F)(F)c1cnc2c(Cl)ncnc2c1]

Synthesis of 4-chloro-7-(trifluoromethyl)pyrido[3,2-d]pyrimidine

Step 1: 3-nitro-5-(trifluoromethyl)picolinonitrile

A microwave reaction vial was charged with 2-chloro-3-nitro-5-(trifluoromethyl)pyridine (2 g, 8.83 mmol), NMP (4.41 ml) and CuCN (0.830 g, 9.27 mmol). The vial was sealed and the mixture was irradiated in the MW at 175° C. for 15 min. Upon cooling to RT, the reaction mixture was poured onto ice and EtOAc was added. The mixture was filtered through Celite, washing with EtOAc and a small amount of MeOH. The layers of the filtrate were separated, and the aqueous portion was extracted again with EtOAc. The combined organic portions were dried with sodium sulfate, filtered and concentrated. The crude material was purified by silica gel chromatography, using a gradient of 0-30% EtOAc in heptane to provide 3-nitro-5-(trifluoromethyl)picolinonitrile (645 mg, 2.97 mmol, 33.7% yield) as a yellow oil that solidified upon standing. LC/MS (ESI) m/z=218.1 (M+H).

Step 2: 3-nitro-5-(trifluoromethyl)picolinamide

A round bottom flask was charged with 3-nitro-5-(trifluoromethyl)picolinonitrile (910 mg, 4.19 mmol) and sulfuric acid (4192 µl, 4.19 mmol), and the mixture was stirred at 60° C. for 16 h. Upon cooling to RT the crude mixture was poured onto ice, and the resulting solids were filtered, washed with water and dried. 3-nitro-5-(trifluoromethyl)picolinamide (850 mg, 3.62 mmol, 86% yield) was isolated as a light yellow solid. LC/MS (ESI⁺) m/z=236.1 (M+H).

Step 3: 3-amino-5-(trifluoromethyl)picolinamide

A round bottom flask was charged with 3-nitro-5-(trifluoromethyl)picolinamide (850 mg, 3.62 mmol) and wet 5 wt. % Pd/C (769 mg, 0.362 mmol) and was purged with nitrogen. EtOAc (7230 µl) and then MeOH (7230 µl) were added, and the flask was evacuated and filled with hydrogen. The reaction was stirred at RT under hydrogen atmosphere for 17 h. The mixture was filtered through Celite and washed with EtOAc and MeOH. The filtrate was concentrated to provide 3-amino-5-(trifluoromethyl)picolinamide (720 mg, 3.51 mmol, 97% yield) as a white solid. LC/MS (ESI⁺) m/z=206.1 (M+H).

Step 4: 7-(trifluoromethyl)pyrido[3,2-d]pyrimidin-4(3H)-one

A vial was charged with 3-amino-5-(trifluoromethyl)picolinamide (615 mg, 3.00 mmol) and triethyl orthoformate (2496 µl, 14.99 mmol). The vial was sealed and the mixture was heated at 120° C. for 17 h. Upon cooling, the heterogeneous mixture was filtered and the solids were washed with heptane. 7-(trifluoromethyl)pyrido[3,2-d]pyrimidin-4(3H)-one (540 mg, 2.51 mmol, 84% yield) was isolated as a tan solid. LC/MS (ESI) m/z=216.0 (M+H).

Step 5: 4-chloro-7-(trifluoromethyl)pyrido[3,2-d]pyrimidine

A pressure bottle was charged with 7-(trifluoromethyl)pyrido[3,2-d]pyrimidin-4(3H)-one (540 mg, 2.51 mmol), toluene (10.000 mL) and Hunig's base (1.315 mL, 7.53 mmol). POCl₃ (0.702 mL, 7.53 mmol) was added, and the bottle was sealed. The mixture was heated to 115° C. for 4 h. After cooling to RT, the mixture was diluted with EtOAc and water, and the layers were separated. The aqueous portion was extracted with additional EtOAc, and the combined organic portions were washed with saturated sodium bicarbonate, dried over sodium sulfate, filtered and concentrated. 4-chloro-7-(trifluoromethyl)pyrido[3,2-d]pyrimidine (560 mg, 2.397 mmol, 96% yield) was isolated as a brown solid. LC/MS (ESI⁺) m/z=234.0 (M+H).

Intermediate 60

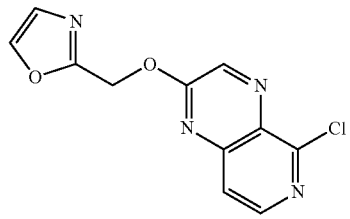 [SMILES: Clc1nccc2nc(OCc3ncco3)cnc12]

Synthesis of 2-(((5-Chloropyrido[3,4-b]pyrazin-2-yl)oxy)methyl)oxazole

The title compound was prepared as described for Intermediate 55, except that oxazol-2-ylmethanol was used instead of (5-methyloxazol-2-yl)methanol in Step 2, in 16% yield. LC/MS (ESI⁺) m/z: 263.0 (M+H⁺).

Intermediate 61

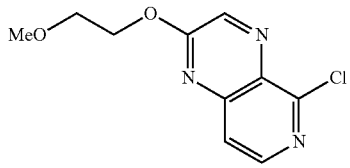 [SMILES: COCCOc1cnc2c(Cl)nccc2n1]

Synthesis of 5-Chloro-2-(2-methoxyethoxy)pyrido[3,4-b]pyrazine

The title compound was prepared as described for Intermediate 55, except that 2-methoxyethanol was used instead of (5-methyloxazol-2-yl)methanol in Step 2, as a mixture with diisopropyl hydrazine-1,2-dicarboxylate. The isolated product was used in subsequent reactions without further purification. LC/MS (ESI⁺) m/z: 240.1 (M+H⁺).

Intermediate 62

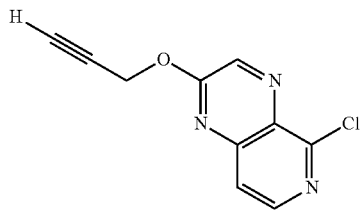 [SMILES: C#CCOc1cnc2c(Cl)nccc2n1]

Synthesis of 5-Chloro-2-(prop-2-yn-1-yloxy)pyrido[3,4-b]pyrazine

The title compound was prepared as described for Intermediate 55, except that propargyl alcohol was used instead of (5-methyloxazol-2-yl)methanol in Step 2, as a mixture with diisopropyl hydrazine-1,2-dicarboxylate. The isolated product was used in subsequent reactions without further purification. LC/MS (ESI⁺) m/z: 219.9 (M+H⁺).

Intermediate 63

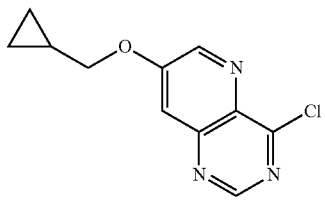 [SMILES: Clc1ncnc2cc(OCC3CC3)cnc12]

Synthesis of 4-chloro-7-(cyclopropylmethoxy)pyrido[3,2-d]pyrimidine

Step 1: Synthesis of 7-(cyclopropylmethoxy)pyrido[3,2-d]pyrimidin-4(1H)-one

To a glass microwave reaction vessel (2-5 ml) were charged with cyclopropylmethanol (3.1 ml, 38.6 mmol) and sodium hydride (60% dispersion in mineral oil) (416 mg, 17.35 mmol). The reaction mixture was stirred at RT for several min. Finally 7-chloropyrido[3,2-d]pyrimidin-4(1H)-one (350 mg, 1.928 mmol) (from intermediate 11, step 1 & 2) was added, and the mixture was heated in a Initiator microwave reactor at 140° C. for 10 min. Then it was quenched with water and sat. NH₄Cl and extracted with EtOAc for five times. The organic extract was washed with brine and dried over MgSO4. The solution was filtered and concentrated to give the crude material as a mixture. It was washed with Et2O and the brown solid was collected by filtration to yield 7-(cyclopropylmethoxy)pyrido[3,2-d]pyrimidin-4(1H)-one (50 mg, 0.230 mmol, 12% yield) as brown solid which was used for next step directly. MS m/z=218.1 (M+H).

Step 2: Synthesis of 4-chloro-7-(cyclopropylmethoxy)pyrido[3,2-d]pyrimidine

To a mixture of 7-(cyclopropylmethoxy)pyrido[3,2-d]pyrimidin-4(1H)-one (50 mg, 0.230 mmol) in Toluene (1.6 ml) were added diisopropylethylamine (122 µl, 0.702 mmol) and phosphorus oxychloride (65.3 µl, 0.714 mmol). The resulting reaction mixture was refluxed at 130° C. for 15 min. It was concentrated and the residue was dissolved in DCM and neutralized with sat. NaHCO₃ until PH=6-7. The mixture was passed through silica plug. The filtrate was diluted with water and extracted with DCM for three times. The organic extract was washed with brine and dried over MgSO4. The solution was filtered and concentrated to give the crude material as a dark brown solid. It was used for next step directly. MS m/z=236.1 (M+H).

Intermediate 64

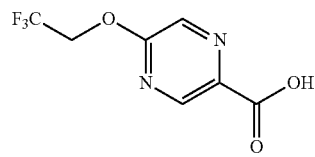 [SMILES: O=C(O)c1cnc(OCC(F)(F)F)cn1]

Synthesis of 5-(2,2,2-trifluoroethoxy)pyrazine-2-carboxylic acid

Step 1: methyl 5-(2,2,2-trifluoroethoxy)pyrazine-2-carboxylate

To a mixture of methyl 5-chloropyrazine-2-carboxylate (1 g, 5.79 mmol) and 2,2,2-trifluoroethanol (2.111 ml, 29.0 mmol) was added potassium carbonate (0.801 g, 5.79 mmol). The reaction was stirred at ambient temperature for 16 hrs. The reaction was partitioned between ethyl acetate and water. The organic portion was concentrated and purified in 10-60% EtOAc/Heptane to give the title compound (1.1 g, 4.66 mmol, 80%). MS m/z=237.1 (M+H).

Step 2: 5-(2,2,2-trifluoroethoxy)pyrazine-2-carboxylic acid

To a mixture of methyl 5-(2,2,2-trifluoroethoxy)pyrazine-2-carboxylate (200 mg, 0.847 mmol) in Dioxane (1.2 mL) was added aqueous 2N HCl (1.0 mL). The reaction was stirred at 80° C. for 16 hrs. The reaction was concentrated in vacuo to afford the title compound quantitatively (188 mg, 0.847 mmol). MS m/z=223.1 (M+H).

Intermediate 65

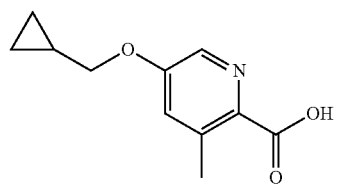

Synthesis of 5-(cyclopropylmethoxy)-3-methylpicolinic acid

Step 1: Synthesis of 5-(cyclopropylmethoxy)-3-methylpicolinonitrile

To a cooled mixture of 5-hydroxy-3-methylpicolinonitrile (1.00 g, 7.46 mmol) and triphenylphosphine (2.70 g, 10.29 mmol) in THF (25 mL) at 0° C. was added diisopropyl azodicarboxylate (2.00 ml, 10.18 mmol) and cyclopropylmethanol (1.10 ml, 13.79 mmol). The reaction mixture was allowed to warm to RT for overnight. The reaction mixture was evaporated onto silica gel and purified by flash chromatography eluting with 0% to 50% EtOAc in hexanes to give 1.172 g (84%) of 5-(cyclopropylmethoxy)-3-methylpicolinonitrile as a white crystalline solid. MS m/z: 189.1 [M+1].

Step 2: Synthesis of 5-(cyclopropylmethoxy)-3-methylpicolinic acid

To a solution of 5-(cyclopropylmethoxy)-3-methylpicolinonitrile (1.00 g, 5.31 mmol) in EtOH (20 mL) was added 5N sodium hydroxide (5 mL, 25.00 mmol) and the reaction was heated at 80° C. for overnight. The reaction was cooled to RT and acidified to pH 3 with 5 M HCl (aq.). The mixture was extracted with EtOAc (3×) and the combined organic layers were dried over MgSO$_4$, filtered and concentrated to give 1.075 g (98%) of an off-white amorphous solid. MS m/z: 208.1 [M+H].

Intermediate 66

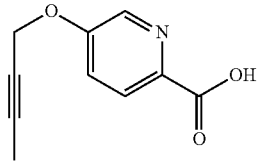

Synthesis of 5-(But-2-yn-1-yloxy)picolinic acid

Step 1: Methyl 5-(but-2-yn-1-yloxy)picolinate

To a solution of methyl 5-hydroxypicolinate (100 mg, 0.653 mmol) and potassium carbonate (135 mg, 0.980 mmol) in DMF (3 ml) 1-bromo-2-butyne (0.069 ml, 0.784 mmol) was added. The reactions were stirred at 50° C. overnight. The crude reaction mixture was partitioned between 30 mL water and 30 mL ethyl acetate. The aqueous layers were extracted with ethyl acetate; the combined organic layers were washed with water and brine and dried with sodium sulfate. The crude product was adsorbed onto a silica-gel loading column and purified by column chromatography, eluting with 0-100% ethyl acetate in DCM, to provide methyl 5-(but-2-yn-1-yloxy)picolinate (72 mg, 54%) as a tan solid.

Step 2: 5-(but-2-yn-1-yloxy)picolinic acid

To a solution of 5-(but-2-yn-1-yloxy)picolinate (72 mg, 0.35 mmol) in methanol (1 ml), dioxane (1 ml) and water (0.1 ml) was added lithium hydroxide (31 mg, 1.3 mmol). The reactions were stirred at ambient temperature for 2 h. The solvents were removed in vacuo. The residue from the reaction was triturated with 0.5 mL 1 N aqueous HCl. The tan precipitate was collected by vacuum filtration, washed with water, and dried in vacuo to generate 5-(but-2-yn-1-yloxy) picolinic acid (56 mg, 0.293 mmol, 83% yield) as a tan powder. LC/MS (ESI$^+$) m/z=192 (M+H).

Intermediate 67

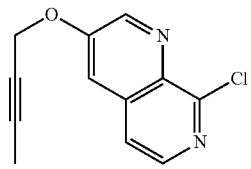 [SMILES: CC#CCOc1cnc2c(Cl)nccc2c1]

Synthesis of 3-(but-2-yn-1-yloxy)-8-chloro-1,7-naphthyridine

Step 1: Synthesis of 8-chloro-1,7-naphthyridin-3-ol

To a 75 mL pressure vessel were charged with 8-chloro-3-methoxy-1,7-naphthyridine (0.8 g, 4.11 mmol) and DCE (10 ml). To this was added boron tribromide, 1.0M in dichloromethane (20.55 ml, 20.55 mmol) slowly. The brown heterogeneous mixture was stirred at RT and then was heated to 60° C. in oil bath and stirred for 3 h. It was cooled to 0° C. by ice bath and quenched with sat. Na$_2$CO$_3$ very slowly. Organic solvents were reduced, and 100 ml EtOH was added to the resulting residue. The white precipitate was filtered out. The filtrate was concentrated to yield 8-chloro-1,7-naphthyridin-3-ol as crude product which was used for next step directly. MS m/z: 181.2 [M+H].

Step 2: Synthesis of 3-(but-2-yn-1-yloxy)-8-chloro-1,7-naphthyridine

To a solution of 8-chloro-1,7-naphthyridin-3-ol (618 mg, 3.42 mmol) in DMF (11 ml) were added bromobutyne (882 mg, 6.67 mmol), cesium carbonate (3233 mg, 9.92 mmol). The reaction mixture was heated at 50° C. for 0.5 h. It was quenched with water, and light brown precipitate was formed. It was then collected by Buchner funnel to yield 3-(but-2-yn-1-yloxy)-8-chloro-1,7-naphthyridine (550 mg, 74% yield) as light brown solid. MS m/z: 233.1 [M+H].

Intermediate 68

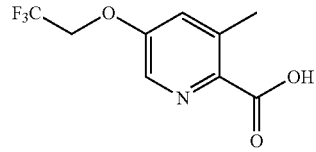 [SMILES: Cc1cc(OCC(F)(F)F)cnc1C(=O)O]

Synthesis of 3-methyl-5-(2,2,2-trifluoroethoxy)picolinic acid

To a solution of 5-hydroxy-3-methylpicolinonitrile (0.487 g, 3.63 mmol) in DMF (5 mL) were added cesium carbonate (1.538 g, 4.72 mmol) and 2,2,2-trifluoroethyl trifluoromethanesulfonate (1.011 ml, 4.36 mmol) and the resulting suspension was stirred at rt overnight. The reaction was diluted with water and EtOAc. The organic layer was washed with 1M LiCl solution and brine before drying over magnesium sulfate and concentrating under reduced pressure. The material was taken up in EtOH (20 mL) and NaOH, 1.0M aq (10.89 ml, 10.89 mmol) was added. The reaction was heated to 80° C. and stirred for 6 hours. The reaction was heated to reflux and stirred overnight. The reaction was continued at reflux for a total of 4 days. The reaction was cooled to rt and diluted with ether and water. The organic layer was washed with additional water and the combined aqueous layers were acidified to pH=1 (pH paper) by the addition of 1M HCl. The aqueous layer was extracted with DCM (2×) and the combined organics were brined, dried over magnesium sulfate and concentrated under reduced pressure to afford 3-methyl-5-(2,2,2-trifluoroethoxy)picolinic acid (0.754 g, 3.21 mmol, 88% yield). LC/MS (ESI+) m/z=236 (M+H).

Intermediate 69

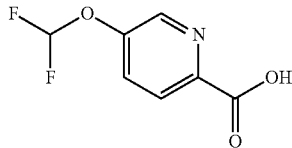 [SMILES: O=C(O)c1ccc(OC(F)F)cn1]

Synthesis of 5-(difluoromethoxy)picolinic acid

Step 1: Synthesis of methyl 5-(difluoromethoxy)picolinate

To a RBF were added 5-hydroxy-2-pyridinecarboxylic acid methyl ester (1.2 ml, 9.94 mmol), sodium chlorodifluoroacetate (3.3 g, 21.54 mmol), and cesium carbonate (9.7 g, 29.8 mmol) in DMF (20 ml). The reaction mixture was heated to 100° C. for 3 h. Then it was cooled to RT. The reaction mixture was diluted with water and extracted with EtOAc. The organic extract was washed with water, brine and dried over MgSO4. It was filtered and concentrated. The crude product was purified by flash chromatography eluting with a gradient of 5% to 50% EtOAc in hexane, to provide methyl 5-(difluoromethoxy)picolinate (1.4962 g, 7.37 mmol, 74.1% yield). MS m/z: 204.3 [M+H].

Step 2: Synthesis of 5-(difluoromethoxy)picolinic acid

To a solution of methyl 5-(difluoromethoxy)picolinate (0.750 g, 3.69 mmol) in 1,4-dioxane (18.46 ml) was added sodium hydroxide, 1N aqueous solution (7.4 ml, 7.4 mmol) and the reaction mixture was stirred at RT for overnight. Then hydrogen chloride, 4.0M solution in 1,4-dioxane (1.8 ml, 7.38 mmol) was added and stirred for 1 h. The reaction mixture was concentrated and was diluted with water and extracted with EtOAc. The organic extract was dried over MgSO$_4$, filtered and concentrated to give 5-(difluoromethoxy)picolinic acid (0.6013 g, 3.18 mmol, 86% yield). MS m/z: 190.2 [M+H].

Intermediate 70

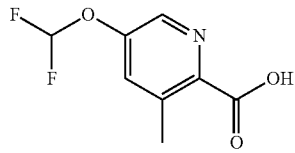

Synthesis of 5-(difluoromethoxy)-3-methylpicolinic acid

Step 1: Synthesis of 5-(difluoromethoxy)-3-methylpicolinonitrile

A mixture of 2-chloro-5-(difluoromethoxy)-3-methylpyridine (12.4 g, 64.1 mmol), zinc cyanide (4.07 mL, 64.1 mmol), 1,1'-bis(diphenylphosphino)ferrocene (2.5 g, 4.51 mmol) and tris(dibenzylideneacetone)dipalladium(0) (2.1 g, 2.93 mmol) in DMA (50 mL) was heated to 110° C. under N$_2$ for 18 h. The reaction mixture was diluted with water and extracted with ethyl acetate. The organic phase obtained was concentrated under reduced pressure and the residue was purified by silica gel chromatography eluting with 0-70% EtOAc/hex to give 5-(difluoromethoxy)-3-methylpicolinonitrile (5.88 g, 31.9 mmol, 49.8% yield). MS m/z: 185.0 [M+H].

Step 2: Synthesis of 5-(difluoromethoxy)-3-methylpicolinic acid

A solution of 5-(difluoromethoxy)-3-methylpicolinonitrile (5.8 g, 31.5 mmol) and sodium hydroxide 1.0 normal (100 ml, 100 mmol) in EtOH (50 ml) was heated to 80° C. for 18 h. The reaction mixture was concentrated and diluted with water and extracted with ether (2×). The aqueous layer was acidified to pH 3 with 1N HCl solution and extracted with TBME (2×). The combined organic layers were dried over sodium sulfate, filtered, and concentrated to give desired product 5-(difluoromethoxy)-3-methylpicolinic acid (4.6 g, 22.64 mmol, 71.9% yield) as a tan solid. MS m/z: 204.1 [M+H].

Intermediate 71

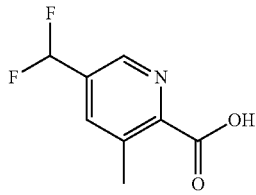

Synthesis of 5-Difluoromethyl-3-methyl-pyridine-2-carboxylic acid

Step 1: 2-Chloro-5-difluoromethyl-3-methyl-pyridine

To a precooled solution of 6-chloro-5-methyl-pyridine-3-carbaldehyde (500 mg, 3.21 mmol) in DCM (15 ml) was added at −78° C. DAST (0.632 ml, 0.777 g, 4.82 mmol). The reaction mixture was stirred for 18 h at −78° C. to rt, then quenched at 0° C. with saturated aq. NaHCO$_3$ solution, diluted with water and extracted with DCM. The organic layer was washed with water and dried over sodium sulfate, filtered, and concentrated. 2-Chloro-5-difluoromethyl-3-methyl-pyridine was obtained as a yellow oil after flash chromatography on silica gel (cyclohexane/EtOAc gradient 0-5 min 100:0, 5-40 min 100:0 to 80:20). ESI MS: 178 [M+H]; $^1$H NMR (400 MHz, CDCl$_3$): δ=8.38 (d, 1H) 7.72 (d, 1H), 6.69 (t, 1H), 2.46 (s, 3H).

Step 2:
5-Difluoromethyl-3-methyl-pyridine-2-carbonitrile

A solution of 2-chloro-5-difluoromethyl-3-methyl-pyridine (337 mg, 1.898 mmol), Zn(CN)$_2$ (159 mg, 1.328 mmol) and Pd(PPh$_3$)$_4$ (132 mg, 0.114 mmol) in DMF (10 ml) was stirred for 10 min at 120° C. in a microwave, filtered over hyflo and washed with water and brine. The combined aqueous layers were extracted with TBME, the combined organic layers were dried over sodium sulfate, filtered and concentrated. 5-Difluoromethyl-3-methyl-pyridine-2-carbonitrile was obtained as a yellow oil after flash chromatography on silica gel (cyclohexane/EtOAc gradient 0-3 min 100:0, 3-35 min 100:0 to 80:20). ESI MS: 169 [M+H]; $^1$H NMR (400 MHz, CDCl$_3$): δ=8.68 (s, 1H), 7.84 (s, 1H), 6.75 (t, 1H), 2.65 (s, 3H).

Step 3:
5-Difluoromethyl-3-methyl-pyridine-2-carboxylic acid

A solution of 5-difluoromethyl-3-methyl-pyridine-2-carbonitrile (209 mg, 0.787 mmol) in concentrated aqueous HCl solution (2 ml) was stirred for 2 h at 120° C. in a sealed tube. The reaction mixture was cooled to rt, diluted with TBME and extracted twice with water. The combined aqueous layers were washed with TBME and lyophilized. The residue was dissolved in water, 1M aqueous NaOH solution was added to adjust the pH to 2 and the solution was extracted three times with DCM. The combined organic layers were dried over sodium sulfate, filtered and concentrated to afford 5-Difluoromethyl-3-methyl-pyridine-2-carboxylic acid. ESI MS: 188 [M+H]; $^1$H NMR (400 MHz, CD$_3$OD): δ=8.62 (s, 1H), 7.98 (s, 1H), 6.95 (t, 1H), 2.65 (s, 3H).

Intermediate 72

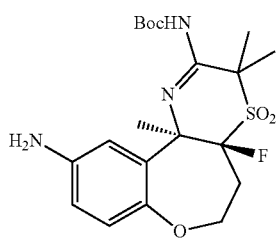 [SMILES: CC(C)(C)OC(=O)NC1=N[C@]2(C)c3cc(N)ccc3OCC[C@@]2(F)S(=O)(=O)C1(C)C]

Synthesis of tert-butyl ((4aR,11bR)-10-amino-4a-fluoro-3,3,11b-trimethyl-4,4-dioxido-4a,5,6,11b-tetrahydro-3H-benzo[6,7]oxepino[4,5-b][1,4]thiazin-2-yl)carbamate Step 1: Tert-butyl ((4aR,11bR)-4a-fluoro-3,3,11b-trimethyl-10-nitro-4,4-dioxido-4a,5,6,11b-tetrahydro-3H-benzo[6,7]oxepino[4,5-b][1,4]thiazin-2-yl)carbamate To an oven dried flask was added tert-butyl N-[(4aR,11bR)-4a-fluoro-3,3,11b-trimethyl-10-nitro-4,4-dioxo-5,6-dihydro-[1]benzoxepino[4,5-b][1,4]thiazin-2-yl]-N-tert-butoxycarbonyl-carbamate (See procedure for Intermediate 24, Step 1) (0.260 g, 0.475 mmol) and THF (3.17 mL). The resulting mixture was cooled to −78° C. and LHMDS (1 M in THF; 0.712 mL, 0.712 mmol) was added and the mixture was stirred for 40 minutes and then oxirane (7.91 mL, 9.50 mmol) was added. The dry ice/acetone bath was removed and the mixture was stirred for 30 minutes. The resulting mixture was treated with saturated aqueous ammonium chloride and extracted with EtOAc. The organic layer was concentrated and the crude material was eluted through a silica gel column using 10-50% EtOAc/Heptane. The desired fractions were combined and concentrated down to yield tert-butyl ((4aR,11bR)-4a-fluoro-3,3,11b-trimethyl-10-nitro-4,4-dioxido-4a,5,6,11b-tetrahydro-3H-benzo[6,7]oxepino[4,5-b][1,4]thiazin-2-yl)carbamate (0.090 g, 0.191 mmol, 40.2% yield)). ESI MS: 494.1 [M+Na] and a mixture of tert-butyl ((4aR,11bR)-4a-fluoro-3,3,11b-trimethyl-10-nitro-4,4-dioxido-4a,5,6,11b-tetrahydro-3H-benzo[6,7]oxepino[4,5-b][1,4]thiazin-2-yl)carbamate and tert-butyl N-[(4aR,11bR)-4a-fluoro-3,3,11b-trimethyl-10-nitro-4,4-dioxo-5,6-dihydro-[1]benzoxepino[4,5-b][1,4]thiazin-2-yl]-N-tert-butoxycarbonyl-carbamate (89 mg, 0.156 mmol, 32.8% yield) ESI MS: 494.1/594.1 [M+Na].

Step 2: Tert-butyl ((11bR)-10-amino-4a-fluoro-3,3,11b-trimethyl-4,4-dioxido-4a,5,6,11b-tetrahydro-3H-benzo[6,7]oxepino[4,5-b][1,4]thiazin-2-yl)carbamate A round bottom flask was charged with Pd/C (0.020 g, 0.019 mmol) and put under a nitrogen atmosphere. A solution of tert-butyl ((11bR)-4a-fluoro-3,3,11b-trimethyl-10-nitro-4,4-dioxido-4a,5,6,11b-tetrahydro-3H-benzo[6,7]oxepino[4,5-b][1,4]thiazin-2-yl)carbamate (0.090 g, 0.191 mmol) in EtOAc (477 µl) and MeOH (477 µl) was added via syringe and the flask was evacuated and filled with hydrogen. The mixture was stirred at RT under hydrogen atmosphere for 17 hours. The mixture was filtered through Celite and washed with EtOAc and the filtrate was concentrated to yield tert-butyl ((11bR)-10-amino-4a-fluoro-3,3,11b-trimethyl-4,4-dioxido-4a,5,6,11b-tetrahydro-3H-benzo[6,7]oxepino[4,5-b][1,4]thiazin-2-yl)carbamate (0.071 mg, 0.161 mmol, 84% yield) as a light yellow solid. LC/MS (ESI$^+$) m/z=442.3.

Intermediate 73-Trans and 73-Cis

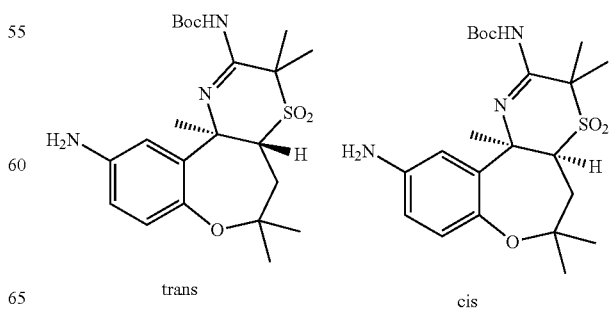

trans                cis

Synthesis of tert-butyl ((4aR,11bR)-10-amino-3,3,6,6,11b-pentamethyl-4,4-dioxido-4a,5,6,11b-tetrahydro-3H-benzo[6,7]oxepino[4,5-b][1,4]thiazin-2-yl)carbamate (trans/cis) and tert-butyl ((4aS,11bR)-10-amino-3,3,6,6,11b-pentamethyl-4,4-dioxido-4a,5,6,11b-tetrahydro-3H-benzo[6,7]oxepino[4,5-b][1,4]thiazin-2-yl)carbamate Step 1: tert-butyl ((4aR,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate and tert-butyl ((4aS,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate To a 25-mL RBF was added tert-butyl N-tert-butoxycarbonyl-N-[(3R)-3-(2-fluoro-5-nitro-phenyl)-3,6,6-trimethyl-1,1-dioxo-2H-1,4-thiazin-5-yl]carbamate (450 mg, 0.850 mmol) in THF (5.6 ml). The reaction solution was cooled to −78° C., then LHMDS (1.0M in THF; 2124 µl, 2.124 mmol) was added slowly. The brown solution was stirred for 15 min, then 1,1-dimethyloxirane (377 µl, 4.25 mmol) was added at −78° C. The reaction mixture was stirred from −78° C. to RT by removing dry-ice bath. 35 min later, it was quenched by 8 mL sat. aq. NH₄Cl. The reaction mixture was diluted with water and extracted with EtOAc. The organic extract was washed with satd NaCl and dried over MgSO₄. The solution was filtered and concentrated to give the crude material as a brown oil. The crude mixture was dissolved in 6 ml tBuOH and potassium tert-butoxide, 1.0M solution in THF (2.5 ml, 2.55 mmol). It was stirred at RT. 20 min later, 8 mL of aq. NH₄Cl was added and extracted with EtOAc. The organic extract was concentrated and was purified using 40 g Puriflash column in 20% to 35% to 50% EtOAc/Heptanes to give 56 mg of tert-butyl ((4aR,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate (13% yield, less polar by TLC), and 90 mg of tert-butyl ((4aS,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate (22% yield, containing impurity, more polar by TLC). MS m/z=504.0 (M+Na).

Step 2: Synthesis of tert-butyl ((4aR,11bR)-10-amino-3,3,6,6,11b-pentamethyl-4,4-dioxido-4a,5,6,11b-tetrahydro-3H-benzo[6,7]oxepino[4,5-b][1,4]thiazin-2-yl)carbamate Solution of tert-butyl ((4aR,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate (56 mg, 0.116 mmol) in THF (1.1 ml) was purged with N₂, and hydrogenated under hydrogen balloon in the presence of palladium 10 wt. % Pd on activated carbon (37.1 mg, 0.035 mmol) for 4.5 h. The mixture was filtered through the plug of Celite, and the filter cake was washed with ethyl acetate. The combined filtrate was concentrated to afford the crude tert-butyl ((4aR,11bR)-10-amino-3,3,6,6,11b-pentamethyl-4,4-dioxido-4a,5,6,11b-tetrahydro-3H-benzo[6,7]oxepino[4,5-b][1,4]thiazin-2-yl)carbamate which was used for next step directly. MS m/z=452.1 (M+H).

Under the similar reaction condition, solution of tert-butyl ((4aS,11bR)-3,3,6,6,11b-pentamethyl-10-nitro-4,4-dioxido-4a,5,6,11b-tetrahydro-3H-benzo[6,7]oxepino[4,5-b][1,4]thiazin-2-yl)carbamate (90 mg, 0.187 mmol) in THF (2 ml) was purged with N₂, and hydrogenated under hydrogen balloon in the presence of 10 wt % Pd/C (70 mg, 0.066 mmol) for 3 h. The mixture was filtered through the plug of Celite, filter cake was washed with ethyl acetate. Combined filtrate was concentrated ton afford and tert-butyl ((4aS,11bR)-10-amino-3,3,6,6,11b-pentamethyl-4,4-dioxido-4a,5,6,11b-tetrahydro-3H-benzo[6,7]oxepino[4,5-b][1,4]thiazin-2-yl)carbamate which were used without further purification. MS m/z=452.1 (M+H).

General Methods

The following General Methods 3-11 describe procedures used with the intermediates, as listed in Table 1, (unless otherwise specified herein) to prepare the Examples, as non-limiting representative compounds of the invention, described in Table 1.

Method 3

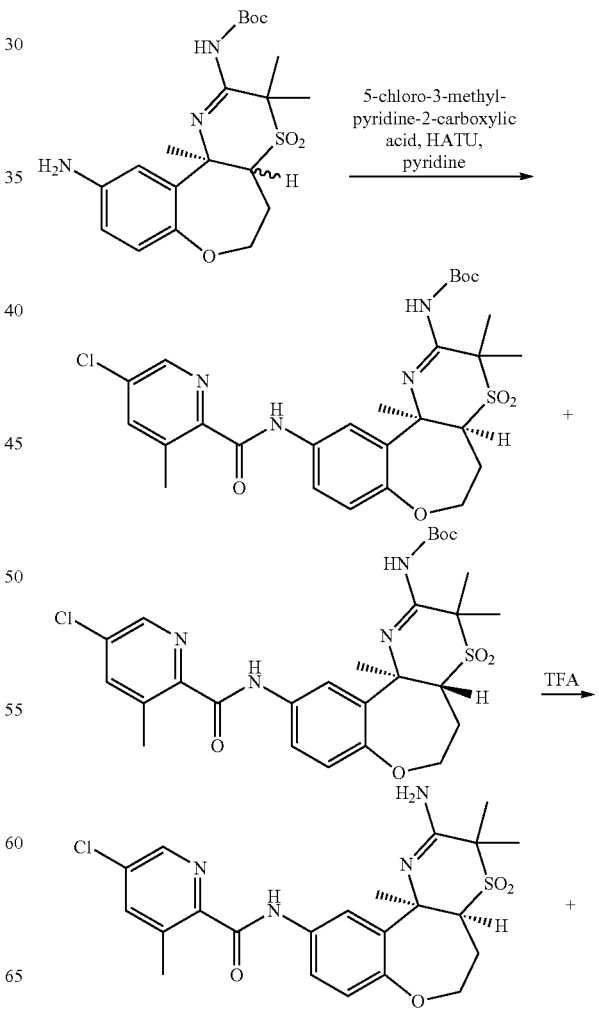

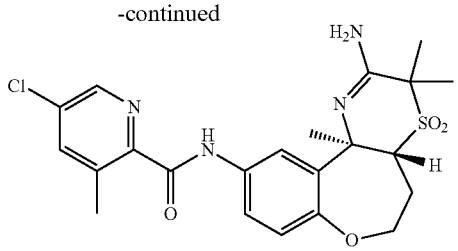

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide and N-((4aS,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide Step 1: tert-butyl ((4aR,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate and tert-butyl ((4aS,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate To the crude tert-butyl ((11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (190 mg, 0.449 mmol) from (prepared in Step 4, Method 2) (~2:1 trans/cis mixture) dissolved in DMF (2 ml), was added 5-chloro-3-methylpyridine-2-carboxylic acid (92 mg, 0.538 mmol), pyridine (0.109 ml, 1.346 mmol) and HATU (256 mg, 0.673 mmol) and resulting solution was stirred for 1 hr at RT. The mixture was diluted with EtOAc (8 ml) and saturated NaHCO₃ solution (3 ml). Water was added to dissolve precipitated solids. The organic layer was separated, washed with water, brine and concentrated. The residue was and purified by silica gel chromatography on 12 g RediSep Gold column using 10-70% EtOAc in heptane to afford major less polar trans-isomer tert-butyl ((4aR,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (110 mg, 0.191 mmol, 42.5% yield and more polar minor cis-isomer tert-butyl ((4aS,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (70 mg, 0.121 mmol, 27% yield).

Step 2: N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide and N-((4aS,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide A solution of trans-isomer tert-butyl ((4aR,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (110 mg, 0.191 mmol) in DCM (2 ml) was treated with TFA (0.7 ml, 9.53 mmol) for 10 min at RT. The mixture was concentrated to dryness, redissolved in 0.5 ml of MeOH and neutralized with saturated solution NaHCO₃. Precipitated material was extracted with ethyl acetate, organic extract was washed with water, brine, filtered through pad of celite and concentrated to afford N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide (89 mg, 0.187 mmol, 98% yield). LC/MS (ESI⁺) m/z=477.

In a deprotection step analogous to Step 2 above, the cis-isomer tert-butyl ((4aS,11bR)-10-(5-chloro-3-methylpicolinamido)-3,3,11b-trimethyl-4,4-dioxido-4a,5,6,11b-tetrahydro-3H-benzo[6,7]oxepino[4,5-b][1,4]thiazin-2-yl)carbamate (70 mg, 0.121 mmol) was converted to N-((4aS,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide (55 mg, 0.115 mmol, 95% yield). LC/MS (ESI⁺) m/z=477.

Method 4

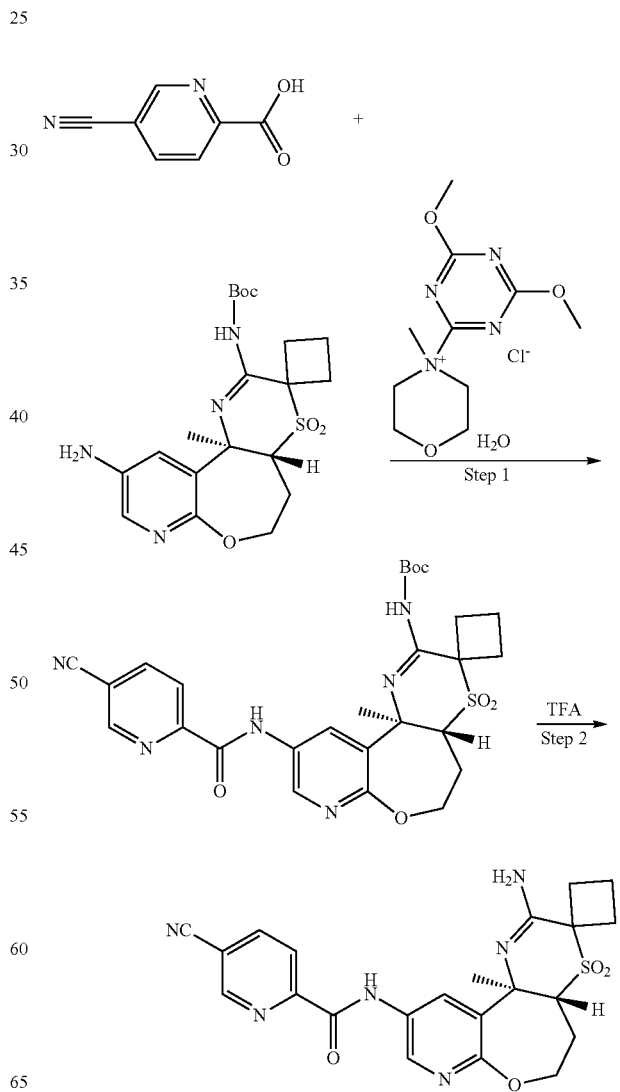

Synthesis of N-((4a'R,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-cyanopicolinamide

Step 1: tert-butyl ((4a'R,11b'R)-10'-(5-cyanopicolinamido)-11b'-methyl-4',4'-dioxido-4a',5',6',11b'-tetrahydro spiro[cyclobutane-1,3'-pyrido[3',2':6,7]oxepino[4,5-b][1,4]thiazin]-2'-yl)carbamate To a solution of tert-butyl ((4a'R,11b'R)-10'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate (0.086 g, 0.197 mmol) in THF/MeOH (3/0.9 mL) was added 5-cyano-2-pyridinecarboxylic acid (0.035 g, 0.236 mmol) and 4-(4,)dimethoxy[1.3.5]triazin-2-yl)-4-methylmorpholinium chloride hydrate, 99+% (0.070 g, 0.236 mmol) and the resulting mixture was stirred at rt for 1.5 h. The reaction was quenched with sat. NaHCO₃ and extracted with DCM. The combined organics were dried over Na₂SO₄, filtered, concentrated. The residue was purified by silica gel chromatography using a gradient 0-3% MeOH/DCM solvent system to afford a white solid as tert-butyl ((4a'R,11b'R)-10'-(5-cyanopicolinamido)-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate as a white solid. MS m/z=588.9 (M+Na).

Step 2: N-((4a'R,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-cyanopicolinamide To tert-butyl ((4a'R,11b'R)-10'-(5-cyanopicolinamido)-11b'-methyl-4',4'-dioxido-4a',5',6',11b'-tetrahydrospiro[cyclobutane-1,3'-pyrido[3',2':6,7]oxepino[4,5-b][1,4]thiazin]-2'-yl)carbamate was added TFA (0.015 ml, 0.197 mmol) and the resulting solution was stirred at rt for 15 min. The reaction mixture was poured into water and the pH was brought to >10 using sat. NaHCO₃ and 5 N NaOH, then extracted with DCM. The combined organics were dried over Na₂SO₄, filtered, concentrated and purified by silica gel chromatography using a gradient 0-3% MeOH/DCM solvent system to afford a white solid as N-((4a'R,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-cyanopicolinamide (0.030 g, 0.064 mmol, 32.6% yield). MS m/z=466.9 (M+H).

Method 5

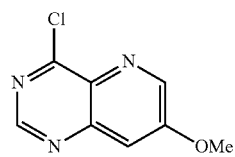

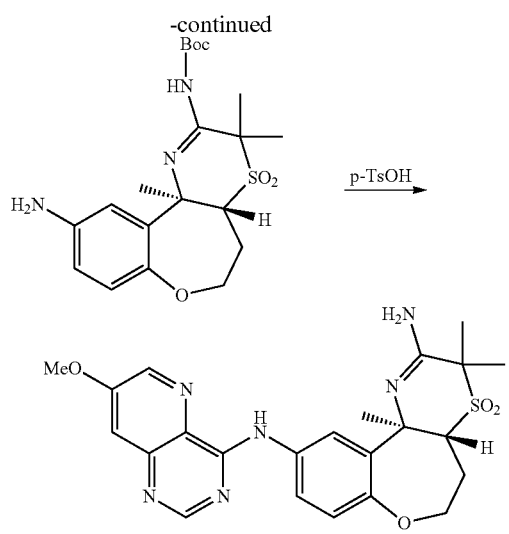

Synthesis of (4aR,11bR)-2-amino-10-((7-methoxypyrido[3,2-d]pyrimidin-4-yl)amino)-3,3,11b-trimethyl-4a,5,6,11b-tetrahydro-3H-benzo[6,7]oxepino[4,5-b][1,4]thiazine 4,4-dioxide A disposable tube was charged with tert-butyl ((4aR,11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (60 mg, 0.142 mmol), 4-chloro-7-methoxypyrido[3,2-d]pyrimidine (30.5 mg, 0.156 mmol) and 2-propanol (708 µl, 0.142 mmol), followed by p-toluenesulfonic acid monohydrate (53.9 mg, 0.283 mmol). The resulting mixture was stirred from rt to 90° C. for 25 min. The reaction mixture was diluted with sat. NaHCO₃ and extracted with EtOAc to yield the crude product as a yellow solid. The crude material was absorbed onto a plug of silica gel and purified by column chromatography through a Redi-Sep pre-packed silica gel column (12 g), eluting with a gradient of 20% to 35% to 50% EtOAc/MeOH/NEt₃ (80/20/2) in (40% EtOAc in Heptane), to provide (4aR,11bR)-2-amino-10-((7-methoxypyrido[3,2-d]pyrimidin-4-yl)amino)-3,3,11b-trimethyl-4a,5,6,11b-tetrahydro-3H-benzo[6,7]oxepino[4,5-b][1,4]thiazine 4,4-dioxide (42 mg, 0.087 mmol, 61.4% yield) as white solid. MS m/z=483.2 (M+H).

Method 6

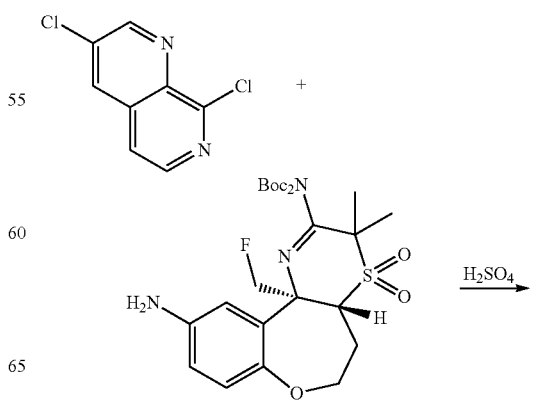

Synthesis of (4aR,11bS)-2-amino-10-((3-chloro-1,7-naphthyridin-8-yl)amino)-11b-(fluoromethyl)-3,3-dimethyl-4a,5,6,11b-tetrahydro-3H-benzo[6,7]oxepino[4,5-b][1,4]thiazine 4,4-dioxide

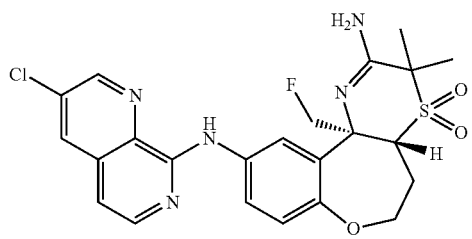

To a 15-mL reaction vial was added tert-butyl N-[(4aR,11bS)-10-amino-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate (103 mg, 0.190 mmol), 3,8-dichloro-1,7-naphthyridine (41.6 mg, 0.209 mmol), isopropanol (3 mL) and a couple of β-drops of $H_2SO_4$. The vial was closed and heated at 90° C. for 1 h. The reaction mixture was allowed to cool to room temperature. The reaction mixture was diluted with 1N NaOH (5 mL) and extracted with DCM (8 mL×3). The organic extracts were dried over $Na_2SO_4$. The solution was filtered and concentrated in vacuo to give the crude material. The crude material was absorbed onto a plug of silica gel and purified by chromatography through a Redi-Sep pre-packed silica gel column (12 g), eluting with a gradient of 0% to 2% 2M $NH_3.MeOH$ in DCM, to provide (4aR,11bS)-2-amino-10-((3-chloro-1,7-naphthyridin-8-yl)amino)-11b-(fluoromethyl)-4a,5,6,11b-tetrahydro-3H-benzo[6,7]oxepino[4,5-b][1,4]thiazine 4,4-dioxide (78 mg, 0.155 mmol, 81% yield) as yellow solid. MS m/z=503.9 (M+H).

Method 7

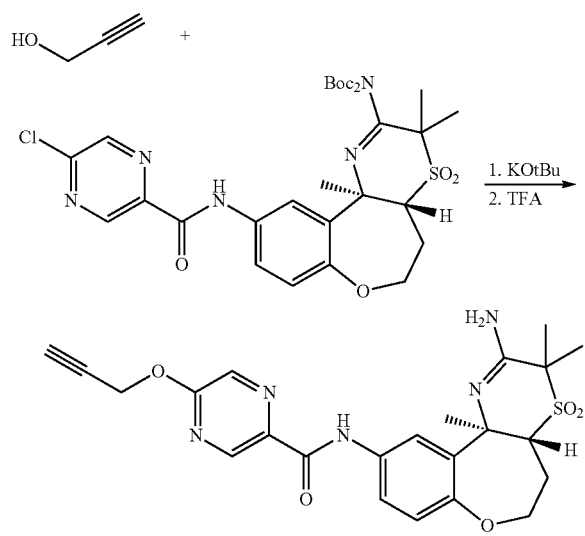

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(prop-2-yn-1-yloxy)pyrazine-2-carboxamide To a solution of tert-butyl N-[(4aR,11bR)-10-[(5-chloropyrazine-2-carbonyl)amino]-3,3,11b-trimethyl-4,4-dioxo-5,6-dihydro-4aH-[1]benzoxepino[4,5-b][1,4]thiazin-2-yl]-N-tert-butoxycarbonyl-carbamate (126 mg, 0.190 mmol) in DMF (2 mL) was added a mixture of potassium tert-butoxide (63.9 mg, 0.569 mmol) in propargyl alcohol (0.224 mL, 3.79 mmol). The reaction was stirred at ambient temperature for 1 h. The reaction mixture was partitioned between water and ethyl acetate, and the organic layer was concentrated. The crude residue was diluted with DCM (3 mL) and TFA (0.292 mL, 3.79 mmol) was added and the reaction was stirred at ambient temperature. After 1 h, the reaction mixture was diluted with DCM, washed with saturated aqueous sodium bicarbonate, and concentrated. The crude product was purified by column chromatography, eluting with 20-80% (3:1 ethyl acetate/ethanol) in heptane, to provide N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(prop-2-yn-1-yloxy)pyrazine-2-carboxamide (82 mg, 0.170 mmol, 89% yield) as an off-white powder. MS m/z=484.0 (M+H).

Method 8

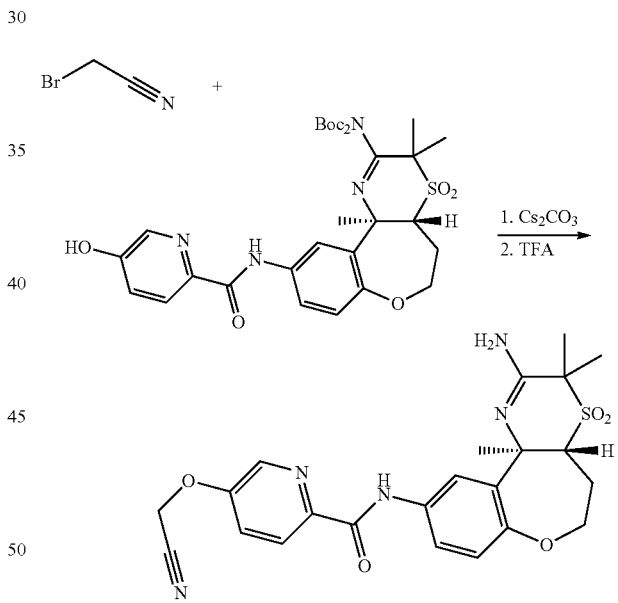

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(cyanomethoxy)picolinamide A vial was charged with tert-butyl N-[(4aR,11bR)-10-[(5-hydroxypyridine-2-carbonyl)amino]-3,3,11b-trimethyl-4,4-dioxo-5,6-dihydro-4aH-[1]benzoxepino[4,5-b][1,4]thiazin-2-yl]-N-tert-butoxycarbonyl-carbamate (150 mg, 0.233 mmol), cesium carbonate (152 mg, 0.465 mmol) and DMF (1163 μl). To this slurry was added 2-bromoacetonitrile (19.81 μl, 0.244 mmol), and the reaction was stirred at RT for 3 h. Water and EtOAc were added and the layers were separated. The organic portion was dried, filtered and concentrated. The crude material was dissolved in 1 mL DCM, and TFA (358 µL, 4.65 mmol) was added and the reaction was stirred for 1 h. EtOAc and saturated NaHCO₃ were added, and the layers were separated. The organic portion was dried, filtered and concentrated. The crude product was purified by silica gel chromatography, using a gradient 0-50% 90/10 DCM/MeOH in DCM. The product was further purified by reverse phase chromatography on the Isolera using 0-75% 0.1% TFA/ACN in water solvent system followed by isolation using an SCX column to give N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(cyanomethoxy)picolinamide. MS m/z=484.1 (M+H).

Method 9

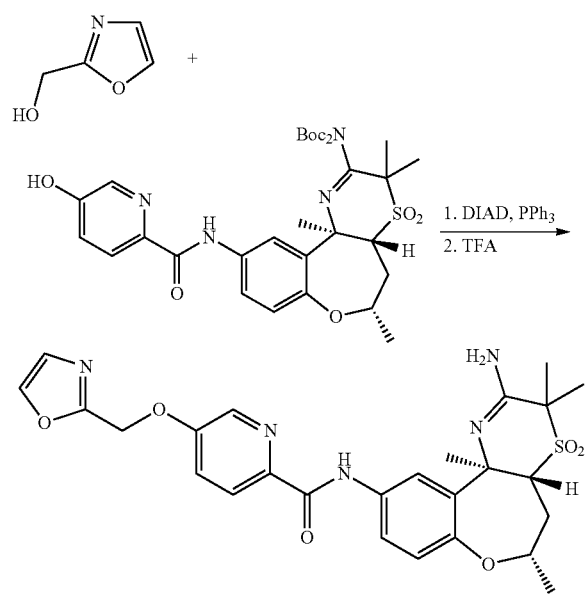

Synthesis of N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-(oxazol-2-ylmethoxy)picolinamide Step 1: tert-butyl N-[(4aR,6S,11bR)-3,3,6,11b-tetramethyl-10-[[5-(oxazol-2-ylmethoxy)pyridine-2-carbonyl]amino]-4,4-dioxo-5,6-dihydro-4aH-[1]benzoxepino[4,5-b][1,4]thiazin-2-yl]-N-tert-butoxycarbonyl-carbamate To a 0° C. solution of tert-butyl N-[(4aR,6S,11bR)-10-[(5-hydroxypyridine-2-carbonyl)amino]-3,3,6,11b-tetramethyl-4,4-dioxo-5,6-dihydro-4aH-[1]benzoxepino[4,5-b][1,4]thiazin-2-yl]-N-tert-butoxycarbonyl-carbamate (80 mg, 0.121 mmol), 2-oxazolemethanol (0.096 mL, 1.214 mmol) and triphenylphosphine (96 mg, 0.364 mmol) in THF (3 mL) was added diisopropyl azodicarboxylate (0.072 mL, 0.364 mmol) dropwise. The reaction was stirred at ambient temperature for 16 h. The reaction mixture was partitioned between water and ethyl acetate and the organic layer was concentrated. The crude product was purified by silica gel column chromatography, eluting with 20-100% ethyl acetate in heptane, to provide tert-butyl N-[(4aR,6S,11bR)-3,3,6,11b-tetramethyl-10-[[5-(oxazol-2-ylmethoxy)pyridine-2-carbonyl]amino]-4,4-dioxo-5,6-dihydro-4aH-[1]benzoxepino[4,5-b][1,4]thiazin-2-yl]-N-tert-butoxycarbonyl-carbamate (19 mg, 0.026 mmol, 21.15% yield) as a colorless oil. MS m/z=762.0 (M+Na).

Step 2: N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-(oxazol-2-ylmethoxy)picolinamide To a solution tert-butyl N-[(4aR,6S,11bR)-3,3,6,11b-tetramethyl-10-[[5-(oxazol-2-ylmethoxy)pyridine-2-carbonyl]amino]-4,4-dioxo-5,6-dihydro-4aH-[1]benzoxepino[4,5-b][1,4]thiazin-2-yl]-N-tert-butoxycarbonyl-carbamate (19 mg, 0.026 mmol) in DCM (2 mL) was added TFA (0.049 mL, 0.642 mmol). The reaction was stirred at ambient temperature for 2 h. The reaction mixture was diluted with DCM and neutralized with saturated aqueous sodium bicarbonate. The crude product was purified by column chromatography, eluting with 20-100% (3:1 ethyl acetate/ethanol) in heptane, to provide N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-(oxazol-2-ylmethoxy)picolinamide (12 mg, 0.022 mmol, 87% yield) as a white powder. MS m/z=540.0 (M+H).

Method 10

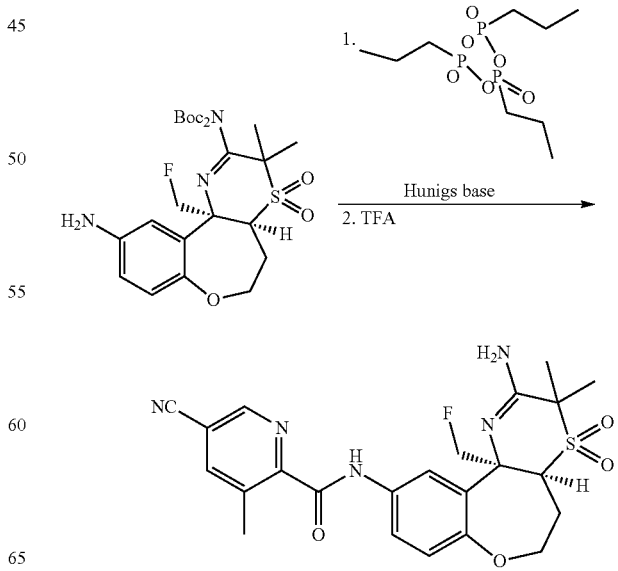

Synthesis of N-((4aS,11bS)-2-amino-11b-(fluoromethyl)-3,3-dimethyl-4,4-dioxido-4a,5,6,11b-tetrahydro-3H-benzo[6,7]oxepino[4,5-b][1,4]thiazin-10-yl)-5-cyano-3-methylpicolinamide Step 1: tert-butyl N-[(4aS,11bS)-10-[(5-cyano-3-methyl-pyridine-2-carbonyl)amino]-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate To a 50-mL round-bottomed flask, tert-butyl N-[(4aS,11bS)-10-amino-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate (102 mg, 0.188 mmol), 5-cyano-3-methylpicolinic acid (36.6 mg, 0.226 mmol), Hunig's base (0.043 mL, 0.245 mmol), and 1-propanephosphonic acid cyclic anhydride (0.120 mL, 0.188 mmol) were added then dissolved in DCM (5 mL). The reaction mixture was stirred at RT for 3 h. The reaction mixture was then diluted with saturated NaHCO$_3$ and extracted with EtOAc (15 mL). The organic extract was washed with water, brine (10 mL) and dried over Na$_2$SO$_4$. The solution was filtered and concentrated in vacuo to give tert-butyl N-[(4aS,11bS)-10-[(5-cyano-3-methyl-pyridine-2-carbonyl)amino]-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate as a white solid that was used without further purification. MS m/z=708.0 (M+Na).

Step 2: N-((4aS,11bS)-2-amino-11b-(fluoromethyl)-3,3-dimethyl-4,4-dioxido-4a,5,6,11b-tetrahydro-3H-benzo[6,7]oxepino[4,5-b][1,4]thiazin-10-yl)-5-cyano-3-methylpicolinamide To a 50-mL round-bottomed flask was added tert-butyl N-[(4aS,11bS)-10-[(5-cyano-3-methyl-pyridine-2-carbonyl)amino]-11b-(fluoromethyl)-3,3-dimethyl-4,4-dioxo-5,6-dihydro-4aH-[1]benzoxepino[4,5-b][1,4]thiazin-2-yl]-N-tert-butoxycarbonyl-carbamate (129 mg, 0.188 mmol), DCM (3 mL), and TFA (2 mL). The reaction mixture stirred at RT for 30 min. The solvent was removed under vacuum. The reaction mixture was diluted with saturated aqueous NaHCO$_3$ and extracted with DCM (3 mL) (3 times). The organic extract was dried over Na$_2$SO$_4$. The crude material was absorbed onto a plug of silica gel and purified by chromatography through a Redi-Sep pre-packed silica gel column (12 g), eluting with a gradient of 0% to 2% 2M NH$_3$.MeOH in DCM, to provide N-((4aS,11bS)-2-amino-11b-(fluoromethyl)-3,3-dimethyl-4,4-dioxido-4a,5,6,11b-tetrahydro-3H-benzo[6,7]oxepino[4,5-b][1,4]thiazin-10-yl)-5-cyano-3-methylpicolinamide (62 mg, 0.128 mmol, 67.9% yield) as an off-white solid. MS m/z=486.0 (M+H).

Method 11

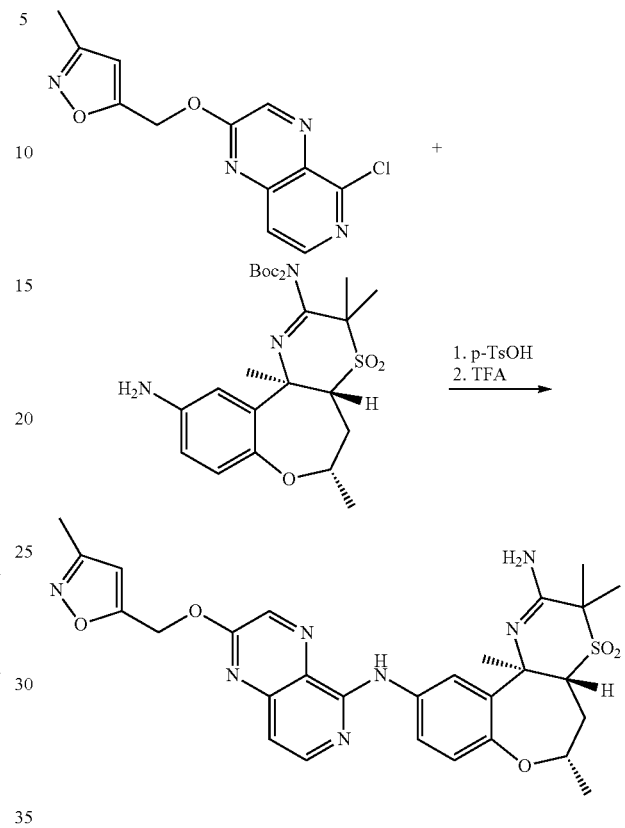

Synthesis of (4aR,6S,11bR)-2-Amino-3,3,6,11b-tetramethyl-10-((2-((5-methyloxazol-2-yl)methoxy)pyrido[3,4-b]pyrazin-5-yl)amino)-4a,5,6,11b-tetrahydro-3H-benzo[6,7]oxepino[4,5-b][1,4]thiazine 4,4-dioxide A suspension of p-toluenesulfonic acid monohydrate (35 mg, 0.19 mmol), 2445-chloropyrido[3,4-b]pyrazin-2-yl)oxy)methyl)-5-methyloxazole (57 mg, 0.21 mmol) and tert-butyl N-[(4aR,6S,11bR)-10-amino-3,3,6,11b-tetramethyl-4,4-dioxo-5,6-dihydro-4aH-[1]benzoxepino[4,5-b][1,4]thiazin-2-yl]-N-tert-butoxycarbonyl-carbamate (100 mg, 0.19 mmol) in 2-propanol (3 mL) was stirred at 85° C. After 3 hours, the reaction mixture was partitioned between saturated aqueous sodium bicarbonate and ethyl acetate. The organic layer was concentrated and redissolved in DCM (3 mL). To the solution was added trifluoroacetic acid (0.39 mL, 4.7 mmol), and the reaction was stirred at ambient temperature for 30 minutes. The reaction mixture was diluted with DCM, washed with saturated aqueous sodium bicarbonate, and concentrated. The crude product was purified by column chromatography, eluting with 15-75% (3:1 ethyl acetate/ethanol) in heptane, to provide the title compound (55 mg, 0.095 mmol, 51% yield) as a yellow solid. LC/MS (ESI$^+$) m/z: 578.2 (M+H$^+$).

The following examples were not prepared by the General Methods described herein:

Example 17

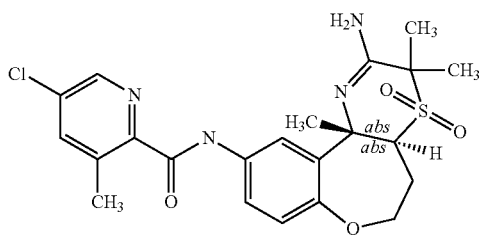

Synthesis of N-((4aS,11bS)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-methylpicolinamide Example 17 was prepared according to Method 1. The racemic product (Example 4) was purified via SFC: Chiralpak IC column (4.6×100 mm), 40% methanol (0.2% diethylamine)/CO$_2$, 100 bar, 50 ml/min, detection at 220 nm to provide Example 17 with >99% ee. LC/MS (ESI+) m/z=477.

Example 31

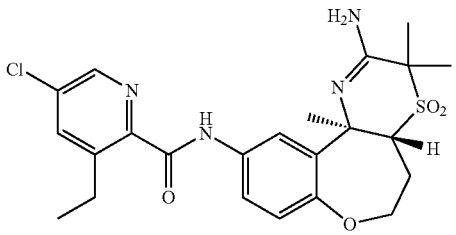 [SMILES: CCc1cc(Cl)cnc1C(=O)Nc1ccc2c(c1)[C@@]1(C)N=C(N)C(C)(C)S(=O)(=O)[C@@H]1CCO2]

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-ethylpicolinamide Step 1: 5-chloro-3-vinylpicolinonitrile A microwave vial was charged with 3-bromo-5-chloropicolinonitrile (1.40 g, 6.44 mmol) and dichlorobis(triphenylphosphine)palladium (II) (0.54 g, 0.77 mmol). The vial was evacuated and backfilled with nitrogen and 1,4-dioxane (10 mL) was added, followed by tri-n-butyl(vinyl)tin (2.45 mL, 7.73 mmol). The reaction mixture was heated at 100° C. for 1 h. The reaction mixture was diluted with water and EtOAc. The solvent was removed under reduced pressure. The crude material was absorbed onto a plug of silica gel and purified by chromatography through a Redi-Sep pre-packed silica gel column (40 g), eluting with a gradient of 10% to 50% EtOAc in hexane, to provide 5-chloro-3-vinylpicolinonitrile (0.72 g, 4.37 mmol, 67.9% yield) as white solid.

$^1$H NMR (400 MHz, CHLOROFORM-d) δ 8.54 (d, J=2.25 Hz, 1H), 7.97 (dd, J=0.44, 2.30 Hz, 1H), 7.05 (dd, J=11.20, 17.56 Hz, 1H), 6.05 (d, J=17.41 Hz, 1H), 5.76 (d, J=11.05 Hz, 1H)

Step 2: 5-chloro-3-vinylpicolinic acid

A cloudy solution of 5-chloro-3-vinylpicolinonitrile (0.72 g, 4.37 mmol) in EtOH (6 mL) and NaOH (1M, 12 mL) was heated to 100° C. After 15 min reaction time full conversion and formation of amide was observed. The reaction mixture was partitioned between water and EtOAc. The aqueous phase contained the carboxylic acid and was neutralized with 6 N HCl. The acid was back-extracted with EtOAc. The organic phase was separated and dried over MgSO4. The solvent was removed under reduced pressure to afford 5-chloro-3-vinylpicolinic acid (0.37 g, 2.02 mmol, 31.3% yield) as a white solid. $^1$H NMR (400 MHz, DMSO-d$_6$) δ 8.57 (d, J=2.25 Hz, 1H), 8.32 (d, J=2.25 Hz, 1H), 7.11 (dd, J=11.15, 17.61 Hz, 1H), 6.06 (dd, J=0.59, 17.51 Hz, 1H), 5.42-5.66 (m, 1H)

Step 3: tert-butyl ((4aR,11bR)-10-(5-chloro-3-vinylpicolinamido)-3,3,11b-trimethyl-4,4-dioxido-4a,5,6,11b-tetrahydro-3H-benzo[6,7]oxepino[4,5-b][1,4]thiazin-2-yl)carbamate To a solution of tert-butyl ((4aR,11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (0.080 g, 0.19 mmol) in DCM (2.0 ml) were added 5-chloro-3-vinylpicolinic acid (0.036 g, 0.20 mmol), triethylamine (0.053 ml, 0.38 mmol) and HATU (0.079 g, 0.21 mmol). The mixture was stirred at room temperature for 2 h. The reaction mixture was absorbed onto a plug of silica gel and purified by chromatography through a Redi-Sep pre-packed silica gel column (12 g), eluting with a gradient of 10% to 60% EtOAc in hexane, to provide tert-butyl ((4aR,11bR)-10-(5-chloro-3-vinylpicolinamido)-3,3,11b-trimethyl-4,4-dioxido-4a,5,6,11b-tetrahydro-3H-benzo[6,7]oxepino[4,5-b][1,4]thiazin-2-yl)carbamate (0.11 g, 0.19 mmol, 99% yield) as a white solid. m/z (ESI) 589.0 (M+H)$^+$.

Step 4: N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-ethylpicolinamide A mixture of tert-butyl ((4aR,11bR)-10-(5-chloro-3-vinylpicolinamido)-3,3,11b-trimethyl-4,4-dioxido-4a,5,6,11b-tetrahydro-3H-benzo[6,7]oxepino[4,5-b][1,4]thiazin-2-yl)carbamate (0.11 g, 0.19 mmol) and palladium, 10% wt. on activated carbon (0.060 g, 0.056 mmol) in DCM (1.0 ml) was stirred under a balloon of hydrogen at room temperature for 12 h. The reaction mixture was absorbed onto a plug of silica gel and purified by chromatography through a Redi-Sep pre-packed silica gel column (12 g), eluting with a gradient of 10% to 60% EtOAc in hexane, to provide tert-butyl ((4aR,11bR)-10-(5-chloro-3-ethylpicolinamido)-3,3,11b-trimethyl-4,4-dioxido-4a,5,6,11b-tetrahydro-3H-benzo[6,7]oxepino[4,5-b][1,4]thiazin-2-yl)carbamate as white solid. To a solution of this compound in 1 mL of DCM was added trifluoroacetic acid (0.56 ml, 7.47 mmol). The mixture was stirred at room temperature for 30 min. The solvent was evaporated and the residue was absorbed onto a plug of silica gel and purified by chromatography through a Redi-Sep pre-packed silica gel column (12 g), eluting with a gradient of 0% to 5% MeOH in DCM to give N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-chloro-3-ethylpicolinamide (0.010 g, 0.020 mmol, 10.9% yield) as an off-white solid. m/z (ESI) 491.0 (M+H)+.

Examples 68 and 69

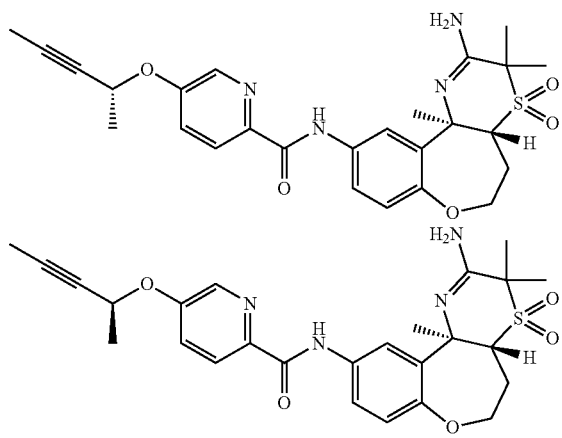

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-((R)-pent-3-yn-2-yloxy)picolinamide and N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-((S)-pent-3-yn-2-yloxy)picolinamide General Method 3 was used with Intermediate 20 and 5-(pent-3-yn-2-yloxy)picolinic acid to prepare the titled compound. The compound was separated into its enantiomers via prep-scale supercritical fluid chromatography using a Chiralpak AD-H column with an isocratic 55% carbon dioxide/45% isopropanol with 0.1% diethyl amine solvent system to yield N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-((R)-pent-3-yn-2-yloxy)picolinamide (27 mg, 0.053 mmol, 27.7% yield) and N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-((S)-pent-3-yn-2-yloxy)picolinamide (19 mg, 0.037 mmol, 19.49% yield). The stereochemistry was assigned arbitrarily. LC/MS (ESI+) m/z=511.1 for both diastereomers.

Examples 70 and 71

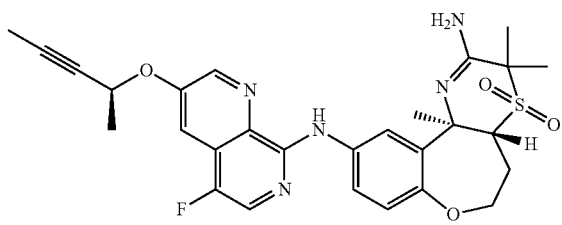

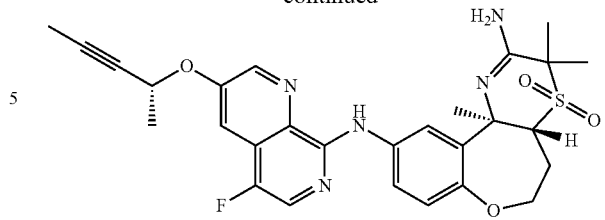

Synthesis of (4aR,11bR)-2-amino-10-((5-fluoro-3-((S)-pent-3-yn-2-yloxy)-1,7-naphthyridin-8-yl)amino)-3,3,11b-trimethyl-4a,5,6,11b-tetrahydro-3H-benzo[6,7]oxepino[4,5-b][1,4]thiazine 4,4-dioxide and (4aR,11bR)-2-amino-10-((5-fluoro-3-((R)-pent-3-yn-2-yloxy)-1,7-naphthyridin-8-yl)amino)-3,3,11b-trimethyl-4a,5,6,11b-tetrahydro-3H-benzo[6,7]oxepino[4,5-b][1,4]thiazine 4,4-dioxide Followed General Method 5 using Intermediate 20 and 8-chloro-5-fluoro-3-(pent-3-yn-2-yloxy)-1,7-naphthyridine. The compound was separated into its enantiomers via prep-scale supercritical fluid chromatography using a Chiralpak AD-H column with an isocratic 40% carbon dioxide/60% isopropanol with 0.2% diethyl amine solvent system to yield (4aR,11bR)-2-amino-10-((5-fluoro-3-((S)-pent-3-yn-2-yloxy)-1,7-naphthyridin-8-yl)amino)-3,3,11b-trimethyl-4a,5,6,11b-tetrahydro-3H-benzo[6,7]oxepino[4,5-b][1,4]thiazine 4,4-dioxide (36 mg, 0.065 mmol, 34.2% yield) and (4aR,11bR)-2-amino-10-((5-fluoro-3-((R)-pent-3-yn-2-yloxy)-1,7-naphthyridin-8-yl)amino)-3,3,11b-trimethyl-4a,5,6,11b-tetrahydro-3H-benzo[6,7]oxepino[4,5-b][1,4]thiazine 4,4-dioxide (38 mg, 0.069 mmol, 36.1% yield). The stereochemistry was assigned arbitrarily. LC/MS (ESI+) m/z=552.1 for both diastereomers.

Example 88

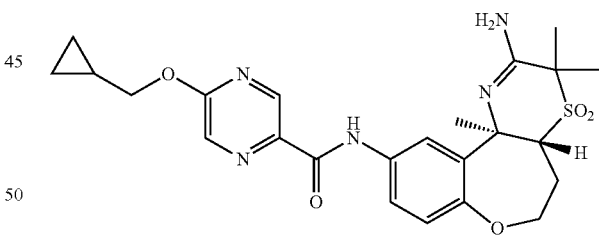

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(cyclopropylmethoxy)pyrazine-2-carboxamide Step 1: tert-butyl N-[(4aR,11bR)-10-[(5-chloropyrazine-2-carbonyl)amino]-3,3,11b-trimethyl-4,4-dioxo-5,6-dihydro-4aH-[1]benzoxepino[4,5-b][1,4]thiazin-2-yl]carbamate Using general method 3 (step 1), trans intermediate 19 (150 mg, 0.354 mmol) and 5-chloropyrazine-2-carboxylic acid (67.4 mg, 0.425 mmol) were combined to afford the title compound (140 mg, 0.248 mmol, 70.1%) as a white solid. MS m/z=564.0 (M+H).

Step 2: tert-butyl N-[(4aR,11bR)-10-[[5-(cyclopropylmethoxy)pyrazine-2-carbonyl]amino]-3,3,11b-trimethyl-4,4-dioxo-5,6-dihydro-4aH-[1]benzoxepino[4,5-b][1,4]thiazin-2-yl]carbamate A solution of hydroxymethyl)cyclopropane (0.10 mL, 1.20 mmol) in THF (1.4 mL) was cooled to 0° C. and treated with sodium hydride (60% wt; 36.1 mg, 0.90 mmol). The reaction was stirred for 30 minutes and then a solution of tert-butyl N-[(4aR,11bR)-10-[(5-chloropyrazine-2-carbonyl)amino]-3,3,11b-trimethyl-4,4-dioxo-5,6-dihydro-4aH-[1]benzoxepino[4,5-b][1,4]thiazin-2-yl]carbamate (113 mg, 0.20 mmol) in 1 mL of THF was added. The reaction was stirred at ambient temperature for 1 hour. The reaction was treated with aqueous ammonium chloride and extracted with ethyl acetate. The organic portion was concentrated. The resulting crude was purified by column chromatography, eluting with 10-50% ethyl acetate/heptane to afford the title compound (100 mg, 0.17 mmol, 83%) as an off-white solid. MS m/z=600.2 (M+H).

Step 3: N-((4aR,11bR)-2-amino-3,3,11b-trimethyl-4,4-dioxido-4a,5,6,11b-tetrahydro-3H-benzo[6,7]oxepino[4,5b][1,4]thiazin-10-yl)-5-(cyclopropylmethoxy)pyrazine-2-carboxamide A solution of tert-butyl N-[(4aR,11bR)-10-[[5-(cyclopropylmethoxy)pyrazine-2-carbonyl]amino]-3,3,11b-trimethyl-4,4-dioxo-5,6-dihydro-4aH-[1]benzoxepino[4,5-b][1,4]thiazin-2-yl]carbamate (100 mg, 0.17 mmol) in dichloromethane (2 mL) was treated with tfa (0.46 mL, 6.01 mmol). The reaction was stirred at ambient temperature for 2 hrs. The reaction mixture was poured into water and the pH was brought to >10 using sat. NaHCO$_3$ and, then extracted with DCM. The combined organics were dried over Na$_2$SO$_4$, filtered, concentrated and purified by column chromatography, eluting with 1-5% methanol/dichloromethane to afford the title compound (10 mg, 0.020 mmol, 10%) as a white solid. MS m/z=500.3 (M+H).

Example 90

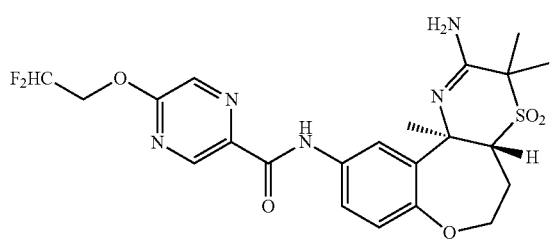 [SMILES: CC1(C)C(N)=N[C@]2(C)c3cc(NC(=O)c4cnc(OCC(F)F)cn4)ccc3OCC[C@H]2S1(=O)=O]

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(2,2-difluoroethoxy)pyrazine-2-carboxamide To a mixture of tert-butyl ((4aR,11bR)-10-(5-chloropyrazine-2-carboxamido)-3,3,11b-trimethyl-4,4-dioxido-4a,5,6,11b-tetrahydro-3H-benzo[6,7]oxepino[4,5-b][1,4]thiazin-2-yl)carbamate (40 mg, 0.071 mmol) and 2,2-difluoroethanol (0.090 mL, 1.418 mmol) in THF was added potassium carbonate (20 mg, 0.142 mmol). The reaction was stirred at 60° C. for 3 hours. The reaction was partitioned between ethyl acetate and water. The organic portion was dried over Na$_2$SO$_4$, filtered and concentrated to afford the boc-protected material. This was suspended in 1 mL of DCM and treated with TFA (0.1 mL). The reaction was stirred for 1 hr. The reaction was then basified using sat. NaHCO$_3$ and, then extracted with DCM. The combined organics were dried over Na$_2$SO$_4$, filtered and concentrated. The resulting crude was purified by column chromatography, eluting with 1-5% methanol/dichloromethane to afford the title compound (28 mg, 0.055 mmol, 77%). MS m/z=510.2 (M+H).

Example 124

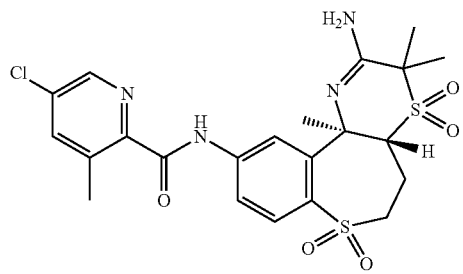 [SMILES: Cc1cc(Cl)cnc1C(=O)Nc1ccc2c(c1)[C@@]1(C)N=C(N)C(C)(C)S(=O)(=O)[C@@H]1CCS2(=O)=O]

Synthesis of N-((4aR,11bR)-2-amino-3,3,11b-trimethyl-4,4,7,7-tetraoxido-4a,5,6,11b-tetrahydro-3H-benzo[6,7]thiepino[4,5-b][1,4]thiazin-10-yl)-5-chloro-3-methylpicolinamide Step 1: Tert-butyl N-[(4aR,11bR)-10-[(5-chloro-3-methyl-pyridine-2-carbonyl)amino]-3,3,11b-trimethyl-4,4-dioxo-5,6-dihydro-4aH-[1]benzothiepino[4,5-b][1,4]thiazin-2-yl]-N-tert-butoxycarbonyl-carbamate Tert-butyl N-[(4aR,11bR)-10-[(5-chloro-3-methyl-pyridine-2-carbonyl)amino]-3,3,11b-trimethyl-4,4-dioxo-5,6-dihydro-4aH-[1]benzothiepino[4,5-b][1,4]thiazin-2-yl]-N-tert-butoxycarbonyl-carbamate was prepared in 84% yield via General Method 4, Step 1 using Intermediate 32-trans and 5-chloro-3-methylpicolinic acid. LC/MS (ESI) m/z=715.2 (M+Na).

Step 2: N-((4aR,11bR)-2-amino-3,3,11b-trimethyl-4,4,7,7-tetraoxido-4a,5,6,11b-tetrahydro-3H-benzo[6,7]thiepino[4,5-b][1,4]thiazin-10-yl)-5-chloro-3-methylpicolinamide A vial was charged with tert-butyl N-[(4aR,11bR)-10-[(5-chloro-3-methyl-pyridine-2-carbonyl)amino]-3,3,11b-trimethyl-4,4-dioxo-5,6-dihydro-4aH-[1]benzothiepino[4,5-b][1,4]thiazin-2-yl]-N-tert-butoxycarbonyl-carbamate (90 mg, 0.130 mmol), THF (556 µl) water (185 µl) and MeOH (556 µl). Oxone (239 mg, 0.389 mmol) was added, and the mixture was stirred at RT for 72 h. Water and EtOAc were added, and the layers were separated. The organic portion was dried, filtered and concentrated. The crude material was dissolved in 1 mL DCM, and TFA (200 µl, 2.60 mmol) was added. The reaction was stirred at RT for 2 h. The solution was loaded onto an SCX column and washed with MeOH. The free base was eluted with ammonia/MeOH. The filtrate was concentrated, and the crude material was triturated in EtOAc, filtered, washed with EtOAc and dried to provide N-((4aR,11bR)-2-amino-3,3,11b-trimethyl-4,4,7,7-tetraoxido-4a,5,6,11b-tetrahydro-3H-benzo[6,7]thiepino[4,5-b][1,4]thiazin-10-yl)-5-chloro-3-methylpicolinamide (35 mg, 0.067 mmol, 51.3% yield) as a white solid. LC/MS (ESI+) m/z=525.1 (M+Na).

Example 130

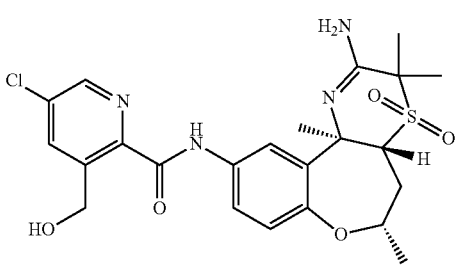

Synthesis of N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(hydroxymethyl)picolinamide Step 1: N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(methoxymethyl)picolinamide N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(methoxymethyl)picolinamide was prepared via General Method 3, using Intermediate 30 and 5-chloro-3-(methoxymethyl)picolinic acid. The product was isolated in 70% yield. LC/MS (ESI+) m/z=521.0 (M+H).

Step 2: N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(hydroxymethyl)picolinamide A round bottom flask was charged with N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(methoxymethyl)picolinamide (125 mg, 0.240 mmol) and DCM (2.4 ml), and the solution was cooled to 0° C. under nitrogen. BBr₃ (47.6 µl, 0.504 mmol) was added dropwise, and the mixture was allowed to warm to RT. After stirring at RT for 1 h, the reaction was quenched with water and neutralized with saturated aqueous sodium bicarbonate. EtOAc was added, and the layers were separated. The aqueous portion was extracted with additional EtOAc, and the combined organic portions were dried over sodium sulfate, filtered and concentrated. The crude material was purified by silica gel chromatography using a gradient of 0-75% 75/25/2 EtOAc/EtOH/NH₄OH in heptane to provide N-((4aR,6S,11bR)-2-amino-3,3,6,11b-tetramethyl-4,4-dioxido-4a,5,6,11b-tetrahydro-3H-benzo[6,7]oxepino[4,5-b][1,4]thiazin-10-yl)-5-chloro-3-(hydroxymethyl)picolinamide (30 mg, 0.059 mmol, 24.66% yield) as a tan solid. LC/MS (ESI+) m/z=507.0 (M+H).

Example 136

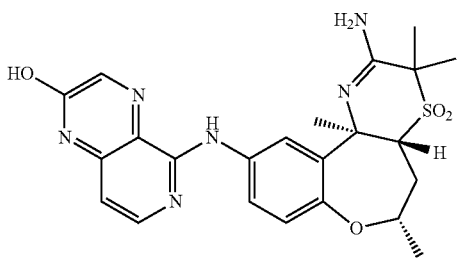 [SMILES: C[C@H]1C[C@@H]2[C@](C)(N=C(N)C(C)(C)S2(=O)=O)c2cc(Nc3nccc4nc(O)cnc34)ccc2O1]

Synthesis of (4aR,6S,11bR)-2-Amino-10-((2-hydroxypyrido[3,4-b]pyrazin-5-yl)amino)-3,3,6,11b-tetramethyl-4a,5,6,11b-tetrahydro-3H-benzo[6,7]oxepino[4,5-b][1,4]thiazine 4,4-dioxide Step 1: 5-Chloro-2-((1-methyl-1H-pyrazol-4-yl)methoxy)pyrido[3,4-b]pyrazine In an analogous reaction to that described for Intermediate 55, Step 2,5-chloropyrido[3,4-b]pyrazin-2-ol and (1-methyl-1H-pyrazol-4-yl)methanol were combined to produce the title compound. LC/MS (ESI+) m/z: 276.0 (M+H+).

Step 2: (4aR,6S,11bR)-2-Amino-10-((2-hydroxypyrido[3,4-b]pyrazin-5-yl)amino)-3,3,6,11b-tetramethyl-4a,5,6,11b-tetrahydro-3H-benzo[6,7]oxepino[4,5-b][1,4]thiazine 4,4-dioxide The title compound was synthesized in 80% yield as described for General Method 11, using 5-Chloro-2-((1-methyl-1H-pyrazol-4-yl)methoxy)pyrido[3,4-b]pyrazine in place of 2-(((5-chloropyrido[3,4-b]pyrazin-2-yl)oxy)methyl)-5-methyloxazole. LC/MS (ESI+) m/z: 483.1 (M+H+).

Example 143

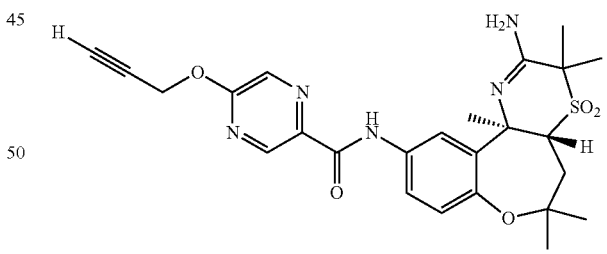

Synthesis of N-((4aR,11bR)-2-Amino-3,3,6,6,11b-pentamethyl-4,4-dioxido-4a,5,6,11b-tetrahydro-3H-benzo[6,7]oxepino[4,5-b][1,4]thiazin-10-yl)-5-(prop-2-yn-1-yloxy)pyrazine-2-carboxamide Step 1: tert-Butyl N-[(4aR,11bR)-10-[(5-chloropyrazine-2-carbonyl)amino]-3,3,6,6,11b-pentamethyl-4,4-dioxo-4a,5-dihydro-[1]-benzoxepino[4,5-b][1,4]thiazin-2-yl]-N-tert-butoxycarbonyl-carbamate In an analogous reaction to that described for Intermediate 36, tert-butyl N-[(4aR,11bR)-10-amino-3,3,6,6,11b-pentamethyl-4,4-dioxo-4a,5-dihydro-[1]benzoxepino[4,5-b][1,4]thiazin-2-yl]-N-tert-butoxycarbonyl-carbamate (100 mg, 0.181 mmol) was converted into the title compound (125 mg, quantitative yield). LC/MS (ESI+) m/z: 715.0 (M+Na+).

Step 2: N-((4aR,11bR)-2-Amino-3,3,6,6,11b-pentamethyl-4,4-dioxido-4a,5,6,11b-tetrahydro-3H-benzo[6,7]oxepino[4,5-b][1,4]thiazin-10-yl)-5-(prop-2-yn-1-yloxy)pyrazine-2-carboxamide Using the reaction sequence described in Method 7, tert-butyl N-[(4aR,6S,11bR)-10-[(5-chloropyrazine-2-carbonyl)amino]-3,3,6,11b-tetramethyl-4,4-dioxo-5,6-dihydro-4aH-[1]benzoxepino[4,5-b][1,4]thiazin-2-yl]-N-tert-butoxycarbonyl-carbamate (126 mg, 0.19 mmol) and propargyl alcohol (0.22 mL, 3.7 mmol) were converted to the title compound (39 mg, 0.076 mmol, 42.2% yield). LC/MS (ESI+) m/z: 498.0 (M+H+).

Example 178

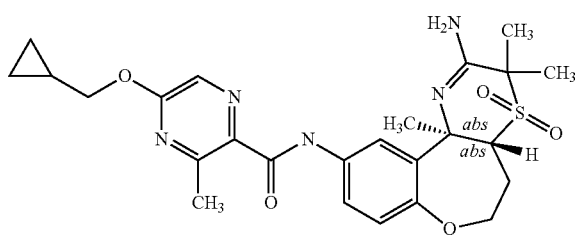

Synthesis of N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(cyclopropylmethoxy)-3-methylpyrazine-2-carboxamide Step 1: tert-butyl ((4aR,11bR)-10-(5-(cyclopropylmethoxy)-3-methylpyrazine-2-carboxamido)-3,3,11b-trimethyl-4,4-dioxido-4a,5,6,11b-tetrahydro-3H-benzo[6,7]oxepino[4,5-b][1,4]thiazin-2-yl)carbamate To a solution of crude tert-butyl ((4aR,11bR)-10-amino-3,3,11b-trimethyl-4,4-dioxido-4a,5,6,11b-tetrahydro-3H-benzo[6,7]oxepino[4,5-b][1,4]thiazin-2-yl)carbamate (0.035 g, 0.083 mmol) in DCM (0.8 ml) were added 5-(cyclopropylmethoxy)-3-methylpyrazine-2-carboxylic acid (0.018 g, 0.087 mmol), triethylamine (0.023 ml, 0.165 mmol) and HATU (0.035 g, 0.091 mmol). The mixture was stirred at RT for 25 min. The reaction mixture was diluted with water and sat. NaHCO₃, and extracted with DCM. The organic extract was washed with brine and dried over MgSO₄. It was filtered and concentrated to give the crude material as a yellow oil which was used for next step directly. MS m/z: 614.1 [M+H].

Step 2: N-((4aR,11bR)-2-amino-3,3,11b-trimethyl-4,4-dioxido-4a,5,6,11b-tetrahydro-3H-benzo[6,7]oxepino[4,5-b][1,4]thiazin-10-yl)-5-(cyclopropylmethoxy)-3-methylpyrazine-2-carboxamide To a reaction mixture of tert-butyl ((4aR,11bR)-10-(5-(cyclopropylmethoxy)-3-methylpyrazine-2-carboxamido)-3,3,11b-trimethyl-4,4-dioxido-4a,5,6,11b-tetrahydro-3H-benzo[6,7]oxepino[4,5-b][1,4]thiazin-2-yl)carbamate (40 mg, 0.065 mmol) in DMF 1 ml was added K2CO3 (40 mg, 0.29 mmol). It was heated to 85° C. for 3 h. It was cooled to RT, diluted with water, and extracted with EtOAc. The organic phase obtained was concentrated under reduced pressure and the residue was purified by silica gel chromatography eluting with 15% to 25% to 40% EtOAc/MeOH/Et3N in (40% EtOAc in Heptane) to yield 23 mg of desired product. MS m/z: 514.2 [M+H].

Tables 1 and 2 below list compound examples, representative of compounds of Formulas I, II and III, and sub-formulas thereof, provided by the present invention, including the compound name, the mass found and/or NMR (Table 1 for examples 4, 6a & 6b) and biological data (BACE enzyme; BACE cell & Cathepsin D enzyme; where available) are listed in Table 2 for all examples:

Table 1

| Example # | Method | Name | Structure | Analytical Data |
|---|---|---|---|---|
| 4 | 1 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide, N-((4aS,11bS)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 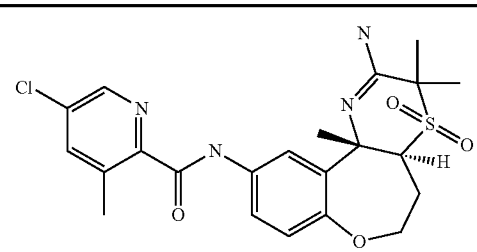 | LC/MS (ESI+) m/z = 436 (M + H). ¹H NMR (400 MHz, DMSO-d₆) δ ppm 10.41 (s, 1 H) 8.88 (d, J = 1.27 Hz, 1 H) 8.40 (d, J = 1.37 Hz, 1 H) 7.75-7.89 (m, 2 H) 7.13 (dd, J = 11.98, 8.85 Hz, 1 H) 6.00 (br. s., 2 H) 4.01 (s, 3 H) 3.47-3.67 (m, 2 H) 1.61 (s, 3 H) 1.56 (s, 3 H) 1.46 (s, 3 H) |

-continued

| Example # | Method | Name | Structure | Analytical Data |
|---|---|---|---|---|
| 6a | 2 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 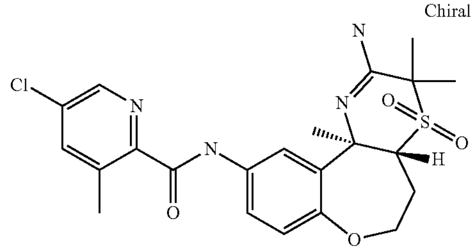 | LC/MS (ESI+) m/z = 477 $^1$H NMR (400 MHz, DMSO-d$_6$) § 10.35 (br s, 1H), 8.57 (dd, J = 0.5, 2.3 Hz, 1H), 8.02 (dd, J = 0.7, 2.3 Hz, 1H), 7.76-7.83 (m, 2H), 6.96 (d, J = 8.31 Hz, 1H), 5.77-6.00 (br s, 2H), 4.51-4.66 (m, 1H), 3.60-3.72 (m, 1H), 3.45-3.58 (m, 1H), 2.56 (s, 3H), 2.26-2.46 (m, 2H), 1.60 (s, 3H), 1.53 (s, 3H), 1.52 (s, 3H). |
| 6b | 2 | N-((4aS,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 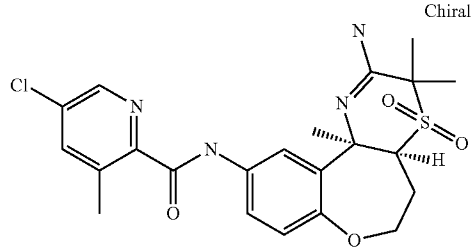 | LC/MS (ESI+) m/z = 477 $^1$H NMR (400 MHz, DMSO-d$_6$) δ 10.32 (br. s, 1H), 8.56 (dd, J = 0.6, 2.3 Hz, 1H), 8.00 (dd, J = 0.6, 2.3 Hz, 1H), 7.70 (dd, J = 2.3, 8.4 Hz, 1H), 7.46 (d, J = 2.3 Hz, 1H), 6.86 (d, J = 8.4 Hz, 1H), 5.96-6.13 (m, 2H), 4.22-4.35 (m, 1H), 3.81-3.94 (m, 1H), 3.66-3.79 (m, 1H), 2.53 (s, 3H), 2.30-2.45 (m, 2H), 1.62 (s, 3H), 1.61 (s, 3H), 1.41 (s, 3H). |
| 12 | 3 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-cyano-3-methyl-2-pyridinecarboxamide | 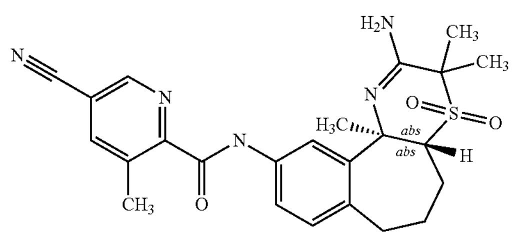 | $^1$H NMR (400 MHz, DMSO-d$_6$) δ ppm 1.40-1.55 (m, 2H), 1.46 (s, 3 H), 1.52 (s, 3H), 1.58 (s, 3 H), 2.01-2.10 (m, 1 H), 2.12-2.24 (m, 1 H), 2.55 (s, 3H), 2.75-2.85 (m, 1H), 3.14-3.24 (m, 2 H), 5.78 (br. s., 2 H), 7.12 (d, J = 8.1 Hz, 1 H) 7.79 (dd, J = 8.1, 2.3 Hz, 1 H) 7.87 (d, J = 2.3 Hz, 1 H) 8.39 (dd, J = 2.0, 0.8 Hz, 1 H) 8.97 (dd, J = 2.0, 0.6 Hz, 1 H) 10.44 (s, 1 H) |
| 22 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-3-methyl-2-pyrazinecarboxamide | 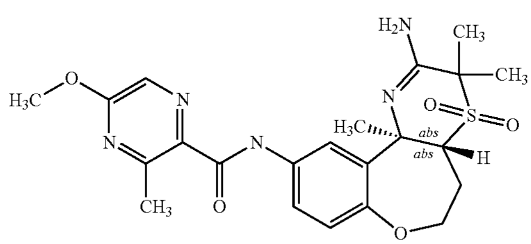 | $^1$H NMR (400 MHz, DMSO-d$_6$) d 10.20 (s, 1H), 8.24 (s, 1H), 7.72-7.89 (m, 2H), 6.95 (d, J = 8.41 Hz, 1H), 5.92 (br. s., 2H), 4.58 (d, J = 12.03 Hz, 1H), 3.99 (s, 3H), 3.56-3.73 (m, 1H), 3.50 (d, J = 10.27 Hz, 1H), 2.76 (s, 3H), 2.41 (d, J = 11.35 Hz, 1H), 2.21-2.36 (m, 1H), 1.59 (s, 3H), 1.53 (d, J = 3.33 Hz, 6H) |

| Example # | Method | Name | Structure | Analytical Data |
|---|---|---|---|---|
| 23 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-methyl-5-(2,2,2-trifluoroethoxy)-2-pyrazinecarboxamide | 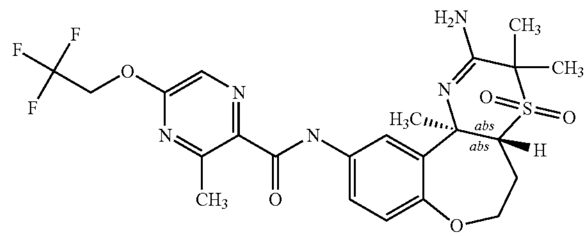 | $^1$H NMR (400 MHz, DMSO-d$_6$) d 10.29 (s, 1H), 8.43 (s, 1H), 7.73-7.90 (m, 2H), 6.97 (d, J = 8.41 Hz, 1H), 5.91 (br. s., 2H), 5.14 (q, J = 8.87 Hz, 2H), 4.59 (d, J = 12.13 Hz, 1H), 3.66 (t, J = 11.25 Hz, 1H), 3.51 (d, J = 11.64 Hz, 1H), 2.77 (s, 3H), 2.27-2.47 (m, 2H), 1.60 (s, 3H), 1.54 (d, J = 3.81 Hz, 6H) |
| 24 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3,5-dichloro-2-pyridinecarboxamide | 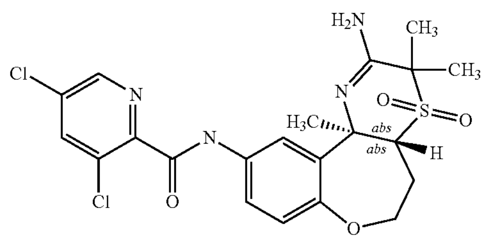 | $^1$H NMR (400 MHz, DMSO-d$_6$) d 10.59 (s, 1H), 8.71 (d, J = 1.96 Hz, 1H), 8.43 (d, J = 2.05 Hz, 1H), 7.63-7.86 (m, 2H), 6.97 (d, J = 8.41 Hz, 1H), 5.88 (br. s., 2H), 4.58 (d, J = 12.03 Hz, 1H), 3.65 (t, J = 11.49 Hz, 1H), 3.53 (d, J = 11.05 Hz, 1H), 2.35-2.46 (m, 1H), 2.24-2.35 (m, 1H), 1.60 (s, 3H), 1.53 (s, 3H), 1.51 (s, 3H) |
| 25 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-chloro-5-(trifluoromethyl)-2-pyridinecarboxamide | 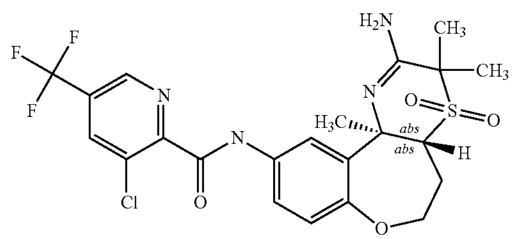 | $^1$H NMR (400 MHz, DMSO-d$_6$) d 10.71 (s, 1H), 8.97-9.17 (m, 1H), 8.55-8.79 (m, 1H), 7.78 (dd, J = 2.69, 8.46 Hz, 1H), 7.72 (d, J = 2.64 Hz, 1H), 6.99 (d, J = 8.51 Hz, 1H), 5.89 (s, 2H), 4.60 (d, J = 12.23 Hz, 1H), 3.66 (t, J = 11.30 Hz, 1H), 3.55 (d, J = 9.78 Hz, 1H), 2.43 (d, J = 10.76 Hz, 1H), 2.24-2.36 (m, 1H), 1.60 (s, 3H), 1.54 (s, 3H), 1.52 (s, 3H) |
| 28 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-6-chloro-3-methylimidazo[1,2-a]pyridine-2-carboxamide | 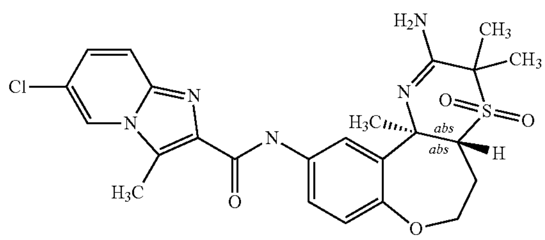 | $^1$H NMR (400 MHz, DMSO-d$_6$) d 9.91 (s, 1H), 8.69 (d, J = 1.17 Hz, 1H), 7.88 (dd, J = 2.54, 8.51 Hz, 1H), 7.82 (d, J = 2.64 Hz, 1H), 7.70 (dd, J = 0.68, 9.68 Hz, 1H), 7.44 (dd, J = 1.96, 9.59 Hz, 1H), 6.96 (d, J = 8.51 Hz, 1H), 5.97 (br. s., 2H), 4.59 (d, J = 12.03 Hz, 1H), 3.59-3.79 (m, 1H), 3.50 (d, J = 11.44 Hz, 1H), 2.82 (s, 3H), 2.36-2.48 (m, 1H), 2.25-2.36 (m, 1H), 1.60 (s, 3H), 1.55 (s, 6H) |

| Example # | Method | Name | Structure | Analytical Data |
|---|---|---|---|---|
| 54 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 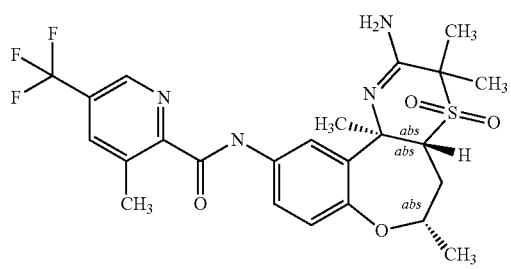 | 1H NMR (400 MHz, DMSO-d6) δ = 10.48 (s, 1H), 8.89 (s, 1H), 8.28 (s, 1H), 7.83-7.76 (m, 2H), 6.97 (d, J = 8.4 Hz, 1H), 5.87 (br. s, 2H), 4.00-3.69 (m, 1H), 3.63-3.41 (m, 1H), 2.59 (s, 3H), 2.41-2.32 (m, 1H), 2.26-2.12 (m, 1H), 1.61 (s, 3H), 1.54 (s, 3H), 1.52 (s, 3H), 1.46 (d, J = 6.3 Hz, 3H) |
| 55 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-methoxy-2-pyrazinecarboxamide | 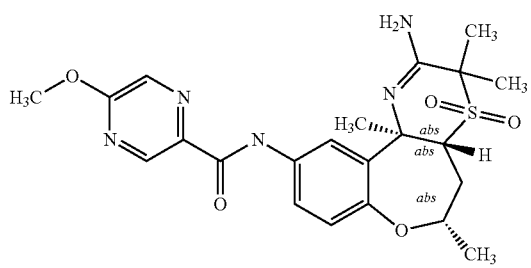 | 1H NMR (400 MHz, DMSO-d6) δ = 10.21 (br. s, 1H), 8.89 (d, J = 1.4 Hz, 1H), 8.41 (d, J = 1.4 Hz, 1H), 7.89 (d, J = 2.6 Hz, 1H), 7.81 (d, J = 8.7 Hz, 1H), 6.96 (d, J = 8.7 Hz, 1H), 5.93 (br. s, 2H), 4.02 (s, 3H), 3.91-3.81 (m, 1H), 3.64-3.42 (m, 1H), 2.42-2.31 (m, 1H), 2.26-2.12 (m, 1H), 1.66-1.51 (m, 9H), 1.45 (d, J = 6.3 Hz, 3H) |
| 56 | 5 | 8-(((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)amino)-1,7-naphthyridine-3-carbonitrile | 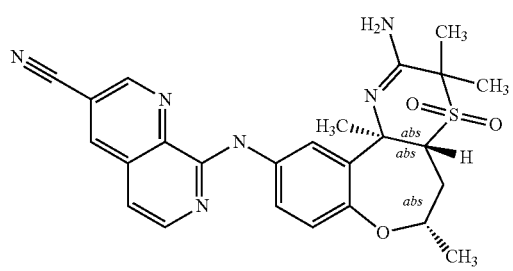 | 1H NMR (400 MHz, DMSO-d6) δ = 9.47 (s, 1H), 9.21 (d, J = 2.1 Hz, 1H), 8.97 (d, J = 2.1 Hz, 1H), 8.19 (d, J = 5.8 Hz, 1H), 8.13 (dd, J = 2.8, 8.5 Hz, 1H), 7.97 (d, J = 2.8 Hz, 1H), 7.19 (d, J = 5.8 Hz, 1H), 6.97 (d, J = 8.5 Hz, 1H), 5.98 (br. s, 2H), 3.92-3.77 (m, 1H), 3.52 (dd, J = 2.3, 12.2 Hz, 1H), 2.42-2.33 (m, 1H), 2.26-2.08 (m, 1H), 1.63 (s, 3H), 1.54 (s, 3H), 1.53 (s, 3H), 1.46 (d, J = 6.2 Hz, 3H) |
| 57 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 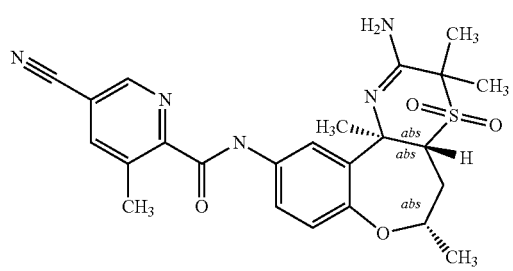 | 1H NMR (400 MHz, DMSO-d6) δ = 10.51 (s, 1H), 8.97 (dd, J = 0.7, 2.0 Hz, 1H), 8.38 (dd, J = 0.7, 2.0 Hz, 1H), 7.84-7.70 (m, 2H), 6.96 (d, J = 8.4 Hz, 1H), 5.88 (br. s, 2H), 3.90-3.78 (m, 1H), 3.59-3.48 (m, 1H), 2.54 (s, 3H), 2.41-2.31 (m, 1H), 2.24-2.09 (m, 1H), 1.60 (s, 3H), 1.53 (s, 3H), 1.51 (s, 3H), 1.45 (d, J = 6.3 Hz, 3H) |

-continued

| Example # | Method | Name | Structure | Analytical Data |
|---|---|---|---|---|
| 65 | 3 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 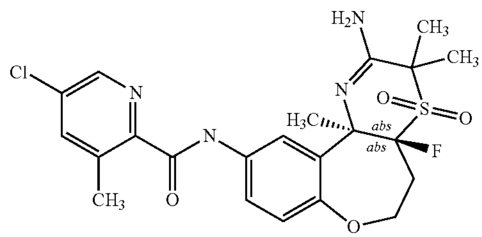 | $^1$H NMR (400 MHz, DMSO-$d_6$) δ 10.36 (s, 1H), 8.57 (d, J = 2.35 Hz, 1H), 8.02 (dd, J = 0.73, 2.30 Hz, 1H), 7.88 (d, J = 2.64 Hz, 1H), 7.82-7.86 (m, 1H), 7.00 (d, J = 8.41 Hz, 1H), 6.13 (s, 2H), 4.52 (dd, J = 3.23, 12.42 Hz, 1H), 3.61-3.72 (m, 1H), 2.69-2.94 (m, 1H), 2.57 (s, 3H), 2.45 (d, J = 5.48 Hz, 1H), 1.72 (s, 3H), 1.57-1.64 (m, 6H) |
| 72 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-methoxy-2-pyridinecarboxamide | 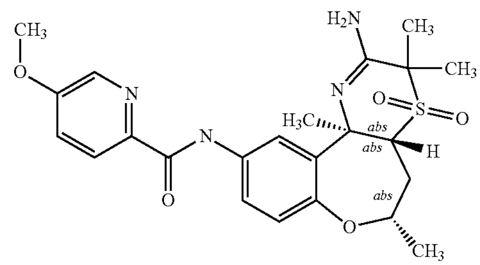 | $^1$H NMR (500 MHz, DMSO-$d_6$) δ ppm 1.45 (d, J = 6.33 Hz, 3 H) 1.53 (d, J = 5.43 Hz, 6 H) 1.61 (s, 3 H) 2.11-2.24 (m, 1 H) 2.37 (d, J = 13.34 Hz, 1 H) 3.51 (d, J = 10.86 Hz, 1 H) 3.85 (dd, J = 10.86, 5.65 Hz, 1 H) 3.93 (s, 3 H) 5.93 (br. s., 2 H) 6.95 (d, J = 8.59 Hz, 1 H) 7.61 (dd, J = 8.71, 2.83 Hz, 1 H) 7.84 (d, J = 4.30 Hz, 2 H) 8.12 (d, J = 8.59 Hz, 1 H) 8.39 (d, J = 2.71 Hz, 1 H) 10.17 (s, 1 H) |
| 73 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-3-chloro-5-(trifluoromethyl)-2-pyridinecarboxamide | 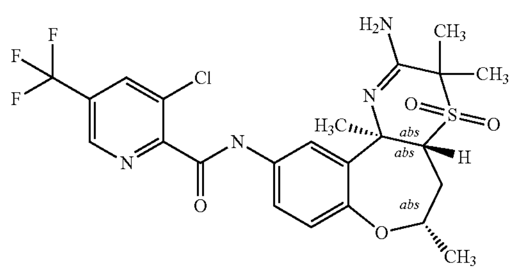 | $^1$H NMR (500 MHz, DMSO-$d_6$) δ ppm 1.46 (d, J = 6.33 Hz, 3 H) 1.50 (s, 3 H) 1.53 (s, 3 H) 1.61 (s, 3 H) 2.19 (d, J = 12.67 Hz, 1 H) 2.37 (d, J = 13.57 Hz, 1 H) 3.55 (d, J = 10.86 Hz, 1 H) 3.85 (d, J = 4.52 Hz, 1 H) 5.86 (s, 2 H) 6.98 (d, J = 8.37 Hz, 1 H) 7.69 (d, J = 2.49 Hz, 1 H) 7.77 (dd, J = 8.48, 2.60 Hz, 1 H) 8,67 (s, 1 H) 9.04 (s, 1 H) 10.68 (s, 1 H) |
| 74 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(2,2,2-trifluoroethoxy)-2-pyrazinecarboxamide | 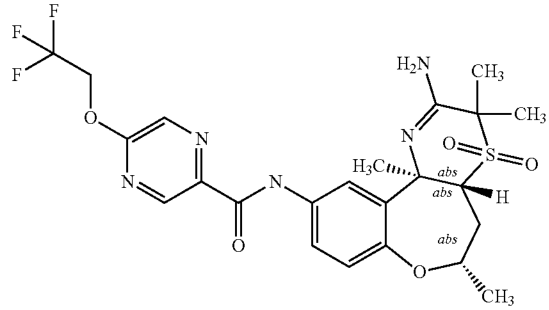 | $^1$H NMR (500 MHz, DMSO-$d_6$) δ ppm 1.45 (d, J = 6.33 Hz, 3 H) 1.53 (d, J = 7.01 Hz, 6 H) 1.60 (s, 3 H) 2.12-2.25 (m, 1 H) 2.37 (d, J = 13.80 Hz, 1 H) 3.51 (d, J = 11.76 Hz, 1 H) 3.85 (dd, J = 9.61, 6.22 Hz, 1 H) 5.16 (q, J = 8.97 Hz, 2 H) 5.89 (s, 2 H) 6.96 (d, J = 8.59 Hz, 1 H) 7.80 (dd, J = 8.48, 2.83 Hz, 1 H) 7.91 (d, J = 2.71 Hz, 1 H) 8.61 (d, J = 1.13 Hz, 1 H) 8.91 (d, J = 1.13 Hz, 1 H) 10.30 (s, 1 H) |

| Example # | Method | Name | Structure | Analytical Data |
|---|---|---|---|---|
| 76 | 7 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(1,3-oxazol-2-ylmethoxy)-2-pyrazinecarboxamide | 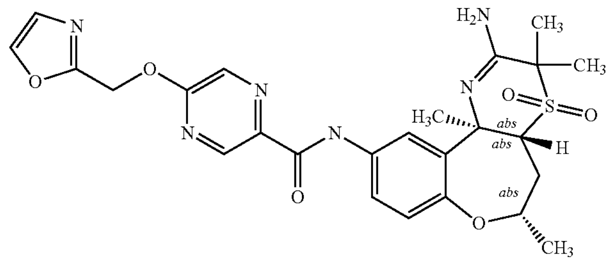 | $^1$H NMR (400 MHz, DMSO-d$_6$) δ ppm 1.45 (d, J = 6.22 Hz, 3 H) 1.53 (d, J = 4.66 Hz, 6 H) 1.60 (s, 3 H) 2.11-2.25 (m, 1 H) 2.30-2.42 (m, 1 H) 3.53 (d, J = 12.13 Hz, 1 H) 3.78-3.92 (m, 1 H) 5.61 (s, 2 H) 5.92 (br. s., 2 H) 6.92-7.01 (m, 1 H) 7.29 (d, J = 0.83 Hz, 1 H) 7.80 (dd, J = 8.50, 2.70 Hz, 1 H) 7.90 (d, J = 2.80 Hz, 1 H) 8.16-8.22 (m, 1 H) 8.50-8.57 (m, 1 H) 8.88 (d, J = 1.35 Hz, 1 H) 10.27 (s, 1 H) |
| 80 | 7 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-((5-methyl-1,3-oxazol-2-yl)methoxy)-2-pyrazinecarboxamide | 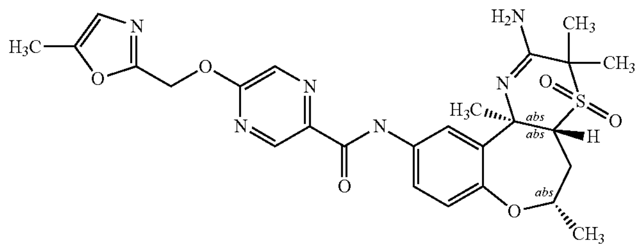 | $^1$H NMR (400 MHz, DMSO-d$_6$) δ ppm 1.45 (d, J = 6.22 Hz, 3 H) 1.55 (br. s., 6 H) 1.62 (br. s., 3 H) 2.13-2.27 (m, 1 H) 2.32 (d, J = 1.04 Hz, 3 H) 2.33-2.40 (m, 1 H) 3.53 (br. s., 1 H) 3.86 (dd, J = 9.93, 5.99 Hz, 1 H) 5.48-5.58 (m, 2 H) 5.92 (br. s., 2 H) 6.90 (d, J = 1.14 Hz, 1 H) 6.97 (d, J = 8.34 Hz, 1 H) 7.82 (d, J = 6.95 Hz, 1 H) 7.90 (d, J = 2.64 Hz, 1 H) 8.52 (d, J = 1.24 Hz, 1 H) 8.82-8.97 (m, 1 H) 10.28 (br. s., 1 H) |
| 83 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylethynyl)-3-methyl-2-pyridinecarboxamide | 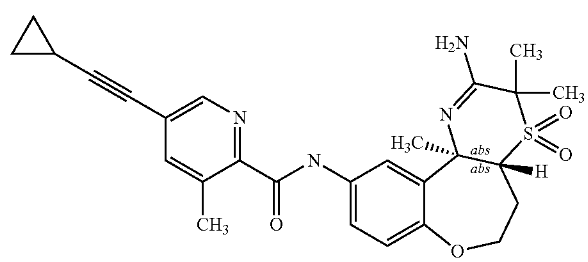 [SMILES: Cc1cc(C#CC2CC2)cnc1C(=O)Nc1ccc2c(c1)[C@@]1(C)N=C(N)C(C)(C)S(=O)(=O)[C@@H]1CCO2] | $^1$H NMR (400 MHz, DMSO-d$_6$) δ ppm 0.77-0.84 (m, 2 H) 0.92-0.99 (m, 2 H) 1.53 (d, J = 4.11 Hz, 6 H) 1.59 (s, 3 H) 1.62 (d, J = 8.31 Hz, 1 H) ) 2.26-2.34 (m, 1 H) 2.35-2.47 (m, 1 H) 2.53 (s, 3 H) 3.51 (d, J = 10.47 Hz, 1 H) 3.60-3.72 (m, 1 H) 4.52-4.64 (m, 1 H) 5.92 (br. s., 2 H) 6.95 (d, J = 8.51 Hz, 1 H) 7.78 (d, J = 2.74 Hz, 1 H) 7.79-7.84 (m, 2 H) 8.48 (d, J = 1.56 Hz, 1 H) 10.34 (s, 1 H) |
| 84 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(trifluoromethyl)-2-pyridinecarboxamide | 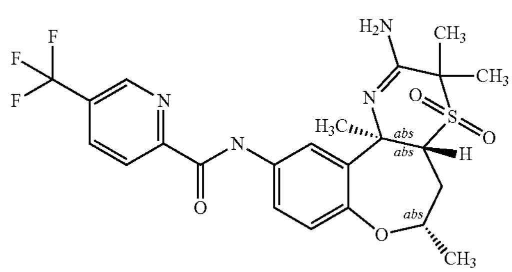 | $^1$H NMR (400 MHz, DMSO-d$_6$) δ ppm 1.46 (d, J = 6.22 Hz, 3 H) 1.54 (d, J = 5.18 Hz, 6 H) 1.61 (s, 3 H) 2.10-2.26 (m, 1 H) 2.38 (d, J = 13.68 Hz, 1 H) 3.53 (dd, J = 12.18, 2.13 Hz, 1 H) 3.78-3.93 (m, 1 H) 5.93 (s, 2 H) 6.98 (d, J = 8.50 Hz, 1 H) 7.85 (dd, J = 8.50, 2.70 Hz, 1 H) 7.92 (d, J = 2.70 Hz, 1 H) 8.33 (d, J = 8.19 Hz, 1 H) 8.49 (dd, J = 8.29, 1.76 Hz, 1 H) 9.06-9.18 (m, 1 H) 10.55 (s, 1 H) |

| Example # | Method | Name | Structure | Analytical Data |
|---|---|---|---|---|
| 85 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-2-pyridinecarboxamide | 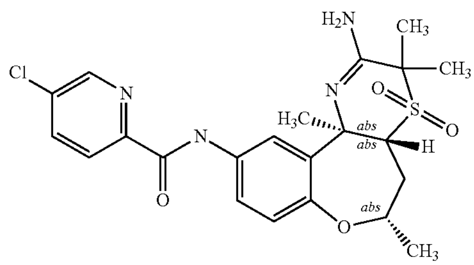 | $^1$H NMR (400 MHz, DMSO-$d_6$) δ ppm 1.45 (d, J = 6.22 Hz, 3 H) 1.53 (d, J = 4.98 Hz, 6 H) 1.60 (s, 3 H) 2.11-2.25 (m, 1 H) ) 2.30-2.42 (m, 1 H) 3.47-3.57 (m, 1 H) 3.78-3.91 (m, 1 H) 5.93 (s, 2 H) 6.96 (d, J = 8.50 Hz, 1 H) 7.83 (dd, J = 8.45, 2.75 Hz, 1 H) 7.89 (d, J = 2.70 Hz, 1 H) 8.11-8.25 (m, 2 H) 8.79 (dd, J = 2.28, 0.73 Hz, 1 H) 10.39 (s, 1 H) |
| 86 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-cyano-2-pyridinecarboxamide | 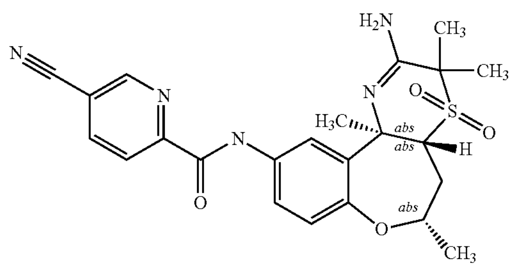 | $^1$H NMR (400 MHz, DMSO-$d_6$) δ ppm 1.45 (d, J = 6.22 Hz, 3 H) 1.53 (d, J = 5.29 Hz, 6 H) 1.60 (s, 3 H) 2.11-2.25 (m, 1 H) 2.30-2.42 (m, 1 H) 3.52 (dd, J = 12.18, 2.23 Hz, 1 H) 3.80-3.93 (m, 1 H) 5.92 (s, 2 H) 6.97 (d, J = 8.50 Hz, 1 H) 7.83 (dd, J = 8.50, 2.80 Hz, 1 H) 7.93 (d, J = 2.80 Hz, 1 H) 8.28 (dd, J = 8.19, 0.83 Hz, 1 H) 8.54-8.63 (m, 1 H) 9.20 (dd, J = 2.02, 0.88 Hz, 1 H) 10.56 (s, 1 H) |
| 93 | 3 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 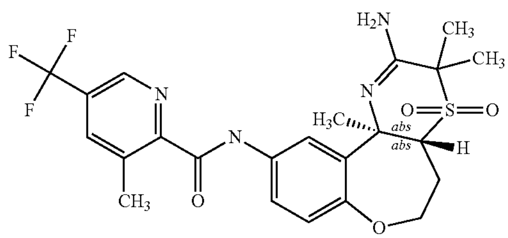 | $^1$H NMR (400 MHz, DMSO-$d_6$) δ ppm 10.49 (s, 1 H) 8.87-8.90 (m, 1 H) 8.27-8.30 (m, 1 H) 7.88 (d, J = 2.64 Hz, 1 H) 7.82-7.86 (m, 1 H) 7.01 (d, J = 8.51 Hz, 1 H) 6.11 (br. s, 2 H) 4.46-4.59 (m, 1 H) 3.59-3.72 (m, 1 H) 2.63-2.94 (m, 2 H) 2.59 (s, 3 H) 1.72 (s, 3 H) 1.61 (m, 6 H) |
| 98 | 3 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 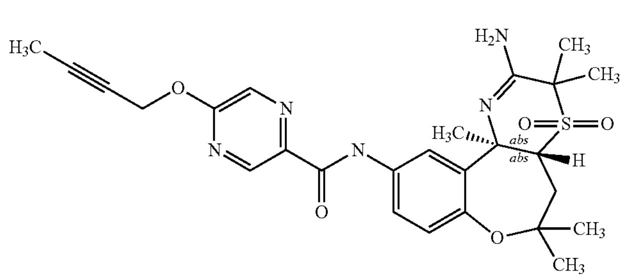 | $^1$H NMR (400 MHz, CHLOROFORM-d) δ ppm 9.49 (s, 1 H) 9.03 (d, J = 1.27 Hz, 1 H) 8.20 (d, J = 1.37 Hz, 1 H) 7.83 (dd, J = 8.51, 2.74 Hz, 1 H) 7.68 (d, J = 2.64 Hz, 1 H) 6.97 (d, J = 8.51 Hz, 1 H) 4.97-5.13 (m, 2 H) 3.39 (dd, J = 12.76, 2.20 Hz, 1 H) 2.56-2.69 (m, 1 H) 2.37-2.47 (m, 1 H) 1.90 (s, 3 H) 1.78-1.86 (m, 3 H) 1.70 (s, 6 H) 1.58-1.66 (m, 3 H) 1.02-1.09 (s, 3 H) |

-continued

| Example # | Method | Name | Structure | Analytical Data |
|---|---|---|---|---|
| 99 | 3 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 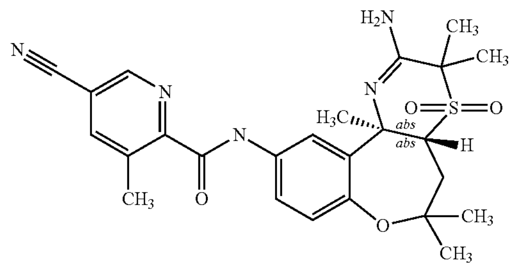 | $^1$H NMR (400 MHz, DMSO-d$_6$) δ ppm 10.79 (s, 1 H) 9.01-9.02 (m, 1 H) 8.44 (d, J = 1.17 Hz, 1 H) 7.90-7.95 (m, 1 H) 7.77 (d, J = 2.54 Hz, 1 H) 7.04 (d, J = 8.03 Hz, 1 H) 5.98 (br. s, 2H) 4.02-4.08 (m, 1 H) 2.58 (s, 3 H) 2.31-2.36 (m, 2 H) 1.92 (s, 3 H) 1.80 (s, 3 H) 1.77 (s, 3 H) 1.58 (s, 3 H) 1.06 (s, 3 H) |
| 104 | 3 | N-((4aR,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 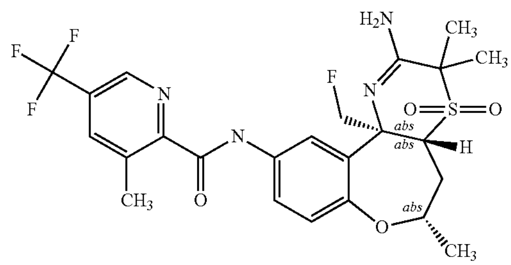 | $^1$H NMR (400 MHz, DMSO-d$_6$) δ ppm 10.53 (s, 1 H) 8.89-8.91 (m, 1 H) 8.29-8.31 (m, 1 H) 7.86 (dd, J = 8.55, 2.75 Hz, 1 H) 7.78 (d, J = 2.70 Hz, 1 H) 7.01 (d, J = 8.50 Hz, 1 H) 6.21 (br. s, 2 H) 5.26-5.53 (m, 1 H) 4.58-4.85 (m, 1 H) 3.89-3.97 (m, 1 H) 3.76-3.82 (m, 1 H) 2.60 (s, 3 H) 2.33-2.39 (m, 1 H) 2.15 (m, 1 H) 1.58 (s, 3 H) 1.55 (s, 3 H) 1.47 (d, J = 6.22 Hz, 3 H) |
| 111 | 3 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 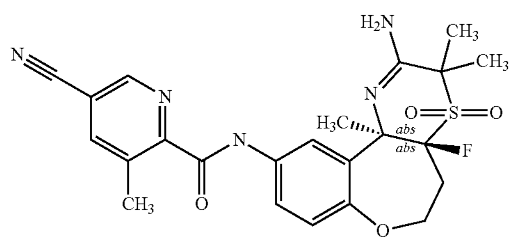 | $^1$H NMR (400 MHz, DMSO-d$_6$) δ ppm 10.47 (s, 1 H) 8.92 (d, J = 1.47 Hz, 1 H) 8.31-8.35 (m, 1 H) 7.75-7.85 (m, 2 H) 6.96 (d, J = 8.61 Hz, 1 H) 6.06 (br. s, 2 H) 4.44-4.52 (m, 1 H) 3.56-3.68 (m, 1 H) 3.34 (d, J = 19.95 Hz, 1 H) 2.62-2.87 (m, 2 H) 1.82 (s, 1 H) 1.75 (s, 1 H) 1.67 (s, 3 H) 1.56 (s, 6 H) |
| 112 | 5 | 8-(((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)amino)-1,7-naphthyridine-3-carbonitrile | 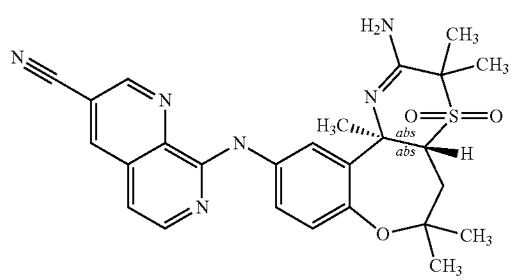 | $^1$H NMR (400 MHz, DMSO-d$_6$) δ ppm 9.46 (s, 1 H) 9.23 (m, 1 H) 8.98 (d, J = 2.07 Hz, 1 H) 8.22 (d, J = 5.70 Hz, 1 H) 8.15 (m, 1 H) 7.98 (d, J = 2.90 Hz, 1 H) 7.20 (d, J = 5.80 Hz, 1 H) 6.88 (d, J = 8.50 Hz, 1 H) 6.00 (br. s, 2 H) 3.98-4.11 (m, 1 H) 2.28-2.42 (m, 2 H) 1.64 (s, 3 H) 1.56 (br. s, 9 H) 1.02 (s, 3 H) |
| 113 | 3 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 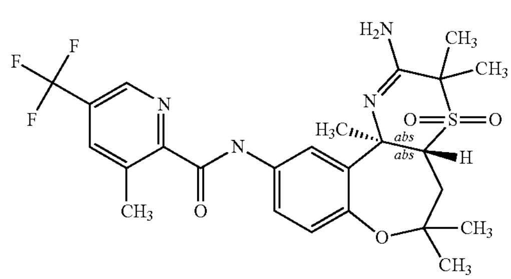 | $^1$H NMR (400 MHz, DMSO-d$_6$) δ ppm 10.46 (s, 1 H) 8.87-8.89 (m, 1 H) 8.26-8.29 (m, 1 H) 7.79 (dd, J = 8.46, 2.69 Hz, 1 H) 7.74-7.76 (m, 1 H) 6.86 (d, J = 8.51 Hz, 1 H) 5.88 (br. s, 2 H) 3.33-3.37 (m, 1 H) 2.58 (s, 3 H) 2.25-2.42 (m, 2 H) 1.60 (s, 3 H) 1.53 (s, 9 H) 0.99 (s, 3 H) |

-continued

| Example # | Method | Name | Structure | Analytical Data |
|---|---|---|---|---|
| 132 | 4 | N-((4aR,11bR)-2-amino-3,3,11b-trimethyl-4,4-dioxido-4a,5,6,11b-tetrahydro-3H-[1]benzothiepino[4,5-b][1,4]thiazin-10-yl)-3-methyl-5-(trifluoromethyl)-2-pyridinecarboxamide | 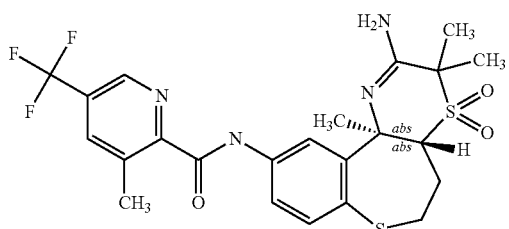 | $^1$H NMR (400 MHz, DMSO-$d_6$) δ ppm 1.55 (s, 3 H) 1.60 (s, 3 H) 1.99 (s, 3 H) 2.33-2.46 (m, 1 H) 2.64 (s, 3 H) 2.83-2.94 (m, 2 H) 3.17-3.25 (m, 1 H) 3.44-3.52 (m, 1 H) 5.85-5.98 (m, 2 H) 7.48-7.56 (m, 1 H) 7.86-7.91 (m, 1 H) 7.93-7.97 (m, 1 H) 8.32-8.39 (m, 1 H) 8.95-8.99 (m, 1 H) 10.65-10.71 (m, 1 H) |
| 133 | 5 | (4aR,6S,11bR)-3,3,6,11b-tetramethyl-N$^{10}$-(7-(trifluoromethyl)-pyrido[3,2-d]pyrimidin-4-yl)-4a,5,6,11b-tetrahydro-3H-[1]benzoxepino[4,5-b][1,4]thiazine-2,10-diamine 4,4-dioxide | 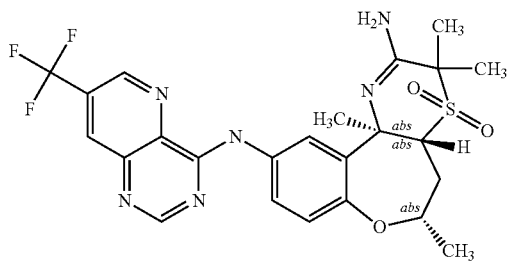 | $^1$H NMR (400 MHz, DMSO-$d_6$) δ ppm 1.47 (d, J = 6.12 Hz, 3 H) 1.54 (s, 6 H) 1.63 (s, 3 H) 2.15-2.26 (m, 1 H) 2.33-2.42 (m, 1 H) 3.48-3.58 (m, 1 H) 3.83-3.93 (m, 1 H) 5.88-6.02 (m, 2 H) 7.01 (d, J = 8.50 Hz, 1 H) 7.92 (dd, J = 8.50, 2.70 Hz, 1 H) 8.13 (d, J = 2.80 Hz, 1 H) 8.64 (d, J = 1.24 Hz, 1 H) 8.73 (s, 1 H) 9.21 (d, J = 1.97 Hz, 1 H) 10.35 (s, 1 H) |
| 138 | Example 136 | (4aR,6S,11bR)-3,3,6,11b-tetramethyl-N$^{10}$-(2-(1,3-oxazol-2-ylmethoxy)-pyrido[3,4-b]pyrazin-5-yl)-4a,5,6,11b-tetrahydro-3H-[1]benzoxepino[4,5-b][1,4]thiazine-2,10-diamine 4,4-dioxide | 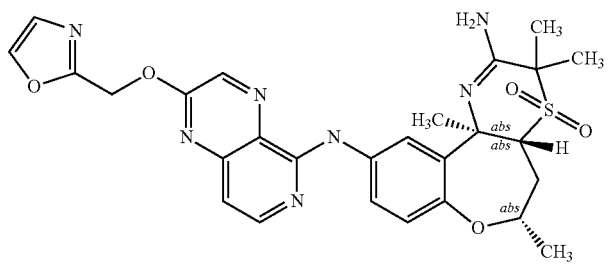 | $^1$H NMR (400 MHz, DMSO-$d_6$) δ ppm 1.46 (d, J = 6.22 Hz, 3 H), 1.51-1.57 (m, 6 H), 1.63 (s, 3 H), 2.11-2.25 (m, 1 H), 2.33-2.41 (m, 1 H), 3.52 (d, J = 11.71 Hz, 1 H), 3.75-3.93 (m, 1 H), 5.66 (s, 2 H), 5.96 (br. s., 2 H), 6.95 (d, J = 8.50 Hz, 1 H), 7.03 (d, J = 5.80 Hz, 1 H), 7.31 (d, J = 0.83 Hz, 1 H), 7.94 (d, J = 2.80 Hz, 1 H), 8.09 (dd, J = 8.50, 2.80 Hz, 1 H), 8.20-8.24 (m, 2 H), 8.65 (s, 1 H), 9.25 (s, 1 H). |
| 146 | 11 | (4aR,6S,11bR)-3,3,6,11b-tetramethyl-N$^{10}$-(2-((1-methyl-1H-pyrazol-3-yl)methoxy)-pyrido[3,4-b]pyrazin-5-yl)-4a,5,6,11b-tetrahydro-3H-[1]benzoxepino[4,5-b][1,4]thiazine-2,10-diamine 4,4-dioxide | 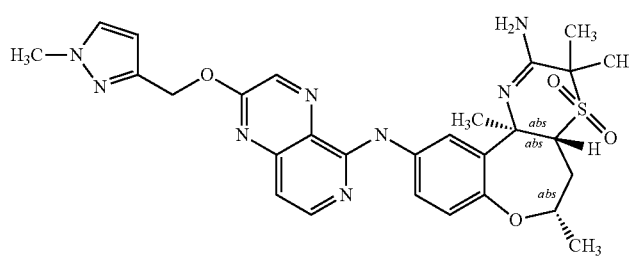 | $^1$H NMR (400 MHz, DMSO-$d_6$) δ ppm 1.46 (d, J = 6.12 Hz, 3 H), 1.54 (s, 6 H), 1.64 (s, 3 H), 2.11-2.25 (m, 1 H), 2.37 (d, J = 13.48 Hz, 1 H), 3.47-3.59 (m, 1 H), 3.85 (m, 4 H), 5.45 (s, 2 H), 5.98 (br. s., 2 H), 6.41 (d, J = 2.07 Hz, 1 H), 6.96 (d, J = 8.50 Hz, 1 H), 7.07 (d, J = 5.80 Hz, 1 H), 7.70 (d, J = 1.66 Hz, 1 H), 7.93 (d, J = 2.49 Hz, 1 H), 8.10 (dd, J = 8.50, 2.18 Hz, 1 H), 8.22 (d, J = 5.91 Hz, 1 H), 8.54 (s, 1 H), 9.21 (br. s., 1 H). |

-continued

| Example # | Method | Name | Structure | Analytical Data |
|---|---|---|---|---|
| 157 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethoxy)-3-methyl-2-pyridinecarboxamide | 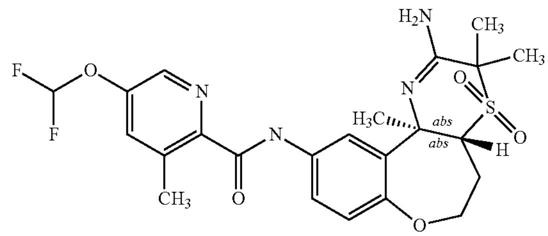 | $^1$H NMR (400 MHz, DMSO-d$_6$) δ ppm 1.52 (s, 3H), 1.53 (s, 3 H) 1.59 (s, 3 H) 2.27-2.45 (m, 2 H) 2.59 (s, 3 H) 3.47-3.57 (m, 1 H) 3.60-3.72 (m, 1 H) 4.54-4.64 (m, 1 H) 5.91 (s, 2 H) 6.95 (d, J = 8.41 Hz, 1 H) 7.23-7.64 (m, 1 H) 7.71 (d, J = 2.05 Hz, 1 H) 7.78 (d, J = 2.64 Hz, 1 H) 7.82 (dd, J = 8.46, 2.69 Hz, 1 H) 8.42 (d, J = 2.45 Hz, 1 H) 10.32 (s, 1 H) |
| 163 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethyl)-3-methyl-2-pyridinecarboxamide | 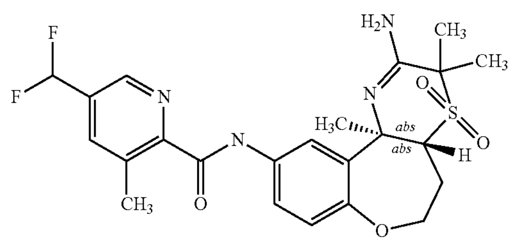 | $^1$H NMR (400 MHz, DMSO-d$_6$) δ ppm 1.53 (s, 3 H) 1.54 (s, 3 H) 1.60 (s, 3 H) 2.28-2.46 (m, 2 H) 2.59 (s, 3 H) 3.51 (dd, J = 11.84, 2.45 Hz, 1 H) 3.61-3.72 (m, 1 H) 4.54-4.63 (m, 1 H) 5.89 (s, 2 H) 6.96 (d, J = 8.31 Hz, 1 H) 7.06-7.38 (m, 1 H) 7.78-7.84 (m, 2 H) 8.03 (s, 1 H) 8.71 (s, 1 H) 10.43 (s, 1 H) |
| 165 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(trifluoromethyl)-2-pyridinecarboxamide | 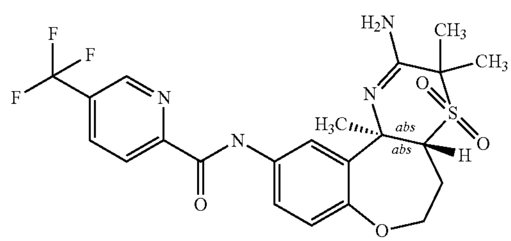 | $^1$H NMR (400 MHz, DMSO-d$_6$) δ ppm 1.48-1.57 (m, 6 H) 1.60 (br. s., 3 H) 1.66-1.96 (m, 2 H) 3.51 (d, J = 10.76 Hz, 1 H) 3.61-3.79 (m, 1 H) 4.59 (d, J = 11.44 Hz, 1 H) 5.93 (br. s., 2 H) 6.92-7.06 (m, 1 H) 7.77-7.89 (m, 1 H) 7.92-7.98 (m, 1 H) 8.34 (d, J = 8.02 Hz, 1 H) 8.50 (d, J = 8.31 Hz, 1 H) 9.06-9.15 (m, 1 H) 10.56 (br. s., 1 H) |
| 166 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-2-pyrazinecarboxamide | 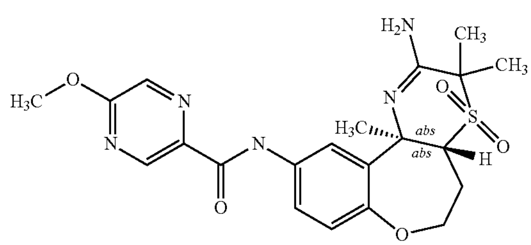 | $^1$H NMR (400 MHz, DMSO-d$_6$) δ ppm 1.54 (s, 3 H) 1.55 (s, 3 H) 1.60 (s, 3 H) 2.29-2.42 (m, 2 H) 3.50 (dd, J = 11.88, 2.59 Hz, 1 H) 3.61-3.74 (m, 1 H) 4.03 (s, 3 H) 4.54-4.63 (m, 1 H) 5.92 (s, 2 H) 6.97 (d, J = 8.51 Hz, 1 H) 7.81 (dd, J = 8.46, 2.79 Hz, 1 H) 7.92 (d, J = 2.74 Hz, 1 H) 8.42 (d, J = 1.37 Hz, 1 H) 8.90 (d, J = 1.37 Hz, 1 H) 10.23 (s, 1 H) |

-continued

| Example # | Method | Name | Structure | Analytical Data |
|---|---|---|---|---|
| 168 | 5 | 8-(((4aR,11bR)-2-amino-3,3,11b-trimethyl-4,4-dioxido-4a,5,6,11b-tetrahydro-3H-[1]benzoxepino[4,5-b][1,4]thiazin-10-yl)amino)-1,7-naphthyridine-3-carbonitrile | 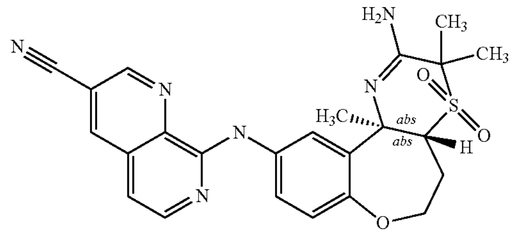 | $^1$H NMR (400 MHz, DMSO-d$_6$) δ ppm 1.55 (s, 6 H) 1.63 (s, 3 H) 2.28-2.47 (m, 2 H) 3.50 (d, J = 9.68 Hz, 1 H) 3.62-3.74 (m, 1 H) 4.53-4.65 (m, 1 H) 5.99 (br. s., 2 H) 6.99 (d, J = 8.61 Hz, 1 H) 7.20 (d, J = 5.87 Hz, 1 H) 8.00 (d, J = 2.74 Hz, 1 H) 8.14 (dd, J = 8.56, 2.79 Hz, 1 H) 8.20 (d, J = 5.77 Hz, 1 H) 8.98 (d, J = 2.05 Hz, 1 H) 9.22 (d, J = 1.96 Hz, 1 H) 9.48 (s, 1 H) |
| 169 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2,2-trifluoroethoxy)-2-pyrazinecarboxamide | 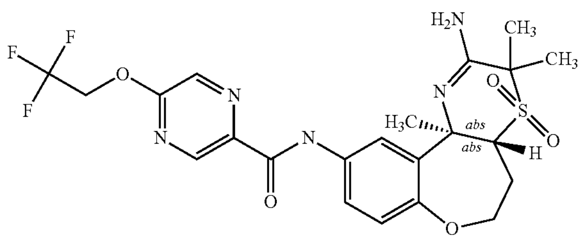 | $^1$H NMR (400 MHz, DMSO-d$_6$) δ ppm 1.53 (s, 3 H) 1.54 (s, 3 H) 1.59 (s, 3 H) 2.28-2.45 (m, 2 H) 3.50 (d, J = 9.78 Hz, 1 H) 3.61-3.72 (m, 1 H) 4.53-4.63 (m, 1 H) 5.16 (q, J = 8.97 Hz, 2 H) 5.91 (s, 2 H) 6.97 (d, J = 8.51 Hz, 1 H) 7.80 (dd, J = 8.56, 2.69 Hz, 1 H) 7.93 (d, J = 2.64 Hz, 1 H) 8.59-8.63 (m, 1 H) 8.88-8.96 (m, 1 H) 10.32 (s, 1 H) |
| 171 | 5 | 8-(((4aR,11bR)-2-amino-3,3,11b-trimethyl-4,4-dioxido-4a,5,6,11b-tetrahydro-3H-[1]benzoxepino[4,5-b][1,4]thiazin-10-yl)amino)-5-fluoro-1,7-naphthyridine-3-carbonitrile | 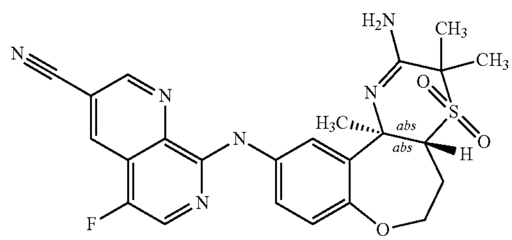 | $^1$H NMR (400 MHz, DMSO-d$_6$) δ ppm 1.54 (s, 3 H) 1.55 (s, 3 H) 1.62 (s, 3 H) 2.28-2.46 (m, 2 H) 3.49 (d, J = 9.78 Hz, 1 H) 3.61-3.72 (m, 1 H) 4.54-4.64 (m, 1 H) 5.97 (br. s., 2 H) 6.97 (d, J = 8.41 Hz, 1 H) 8.00-8.05 (m, 1 H) 8.05-8.07 (m, 1 H) 8.23 (d, J = 1.17 Hz, 1 H) 9.13 (d, J = 1.96 Hz, 1 H) 9.32 (d, J = 1.86 Hz, 1 H) 9.46 (s, 1 H) |
| 176 | 5 | (4aR,11bR)-N$^{10}$-(7-chloropyrido-[3,2-d]pyrimidin-4-yl)-3,3,11b-trimethyl-4a,5,6,11b-tetrahydro-3H-[1]benzoxepino[4,5-b][1,4]thiazine-2,10-diamine 4,4-dioxide | 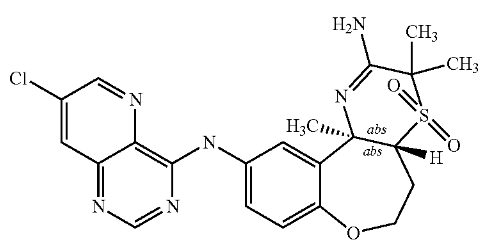 | $^1$H NMR (400 MHz, DMSO-d$_6$) δ ppm 1.55 (s, 6 H) 1.63 (s, 3 H) 2.29-2.48 (m, 2 H) 3.46-3.55 (m, 1 H) 3.65-3.76 (m, 1 H) 4.56-4.66 (m, 1 H) 5.95 (s, 2 H) 7.02 (d, J = 8.51 Hz, 1 H) 7.92 (dd, J = 8.56, 2.69 Hz, 1 H) 8.13 (d, J = 2.74 Hz, 1 H) 8.40 (d, J = 2.35 Hz, 1 H) 8.65 (s, 1 H) 8.94 (d, J = 2.35 Hz, 1 H) 10.19 (s, 1 H) |

| Example # | Method | Name | Structure | Analytical Data |
|---|---|---|---|---|
| 188 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 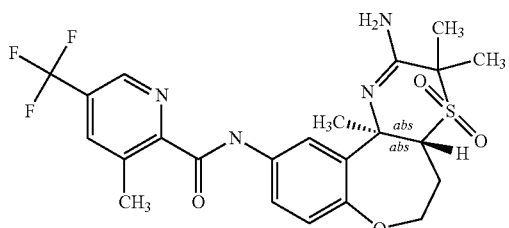 | $^1$H NMR (400 MHz, DMSO-d$_6$) δ ppm 1.53 (s, 3 H) 1.54 (s, 3 H) 1.60 (s, 3 H) 2.27-2.46 (m, 2 H) 2.59 (s, 3 H) 3.52 (dd, J = 11.84, 2.35 Hz, 1 H) 3.60-3.73 (m, 1 H) 4.54-4.64 (m, 1 H) 5.88 (s, 2 H) 6.98 (d, J = 8.41 Hz, 1 H) 7.78-7.83 (m, 2 H) 8.29 (dd, J = 1.47, 0.68 Hz, 1 H) 8.84-8.94 (m, 1 H) 10.49 (s, 1 H) |
| 189 | 3 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 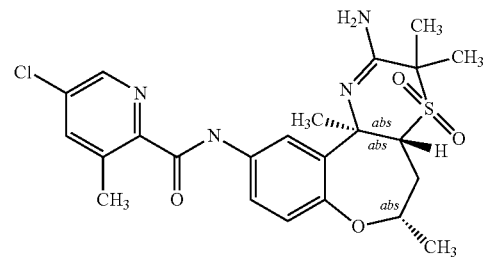 | $^1$H NMR (400 MHz, DMSO-d$_6$) δ ppm 1.45 (d, J = 6.16 Hz, 3 H) 1.52 (s, 3 H) 1.54 (s, 3 H) 1.61 (s, 3 H) 2.12-2.24 (m, 1 H) 2.37 (d, J = 13.40 Hz, 1 H) 2.56 (s, 3 H) 3.53 (d, J = 10.17 Hz, 1 H) 3.85 (dd, J = 10.12, 6.99 Hz, 1 H) 5.89 (s, 2 H) 6.95 (d, J = 8.41 Hz, 1 H) 7.76 (d, J = 2.74 Hz, 1 H) 7.80 (dd, J = 8.46, 2.69 Hz, 1 H) 8.02 (d, J = 1.56 Hz, 1 H) 8.57 (d, J = 2.25 Hz, 1 H) 10.34 (s, 1 H) |
| 190 | 3 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 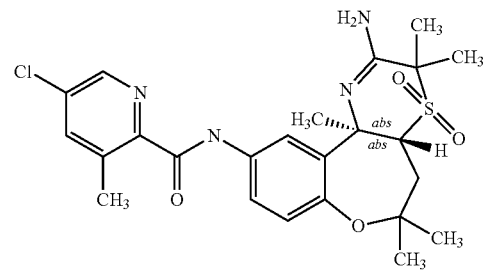 | $^1$H NMR (400 MHz, DMSO-d$_6$) δ ppm 1.00 (s, 3 H) 1.55 (s, 9 H) 1.61 (s, 3 H) 2.26-2.42 (m, 2 H) 2.57 (s, 1 H) 5.90 (br. s., 2 H) 6.86 (d, J = 8.41 Hz, 1 H) 7.76 (d, J = 2.64 Hz, 1 H) 7.81 (dd, J = 8.36, 2.59 Hz, 1 H) 8.02 (dd, J = 2.25, 0.68 Hz, 1 H) 8.58 (d, J = 2.35 Hz, 1 H) 10.33 (s, 1 H) |
| 191 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 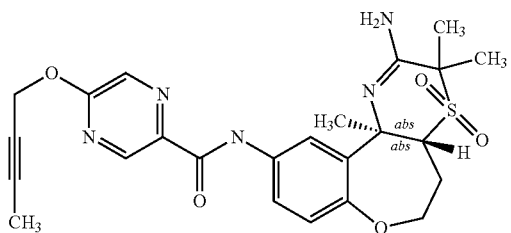 | $^1$H NMR (400 MHz, DMSO-d$_6$) δ ppm 1.53 (m, 6 H) 1.58 (s, 3 H) 1.81-1.88 (m, 3 H) 2.25-2.45 (m, 2 H) 3.49 (d, J = 11.54 Hz, 1 H) 3.61-3.72 (m, 1 H) 4.52-4.62 (m, 1 H) 5.03-5.12 (m, 2 H) 5.91 (br. s., 2 H) 6.96 (d, J = 8.61 Hz, 1 H) 7.80 (dd, J = 8.41, 2.15 Hz, 1 H) 7.91 (d, J = 2.64 Hz, 1 H) 8.42-8.46 (m, 1 H) 8.88 (d, J = 1.27 Hz, 1 H) 10.23 (s, 1 H) |

| Example # | Method | Name | Structure | Analytical Data |
|---|---|---|---|---|
| 192 | 4 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 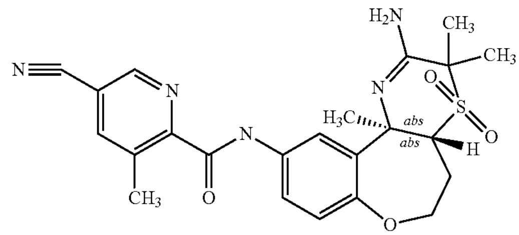 | $^1$H NMR (400 MHz, DMSO-$d_6$) δ ppm 1.53 (s, 3 H) 1.54 (s, 3 H) 1.60 (s, 3 H) 2.32-2.46 (m, 2 H) 2.55 (s, 3 H) 3.52 (dd, J = 11.74, 2.54 Hz, 1 H) 3.62-3.72 (m, 1 H) 4.59 (d, J = 10.86 Hz, 1 H) 5.89 (s, 2 H) 6.94-7.01 (m, 1 H) 7.77-7.83 (m, 2 H) 8.39 (dd, J = 1.96, 0.78 Hz, 1 H) 8.95-9.00 (m, 1 H) 10.52 (s, 1 H) |
| 193 | 3 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropyl-ethynyl)-2-pyridinecarboxamide | 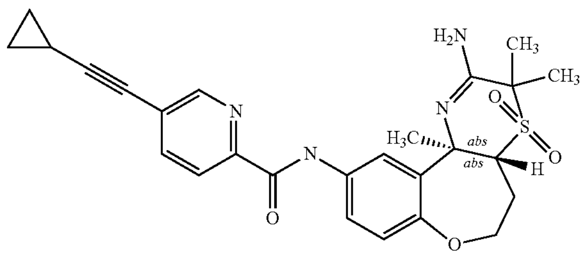 | $^1$H NMR (400 MHz, DMSO-$d_6$) δ ppm 0.80-0.85 (m, 2 H) 0.94-1.00 (m, 2 H) 1.54 (m, 6 H) 1.59 (s, 3 H) 1.62-1.69 (m, 1 H) 2.29-2.45 (m, 2 H) 3.50 (dd, J = 11.69, 2.40 Hz, 1 H) 3.62-3.75 (m, 1 H) 4.51-4.65 (m, 1 H) 5.94 (s, 2 H) 6.97 (d, J = 8.51 Hz, 1 H) 7.85 (dd, J = 8.51, 2.74 Hz, 1 H) 7.90 (d, J = 2.74 Hz, 1 H) 7.99-8.04 (m, 1 H) 8.06-8.13 (m, 1 H) 8.70 (dd, J = 2.05, 0.78 Hz, 1 H) 10.38 (s, 1 H) |

The methods used to prepare the exemplary compounds are included in Table 1. Table I further provides the mass and biological data (average μM IC$_{50}$'s for the enzyme and cell assays) for each compound, where available.

TABLE 2

| Example No | Compound Name | General Method Used | Penultimate Intermediate | MS Found | BACE1 FRET assay IC$_{50}$ (μM) | HEK cell assay IC$_{50}$ (μM) | CatD IC50 (μM) |
|---|---|---|---|---|---|---|---|
| 4 | N-((4aR*,11bR*)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide, N-((4aS,11bS)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | | | 477 | 0.004 | 0.01 | >100 |
| 6a | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | | | 477 | 0.002 | 0.006 | >100 |
| 6b | N-((4aS,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | | | 477 | 0.003 | 0.004 | >100 |
| 7 | 2-(((4aR,11bR)-2-amino-3,3,11b-trimethyl-4,4-dioxido-4a,5,6,11b-tetrahydro-3H-[1]benzoxepino[4,5-b][1,4]thiazin-10-yl)amino)-3-pyridinecarbonitrile | 6 | 19-trans | 426 | 0.116 | 0.124 | 252.0 |
| 8 | N-((4aS,11bR)-2-amino-3,3,11b-trimethyl-4,4-dioxido-3a,5,6,7,11b-hexahydrobenzo[3,4]cyclohepta[1,2-b][1,4]thiazin-10-yl)-5-methoxy-2-pyrazinecarboxamide | 3 | 28-cis | 458 | 0.172 | 0.031 | 1890 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 9 | N-((4a8,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-chloro-3-methyl-2-pyridinecarboxamide | 3 | 28-cis | 475 | 0.021 | 0.02 | 757.2 |
| 10 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-methoxy-2-pyrazinecarboxamide | 3 | 28-trans | 458 | 0.011 | 0.004 | 340.4 |
| 11 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-chloro-3-methyl-2-pyridinecarboxamide | 3 | 28-trans | 475 | 0.005 | 0.008 | 217.0 |
| 12 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-cyano-3-methyl-2-pyridinecarboxamide | 3 | 28-trans | 466 | 0.003 | 0.001 | 1040 |
| 13 | (4aR,11bR)-N⁻10⁻-(3-methoxy-2-pyridinyl)-3,3,11b-trimethyl-4a,5,6,11b-tetrahydro-3H-[1]benzoxepino[4,5-b][1,4]thiazine-2,10-diamine 4,4-dioxide | 6 | 19-trans | 431 | 0.094 | 0.073 | 369.2 |
| 14 | N-((4aR,11bR)-2-amino-3,3,11b-trimethyl-4,4-dioxido-4,5,6,11b-tetrahydro-3H-[1]benzoxepino[4,5-b][1,4]thiazin-10-yl)-5-(((1R)-1-methyl-2-butyn-1-yl)oxy)-2-pyrazinecarboxamide,N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(((1S)-1-methyl-2-butyn-1-yl)oxy)-2-pyrazinecarboxamide | 3 | 20 | 512 | 0.005 | 0.001 | 688.8 |
| 15 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(((1S)-1-methyl-2-butyn-1-yl)oxy)-2-pyrazinecarboxamide | 3 | 20 | 512 | 0.003 | 0.0005 | 1971 |
| 16 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(((1R)-1-methyl-2-butyn-1-yl)oxy)-2-pyrazinecarboxamide | 3 | 20 | 512 | 0.03 | 0.138 | 979.3 |
| 17 | N-((4aS,11bS)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | Example 17 | | 477 | 1.46 | 0.833 | >400 |
| 18 | N-((4aR,11bR)-2-amino-3,3,11b-trimethyl-4,4-dioxido-4a,5,6,11b-tetrahydro-3H-pyrido[3',2':6,7]oxepino[4,5-b][1,4]thiazin-10-yl)-5-chloro-3-methyl-2-pyridinecarboxamide | 4 | 23-trans | 478 | 0.006 | 0.014 | 1289 |
| 19 | (4aR,11bR)-N⁻10⁻-(3-chloro-1,7-naphthyridin-8-yl)-3,3,11b-trimethyl-4a,5,6,11b-tetrahydro-3H-pyrido[3',2':6,7]oxepino[4,5-b][1,4]thiazine-2,10-diamine4,4-dioxide | 6 | 23-trans | 487 | 0.003 | 0.019 | 262.5 |
| 20 | N-((4aS,11bR)-2-amino-3,3,11b-trimethyl-4,4-dioxido-4a,5,6,11b-tetrahydro-3H-pyrido[3',2':6,7]oxepino[4,5-b][1,4]thiazin-10-yl)-5-chloro-3-methyl-2-pyridinecarboxamide | 10 | 23-trans | 478 | 0.019 | 0.022 | 377.2 |
| 21 | N-((4aS,11bR)-2-amino-3,3,11b-trimethyl-4,4-dioxido-4a,5,6,11b-tetrahydro-3H-pyrido[3',2':6,7]oxepino[4,5-b][1,4]thiazin-10-yl)-5-cyano-3-methyl-2-pyridinecarboxamide | 10 | 23-cis | 469 | 0.007 | 0.026 | 1417 |
| 22 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-3-methyl-2-pyrazinecarboxamide | 3 | 19-trans | 474 | 0.017 | 0.007 | 1236 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 23 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-methyl-5-(2,2,2-trifluoroethoxy)-2-pyrazinecarboxamide | 3 | 19-trans | 542 | 0.003 | 0.01 | 1398 |
| 24 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3,5-dichloro-2-pyridinecarboxamide | 3 | 19-trans | 497 | 0.003 | 0.001 | 968.5 |
| 25 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-chloro-5-(trifluoromethyl)-2-pyridinecarboxamide | 3 | 19-trans | 531 | 0.007 | 0.002 | 3533 |
| 26 | N-((4aS,11bR)-2-amino-3,3,4a,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 25 | 491 | 0.003 | 0.001 | 995.0 |
| 27 | N-((4aR,11bR)-2-amino-3,3,4a,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 25 | 491 | 0.15 | 0.264 | 552.8 |
| 28 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-6-chloro-3-methylimidazo[1,2-a]pyridine-2-carboxamide | 3 | 19-trans | 516 | 0.028 | 0.008 | >400 |
| 29 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-ethyl-2-pyridinecarboxamide | 3 | 19-trans | 457 | 0.038 | 0.01 | 1369 |
| 30 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-isoquinolinecarboxamide | 3 | 19-trans | 479 | 0.084 | 0.058 | 1083 |
| 31 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-ethyl-2-pyridinecarboxamide | Example 31 | 19-trans | 491 | 0.015 | 0.016 | 226.0 |
| 32 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-methoxy-3-methyl-2-pyridinecarboxamide | 3 | 28-cis | 471 | 0.073 | 0.021 | 1339 |
| 33 | 8-(((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)amino)-1,7-naphthyridine-3-carbonitrile | 6 | 28-cis | 475 | 0.029 | 0.097 | 286.0 |
| 34 | (4aS,11bR)-N$^{10}$-(3-chloro-1,7-naphthyridin-8-yl)-3,3,11b-trimethyl-3,4a,5,6,7,11b-hexahydrobenzo[3,4]cyclohepta[1,2-b][1,4]thiazine-2,10-diamine 4,4-dioxide | 6 | 28-cis | 484 | 0.071 | 0.464 | 409.0 |
| 35 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-(difluoromethyl)-3-methyl-2-pyridinecarboxamide | 3 | 28-cis | 491 | 0.049 | 0.023 | >400 |
| 36 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-3,5-dichloro-2-pyridinecarboxamide | 3 | 28-cis | 495 | 0.062 | 0.29 | >400 |
| 37 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-cyano-3-methyl-2-pyridinecarboxamide | 3 | 28-cis | 466 | 0.036 | 0.016 | >400 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 38 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-chloro-2-pyridinecarboxamide | 3 | 28-cis | 461 | 0.099 | 0.15 | >400 |
| 39 | N-((4aS,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-(difluoromethoxy)-3-methyl-2-pyridinecarboxamide | 3 | 28-cis | 507 | 0.142 | 0.022 | >400 |
| 40 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-(difluoromethyl)-3-methyl-2-pyridinecarboxamide | 3 | 28-trans | 491 | 0.035 | 0.015 | >400 |
| 41 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-(difluoromethoxy)-3-methyl-2-pyridinecarboxamide | 3 | 28-trans | 507 | 0.018 | 0.005 | 5553 |
| 42 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-methoxy-3-methyl-2-pyridinecarboxamide | 3 | 28-trans | 471 | 0.067 | 0.032 | 2983 |
| 43 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-chloro-2-pyridinecarboxamide | 3 | 28-trans | 461 | 0.012 | 0.019 | 457.7 |
| 44 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-3,5-dichloro-2-pyridinecarboxamide | 3 | 28-trans | 495 | 0.005 | 0.016 | 540.8 |
| 45 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-3-methyl-5-(trifluoromethyl)-2-pyridinecarboxamide | 3 | 28-trans | 509 | 0.018 | 0.006 | 1464 |
| 46 | (4aR,11bR)-N$^{10}$-(3-chloro-1,7-naphthyridin-8-yl)-3,3,11b-trimethyl-3,4a,5,6,7,11b-hexahydrobenzo[3,4]cyclohepta[1,2-b][1,4]thiazine-2,10-diamine 4,4-dioxide | 6 | 28-trans | 484 | 0.01 | 0.102 | 85.9 |
| 47 | 8-(((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)amino)-1,7-naphthyridine-3-carbonitrile | 6 | 28-trans | 475 | 0.008 | 0.042 | 338.1 |
| 48 | (4aR,11bR)-N$^{10}$-(2-methoxypyrido[3,4-b]pyrazin-5-yl)-3,3,11b-trimethyl-3,4a,5,6,7,11b-hexahydrobenzo[3,4]cyclohepta[1,2-b][1,4]thiazine-2,10-diamine 4,4-dioxide | 6 | 28-trans | 481 | 0.041 | 0.041 | 392.5 |
| 49 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-6-chloro-3-methylimidazo[1,2-a]pyridine-2-carboxamide | 3 | 28-trans | 514 | 0.082 | 0.013 | 394.1 |
| 50 | N-((4aR,11bR)-2-amino-3,3,11b-trimethyl-4,4-dioxido-3,4a,5,6,7,11b-hexahydrobenzo[3,4]cyclohepta[1,2-b][1,4]thiazin-10-yl)-5-(2-butyn-1-yloxy)-2-pyrazinecarboxamide | 3 | 28-trans | 496 | 0.0007 | 0.0002 | 119.8 |
| 51 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 3 | 30 | 512 | 0.001 | 0.0004 | 461.0 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 52 | (4aR,6S,11bR)-N⁻10⁻-(5-fluoro-3-methoxy-1,7-naphthyridin-8-yl)-3,3,6,11b-tetramethyl-4a,5,6,11b-tetrahydro-3H-[1]benzoxepino[4,5-b][1,4]thiazine-2,10-diamine 4,4-dioxide | 5 | 30 | 514 | 0.014 | 0.022 | 173.7 |
| 53 | (4aR,6S,11bR)-N⁻10⁻-(2-methoxypyrido[3,4-b]pyrazin-5-yl)-3,3,6,11b-tetramethyl-4a,5,6,11b-tetrahydro-3H-[1]benzoxepino[4,5-b][1,4]thiazine-2,10-diamine 4,4-dioxide | 5 | 30 | 497 | 0.032 | 0.011 | 976.8 |
| 54 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 30 | 525 | 0.006 | 0.001 | 1618 |
| 55 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 30 | 474 | 0.009 | 0.004 | 649.7 |
| 56 | 8-(((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)amino)-1,7-naphthyridine-3-carbonitrile | 5 | 30 | 491 | 0.002 | 0.001 | 544.2 |
| 57 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 3 | 30 | 482 | 0.002 | 0.0007 | 1462 |
| 58 | N-((4a'S,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-chloro-3-methyl-2-pyridinecarboxamide | 4 | 21-cis | 490 | 0.014 | 0.011 | 656.3 |
| 59 | N-((4a'R,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-chloro-3-methyl-2-pyridinecarboxamide | 4 | 21-trans | 490 | 0.050 | 0.057 | >400 |
| 60 | (4a'R,11b'R)-N⁻10⁻-(2-methoxypyrido[3,4-b]pyrazin-5-yl)-11b'-methyl-4a',5',6',11b'-tetrahydrospiro[cyclobutane-1,3'-pyrido[3',2':6,7]oxepino[4,5-b][1,4]thiazine-2',10'-diamine 4',4'-dioxide | 6 | 21-trans | 496 | 0.037 | 0.135 | >400 |
| 61 | (4a'R,11b'R)-N⁻10⁻-(3-chloro-1,7-naphthyridin-8-yl)-11b'-methyl-4a',5',6',11b'-tetrahydrospiro[cyclobutane-1,3'-pyrido[3',2':6,7]oxepino[4,5-b][1,4]thiazine-2',10'-diamine 4',4'-dioxide | 6 | 21-trans | 499 | 0.018 | 0.125 | 679.7 |
| 62 | N-((4a'R,11b'R)-2'-amino-11b'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-cyano-3-methyl-2-pyridinecarboxamide | 4 | 21-trans | 481 | 0.015 | 0.060 | >400 |
| 63 | N-((4a'R,11b'R)-2'-amino-1113'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-cyano-2-pyridinecarboxamide | 4 | 21-trans | 467 | 0.036 | 0.164 | 867.8 |
| 64 | N-((4a'R,11b'R)-2'-amino-1113'-methyl-4',4'-dioxido-4a',5',6',11b'-tetrahydrospiro[cyclobutane-1,3'-pyrido[3',2':6,7]oxepino[4,5-b][1,4]thiazin]-10'-yl)-5-methoxy-3-methyl-2-pyridinecarboxamide | 4 | 21-trans | 486 | 0.059 | 0.184 | >400 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 65 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 72 | 495 | 0.006 | 0.074 | 323.9 |
| 66 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-chloro-2-pyridinecarboxamide | 3 | 72 | 481 | 0.008 | 0.089 | 269.5 |
| 67 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 72 | 478 | 0.022 | 0.115 | 2917 |
| 68 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(((1R)-1-methyl-2-butyn-1-yl)oxy)-2-pyridinecarboxamide | Example 68 | 20 | 511 | 0.002 | 0.001 | 1992 |
| 69 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(((1S)-1-methyl-2-butyn-1-yl)oxy)-2-pyridinecarboxamide | Example 69 | 20 | 511 | 0.081 | 1.01 | 810.8 |
| 70 | (4aR,11bR)-N⁻10⁻-(5-fluoro-3-(((1S)-1-methyl-2-butyn-1-yl)oxy)-1,7-naphthyridin-8-yl)-3,3,11b-trimethyl-4a,5,6,11b-tetrahydro-3H-[1]benzoxepino[4,5-b][1,4]thiazine-2,10-diamine 4,4-dioxide | Example 70 | 20 | 552 | 0.003 | 0.026 | 237.1 |
| 71 | (4aR,11bR)-N1⁻10⁻-(5-fluoro-3-(((1R)-1-methyl-2-butyn-1-yl)oxy)-1,7-naphthyridin-8-yl)-3,3,11b-trimethyl-4a,5,6,11b-tetrahydro-3H-[1]benzoxepino[4,5-b][1,4]thiazine-2,10-diamine 4,4-dioxide | Example 71 | 20 | 552 | 0.12 | 2.36 | 186.0 |
| 72 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-methoxy-2-pyridinecarboxamide | 3 | 30 | 473 | 0.011 | 0.005 | 1391 |
| 73 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-3-chloro-5-(trifluoromethyl)-2-pyridinecarboxamide | 3 | 30 | 545 | 0.011 | 0.004 | 1394 |
| 74 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(2,2,2-trifluoroethoxy)-2-pyrazinecarboxamide | 3 | 30 | 542 | 0.003 | 0.007 | 871.3 |
| 75 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-2-pyrazinecarboxamide | 3 | 30 | 478 | 0.004 | 0.061 | 217.0 |
| 76 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(1,3-oxazol-2-ylmethoxy)-2-pyrazinecarboxamide | 7 | 36 | 541 | 0.002 | 0.0009 | 1050 |
| 77 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-6-chloro-3-methylimidazo[1,2-a]pyridine-2-carboxamide | 3 | 30 | 530 | 0.017 | 0.005 | 395.5 |
| 78 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-((3-methyl-5-isoxazolyl)methoxy)-2-pyrazinecarboxamide | 7 | 36 | 556 | 0.007 | 0.026 | 407.3 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 79 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-propoxy-2-pyrazinecarboxamide | 7 | 36 | 502 | 0.005 | 0.016 | 841.2 |
| 80 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-((5-methyl-1,3-oxazol-2-yl)methoxy)-2-pyrazinecarboxamide | 7 | 36 | 555 | 0.004 | 0.001 | 1488 |
| 81 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-((1-methyl-1H-pyrazol-4-yl)methoxy)-2-pyrazinecarboxamide | 7 | 36 | 554 | 0.016 | 0.072 | 1313 |
| 82 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-((1-methyl-1H-pyrazol-3-yl)methoxy)-2-pyrazinecarboxamide | 7 | 36 | 554 | 0.005 | 0.009 | 583.0 |
| 83 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylethynyl)-3-methyl-2-pyridinecarboxamide | 3 | 20 | 507 | 0.006 | 0.009 | 954.3 |
| 84 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(trifluoromethyl)-2-pyridinecarboxamide | 3 | 30 | 511 | 0.012 | 0.004 | 2759 |
| 85 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-2-pyridinecarboxamide | 3 | 30 | 477 | 0.004 | 0.003 | 607.0 |
| 86 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-cyano-2-pyridinecarboxamide | 3 | 30 | 468 | 0.003 | 0.002 | 1138 |
| 87 | N-((4aS,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 24-cis | 495 | 0.002 | 0.008 | 279.0 |
| 88 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylmethoxy)-2-pyrazinecarboxamide | Example 88 | | 500 | 0.010 | 0.044 | 745.1 |
| 89 | N-((4aS,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 24-cis | 478 | 0.028 | 0.05 | 399.9 |
| 90 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2-difluoroethoxy)-2-pyrazinecarboxamide | Example 90 | | 510 | 0.007 | 0.011 | 918.5 |
| 91 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2-difluoroethoxy)-3-methyl-2-pyrazinecarboxamide | 3 | 19-trans | 524 | 0.019 | 0.027 | 1867 |
| 92 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(methoxymethyl)-2-pyridinecarboxamide | 3 | 19-trans | 473 | 0.122 | 0.026 | 3050 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 93 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 24-trans | 529 | 0.011 | 0.054 | 513.1 |
| 94 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 3 | 24-trans | 516 | 0.000 | 0.008 | >400 |
| 95 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-(difluoromethoxy)-3-methyl-2-pyridinecarboxamide | 3 | 24-trans | 527 | 0.014 | 0.061 | 248.2 |
| 96 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2-difluoroethoxy)-2-pyridinecarboxamide | 3 | 19 | 509 | 0.033 | 0.098 | 1184 |
| 97 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2,2-trifluoroethoxy)-2-pyridinecarboxamide | 3 | 19 | 527 | 0.022 | 0.069 | 973.9 |
| 98 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 3 | 31-trans | 526 | 0.002 | 0.0005 | 318.0 |
| 99 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 3 | 31-trans | 496 | 0.008 | 0.002 | >400 |
| 100 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 31-trans | 488 | 0.025 | 0.012 | 1341 |
| 101 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-methoxy-3-methyl-2-pyrazinecarboxamide | 3 | 31-trans | 502 | 0.029 | 0.019 | 835.1 |
| 102 | N-((4aS,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 3 | 31-trans | 526 | 0.001 | 0.002 | 284.1 |
| 103 | N-((4aS,11bR)-2-amino-3,3,6,6,11b-pentamethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 31-trans | 539 | 0.018 | 0.023 | 143.0 |
| 104 | N-((4aR,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 33-trans | 543 | 0.014 | 0.037 | >400 |
| 105 | N-((4aS,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 33-trans | 543 | 0.004 | 0.013 | 1485 |
| 106 | (4aR,11bR)-3,3,6,6,11b-pentamethyl-N$^{10}$-(7-(trifluoromethyl)pyrido[3,2-d]pyrimidin-4-yl)-4a,5,6,11b-tetrahydro-3H-[1]benzoxepino[4,5-b][1,4]thiazine-2,10-diamine 4,4-dioxide | 5 | 31-trans | 549 | 0.017 | 0.009 | 504.6 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 107 | N-((4aR,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 33-trans | 492 | 0.095 | 0.110 | >400 |
| 108 | N-((4aS,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)-5-methoxy-2-pyrazinecarboxamide | 3 | 33-trans | 492 | 0.013 | 0.018 | 388.1 |
| 109 | 8-(((4aS,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)amino)-1,7-naphthyridine-3-carbonitrile | 5 | 33-trans | 509 | 0.003 | 0.008 | >400 |
| 110 | 8-(((4aR,6S,11bS)-2-amino-11b-(fluoromethyl)-3,3,6-trimethyl-4,4-dioxido-4a,5,6,11b-tetrahydro-3H-[1]benzoxepino[4,5-b][1,4]thiazin-10-yl)amino)-1,7-naphthyridine-3-carbonitrile | 5 | 33-trans | 509 | 0.013 | 0.021 | >400 |
| 111 | N-((4aR,11bR)-2-amino-4a-fluoro-3,3,11b-trimethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 3 | 24-trans | 486 | 0.005 | 0.019 | 330.8 |
| 112 | 8-(((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)amino)-1,7-naphthyridine-3-carbonitrile | 5 | 31 | 505 | 0.003 | 0.002 | 316.4 |
| 113 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 3 | 31 | 539 | 0.006 | 0.002 | 1201 |
| 114 | N-((4aR,11bR)-2-amino-3,3,11b-trimethyl-4,4-dioxido-4a,5,6,11b-tetrahydro-3H-[1]benzothiepino[4,5-b][1,4]thiazin-10-yl)-5-chloro-3-methyl-2-pyridinecarboxamide | 4 | 32-trans | 493 | 0.001 | 0.012 | 292.2 |
| 115 | N-((4aS,11bR)-2-amino-3,3,11b-trimethyl-4,4-dioxido-4a,5,6,11b-tetrahydro-3H-[1]benzothiepino[4,5-b][1,4]thiazin-10-yl)-5-chloro-3-methyl-2-pyridinecarboxamide | 4 | 32-cis | 493 | 0.006 | 0.012 | 276.0 |
| 116 | N-((4aS,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 4 | 22-cis | 529 | 0.011 | 0.014 | >400 |
| 117 | N-((4aR,11bR)-2-amino-3,3,11b-trimethyl-4,4-dioxido-4a,5,6,11b-tetrahydro-3H-[1]benzothiepino[4,5-b][1,4]thiazin-10-yl)-5-methoxy-2-pyrazinecarboxamide | 4 | 32-trans | 476 | 0.014 | 0.003 | 168.5 |
| 118 | N-((4aR,11bR)-2-amino-3,3,11b-trimethyl-4,4-dioxido-4a,5,6,11b-tetrahydro-3H-[1]benzothiepino[4,5-b][1,4 5-(difluoromethoxy)-3-methyl-2-pyridinecarboxamide | 4 | 32-trans | 525 | 0.002 | 0.002 | 207.5 |
| 119 | N-((4aR,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 4 | 22-trans | 529 | 0.024 | 0.019 | 3358 |
| 120 | N-((4aS,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-(trifluoromethyl)-2-pyrazinecarboxamide | 4 | 22-cis | 516 | 0.082 | 0.148 | 752.2 |
| 121 | N-((4aR,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-(trifluoromethyl)-2-pyrazinecarboxamide | 4 | 22-trans | 516 | 0.184 | 0.21 | 994.9 |

TABLE 2-continued

| Example No | Compound Name | General Method Used | Penultimate Intermediate | MS Found | BAC E1 FRET assay $IC_{50}$ (μM) | HEK cell assay $IC_{50}$ (μM) | CatD IC50 (μM) |
|---|---|---|---|---|---|---|---|
| 122 | N-((4aS,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-(difluoromethoxy)-2-pyridinecarboxamide | 4 | 22-cis | 513 | 0.011 | 0.013 | 1029 |
| 123 | N-((4aR,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-(difluoromethoxy)-2-pyridinecarboxamide | 4 | 22-trans | 513 | 0.019 | 0.033 | 4096 |
| 124 | N-((4aR,11bR)-2-amino-3,3,11b-trimethyl-4,4,7,7-tetraoxido-4a,5,6,11b-tetrahydro-3H-[1]benzoxepino[4,5-b][1,4]thiazin-10-yl)-5-chloro-3-methyl-2-pyridinecarboxamide | Example 124 | | 525 | 0.006 | 0.008 | >1.65 |
| 125 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-((1R)-1-cyanoethoxy)-2-pyridinecarboxamide, N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-((1S)-1-cyanoethoxy)-2-pyridinecarboxamide | 8 | 26 | 498 | 0.056 | 0.067 | 1064 |
| 126 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyanomethoxy)-2-pyridinecarboxamide | 8 | 26 | 484 | 0.017 | 0.034 | >1.65 |
| 127 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-3-chloro-5-(trifluoromethyl)-2-pyridinecarboxamide | 3 | 31-trans | 559 | 0.019 | 0.007 | 1024 |
| 128 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-3,5-dichloro-2-pyridinecarboxamide | 3 | 31-trans | 525 | 0.008 | 0.003 | 592.6 |
| 129 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-3,5-dichloro-2-pyridinecarboxamide | 3 | 30 | 511 | 0.003 | 0.002 | 567.0 |
| 130 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-3-(hydroxymethyl)-2-pyridinecarboxamide | Example 130 | | 507 | 0.003 | 0.0008 | 44.8 |
| 131 | (4aR,6S,11bR)-2-amino-3,3,6,11b-tetramethyl-10-((3-(trifluoromethyl)-1,7-naphthyridin-8-yl)amino)-4a,5,6,11b-tetrahydro-3H-benzo[6,7]oxepino[4,5-b][1,4]thiazine 4,4-dioxide | 5 | 30 | 534 | 0.005 | 0.005 | 443.0 |
| 132 | N-((4aR,11bR)-2-amino-3,3,11b-trimethyl-4,4-dioxido-4a,5,6,11b-tetrahydro-3H-[1]benzothiepino[4,5-b][1,4]thiazin-10-yl)-3-methyl-5-(trifluoromethyl)-2-pyridinecarboxamide | 4 | 32-trans | 527 | 0.002 | 0.0008 | 357.1 |
| 133 | (4aR,6S,11bR)-3,3,6,11b-tetramethyl-N⁻10⁻-(7-(trifluoromethyl)pyrido[3,2-d]pyrimidin-4-yl)-4a,5,6,11b-tetrahydro-3H-[1]benzoxepino[4,5-b][1,4]thiazine-2,10-diamine 4,4-dioxide | 5 | 30 | 535 | 0.010 | 0.005 | 427.2 |
| 134 | (4aR,6S,11bR)-3,3,6,11b-tetramethyl-N⁻10⁻-(2-((5-methyl-1,3-oxazol-2-yl)methoxy)pyrido[3,4-b]pyrazin-5-yl)-4a,5,6,11b-tetrahydro-3H-[1]benzoxepino[4,5-b][1,4]thiazine-2,10-diamine 4,4-dioxide | 11 | 30 | 578 | 0.003 | 0.003 | >44.4 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 135 | (4aR,6S,11bR)-3,3,6,11b-tetramethyl-N⁻10⁻-(2-propoxypyrido[3,4-b]pyrazin-5-yl)-4a,5,6,11b-tetrahydro-3H-[1]benzoxepino[4,5-b][1,4]thiazine-2,10-diamine 4,4-dioxide | 11 | 30 | 525 | 0.026 | 0.139 | 104.4 |
| 136 | 5-(((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)amino)pyrido[3,4-b]pyrazin-2(1H)-one | 11 | 30 | 483 | 0.025 | 0.016 | 247.0 |
| 137 | (4aR,6S,11bR)-3,3,6,11b-tetramethyl-N⁻10⁻-(2-((3-methyl-5-isoxazolyl)methoxy)pyrido[3,4-b]pyrazin-5-yl)-4a,5,6,11b-tetrahydro-3H-[1]benzoxepino[4,5-b][1,4]thiazine-2,10-diamine 4,4-dioxide | 11 | 30 | 578 | 0.018 | 0.091 | >133 |
| 138 | (4aR,6S,11bR)-3,3,6,11b-tetramethyl-N⁻10⁻-(2-(1,3-oxazol-2-ylmethoxy)pyrido[3,4-b]pyrazin-5-yl)-4a,5,6,11b-tetrahydro-3H-[1]benzoxepino[4,5-b][1,4]thiazine-2,10-diamine 4,4-dioxide | Example 136 | 30 | 564 | 0.004 | 0.001 | 173.0 |
| 139 | (4aR,6S,11bR)-N⁻10⁻-(2-(2-methoxyethoxy)pyrido[3,4-b]pyrazin-5-yl)-3,3,6,11b-tetramethyl-4a,5,6,11b-tetrahydro-3H-[1]benzoxepino[4,5-b][1,4]thiazine-2,10-diamine 4,4-dioxide | 11 | 30 | 541. | 0.007 | 0.008 | 304.3 |
| 140 | (4aR,6S,11bR)-3,3,6,11b-tetramethyl-N⁻10⁻-(2-(2-propyn-1-yloxy)pyrido[3,4-b]pyrazin-5-yl)-4a,5,6,11b-tetrahydro-3H-[1]benzoxepino[4,5-b][1,4]thiazine-2,10-diamine 4,4-dioxide | 11 | 30 | 521.0 | 0.002 | 0.002 | 610.2 |
| 141 | (4aR,11bR)-3,3,6,6,11b-pentamethyl-N⁻10⁻-(2-(2-propyn-1-yloxy)pyrido[3,4-b]pyrazin-5-yl)-4a,5,6,11b-tetrahydro-3H-[1]benzoxepino[4,5-b][1,4]thiazine-2,10-diamine 4,4-dioxide | 11 | 31-trans | 535.0 | 0.004 | 0.017 | 385.5 |
| 142 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(2-propyn-1-yloxy)-2-pyrazinecarboxamide | 7 | 36 | 498.0 | 0.001 | 0.0005 | 215.5 |
| 143 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-(2-propyn-1-yloxy)-2-pyrazinecarboxamide | Example 143 | 31-trans | 512.1 | 0.002 | 0.0005 | 202.0 |
| 144 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(1,3-oxazol-2-ylmethoxy)-2-pyridinecarboxamide | 9 | 34 | 540.0 | 0.004 | 0.003 | 563.8 |
| 145 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-(2-propyn-1-yloxy)-2-pyridinecarboxamide | 9 | 34 | 497.0 | 0.001 | 0.002 | 329.1 |
| 146 | (4aR,6S,11bR)-3,3,6,11b-tetramethyl-N⁻10⁻-(2-((1-methyl-1H-pyrazol-3-yl)methoxy)pyrido[3,4-b]pyrazin-5-yl)-4a,5,6,11b-tetrahydro-3H-[1]benzoxepino[4,5-b][1,4]thiazine-2,10-diamine 4,4-dioxide | 11 | 30 | 577.0 | 0.005 | 0.004 | 804.5 |
| 147 | N-((4aS,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 10 | 22 | 495 | 0.003 | 0.009 | 1284 |
| 148 | (4aR,11bS)-N⁻10⁻-(3-chloro-1,7-naphthyridin-8-yl)-11b-(fluoromethyl)-3,3-dimethyl-4a,5,6,11b-tetrahydro-3H-[1]benzoxepino[4,5-b][1,4]thiazine-2,10-diamine 4,4-dioxide | 6 | 22 | 504 | 0.012 | 0.093 | 709.5 |

TABLE 2-continued

| Example No | Compound Name | General Method Used | Penultimate Intermediate | MS Found | BACE1 FRET assay IC$_{50}$ (μM) | HEK cell assay IC$_{50}$ (μM) | CatD IC50 (μM) |
|---|---|---|---|---|---|---|---|
| 149 | N-((4aR,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 10 | 22 | 495 | 0.009 | 0.044 | >400 |
| 150 | (4aR,11bS)-11b-(fluoromethyl)-3,3-dimethyl-N⁻10⁻-(2-(1-methylethoxy)pyrido[3,4-b]pyrazin-5-yl)-4a,5,6,11b-tetrahydro-3H-[1]benzoxepino[4,5-b][1,4]thiazine-2,10-diamine 4,4-dioxide | 6 | 22 | 529 | 0.227 | 1.4 | >400 |
| 151 | (4aR,11bS)-11b-(fluoromethyl)-N⁻10⁻-(2-methoxypyrido[3,4-b]pyrazin-5-yl)-3,3-dimethyl-4a,5,6,11b-tetrahydro-3H-[1]benzoxepino[4,5-b][1,4]thiazine-2,10-diamine 4,4-dioxide | 6 | 22 | 501 | 0.037 | 0.068 | >400 |
| 152 | N-((4aR,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-methoxy-3-methyl-2-pyridinecarboxamide | 10 | 22 | 491 | 0.031 | 0.075 | >400 |
| 153 | N-((4aS,11bS)-2-amino-11b-(fluoromethyl)-3,3-dimethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 10 | 22 | 486 | 0.002 | 0.006 | 2075 |
| 154 | (4aS,11bS)-N1⁻10⁻-(3-chloro-1,7-naphthyridin-8-yl)-11b-(fluoromethyl)-3,3-dimethyl-4a,5,6,11b-tetrahydro-3H-[1]benzoxepino[4,5-b][1,4]thiazine-2,10-diamine 4,4-dioxide | 6 | 22 | 504 | 0.003 | 0.032 | 461.6 |
| 155 | (4aS,11bS)-11b-(fluoromethyl)-N⁻10⁻-(2-methoxypyrido[3,4-b]pyrazin-5-yl)-3,3-dimethyl-4a,5,6,11b-tetrahydro-3H-[1]benzoxepino[4,5-b][1,4]thiazine-2,10-diamine 4,4-dioxide | 5 | 22 | 501 | 0.014 | 0.062 | >400 |
| 156 | (4aR,11bR)-N⁻10⁻-(2-methoxypyrido[3,4-b]pyrazin-5-yl)-3,3,11b-trimethyl-4a,5,6,11b-tetrahydro-3H-[1]benzoxepino[4,5-b][1,4]thiazine-2,10-diamine 4,4-dioxide | 5 | 18 | 483 | 0.011 | 0.014 | 1032 |
| 157 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethoxy)-3-methyl-2-pyridinecarboxamide | 4 | 19-trans | 509 | 0.002 | 0.003 | 1205 |
| 158 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-3-methyl-2-pyridinecarboxamide | 4 | 19-trans | 473 | 0.021 | 0.007 | >400 |
| 159 | (4aS,11bR)-N⁻10⁻-(2-methoxypyrido[3,4-b]pyrazin-5-yl)-3,3,11b-trimethyl-4a,5,6,11b-tetrahydro-3H-[1]benzoxepino[4,5-b][1,4]thiazine-2,10-diamine 4,4-dioxide | 5 | 19-cis | 483 | 0.075 | 0.052 | >400 |
| 160 | N-((4aS,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethoxy)-3-methyl-2-pyridinecarboxamide | 4 | 19-cis | 509 | 0.010 | 0.003 | 1166 |
| 161 | N-((4aS,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-3-methyl-2-pyridinecarboxamide | 4 | 19-cis | 473 | 0.032 | 0.008 | 878.0 |
| 162 | (4aR,11bR)-N⁻10⁻-(7-methoxypyrido[3,2-d]pyrimidin-4-yl)-3,3,11b-trimethyl-4a,5,6,11b-tetrahydro-3H-[1]benzoxepino[4,5-b][1,4]thiazine-2,10-diamine 4,4-dioxide | 5 | 18 | 483 | 0.007 | 0.009 | 619.2 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 163 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethyl)-3-methyl-2-pyridinecarboxamide | 4 | 19-trans | 493 | 0.005 | 0.003 | >400 |
| 164 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(trifluoromethyl)-2-pyrazinecarboxamide | 4 | 19-trans | 498 | 0.028 | 0.017 | 1598 |
| 165 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(trifluoromethyl)-2-pyridinecarboxamide | 4 | 19-trans | 497 | 0.006 | 0.004 | 1069 |
| 166 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-2-pyrazinecarboxamide | 4 | 19-trans | 460 | 0.017 | 0.0074 | 1129 |
| 167 | (4aR,11bR)-N1$^{10-}$-(7-(cyclopropylmethoxy)pyrido[3,2-d]pyrimidin-4-yl)-3,3,11b-trimethyl-4a,5,6,11b-tetrahydro-3H-[1]benzoxepino[4,5-b][1,4]thiazine-2,10-diamine 4,4-dioxide | 5 | 18 | 523 | 0.008 | 0.029 | 384.1 |
| 168 | 8-(((4aR,11bR)-2-amino-3,3,11b-trimethyl-4,4-dioxido-4a,5,6,11b-tetrahydro-3H-[1]benzoxepino[4,5-b][1,4]thiazin-10-yl)amino)-1,7-naphthyridine-3-carbonitrile | 5 | 18 | 477 | 0.002 | 0.003 | >44.4 |
| 169 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2,2,2-trifluoroethoxy)-2-pyrazinecarboxamide | 4 | 19-trans | 528 | 0.001 | 0.004 | 1619 |
| 170 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylmethoxy)-3-methyl-2-pyridinecarboxamide | 4 | 19-trans | 513 | 0.014 | 0.026 | 2050 |
| 171 | 8-(((4aR,11bR)-2-amino-3,3,11b-trimethyl-4,4-dioxido-4a,5,6,11b-tetrahydro-3H-[1]benzoxepino[4,5-b][1,4]thiazin-10-yl)amino)-5-fluoro-1,7-naphthyridine-3-carbonitrile | 5 | 19-trans | 495 | 0.003 | 0.010 | >14.8 |
| 172 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-chloro-5-(difluoromethyl)-2-pyridinecarboxamide | 4 | 19-trans | 513 | 0.012 | 0.004 | >400 |
| 173 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-chloro-5-methoxy-2-pyridinecarboxamide | 4 | 19-trans | 493 | 0.005 | 0.007 | >400 |
| 174 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-chloro-5-cyano-2-pyridinecarboxamide | 4 | 19-trans | 488 | 0.002 | 0.002 | 1067 |
| 175 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylmethoxy)-2-pyridinecarboxamide | 4 | 19-trans | 499 | 0.009 | 0.017 | 1508 |
| 176 | (4aR,11bR)-N$^{10-}$-(7-chloropyrido[3,2-d]yrimidin-4-yl)-3,3,11b-trimethyl-4a,5,6,11b-tetrahydro-3H-[1]benzoxepino[4,5-b][1,4]thiazine-2,10-diamine 4,4-dioxide | 5 | 19-trans | 487 | 0.008 | 0.011 | 186.0 |
| 177 | (4aR,11bR)-N$^{10-}$-(5-fluoro-3-methoxy-1,7-naphthyridin-8-yl)-3,3,11b-trimethyl-4a,5,6,11b-tetrahydro-3H-[1]benzoxepino[4,5-b][1,4]thiazine-2,10-diamine 4,4-dioxide | 5 | 19-trans | 500 | 0.018 | 0.111 | 313.5 |
| 178 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5- | Example 178 | 19-trans | 514 | 0.010 | 0.028 | 586.5 |

TABLE 2-continued

| Example No | Compound Name | General Method Used | Penultimate Intermediate | MS Found | BACE1 FRET assay IC$_{50}$ (μM) | HEK cell assay IC$_{50}$ (μM) | CatD IC50 (μM) |
|---|---|---|---|---|---|---|---|
| | (cyclopropylmethoxy)-3-methyl-2-pyrazinecarboxamide | | | | | | |
| 179 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-cyclopropyl-2-pyridinecarboxamide | 4 | 19-trans | 469 | 0.066 | 0.035 | 705.1 |
| 180 | N-((4aR,6R,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 27-trans | 491 | 0.003 | 0.005 | 90.4 |
| 181 | N-((4aS,6R,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 27-cis | 491 | 0.001 | 0.0008 | 124.5 |
| 182 | (4aR,11bR)-N$^-$10$^-$-(3-(2-butyn-1-yloxy)-1,7-naphthyridin-8-yl)-3,3,11b-trimethyl-4a,5,6,11b-tetrahydro-3H-[1]benzoxepino[4,5-b][1,4]thiazine-2,10-diamine 4,4-dioxide | 5 | 19-trans | 520 | 0.003 | 0.014 | >400 |
| 183 | N-((4aS,6S,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 29 | 491 | 0.009 | 0.003 | 44.0 |
| 184 | N-((4aS,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 73 | 505 | 0.008 | 0.004 | 403.3 |
| 185 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-methoxy-2-pyridinecarboxamide | 3 | 19-trans | 459 | 0.021 | 0.013 | 516.4 |
| 186 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-chloro-2-pyridinecarboxamide | 3 | 19-trans | 463 | 0.006 | 0.010 | 278.8 |
| 187 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-methyl-5-(2,2,2-trifluoroethoxy)-2-pyridinecarboxamide | 3 | 19-trans | 541 | 0.016 | 0.064 | 1235 |
| 188 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-3-methyl-5-(trifluoromethyl)-2-pyridinecarboxamide | 4 | 19-trans | 511 | 0.008 | 0.003 | 1549 |
| 189 | N-((4aR,6S,11bR)-2-amino-3,3,6,11b-tetramethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 30 | 491 | 0.003 | 0.001 | 191.3 |
| 190 | N-((4aR,11bR)-2-amino-3,3,6,6,11b-pentamethyl-4,4-dioxido-4a,5,6,11b-tetrahydro-3H-[1]benzoxepino[4,5-b][1,4]thiazin-10-yl)-5-chloro-3-methyl-2-pyridinecarboxamide | 3 | 31-trans | 505 | 0.005 | 0.002 | 441.1 |
| 191 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(2-butyn-1-yloxy)-2-pyrazinecarboxamide | 3 | 19-trans | 498 | 0.0007 | 0.0003 | 624.4 |
| 192 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-cyano-3-methyl-2-pyridinecarboxamide | 4 | 19-trans | 468 | 0.002 | 0.001 | 434.0 |
| 193 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(cyclopropylethynyl)-2-pyridinecarboxamide | 3 | 19-trans | 493 | 0.004 | 0.006 | 994.8 |

TABLE 2-continued

| Example No | Compound Name | General Method Used | Penultimate Intermediate | MS Found | BAC E1 FRET assay IC$_{50}$ (μM) | HEK cell assay IC$_{50}$ (μM) | CatD IC50 (μM) |
|---|---|---|---|---|---|---|---|
| 194 | N-((4aR,11bR)-2-amino-3,3,11b-trimethyl-4,4-dioxido-4a,5,6,11b-tetrahydro-3H-[1]benzoxepino[4,5-b][1,4]thiazin-10-yl)-5-(difluoromethoxy)-2-pyridinecarboxamide | 3 | 19-trans | 495 | 0.008 | 0.003 | 651.6 |

The invention provides further representative examples of Formulas I, II and sub-formulas thereof:

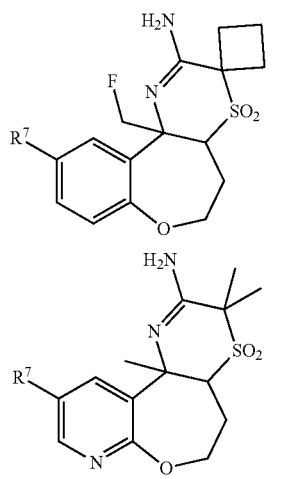
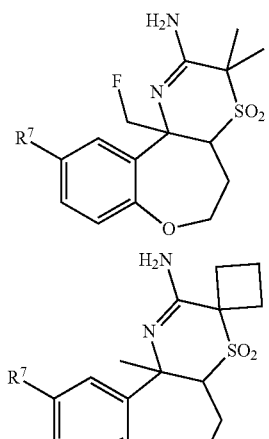
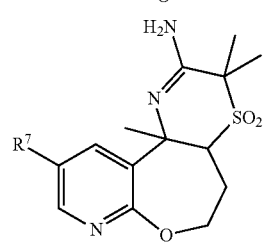
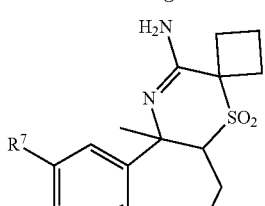
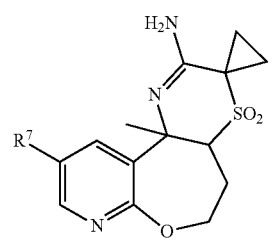

and wherein R$^7$ is

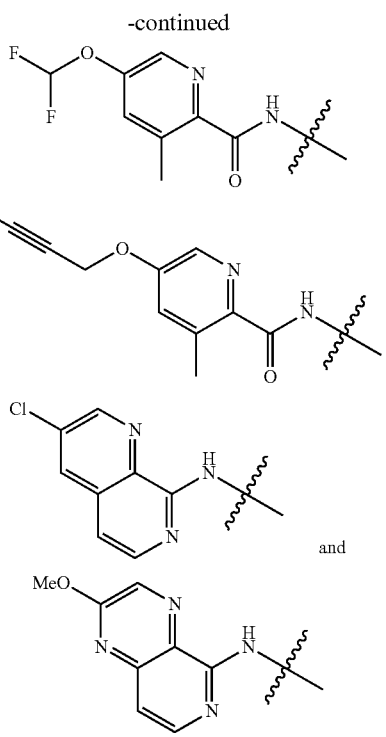

and and more representative examples:

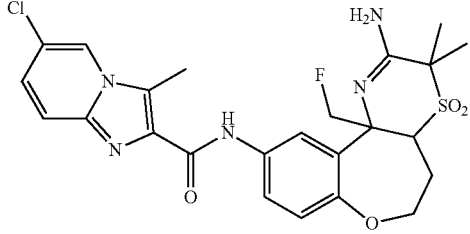

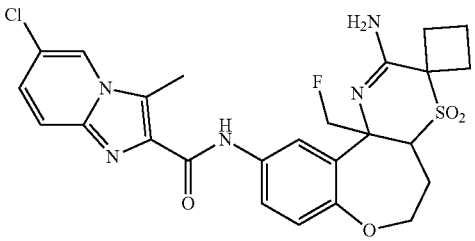

-continued

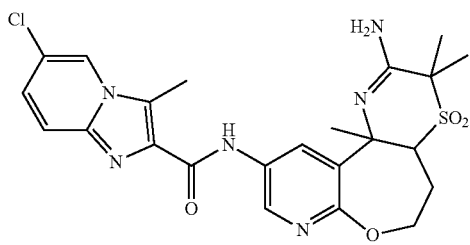

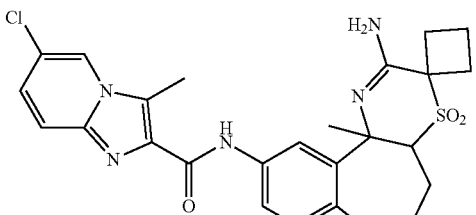

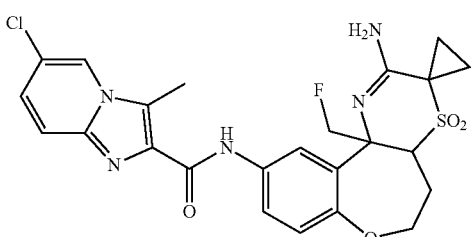

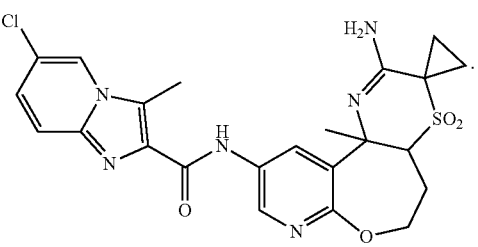

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a process for preparing a compound according to any of Formula I, II or III, the process comprising the step of reacting a compound 20

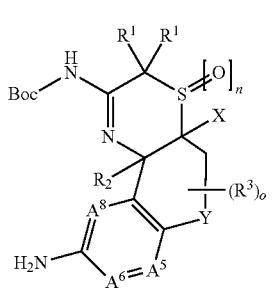

wherein $A^5, A^6, A^8, R^1, R^2, R^3, X, Y$, n and o of compound 20 are as defined herein with respect to Formulas I, II or III, with a compound having the structure or $R^9$—C(=O)OH or $R^9$—Cl, wherein $R^9$ is as defined herein with respect to Formulas I, II or III, to prepare the compound according to any of Formulas I, II or III.

In one embodiment of the invention, there is provided a method of making a compound of Formula II-A having a general structure of

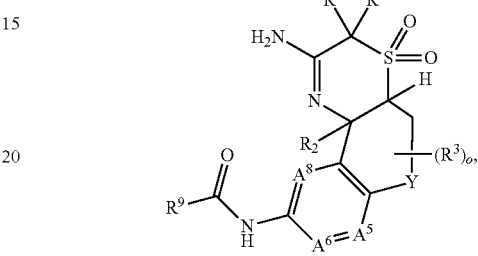

the method comprising the step of reacting a compound 20

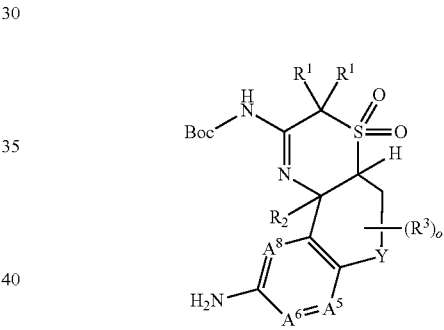

wherein $A^5, A^6, A^8$, each $R^1, R^2, R^3$, Y and o of Formula II-A are as defined herein, with a compound having the structure $R^9$—COOH, wherein $R^9$ is as defined herein, to make a compound of Formula II-A.

In one embodiment of the invention, there is provided a method of making a compound of Formula II-B having a general structure of

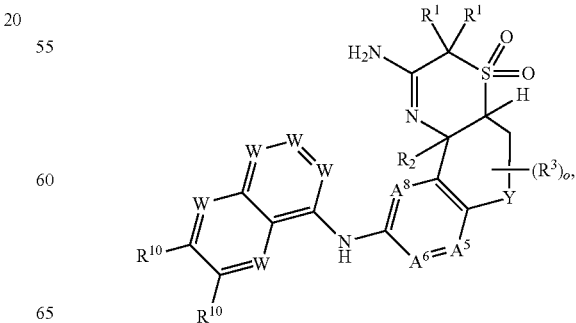

the method comprising the step of reacting a compound 20

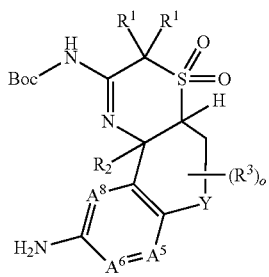

wherein $A^4$, $A^5$, $A^6$, $A^8$, each $R^1$, $R^2$, each $R^3$, Y and o of Formula II-B are as defined herein, with a compound having the structure

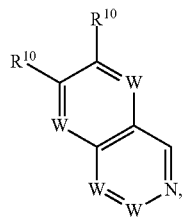

wherein each W and each $R^{10}$ are, independently, as defined herein, in the presence of acid to make a compound of Formula II-B.

In one embodiment of the invention, there is provided a method of making a compound of Formula II-C

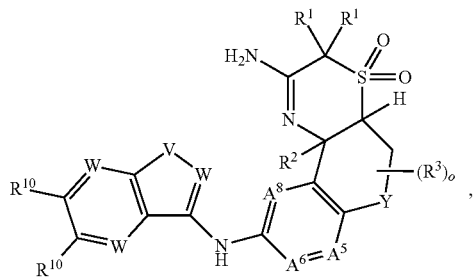

the method comprising the step of reacting a compound 20

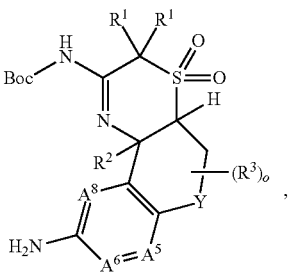

wherein $A^4$, $A^5$, $A^6$, $A^8$, each $R^1$, $R^2$, each $R^3$, Y and o of Formula II-C are as defined herein, with a compound having the structure

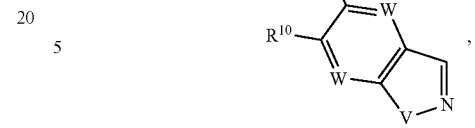

wherein V, each W and each $R^{10}$ are, independently, as defined herein, to make a compound of Formula II-C.

In another embodiment of the invention, there is provided a method of making a compound of Formula III-A having a general formula of

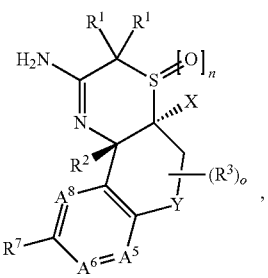

the method comprising the step of reacting a compound 20

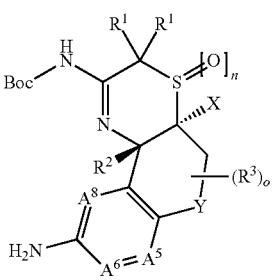

wherein $A^5$, $A^6$, $A^8$, each $R^1$, $R^2$, each $R^3$, X, Y, n and o of Formula III are as defined herein, with a compound having either structure of $R^7$—COOH in the presence of a base or $R^7$ in the presence of an acid, wherein $R^7$ is as defined herein, to make a compound of Formula III-A.

In another embodiment of the invention, there is provided a method of making a compound of Formula III-B having a general formula of

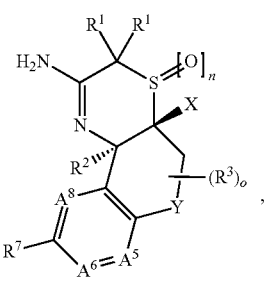

the method comprising the step of reacting a compound 20

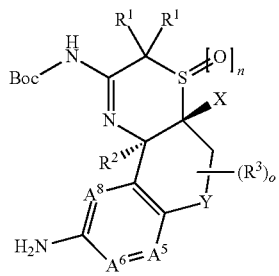

wherein $A^5$, $A^6$, $A^8$, each $R^1$, $R^2$, each $R^3$, X, Y, n and o of Formula III are as defined herein, with a compound having either structure of $R^7$—COOH in the presence of a base or $R^7$ in the presence of an acid, wherein $R^7$ is as defined herein, to make a compound of Formula III-B.

In another embodiment of the invention, there is provided a method of making a compound of Formula III-C having a general formula of

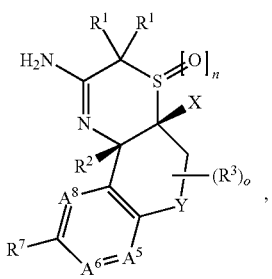

the method comprising the step of reacting a compound 20

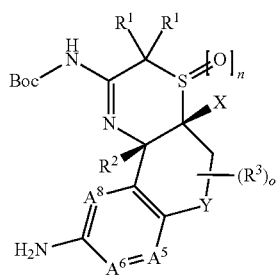

wherein $A^5$, $A^6$, $A^8$, each $R^1$, $R^2$, each $R^3$, X, Y, n and o of Formula III are as defined herein, with a compound having either structure of $R^7$—COOH in the presence of a base or $R^7$ in the presence of an acid, wherein $R^7$ is as defined herein, to make a compound of Formula III-C.

In another embodiment of the invention, there is provided a method of making a compound of Formula III-D having a general formula of

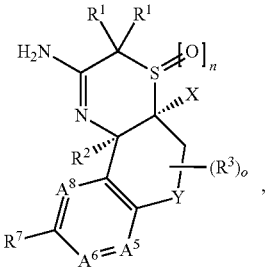

the method comprising the step of reacting a compound 20

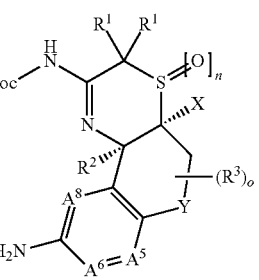

wherein $A^5$, $A^6$, $A^8$, each $R^1$, $R^2$, each $R^3$, X, Y, n and o of Formula III are as defined herein, with a compound having either structure of $R^7$—COOH in the presence of a base or $R^7$ in the presence of an acid, wherein $R^7$ is as defined herein, to make a compound of Formula III-D.

In another embodiment of the invention, there is provided a method of making a compound of Formula III-B-2 having the formula:

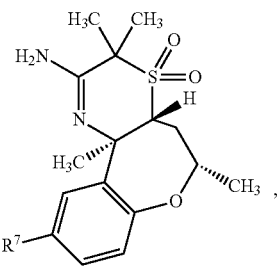

the method comprising the step of reacting a compound 20

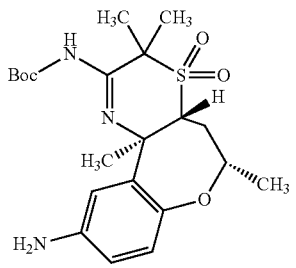

with a compound having the structure of either (1) $R^7$—COOH in the presence of a base; or (2) $R^7$ in the presence of an acid, wherein $R^7$ is

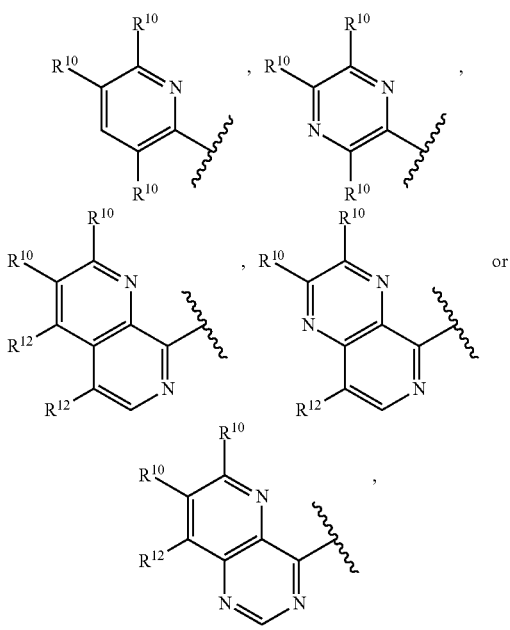

wherein each R[10], independently, is H, halo, haloalkyl, CN, OH, NO$_2$, NH$_2$, SF$_5$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, tetrahydropyrrolyl, piperazinyl, oxetan-3-yl, dioxolyl, NHC(O)R[11]— or C(O)NHR[11]—, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$; and each R[12], independently, is H, F or Cl, to make a compound of Formula III-B-2.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$;

acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$ (deuterium), $^3H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Deuterated ($^2H$), Tritiated ($^3H$) and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table 2.

In Vitro BACE Cell-Based Assay

The cell-based assay measures inhibition or reduction of Aβ340 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table 2.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p 379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorgenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 2).

Where available, the in-vitro Cat D FRET assay data for each of the Examples is provided in Table 2. A vast majority of the compounds representative of the present invention exhibit Cat D $IC_{50}$ values of >400 µM. In fact, many of those compounds exhibit Cat D $IC_{50}$ values of >800 µM. See, for instance, examples 8, 12, 15, 16, 18, 21-23, 24, 25, 26, 29, 30, 32, 41-42, 45, 53, 54, 57, 63, 67-69, 72-74, 76, 79-81, 83 & 84 (to point to just a few; referring to data in Table 2). Further, many of those compounds exhibit Cat D $IC_{50}$ values of >1200 µM. See, for instance, examples 8, 12, 15, 18, 21-23, 25, 29, 30, 32, 41-42, 45, 54, 57, 67-68, 72-73, 76, 80-81, 84, 86, 91-92 & 100 (to point out those from compound examples 1-100; and with reference to data in Table 2). There are many more compounds from examples 101-194 (See Table 2) which also exhibit Cat D $IC_{50}$ values of >400 µM; >800 µM; and >1200 µM. As shown by the high micromolar Cat D data (very poorly active or inactive against Cat D), the compounds of the present invention possess the unexpected property of little to no ability to inhibit the activity of Cat D. The compounds of the present invention are believed to minimize, reduce or eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, Journal of Neurochemistry, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, Journal of Pharmacology and Experimental Therapeutics, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
  IV: 5% EtOH, 45% Propylene Glycol in 5% Dextrose The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
|---|---|---|
| 54 | 76 | 63 |
| 55 | 74 | 70 |
| 56 | 70 | 61 |
| 84 | 70 | 68 |
| 85 | 79 | 78 |
| 86 | 79 | 79 |
| 104 | 36 | 11 |
| 106 | 36 | 36 |
| 127 | 37 | 15 |
| 129 | 21 | 18 |
| 133 | 63 | 51 |
| 138 | 46 | 38 |
| 140 | 71 | 72 |

Indications

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. Arch Neurol. 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, Cell, (120): 545-555, 2005; Walsh and Selkoe, Neuron, (44): 181-193, 2004). Although the precise mechanisms of Ab toxicity are unclear, oligomeric forms of Ab may contribute to cognitive decline by altering synaptic structure and function (Palop and Mucke, Nat. Neuroscience, (13): 812-818, 2010; Selkoe, Behavioral Brain Res., (192): 106-113, 2008; Shankar et al., Nat. Medicine (14): 837-842, 2008). Transgenic mouse models that overexpress mutant APP and produce high levels of Ab show amyloid plaque deposition, synaptic deficits, learning and memory impairments, and other behavioral abnormalities (Games et al., Nature, (373): 523-527, 1995; Götz et al., Molecular Psychiatry (9): 664-683, 2004; Hsia et al., Proc. Natl. Academy of Science USA (96): 3228-3233, 1999; Hsiao et al., Science (274): 99-102, 1996, citing Harris et al, Neuron (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

Bapineuzamab, a monoclonal amino-terminus specific anti-amyloid antibody is presently in Phase III clinical trials for the treatment of AD. Alzheimer's Research & Therapy, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier amd more common. It is firmly believed that by reducing the formation of A-beta, one can begin to pre-treat AD. Vassar et al, Journal of Neuroscience, 29 (41):12787-12794, 2009. One published pathway for treatment of AD is inhibition of beta-secretase. Tirrell, Bloomberg News, The Boston Globe, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from pre-clinical animal models to man. Because of toxicology findings identified in longer-term preclinical studies, this compound is no longer progressing in clinical development. However, BACE1 remains a viable target because the potential adverse effects discussed herein were recapitulated in LY2811376-treated BACE1 KO mice and thus are unrelated to BACE1 inhibition. The magnitude and duration of central Aβ reduction obtainable with BACE1 inhibition positions this protease as a tractable small-molecule target through which to test the amyloid hypothesis in man. *Neuroscience*, 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages

What is claimed is:

1. A compound of Formula I

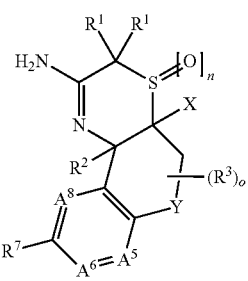

I or a stereoisomer, tautomer, or pharmaceutically acceptable salt thereof, wherein $A^5$ is $CR^5$ or N;

$A^6$ is $CR^6$ or N;

$A^8$ is $CR^8$ or N, provided that no more than one of $A^5$, $A^6$ and $A^8$ is N;

each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$alkyl, $C_{1-3}$alkoxyl, $CH_2OC_{1-2}$alkyl or $C_{1-3}$haloalkyl;

$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;

each $R^3$, independently, is halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NHC(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —$C(O)NHCH_3$, oxo, $C_{1-6}$ alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thio-alkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)$R^{11}$— or —C(O)NH$R^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

$R^{11}$ is $C_{1-6}$alkyl, $C_{1-6}$alkoxyl or $C_{3-6}$cycloalkyl;

X is H, F, $CH_3$, $CH_2CH_3$, cyclopropyl or CN;

Y is —$SCR^4R^4$—, —$CR^4R^4S$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;

n is 0, 1 or 2; and o is 0, 1 or 2.

2. The compound according to claim 1, or a stereoisomer or pharmaceutically acceptable salt thereof, wherein n is 2.

3. The compound according to claim 2, or a stereoisomer or pharmaceutically acceptable salt thereof, wherein $R^7$ is —NH—$R^9$ or —NH—C(=O)—$R^9$;

or $R^7$ is

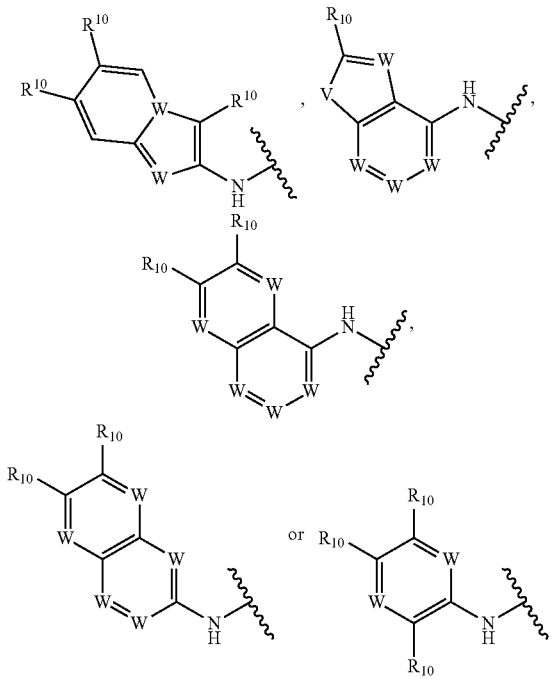

wherein V is $NR^{10}$, O or S; and each W, independently, is CH, CF, CCl, $CCH_3$ or N.

4. The compound according to claim 3, or a stereoisomer or pharmaceutically acceptable salt thereof, wherein A⁵ is CR⁵ or N;

A⁶ is CR⁶;

A⁸ is CR⁸;

each R¹, independently, is H, F, Cl, CF₃, OCF₃, methyl, ethyl, CN, OCH₃, SCH₃, NHCH₃, C(O)CH₃ or CH₂OCHF₂;

R² is CH₃, CH₂F or CHF₂;

each R³, independently, is F, Cl, CF₃, OCF₃, methyl, ethyl, CN, OCH₃ or CH₂OCHF₂; and each of R⁵, R⁶ and R⁸, independently, is H, F, Cl, CF₃, OCF₃, methyl, ethyl, CN, OH, OCH₃, SCH₃, NHCH₃ or C(O)CH₃.

5. The compound according to claim 1, or a stereoisomer or pharmaceutically acceptable salt thereof, R⁷ is —NH—R⁹, —NH—C(=O)—R⁹ or

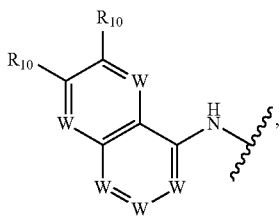

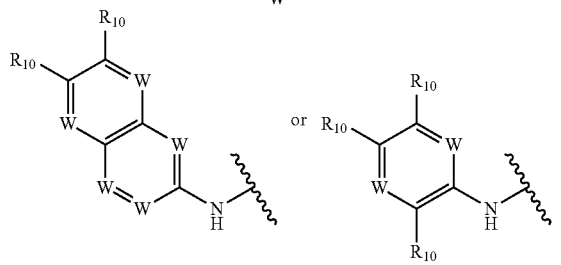

wherein each W, independently, is CH, CF, CCl, CCH₃ or N.

6. The compound according to claim 1, or a stereoisomer or pharmaceutically acceptable salt thereof, wherein R⁷ is —NH—C(=O)—R⁹.

7. The compound according to claim 1, or a stereoisomer or pharmaceutically acceptable salt thereof, wherein R⁷ is —NH—R⁹.

8. The compound according to claim 1, or a stereoisomer or pharmaceutically acceptable salt thereof, wherein R⁷ is

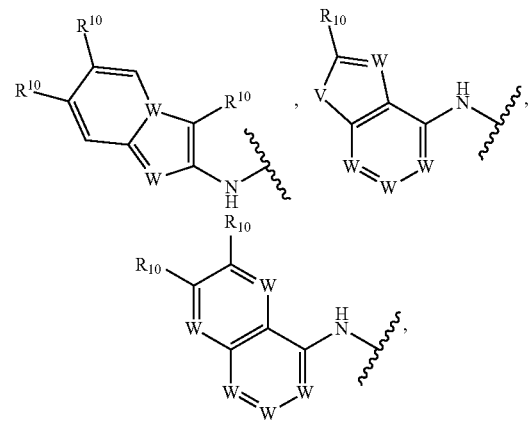

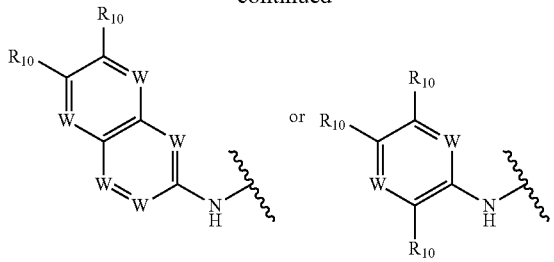

wherein V is NR¹⁰ or S; and each W, independently, is CH, CF, CCl, CCH₃ or N.

9. The compound according to claim 3, or a stereoisomer or pharmaceutically acceptable salt thereof, wherein A⁵ is CR⁵;

A⁶ is CR⁶; and

A⁸ is CR⁸; wherein each of R⁵, R⁶ and R⁸, independently, is H, F, CF₃, CF₂H, CH₂F or CH₃.

10. A compound according to claim 1, or a stereoisomer, tautomer, or pharmaceutically acceptable salt thereof, having a Formula II:

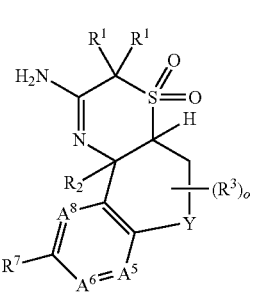

II wherein

A⁵ is CR⁵ or N;

A⁶ is CR⁶ or N;

A⁸ is CR⁸ or N, provided that no more than one of A⁴, A⁵, A⁶ and A⁸ is N;

each R¹, independently, is H, F, Cl, C₁₋₆-alkyl, C₂₋₄alkenyl, C₂₋₄alkynyl, CN, —CH₂OC₁₋₆-alkyl, —OC₁₋₆-alkyl, —S(O)ₒC₁₋₆-alkyl, —NHC₁₋₆-alkyl or —C(O)C₁₋₆-alkyl, wherein each of the C₁₋₆-alkyl, C₂₋₄alkenyl, C₂₋₄alkynyl, and C₁₋₆-alkyl portion of —CH₂OC₁₋₆-alkyl, —OC₁₋₆-alkyl, —S(O)ₒC₁₋₆-alkyl, —NHC₁₋₆-alkyl and —C(O)C₁₋₆-alkyl are optionally substituted with 1-4 substituents of F, oxo or OH;

alternatively, each R¹ taken together with the carbon atom to which they are attached form a C₃₋₆spirocarbocyclic ring optionally including one heteroatom selected from O and N and optionally substituted with 1-4 F atoms on the carbon atoms and a substituent of C₁₋₃alkyl, CH₂OC₁₋₂alkyl or C₁₋₃haloalkyl on the nitrogen atom;

R² is CH₃, CH₂F or CHF₂;

each R³, independently, is halo, C₁₋₄alkyl, CH₂OC₁₋₄alkyl, CH₂OH, C₁₋₄haloalkyl or cyclopropyl, wherein each of the CH₂OC₁₋₄alkyl and cyclopropyl is optionally substituted with 1-4 F atoms;

each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is $-NH-R^9$ or $-NH-C(=O)-R^9$;

or $R^7$ is

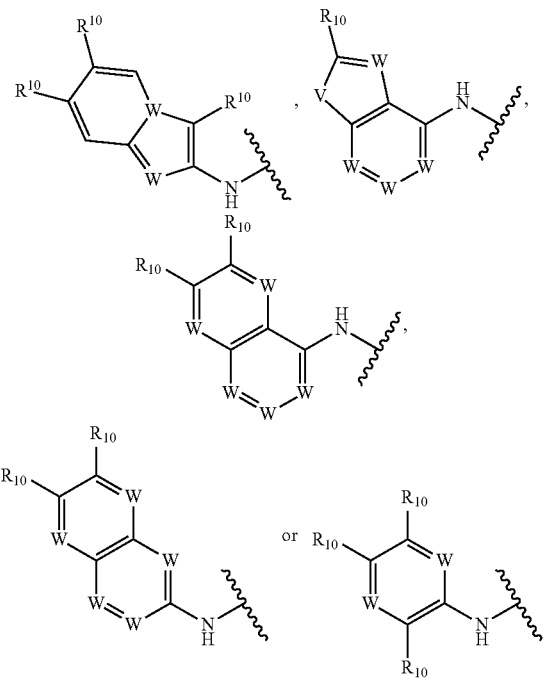

wherein V is $NR^{10}$ or S; and
each W, independently, is CH, CF, CCl, $CCH_3$ or N;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, oxazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, $-C(O)NHCH_3$, oxo, $C_{1-6}$ alkyl, $C_{2-6}$ alkenyl, $C_{2-6}$ alkynyl, $C_{3-6}$ cycloalkyl, $C_{1-6}$alkylamino-, $C_{1-6}$dialkylamino-, $C_{1-6}$ alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

Y is $-SCR^4R^4-$, $-S(O)_2CR^4R^4-$, $-OCR^4R^4-$, $-CR^4R^4O-$ or $-CR^4R^4CR^4R^4-$, wherein each $R^4$, independently, is H, F, $C_{1-3}$alkyl or $C_{1-3}$haloalkyl; and o is 0, 1 or 2.

11. The compound according to claim 10, or a stereoisomer, tautomer or pharmaceutically acceptable salt thereof, wherein $A^5$ is $CR^5$ or N;
$A^6$ is $CR^6$ or N;
$A^8$ is $CR^8$ or N, provided no more than one of $A^5$, $A^6$ and $A^8$ is N;

each $R^1$, independently, is H, F, Cl, $CF_3$, $OCF_3$, methyl, ethyl, CN, $OCH_3$, $SCH_3$, $NHCH_3$, $C(O)CH_3$ or $CH_2OCHF_2$;

each $R^3$, independently, is F, Cl, $CF_3$, methyl, ethyl or $CH_2OCHF_2$; and each of $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$.

12. The compound according to claim 10, or a stereoisomer or pharmaceutically acceptable salt thereof, wherein $A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$;

each $R^3$, independently, is F, Cl, $CF_3$, methyl, ethyl or $CH_2OCHF_2$; and $R^7$ is $-NH-C(=O)-R^9$ or

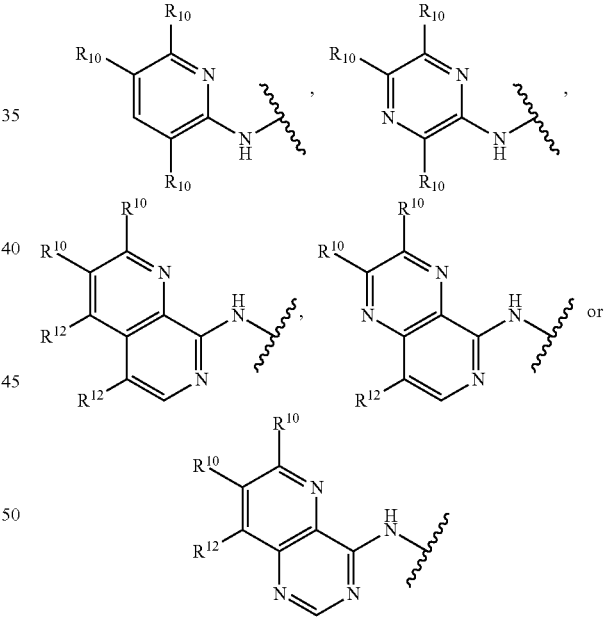

wherein each $R^{10}$, independently, is H, F, Cl, CN, OH, $C_{2-3}$alkenyl, $C_{2-3}$alkynyl, $C_{3-6}$cycloalkyl, $C_{1-6}$alkoxyl, $C_{1-6}$thioalkoxyl, 2-propyn-1-yloxy, 2-butyn-1-yloxy, wherein each of the $C_{1-6}$alkyl, $C_{2-3}$alkenyl, $C_{2-3}$alkynyl, $C_{3-6}$cycloalkyl, $C_{1-6}$alkoxyl, $C_{1-6}$thioalkoxyl, 2-propyn-1-yloxy or 2-butyn-1-yloxy, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$; and each R$^{12}$, independently, is H, F, Cl or CH$_3$.

13. The compound according to claim 12, or a stereoisomer or pharmaceutically acceptable salt thereof, wherein R$^7$ is —NH—C(=O)—R$^9$.

14. The compound according to claim 12, or a stereoisomer or pharmaceutically acceptable salt thereof, wherein R$^7$ is

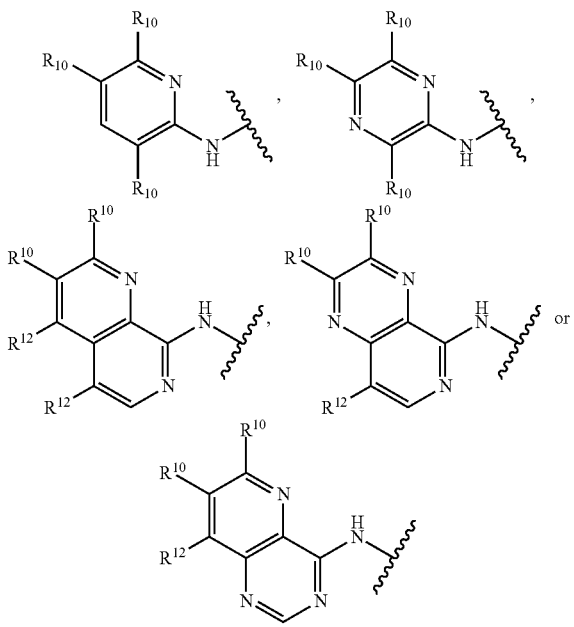

wherein each R$^{12}$, independently, is H, F or Cl.

15. The compound according to claim 1, or a stereoisomer or pharmaceutically acceptable salt thereof, having a Formula II-A

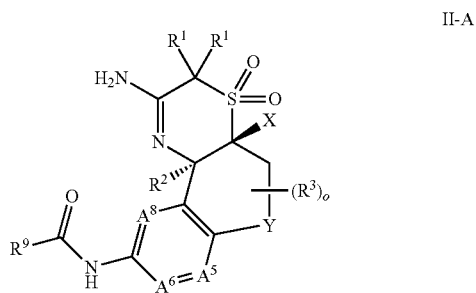

II-A wherein
A$^5$ is CR$^5$ or N;
A$^6$ is CR$^6$ or N;
A$^8$ is CR$^8$ or N, provided that no more than one of A$^5$, A$^6$ and A$^8$ is N;
each R$^1$, independently, is H, F, Cl, C$_{1-4}$-alkyl, C$_{2-4}$alkenyl, C$_{2-4}$alkynyl, CN, —CH$_2$OC$_{1-3}$-alkyl, —OC$_{1-3}$-alkyl, wherein each of the C$_{1-4}$-alkyl, C$_{2-4}$alkenyl, C$_{2-4}$alkynyl and C$_{1-4}$-alkyl portion of —CH$_2$OC$_{1-3}$-alkyl and —OC$_{1-3}$-alkyl are optionally substituted with 1-4 substituents of F;
alternatively, each R$^1$ taken together with the carbon atom to which they are attached form a C$_{3-6}$ spirocarbocyclic ring optionally including one heteroatom selected from O and N and optionally substituted with 1-4 F atoms on the carbon atoms and a subsistent of C$_{1-3}$alkyl, CH$_2$OC$_{1-2}$alkyl or C$_{1-3}$haloalkyl on the nitrogen atom;
R$^2$ is CH$_3$, CH$_2$F or CHF$_2$;
each R$^3$, independently, is halo, C$_{1-4}$alkyl, CH$_2$OC$_{1-4}$alkyl, CH$_2$OH, C$_{1-4}$haloalkyl or cyclopropyl, wherein each of the CH$_2$OC$_{1-4}$alkyl and cyclopropyl is optionally substituted with 1-4 F atoms;
each of R$^5$, R$^6$ and R$^8$, independently, is H or F;
R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, furanyl, dihydrofuranyl, thienyl, and pyrrolyl, wherein the C$_{1-6}$-alkyl, C$_{2-4}$alkenyl, C$_{2-4}$alkynyl and ring are optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHCH$_3$, oxo, C$_{1-6}$ alkyl, C$_{2-6}$ alkenyl, C$_{2-6}$ alkynyl, C$_{3-6}$ cycloalkyl, C$_{1-6}$ alkylamino-, C$_{1-6}$dialkylamino-, C$_{1-6}$ alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)R$^{11}$— or —C(O)NHR$^{11}$—, wherein each of the C$_{1-6}$alkyl, C$_{2-6}$alkenyl, C$_{2-6}$ alkynyl, C$_{3-6}$ cyclo alkyl, C$_{1-6}$ alkylamino-, C$_{1-6}$ dialkylamino-, C$_{1-6}$ alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$;
X is H or F;
Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, C$_{1-3}$alkyl or C$_{1-3}$haloalkyl; and
o is 0, 1 or 2.

16. The compound according to claim 15, or a stereoisomer, tautomer or
pharmaceutically acceptable salt thereof, wherein
A$^5$ is CR$^5$;
A$^6$ is CR$^6$;
A$^8$ is CR$^8$; wherein each of R$^4$, R$^5$, R$^6$ and R$^8$, independently, is H or F;
each R$^1$, independently, is H, F, CH$_3$, C$_2$H$_5$, CF$_2$H, CH$_2$F, CH$_2$OCH$_2$F, CH$_2$OCF$_2$H or CH$_2$OCF$_3$;
alternatively, each R$^1$ taken together with the carbon atom to which they are attached form a C$_{3-6}$ spirocarbocyclic ring optionally including one heteroatom selected from O and N and optionally substituted with 1-3 F atoms;
R$^2$ is CH$_3$, CH$_2$F or CHF$_2$;
each R$^3$, independently, is F, CH$_3$, C$_2$H$_5$, CH$_2$F, CF$_2$H, CF$_3$ or CH$_2$CF$_3$;
R$^9$ is a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, imidazo-pyridyl, pyrido-pyrazinyl, pyrido-pyrimidinyl, pyranyl, dihydropyranyl, furanyl, dihydrofuranyl, thienyl, and pyrrolyl, wherein the ring is optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$ alkyl, $C_{2-6}$ alkenyl, $C_{2-6}$ alkynyl, $C_{3-6}$ cycloalkyl, $C_{1-6}$alkylamino-, $C_{1-6}$dialkylamino-, $C_{1-6}$ alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)$R^{11}$— or —C(O)NHR$^{11}$—, wherein each of the $C_{1-6}$alkyl, $C_{2-6}$alkenyl, $C_{2-6}$ alkynyl, $C_{3-6}$ cycloalkyl, $C_{1-6}$ alkylamino-, $C_{1-6}$ dialkylamino-, $C_{1-6}$ alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$ alkylamino-, $C_{1-3}$ dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$;

Y is —SCR$^4$R$^4$—, —S(O)$^2$CR$^4$R$^4$—, —OCR$^4$R$^4$— or —CR$^4$R$^4$CR$^4$R$^4$—, wherein each R$^4$, independently, is H, F or CH$_3$; and o is 0, 1 or 2.

17. The compound according to claim 15, or a stereoisomer or pharmaceutically acceptable salt thereof, wherein
A$^5$ is CR$^5$ or N;
A$^6$ is CR$^6$ or N;
A$^8$ is CR$^8$ or N, wherein each of R$^4$, R$^5$, R$^6$ and R$^8$, independently, is H or F and provided no more than one of A$^5$, A$^6$ and A$^8$ is N;
each R$^1$, independently, is H, F, Cl, CF$_3$, CH$_3$, CF$_2$H or CH$_2$F;
R$^2$ is CH$_3$ or CH$_2$F;
each R$^3$, independently, is CF$_3$, CH$_3$, CF$_2$H or CH$_2$F; and
o is 0 or 1.

18. The compound according to claim 1, or a stereoisomer, tautomer, or pharmaceutically acceptable salt thereof, having a Formula II-B:

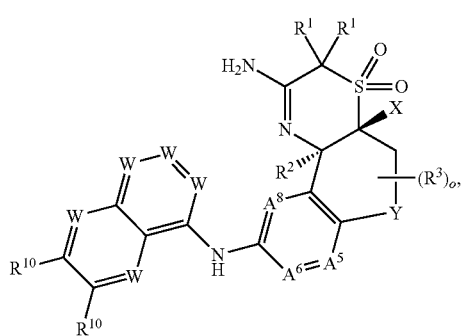

II-B wherein
A$^5$ is CR$^5$ or N;
A$^6$ is CR$^6$ or N;

A$^8$ is CR$^8$ or N, provided that no more than one of A$^5$, A$^6$ and A$^8$ is N;
each R$^1$, independently, is H, F, Cl, $C_{1-4}$-alkyl, $C_{2-4}$alkenyl, $C_{2-4}$alkynyl, CN, CH$_2$OC$_{1-3}$-alkyl, —OC$_{1-3}$-alkyl, wherein each of the $C_{1-4}$-alkyl, $C_{2-4}$ alkenyl, $C_{2-4}$ alkynyl and $C_{1-3}$-alkyl portion of —CH$_2$OC$_{1-3}$-alkyl and —OC$_{1-3}$-alkyl are optionally substituted with 1-4 substituents of F;
alternatively, each R$^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, CH$_2$OC$_{1-2}$alkyl or $C_{1-3}$haloalkyl on the nitrogen atom;
R$^2$ is CH$_3$, CH$_2$F or CHF$_2$;
each R$^3$, independently, is halo, $C_{1-4}$alkyl, CH$_2$OC$_{1-4}$alkyl, CH$_2$OH, $C_{1-4}$haloalkyl or cyclopropyl, wherein each of the CH$_2$OC$_{1-4}$alkyl and cyclopropyl is optionally substituted with 1-4 F atoms;
each of R$^5$, R$^6$ and R$^8$, independently, is H or F;
each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)$R^{11}$— or —C(O)NHR$^{11}$—, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$;
each W, independently, is CH, CF, CCl, CCH$_3$ or N;
X is H or F;
Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, $C_{1-3}$alkyl or $C_{1-3}$haloalkyl; and
o is 0, 1 or 2.

19. The compound according to claim 18, or a stereoisomer or pharmaceutically acceptable salt thereof, wherein
A$^5$ is CR$^5$;
A$^6$ is CR$^6$;
A$^8$ is CR$^8$; wherein each of R$^5$, R$^6$ and R$^8$, independently, is H or F;
each R$^1$, independently, is H, F, CH$_3$, C$_2$H$_5$, CF$_2$H, CH$_2$F, CH$_2$OCH$_2$F, CH$_2$OCF$_2$H or CH$_2$OCF$_3$;
alternatively, each R$^1$ taken together with the carbon atom to which they are attached form a $C_{3-6}$ spirocarbocyclic ring optionally including one heteroatom selected from O and N and optionally substituted with 1-3 F atoms;
R$^2$ is CH$_3$ or CH$_2$F;
each R$^3$, independently, is CF$_3$, CH$_3$, CF$_2$H or CH$_2$F; and
o is 0 or 1.

20. The compound according to claim 18, or a stereoisomer or pharmaceutically acceptable salt thereof, wherein $A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^5$, $A^6$ and $A^8$ is N;
each $R^1$, independently, is H, F, Cl, $CF_3$, $CH_3$, $CF_2H$ or $CH_2F$;
$R^2$ is $CH_3$ or $CH_2F$;
each $R^3$, independently, is $CF_3$, $CH_3$, $CF_2H$ or $CH_2F$; and o is 0 or 1.

21. The compound according to claim 1, or a stereoisomer, tautomer, or pharmaceutically acceptable salt thereof, having a Formula II-D:

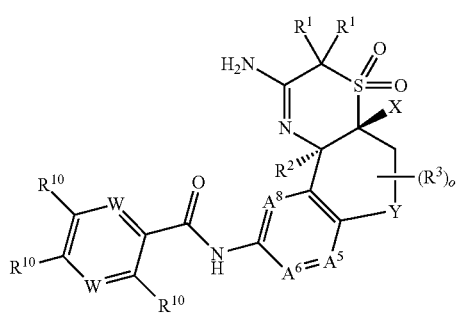

II=D wherein
$A^5$ is $CR^5$ or N;
$A^6$ is $CR^6$ or N;
$A^8$ is $CR^8$ or N, provided that no more than one of $A^5$, $A^6$ and $A^8$ is N;
each $R^1$, independently, is H, F, Cl, $C_{1-4}$-alkyl, $C_{2-4}$alkenyl, $C_{2-4}$alkynyl, CN, $CH_2OC_{1-3}$-alkyl, —$OC_{1-3}$-alkyl, wherein each of the $C_{1-4}$-alkyl, $C_{2-4}$ alkenyl, $C_{2-4}$ alkynyl and $C_1$-3-alkyl portion of —$CH_2OC_{1-3}$-alkyl and —$OC_{1-3}$-alkyl are optionally substituted with 1-4 substituents of F;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
$R^2$ is $CH_3$, $CH_2F$ or $CHF_2$;
each $R^3$, independently, is halo, $C_{1-4}$alkyl, $CH_2OC_{1-4}$alkyl, $CH_2OH$, $C_{1-4}$haloalkyl or cyclopropyl, wherein each of the $CH_2OC_{1-4}$alkyl and cyclopropyl is optionally substituted with 1-4 F atoms;
each of $R^5$, $R^6$ and $R^8$, independently, is H or F;
each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —$NHC(O)R^{11}$— or —$C(O)NHR^{11}$—, wherein each of the $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;
each W, independently, is CH, CF, CCl, $CCH_3$ or N;
X is H or F;
Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, $C_{1-3}$alkyl or $C_{1-3}$haloalkyl; and
o is 0, 1 or 2.

22. The compound according to claim 21, or a stereoisomer or pharmaceutically acceptable salt thereof, wherein
$A^5$ is $CR^5$ or N;
$A^6$ is $CR^6$;
$A^8$ is $CR^8$; wherein each of $R^5$, $R^6$ and $R^8$, independently, is H or F;
each $R^1$, independently, is H, F, $CH_3$, $C_2H_5$, $CF_2H$, $CH_2F$, $CH_2OCH_2F$, $CH_2OCF_2H$ or $CH_2OCF_3$;
alternatively, each $R^1$ taken together with the carbon atom to which they are attached form a $C_{3-6}$ spirocarbocyclic ring optionally including one heteroatom selected from O and N and optionally substituted with 1-3 F atoms;
$R^2$ is $CH_3$ or $CH_2F$;
each $R^3$, independently, is $CF_3$, $CH_3$, $CF_2H$ or $CH_2F$; and
o is 0 or 1.

23. The compound according to claim 21, or a stereoisomer or pharmaceutically acceptable salt thereof, wherein
$A^5$ is $CR^5$ or N;
$A^6$ is $CR^6$;
$A^8$ is $CR^8$, wherein each of $R^5$, $R^6$ and $R^8$, independently, is H or F;
each $R^1$, independently, is H, F, Cl, $CF_3$, $CH_3$, $CF_2H$ or $CH_2F$;
$R^2$ is $CH_3$ or $CH_2F$; and
o is 0.

24. The compound of claim 1, or a pharmaceutically acceptable salt thereof, having a
formula III-C or III-D

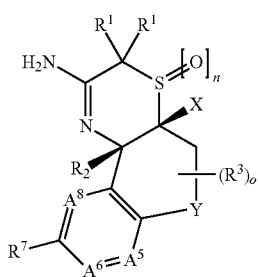

III-C

-continued

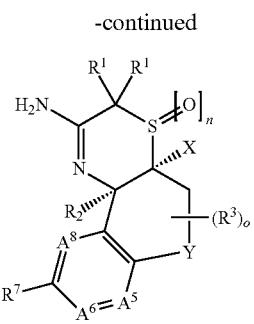

III-D wherein
$A^5$ is $CR^5$ or N;
$A^6$ is $CR^6$ or N;
$A^8$ is $CR^8$ or N, provided that no more than one of $A^5$, $A^6$ and $A^8$ is N;
each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, $C_{1-3}$ alkyl, $C_{1-3}$alkoxyl, $CH_2OC_{1-2}$ alkyl or $C_{1-3}$haloalkyl;
$R^2$ is $C_{1-4}$alkyl, $CH_2OC_{1-4}$alkyl, $CH_2OH$, $CH_2CN$, $C_{3-6}$cycloalkyl or CN, wherein each of the $C_{1-4}$alkyl, $CH_2OC_{1-4}$alkyl and $C_{3-6}$cycloalkyl is optionally substituted with 1-4 F atoms;
each $R^3$, independently, is halo, $C_{1-4}$alkyl, $OC_{1-4}$alkyl, $CH_2OC_{1-4}$alkyl, $CH_2OH$, $C_{1-4}$haloalkyl, cyclopropyl or CN, wherein each of the $OC_{1-4}$alkyl, $CH_2OC_{1-4}$alkyl and cyclopropyl is optionally substituted with 1-4 F atoms;
each of $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NHC(═O)—$R^9$, —C(═O)NH—$R^9$, —O—$R^9$ or —S—$R^9$;
$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;
each $R^{10}$, independently, is H, halo, haloalkyl, CN, OH, $NO_2$, $NH_2$, $SF_5$, acetyl, —$C(O)NHCH_3$, oxo, $C_{1-6}$ alkyl, $C_{2-6}$ alkenyl, $C_{2-6}$ alkynyl, $C_{3-6}$ cycloalkyl, $C_{1-6}$alkylamino-, $C_{1-6}$dialkylamino-, $C_{1-6}$ alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)$R^{11}$— or —C(O)NHR$^{11}$—, wherein each of the $C_{1-6}$alkyl, $C_{2-6}$alkenyl, $C_{2-6}$ cycloalkyl, $C_{1-6}$ alkylamino-, $C_{1-6}$dialkylamino-, $C_{1-6}$ alkoxyl, $C_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;
$R^{11}$ is $C_{1-6}$alkyl, $C_{1-6}$alkoxyl or $C_{3-6}$cycloalkyl;
X is H, F, $CH_3$, $CH_2CH_3$, cyclopropyl or CN;
Y is —$SCR^4R^4$—, —$S(O)_2CR^4R^4$—, —$OCR^4R^4$—, —$CR^4R^4O$— or —$CR^4R^4CR^4R^4$—, wherein each $R^4$, independently, is H, F, OH, $C_{1-6}$alkyl, $OC_{1-6}$alkyl or $C_{1-6}$haloalkyl;
n is 0, 1 or 2; and
o is 0, 1 or 2.

25. The compound of claim 1, or a pharmaceutically acceptable salt thereof, having a
formula III-A or III-B

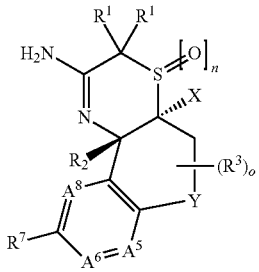

III-A

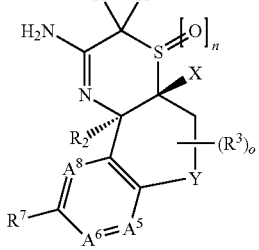

III-B wherein
$A^5$ is $CR^5$ or N;
$A^6$ is $CR^6$ or N;
$A^8$ is $CR^8$ or N, provided that no more than one of $A^5$, $A^6$ and $A^8$ is N;
each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)C_{1-6}$-alkyl or $C_{3-6}$cycloalkyl, wherein each of the $C_{1-6}$-alkyl, $C_{2-4}$alkenyl, $C_{2-4}$alkynyl, $C_{3-6}$cycloalkyl and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^1$ taken together with the carbon atom to which they are attached form a $C_{3-6}$ spirocarbocyclic ring optionally including one heteroatom selected from O and N and optionally substituted, independently, with 1-4 substituents of F, OH, C$_{1-3}$alkyl, C$_{1-3}$alkoxyl, CH$_2$OC$_{1-2}$alkyl or C$_{1-3}$haloalkyl;

R$^2$ is C$_{1-4}$alkyl, CH$_2$OC$_{1-4}$alkyl, CH$_2$OH, CH$_2$CN, C$_{3-6}$cycloalkyl or CN, wherein each of the C$_{1-4}$alkyl, CH$_2$OC$_{1-4}$alkyl and C$_{3-6}$cycloalkyl is optionally substituted with 1-4 F atoms;

each R$^3$, independently, is halo, C$_{1-4}$alkyl, OC$_{1-4}$alkyl, CH$_2$OC$_{1-4}$alkyl, CH$_2$OH, C$_{1-4}$haloalkyl, cyclopropyl or CN, wherein each of the OC$_{1-4}$alkyl, CH$_2$OC$_{1-4}$alkyl and cyclopropyl is optionally substituted with 1-4 F atoms;

each of R$^5$, R$^6$ and R$^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

R$^7$ is —NH—R$^9$, —NHC(=O)—R$^9$, —C(=O)NH—R$^9$, —O—R$^9$ or —S—R$^9$;

R$^9$ is acetyl, C$_{1-6}$-alkyl, C$_{2-4}$alkenyl, C$_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$;

each R$^{10}$, independently, is H, halo, haloalkyl, CN, OH, NO$_2$, NH$_2$, SF$_5$, acetyl, —C(O)NHCH$_3$, oxo, C$_{1-6}$ alkyl, C$_{2-6}$ alkenyl, C$_{2-6}$ alkynyl, C$_{3-6}$ cycloalkyl, C$_{1-6}$alkylamino-, C$_{1-6}$dialkylamino-, C$_{1-6}$ alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolyl, pyrrolidinyl, piperazinyl, oxetan-3-yl, dioxolyl, —NHC(O)R$^{11}$— or —C(O)NHR$^{11}$—, wherein each of the C$_{1-6}$alkyl, C$_{2-6}$alkenyl, C$_{2-6}$ alkynyl, C$_{3-6}$ cyclo alkyl, C$_{1-6}$alkylamino-, C$_{1-6}$dialkylamino-, C$_{1-6}$alkoxyl, C$_{1-6}$thioalkoxyl, 2-propyn-1-yloxy, 2-butyn-1-yloxy, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxy, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or CH$_3$;

R$^{11}$ is C$_{1-6}$alkyl, C$_{1-6}$alkoxyl or C$_{3-6}$cycloalkyl;

X is H, F, CH$_3$, CH$_2$CH$_3$, cyclopropyl or CN;

Y is —SCR$^4$R$^4$—, —S(O)$_2$CR$^4$R$^4$—, —OCR$^4$R$^4$—, —CR$^4$R$^4$O— or —CR$^4$R$^4$CR$^4$R$^4$—, wherein each R$^4$, independently, is H, F, OH, C$_{1-6}$alkyl, OC$_{1-6}$alkyl or C$_{1-6}$haloalkyl;

n is 0, 1 or 2; and o is 0, 1 or 2.

26. The compound of claim 25, or a stereoisomer, tautomer or pharmaceutically acceptable salt thereof, having a formula III-B-1

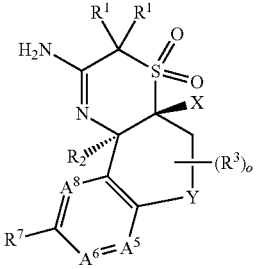

III-B-1 wherein A$^5$ is CR$^5$ or N;
A$^6$ is CR$^6$;
A$^8$ is CR$^8$, wherein each of R$^5$, R$^6$ and R$^8$, independently, is H or F;
each R$^1$, independently, is CH$_3$;
R$^2$ is CH$_3$ or CH$_2$F;
R$^7$ is —NH—C(=O)—R$^9$, or
R$^7$ is

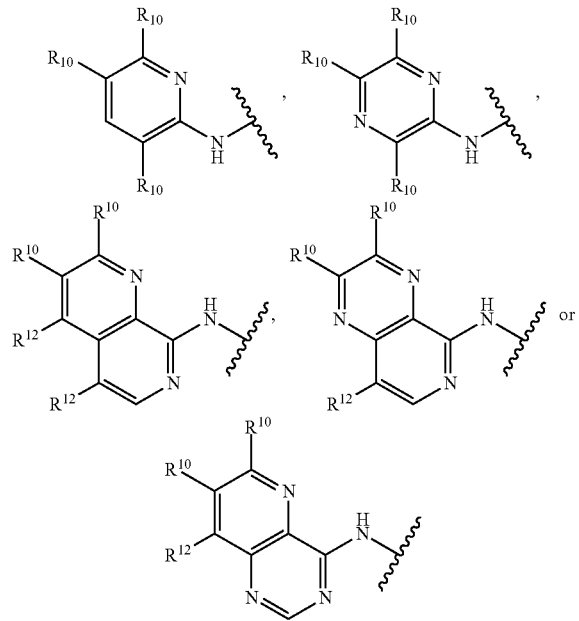

R$^9$ is a ring selected from phenyl, pyridyl, pyrimidyl, pyrazinyl, pyridazinyl, naphthyl, quinolinyl, isoquinolinyl, quinazolinyl, naphthyridinyl, phthalazinyl, imidazo[1,2-a]pyridyl, pyrido[3,4-b]pyrazin-5-yl or pyrido[3,2-d]pyrimidin-4-yl, wherein the ring is optionally substituted, independently, with 1-5 substituents of R$^{10}$;

each R$^{10}$, independently, is H, F, Cl, C$_{1-3}$alkyl, C$_{1-3}$haloalkyl, CN, OH, C$_{2-3}$alkenyl, C$_{2-3}$alkynyl, C$_{3-6}$ cycloalkyl, C$_{1-6}$ alkoxyl, C$_{1-6}$thioalkoxyl, 2-propyn-1-yloxy, 2-butyn-1-yloxy, wherein each of the C$_{1-6}$alkyl, C$_{2-3}$alkenyl, C$_{2-3}$alkynyl, C$_{3-6}$cycloalkyl, C$_{1-6}$alkoxyl, C$_{1-6}$thioalkoxyl, 2-propyn-1-yloxy or 2-butyn-1-yloxy, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C$_{1-3}$thioalkoxyl, oxetan-3yl, oxazolyl, isoxazolyl, imidazolyl or pyrazolyl, wherein each of the oxazolyl, isoxazolyl, imidazolyl or pyrazolyl is optionally substituted with 1-3 substituents of F or $CH_3$;

each $R^{12}$, independently, is H, F, Cl or $CH_3$;

X is H or F;

Y is —$SCR^4R^4$—, —$S(O)^2CR^4R^4$—, —$OCR^4R^4$—, —$CR^4R^{40}$— or —$CR^4R^4CR^4R^4$—, wherein each $R^4$, independently, is H, F, $CH_3$, $CH_2F$ or $CF_3$; and o is 0.

27. The compound of claim 1, or a stereoisomer, tautomer or pharmaceutically acceptable salt thereof, selected from

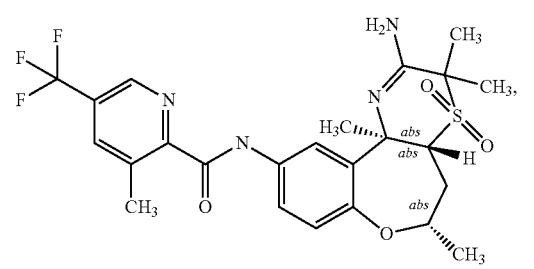

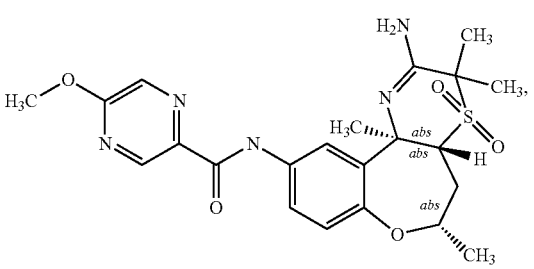

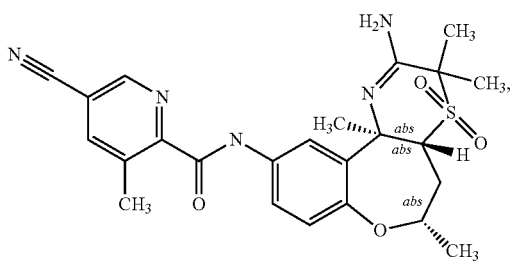

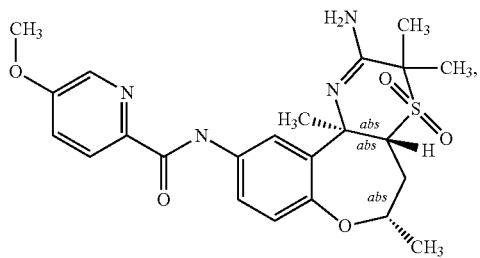

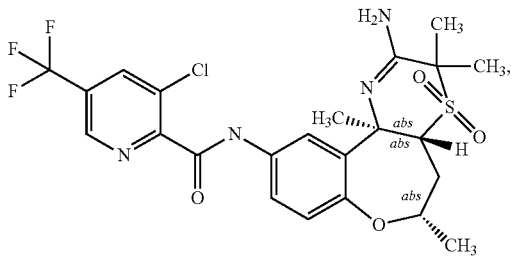

-continued

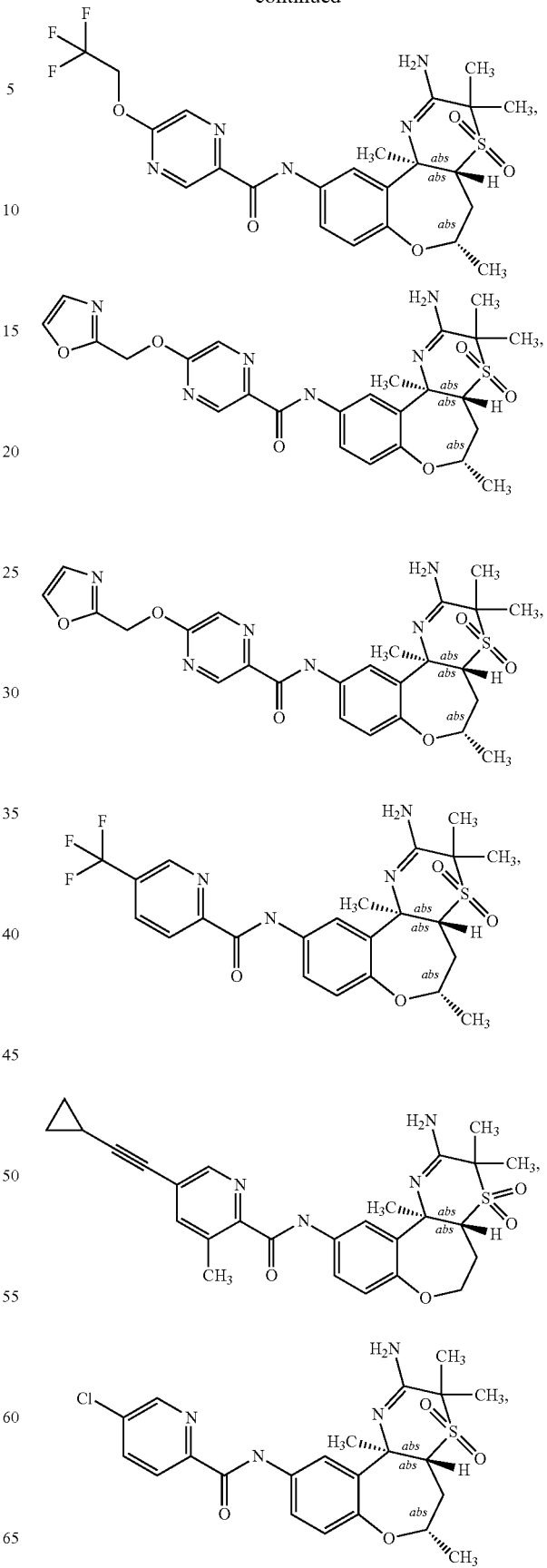

265
-continued
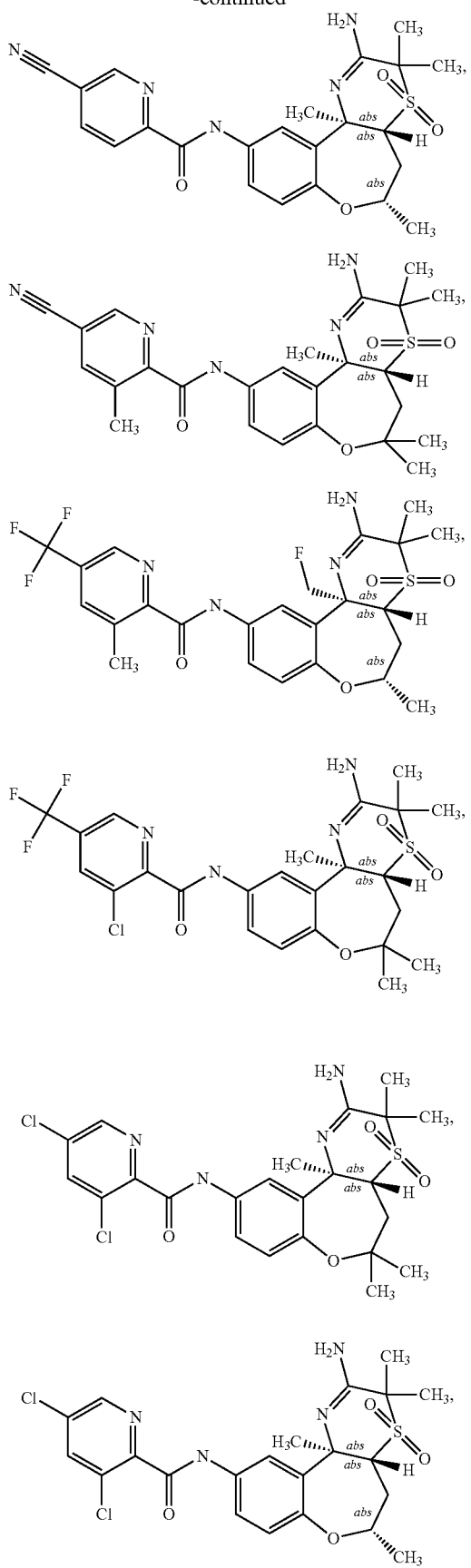
266
-continued
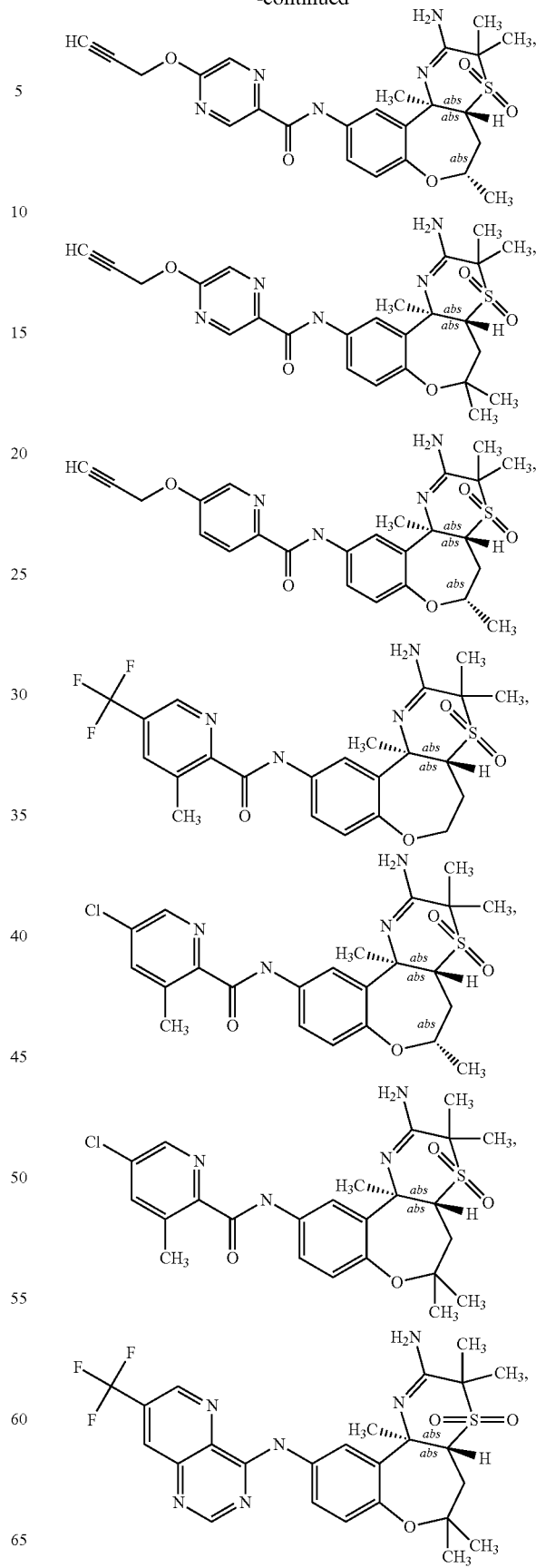

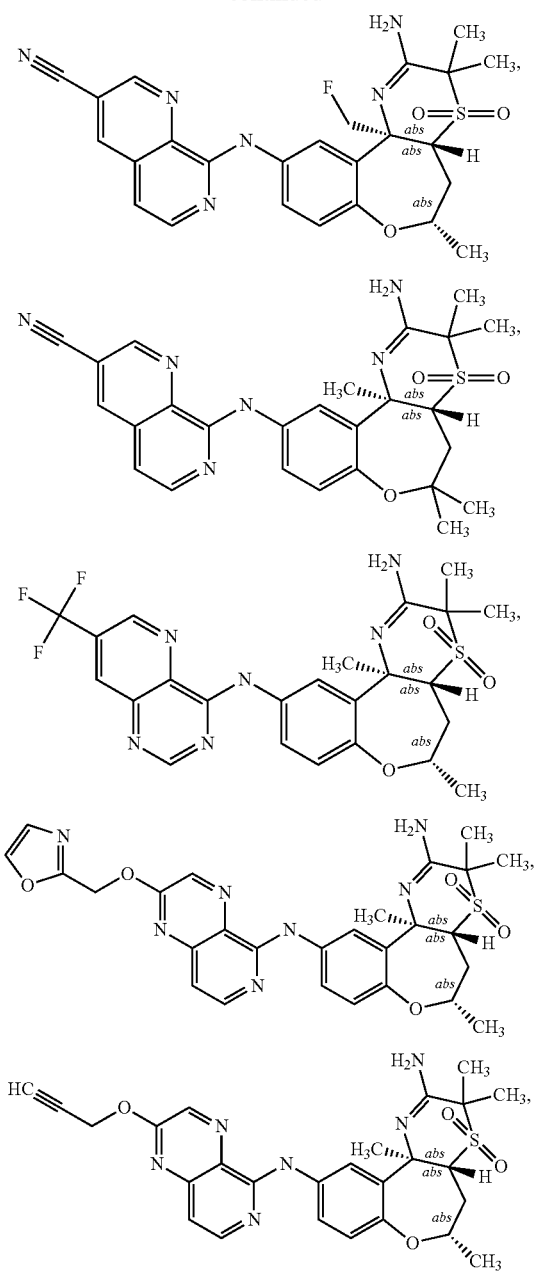

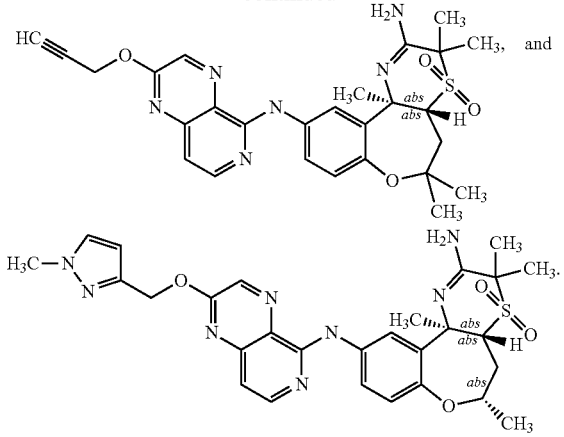

28. A pharmaceutical composition comprising a compound according to claim 1 and a pharmaceutically acceptable excipient.

29. A pharmaceutical composition comprising a compound according to claim 26 and a pharmaceutically acceptable excipient.

30. A pharmaceutical composition comprising a compound according to claim 27 and a pharmaceutically acceptable excipient.

31. A process for preparing a compound according to claim 1, the process comprising the step of reacting a compound 20

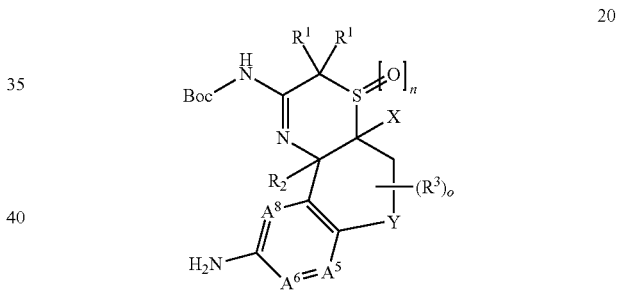

wherein $A^5, A^6, A^8, R^1, R^2, R^3, X, Y, n$ and $o$ of compound 20 are as defined in claim 1, with a compound having the structure or $R^9$—C(=O)OH in the presence of an acid activating agent or $R^9$—Cl in the presence of acid, wherein $R^9$ is as defined in claim 1 to prepare the compound according to of claim 1.

* * * * *